United States Patent
Baker et al.

(10) Patent No.: US 8,187,855 B2
(45) Date of Patent: May 29, 2012

(54) LARGE-SCALE PRODUCTION OF SOLUBLE HYALURONIDASE

(75) Inventors: David Baker, San Diego, CA (US); Louis H. Bookbinder, San Diego, CA (US)

(73) Assignee: Halozyme, Inc., San Diego, CA (US)

( * ) Notice: Subject to any disclaimer, the term of this patent is extended or adjusted under 35 U.S.C. 154(b) by 0 days.

(21) Appl. No.: 12/735,868

(22) PCT Filed: Mar. 6, 2009

(86) PCT No.: PCT/US2009/001455
§ 371 (c)(1),
(2), (4) Date: Nov. 9, 2010

(87) PCT Pub. No.: WO2009/111066
PCT Pub. Date: Sep. 11, 2009

(65) Prior Publication Data
US 2011/0053247 A1   Mar. 3, 2011

Related U.S. Application Data

(60) Provisional application No. 61/068,622, filed on Mar. 6, 2008.

(51) Int. Cl.
C12N 9/26 (2006.01)
C12N 15/00 (2006.01)
A61K 38/46 (2006.01)
A61K 38/00 (2006.01)

(52) U.S. Cl. .......... 435/201; 424/94.62; 435/320.1; 514/44 R

(58) Field of Classification Search .......... 424/94.3, 424/94.62; 435/200, 201, 320.1; 514/1.1, 514/44 R
See application file for complete search history.

(56) References Cited

U.S. PATENT DOCUMENTS

| | | | |
|---|---|---|---|
| 5,292,509 A | 3/1994 | Hageman | 424/94.61 |
| 5,705,364 A | 1/1998 | Etcheverry et al. | 435/70.3 |
| 6,528,286 B1 | 3/2003 | Ryll | 435/69.7 |
| 6,745,776 B2 | 6/2004 | Soll | 128/898 |
| 7,767,429 B2 | 8/2010 | Bookbinder | 435/201 |
| 2004/0268425 A1 | 12/2004 | Bookbinder et al. | 800/18 |
| 2005/0260186 A1 | 11/2005 | Bookbinder et al. | 424/94.61 |
| 2006/0104968 A1 | 5/2006 | Bookbinder et al. | 424/94.61 |
| 2007/0134228 A1 | 6/2007 | Stern et al. | 424/94.61 |
| 2009/0123367 A1 | 5/2009 | Bookbinder et al. | 424/1.49 |
| 2009/0181013 A1 | 7/2009 | Bookbinder et al. | 424/130.1 |
| 2009/0181032 A1 | 7/2009 | Bookbinder et al. | 424/141.1 |
| 2009/0214505 A1 | 8/2009 | Bookbinder et al. | 424/94.1 |
| 2009/0253175 A1 | 10/2009 | Bookbinder et al. | 435/69.1 |
| 2009/0304665 A1 | 12/2009 | Frost et al. | 424/94.5 |
| 2009/0311237 A1 | 12/2009 | Frost | 424/94.62 |
| 2010/0003238 A1 | 1/2010 | Frost et al. | 424/94.62 |
| 2010/0074885 A1 | 3/2010 | Schiff et al. | 424/130.1 |
| 2010/0143457 A1 | 6/2010 | Wei et al. | 424/450 |
| 2010/0196423 A1 | 8/2010 | Bookbinder et al. | 424/247.1 |
| 2010/0211015 A1 | 8/2010 | Bookbinder et al. | 604/187 |

FOREIGN PATENT DOCUMENTS

| | | |
|---|---|---|
| CN | 1942588 | 9/2004 |
| WO | WO 88/02261 | 4/1988 |
| WO | WO 2004/078140 | 9/2004 |

OTHER PUBLICATIONS

U.S. Appl. No. 12/802,864, filed Jun. 15, 2010.
U.S. Appl. No. 12/807,991, filed Sep. 16, 2010.
Altschul, S., "Basic local alignment search tool," J Molec Biol 215(3):403-410 (1990).
Baumgartner et al., "Phase I study in chemoresistant loco-regional malignant disease with hyaluronidase," Reg. Cancer Treat. 1:55-58 (1988).
Bjermer, "Hyaluronate and type III procollagen peptide concentrations in bronchoalveolar lavage fluid as markers of disease activity in farmer's lung," Br Med J Clin Res Ed. 295(6602):803-806 (1987).
Carrillo, H. and D. Lipman, "The multiple-sequence alignment problem in biology," SIAM J Applied Math 48(5):1073-1082 (1988).
Danilkovitch-Miagkova, et al., "Hyaluronidase 2 negatively regulates RON receptor tyrosine kinase and mediates transformation of epithelial cells by jaagsiekte sheep retrovirus," Proc Natl Acad Sci USA. 100(8):4580-4585 (2003).
De Maeyer et al., "The growth rate of two transplantable murine tumors, 3LL lung carcinoma and B16F10 melanoma, is influenced by Hyal-1, a locus determining hyaluronidase levels and polymorphism," Int. J. Cancer 51:657-660 (1992).
Delpech et al., "Enzyme-linked hyaluronectin: a unique reagent for hyaluronan assay and tissue location and for hyaluronidase activity detection," Anal. Biochem. 229(1):35-41 (1995).
Derwent Abstract for WO 1988002261. Inventor: Baumgartne et al., WPI Acc No. 1988 105412/198815, Dialog File No. 351. Abstract published 1988 [2 pages].
Devereux et al, "A comprehensive set of sequence analysis programs for the VAX," Nucleic Acids Research 12:387-395 (1984).
Dubensky et al., "Direct transfection of viral and plasmid DNA into the liver or spleen of mice," Proc Natl Acad Sci U S A 81(23):7529-7533 (1984).
Elder et. al, "Intra-arterial hyaluronidase in severe peripheral arterial disease," Lancet 648-649 (1980).
Favre et al, "Hyaluronidase enhances recombinant adeno-associated virus (rAAV)-mediated gene transfer in the rat skeletal muscle," Gene Ther 7(16):1417-1420 (2000).
Few, B., "Hyaluronidase for treating intravenous extravasations," MCN Amer. J. Matern. Child Nurs. 12(1):23-26 (1987).

(Continued)

*Primary Examiner* — Herbert J Lilling
(74) *Attorney, Agent, or Firm* — McKenna Long & Aldridge LLP; Stephanie Seidman

(57) ABSTRACT

Provided are methods for preparing large-scale preparations of soluble hyaluronidases. The methods employ cells that contain a plurality of active copies of nucleic acid encoding the soluble hyaluronidase and a plurality of feedings and temperature changes, whereby the encoded soluble hyaluronidase is secreted into the cell culture medium.

16 Claims, No Drawings

OTHER PUBLICATIONS

Frost, G. and R. Stern, "A microtiter-based assay for hyaluronidase activity not requiring specialized reagents," Anal. Biochem. 251:263-269 (1997).

Frost et al., "Purification, cloning, and expression of human plasma hyaluronidase," Biochem. Biophys. Res. Commun. 236:10-15 (1997).

Gribskov et al., "Sigma factors from *E. coli, B. subtilis*, phage SP01, and phage T4 are homologous proteins," Nucl. Acids Res. 14:6745-6763 (1986).

Hallgren et al, "Accumulation of hyaluronan (hyaluronic acid) in myocardial interstitial tissue parallels development of transplantation edema in heart allografts in rats," J Clin Invest 85:668-673 (1990).

Hallgren et al, "Hyaluronic acid accumulation and redistribution in rejecting rat kidney graft. Relationship to the transplantation edema," J Exp Med. 171:2063-2076 (1990).

Harvey et al., "Mutagenesis of the gamma-carboxyglutamic acid domain of human factor VII to generate maximum enhancement of the membrane contact site," J Biol Chem 278(10):8363-8369 (2003).

IUPAC-IUB Commission on Biochemical Nomenclature, "Abbreviated nomenclature of synthetic poypeptides-polymerized amino acids-revised recommendations," Biochemistry 11:1726-1731 (1972).

IUPAC-IUB Commission on Biochemical Nomenclature, "A One-Letter Notation for Amino Acid Sequences: Tentative Rules," J. Biol. Chem. 243:3557-3559 (1968).

Kolodgie et al, "Differential accumulation of proteoglycans and hyaluronan in culprit lesions: insights into plaque erosion," Arterioscler Thromb Vasc Biol. 22(10):1642-1648 (2002).

Laurent et al, "Hyaluronan in human cerebrospinal fluid," Acta Neurol Scand 94(3):194-206 (1996).

Maclean, et. al., "Hyaluronidase-induced reductions in myocardial infarct size," Science 194(4261):199-200 (1976).

Maun et al., "Disulfide locked variants of factor VIIa with a restricted beta-strand conformation have enhanced enzymatic activity," Prot Sci 14:1171-1180 (2005).

Needleman, S. and C. Wunsch "A general method applicable to the search for similarities in the amino acid sequence of two proteins," J Mol Biol. 48:443-453 (1970).

Nettelbladt et al, "Accumulation of hyaluronic acid in the alveolar interstitial tissue in bleomycin-induced alveolitis," Am Rev Resp Dis 139:759-762 (1989).

Paul, A. and D. Sochart, "Improving the results of ganglion aspiration by the use of hyaluronidase," J Hand Surg 22(2):219-221 (1997).

Pawlowski et al., "The effects of hyalurodinase upon tumor formation in BALB/c mice painted with 7,12-dimethylbenz-(a)anthracene," Int. J. Cancer 23:105-109 (1979).

Pearson, W. and D. Lipman "Improved tools for biological sequence comparison," Proc. Natl. Acad. Sci. USA 85:2444-2448 (1988).

Przysiecki et al., "Occurrence of beta-hydroxylated asparagine residues in non-vitamin K-dependent proteins containing epidermal growth factor-like domains," Proc Natl Acad Sci USA. 84(22):7856-7860 (1987).

Schwartz, R. and M. Dayhoff, eds., Atlas of Protein Sequence And Structure, National Biomedical Research Foundation, pp. 353-358 (1979).

Smith, T. and M. Waterman, "Comparison of biosequences," Advances in Applied Mathematics 2:482-489 (1981).

St Croix et al., "Reversal of intrinsic and acquired forms of drug resistance by hyaluronidase treatment of solid tumors," Cancer Lett 131(1):35-44 (1998).

Takahashi et al., "A fluorimetric Morgan-Elson assay method for hyaluronidase activity ," Anal. Biochem. 322:257-263 (2003).

Waldenstrom et al, "Coxsackie B3 myocarditis induces a decrease in energy charge and accumulation of hyaluronan in the mouse heart," Eur J Clin Invest 23:277-282 (1993).

Waldenstrom et al, "Accumulation of hyaluronan and tissue edema in experimental myocardial infarction," J Clin Invest 88(5):1622-1628 (1991).

Wallander et al, "Intestinal distribution of hyaluronan in small bowel allografting in the rat," Transplant Int 6:133-137 (1993).

Wells et al, "The localization of hyaluronan in normal and rejected human kidneys," Transplantation 50:240-243 (1990).

Zanker et al., "Induction of response in previous chemotherapy resistant patients by hyaluronidase," Proc. Amer. Assoc. Cancer Res. 27:390 Abstract 1550 (1986).

Foreign Office Action, issued Nov. 8, 2011 (received Dec. 21, 2011), in connection with Chinese Patent Application No. 200980107850.9, [English language translation], 6 pages.

LARGE-SCALE PRODUCTION OF SOLUBLE HYALURONIDASE

RELATED APPLICATIONS

This application is the National Stage of International Application No. PCT/US2009/001455, filed 6 Mar., 2009, which claims benefit of priority to U.S. Provisional Application Ser. No. 61/068,622, to David Baker and Louis Bookbinder, entitled "LARGE-SCALE PRODUCTION OF SOLUBLE HYALURONIDASE," filed Mar. 6, 2008.

This application is related to U.S. application Ser. No. 11/238,171 to Louis Bookbinder, Anirban Kundu, Gregory I. Frost, Michael F. Haller, Gilbert A. Keller, and Tyler M. Dylan, entitled SOLUBLE GLYCOSAMINOGLYCANS AND METHODS OF PREPARING AND USING SOLUBLE GLYCOSAMINOGLYCANS, filed Sep. 27, 2005 and published as U.S. Publication No. 20060104968, which is a continuation-in-part of U.S. application Ser. No. 11/065,716 to Louis Bookbinder, Anirban Kundu, Gregory I. Frost, Michael F. Haller, Gilbert A. Keller, and Tyler M. Dylan, entitled SOLUBLE GLYCOSAMINOGLYCANS AND METHODS OF PREPARING AND USING SOLUBLE GLYCOSAMINOGLYCANS, filed Feb. 23, 2005 and published as U.S. Publication No. 20050260186, which is a continuation-in-part of U.S. application Ser. No. 10/795,095 to Louis Bookbinder, Anirban Kundu and Gregory I. Frost, entitled SOLUBLE HYALURONIDASE GLYCOPROTEIN (SHASEGP), PROCESS FOR PREPARING THE SAME, USES AND PHARMACEUTICAL COMPOSITIONS COMPRISING THEREOF, filed Mar. 5, 2004 and published as U.S. Publication No. 20040268425. The subject matter of each of the above-noted applications is incorporated by reference in its entirety.

FIELD OF THE INVENTION

Provided are methods for large-scale production of a recombinant human protein.

BACKGROUND

Hyaluronidases are a family of enzymes that degrade hyaluronic acid (also known as hyaluronan or hyaluronate), an essential component of the extracellular matrix and a major constituent of the interstitial barrier. By catalyzing the hydrolysis of hyaluronic acid, hyaluronidase lowers the viscosity of hyaluronic acid, thereby increasing tissue permeability. As such, hyaluronidases have been used, for example, as a spreading or dispersing agent in conjunction with other agents, drugs and proteins to enhance their dispersion and delivery. Hyaluronidases also have other therapeutic and cosmetic uses. Because of the increasing use of hyaluronidases for therapeutic and cosmetic uses, there is a need for large-scale quantities of purified hyaluronidase. Therefore, among the objects herein, it is an object to provide methods for the production and purification of hyaluronidases.

SUMMARY

Provided herein are methods for the production and purification of soluble hyaluronidases. In particular, provided herein are methods for the production and purification of soluble rHuPH20. Also provided herein are cell medium and harvested cell culture fluid that contain soluble rHuPH20. The methods provided herein can be used to produce and purify any quantity of soluble hyaluronidase, such as rHuPH20. For example, the methods and steps described herein are amendable for scale-up or scale-down, as would be apparent to one of skill in the art.

The methods provided herein can be used to produce and purify large-scale quantities of soluble rHuPH20. The methods provided herein for producing soluble rHuPH20 can include a) inoculating cell medium in a bioreactor with an inoculum of cells that encode soluble rHuPH20 to produce a cell culture, wherein cells contain between 150 and 300 copies of nucleic acid encoding soluble rHuPH20, the bioreactor contains at least 100 liters of cell culture and about $10^{10}$-$10^{11}$ cells are inoculated per 100 liters cell culture and cells are cultured at a set temperature; b) feeding the cells with a first feed medium containing glucose, L-alanyl-L-glutamine, human insulin and yeast extract in amounts sufficient to increase cell growth and peak cell density, and to increase soluble rHuPH20 synthesis, wherein the feed medium is added to the culture at a volume of 4% of the cell culture volume; c) feeding the cells with a second feed medium containing glucose, L-alanyl-L-glutamine, yeast extract and sodium butyrate in amounts sufficient to increase soluble rHuPH20 synthesis and induce cell cycle arrest, wherein the amount of L-alanyl-L-glutamine is decreased compared to the amount of L-alanyl-L-glutamine in the second step, and the amount of yeast extract is increased compared to the amount of yeast extract in step b), and the feed medium is added to the culture at a volume of 4% of the cell culture volume and the temperature is lowered compared to the temperature in the step a) to a temperature sufficient to increase cell cycle arrest, increase cell viability and stabilize the soluble hyaluronidase; d) feeding the cells with a third feed medium containing glucose, L-alanyl-L-glutamine, yeast extract and sodium butyrate in amounts sufficient to increase soluble rHuPH20 synthesis and increase cell cycle arrest, wherein the feed medium is added to the culture at a volume of 4% of the cell culture volume, the amount of L-alanyl-L-glutamine and glucose is decreased compared to the amount of L-alanyl-L-glutamine and glucose in step c), and the amount of yeast extract and sodium butyrate is increased compared to the amount of yeast extract and sodium butyrate in step c), and the temperature is lowered compared to the temperature in step c) to a temperature sufficient to increase cell cycle arrest, increase cell viability and stabilize the soluble hyaluronidase; e) feeding the cells with a fourth feed medium containing glucose, L-alanyl-L-glutamine, yeast extract and sodium butyrate in amounts sufficient to increase soluble rHuPH20 synthesis and increase cell cycle arrest, wherein the amount of L-alanyl-L-glutamine and glucose is decreased compared to the amount of L-alanyl-L-glutamine and glucose in step d), the amount of sodium butyrate is decreased compared to the amount of sodium butyrate in step d), the temperature is lowered compared to the temperature in step d) to a temperature sufficient to increase cell cycle arrest, increase cell viability and stabilize the soluble hyaluronidase and feed medium is added to the culture at a volume of 4% of the cell culture volume; f) culturing the cells until the viability drops below at least or about 50%; g) obtaining the harvest cell culture fluid; and h) the soluble rHuPH20 is purified from the harvest culture fluid.

The harvest cell culture fluid can be filtered prior to purification. In some examples, the temperature in step a) is 37° C., the temperature in step c) is 36.5° C., the temperature in step d) is 36° C. and the temperature in step d) is 35.5° C. The soluble rHuPH20 purification can be effected by column chromatography, such as beaded crosslinked agarose column chromatography, beaded crosslinked phenyl-substituted agarose column chromatography, amino phenyl boronate column chromatography and hydroxyapatite column chromatography.

In one example, the method for producing soluble rHuPH20, includes steps of a) inoculating cell medium in a bioreactor with an inoculum of cells that encode soluble rHuPH20 to produce a cell culture, wherein the cells contain between 150 and 300 copies of nucleic acid encoding soluble rHuPH20, the bioreactor contains at least 100 liters of cell culture, the inoculation cell density is at or about $4 \times 10^5$ cells/mL and the cells are cultured at 37° C.; b) feeding the cells with a first feed medium containing at or about 33 g/L glucose, 32 mM L-alanyl-L-glutamine, 16.6 g/L yeast extract and 33 mg/L insulin, wherein the feed medium is added to the culture at a volume of 4% of the cell culture volume; c) feeding the cells with a second feed medium containing at or about 33 g/L glucose, 16 mM L-alanyl-L-glutamine, 33.4 g/L yeast extract and 0.92 g/L sodium butyrate, wherein the feed medium is added to the culture at a volume of 4% of the cell culture volume and the temperature is lowered to 36.5° C.; d) feeding the cells with a third feed medium containing at or about 50 g/L glucose, 10 mM L-alanyl-L-glutamine, 50 g/L yeast extract and 1.8 g/L sodium butyrate, wherein the feed medium is added to the culture at a volume of 4% of the cell culture volume and the temperature is lowered to 36° C.; e) feeding the cells with a fourth feed medium containing at or about 33 g/L glucose, 6.6 mM L-alanyl-L-glutamine, 50 g/L yeast extract and 0.92 g/L sodium butyrate, wherein the feed medium is added to the culture at a volume of 4% of the cell culture volume and the temperature is lowered to 36° C.; f) continuing to culture the cells until viability drops below at least or about 50%; g) obtaining the harvest cell culture fluid; h) filtering the harvest cell culture fluid; and i) purifying the rHuPH20 from the harvest culture fluid using beaded crosslinked agarose column chromatography, beaded crosslinked phenyl-substituted agarose column chromatography, amino phenyl boronate column chromatography and hydroxyapatite column chromatography.

In another example, the method for producing soluble rHuPH20 includes the steps of a) inoculating cell medium in a bioreactor with an inoculum of cells that encode soluble rHuPH20 to produce a cell culture, wherein the cells comprise between 150 and 300 copies of nucleic acid encoding soluble rHuPH20; the bioreactor contains at least 100 liters of cell culture; the inoculation cell density is at or about $4 \times 10^5$ cells/mL; and the cells are cultured at or about 37° C.; b) feeding the cells with a first feed medium containing or containing about 33 g/L glucose, 32 mM L-alanyl-L-glutamine, 83.3 g/L yeast extract and 33 mg/L insulin, wherein the feed medium is added to the culture at a volume of 4% or about 4% of the cell culture volume; c) feeding the cells with a second feed medium containing or containing about 33 g/L glucose, 13 mM L-alanyl-L-glutamine, 166.7 g/L yeast extract and 0.92 g/L sodium butyrate, wherein the feed medium is added to the culture at a volume of at or about 4% of the cell culture volume and the temperature is lowered to 36.5° C.; d) feeding the cells with a third feed medium containing or containing about 50 g/L glucose, 10 mM L-alanyl-L-glutamine, 250 g/L yeast extract and 1.8 g/L sodium butyrate, wherein the feed medium is added to the culture at a volume of 4% or about 4% of the cell culture volume and the temperature is lowered to 36° C.; e) feeding the cells with a fourth feed medium containing or containing about 33 g/L glucose, 6.7 mM L-alanyl-L-glutamine, 250 g/L yeast extract and 0.92 g/L sodium butyrate, wherein the feed medium is added to the culture at a volume of 4% or about 4% of the cell culture volume and the temperature is lowered to 36° C.; f) continuing to culture the cells until viability drops below at least or about 50%; g) obtaining the harvest cell culture fluid; h) filtering the harvest cell culture fluid; and i) purifying the rHuPH20 from the harvest culture fluid using beaded crosslinked agarose column chromatography, beaded crosslinked phenyl-substituted agarose column chromatography, amino phenyl boronate column chromatography and hydroxyapatite column chromatography.

In some examples, the volume of cell culture in the bioreactor is or is about 200, 300, 400, 500, 1000, 1500, 2000, 2500, 3000 or 3500 liters. In some examples, the amount of soluble rHuPH20 is produced per 100 L of cell culture using the methods provided herein at least or about 1, 5, 10, 15, 20, 25, 30, 35 or 40 grams of soluble rHuPH20. The specific activity of the soluble rHuPH20 can be at least or about 80000, 100000, 120000, 140000, 160000 or 180,000 units/mg. The cells that encode soluble rHuPH20 can, in some instances, be DG44 CHO cells. Further, the rHuPH20 can be encoded by nucleic acid set forth in SEQ ID NO:47.

Provided herein are cell culture media containing soluble rHuPH20 with an enzymatic activity of greater than 5000 units/mL, such as 10,000, 12,000, 14,000, 16,000, 18,000, 20,000, 22,000 or 24,000 units/mL. Also provided herein are harvested cell culture fluid containing soluble rHuPH20 with an enzymatic activity of greater than 5000 units/mL, such as 10,000, 12,000, 14,000, 16,000, 18,000, 20,000, 22,000 or 24,000 units/mL.

DETAILED DESCRIPTION

Outline

A. Definitions
B. Overview
C. Hyaluronidase
 1. Structure and function
 2. PH20
 3. Therapeutic uses of hyaluronidases
  a. Use as a spreading agent
  b. Use in hypodermoclysis
  c. Use in vitrectomy and ophthalmic disorders and conditions
  d. Use in gene therapy
  e. Cosmetic uses
  f. Use in organ transplantation
  g. Use in cancer treatment
  h. Use in treatment of glycosaminoglycan accumulation in the brain
  i. Use in treatment of glycosaminoglycan accumulation in cardiovascular disease
  j. Use in pulmonary disease
  k. Other uses
D. Hyaluronidase-expressing cells
 a. 3D35M cells
 b 2B2 cells
E. Cell culture expansion
F. Protein production
G. Protein concentration and buffer exchange
H. Purification
 1. Beaded crosslinked agarose column
 2. Beaded crosslinked phenyl-substituted agarose column
 3. Amino Phenyl Boronate column
 4. Hydroxyapatite column
 6. Virus removal, protein concentration and buffer exchange
I. Filling
J. Monitoring and assays 1. Monitoring conditions
2. Monitoring soluble rHuPH20 production
K. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, hyaluronidase refers to an enzyme that degrades hyaluronic acid. Hyaluronidases include bacterial hyaluronidases (EC 4.2.99.1), hyaluronidases from leeches, other parasites, and crustaceans (EC 3.2.1.36), and mammalian-type hyaluronidases (EC 3.2.1.35). Hyaluronidases also include any of non-human origin including, but not limited to, murine, canine, feline, leporine, avian, bovine, ovine, porcine, equine, piscine, ranine, bacterial, and any from leeches, other parasites, and crustaceans. Exemplary non-human hyaluronidases include, hyaluronidases from cows (SEQ ID NO:10), yellow jacket wasp (SEQ ID NOS:11 and 12), honey bee (SEQ ID NO:13), white-face hornet (SEQ ID NO:14), paper wasp (SEQ ID NO:15), mouse (SEQ ID NOS:16-18, 29), pig (SEQ ID NOS:19-20), rat (SEQ ID NOS:21-23, 28), rabbit (SEQ ID NO:24), sheep (SEQ ID NO:25), orangutan (SEQ ID NO:26), cynomolgus monkey (SEQ ID NO:27), guinea pig (SEQ ID NO:30), *Staphylococcus aureus* (SEQ ID NO:31), *Streptococcus pyogenes* (SEQ ID NO:32), and *Clostridium perfringens* (SEQ ID NO:33). Exemplary human hyaluronidases include HYAL1 (SEQ ID NO:34), HYAL2 (SEQ ID NO:35), HYAL3 (SEQ ID NO:36), HYAL4 (SEQ ID NO:37), and PH20 (SEQ ID NO:1). Also included amongst hyaluronidases are soluble human PH20 and soluble rHuPH20.

Reference to hyaluronidases includes precursor hyaluronidase polypeptides and mature hyaluronidase polypeptides (such as those in which a signal sequence has been removed), truncated forms thereof that have activity, and includes allelic variants and species variants, variants encoded by splice variants, and other variants, including polypeptides that have at least 40%, 45%, 50%, 55%, 60%, 65%, 70%, 75%, 80%, 85%, 90%, 95%, 96%, 97%, 98%, 99% or more sequence identity to the precursor polypeptides set forth in SEQ ID NOS: 1 and 10-37, or the mature form thereof. For example, reference to hyaluronidase also includes the human PH20 precursor polypeptide variants set forth in SEQ ID NOS:48-49. Hyaluronidases also include those that contain chemical or posttranslational modifications and those that do not contain chemical or posttranslational modifications. Such modifications include, but are not limited to, pegylation, albumination, glycosylation, farnesylation, carboxylation, hydroxylation, phosphorylation, and other polypeptide modifications known in the art.

As used herein, soluble human PH20 or sHuPH20 include mature polypeptides lacking all or a portion of the glycosylphospatidyl inositol (GPI) attachment site at the C-terminus such that upon expression, the polypeptides are soluble. Exemplary sHuPH20 polypeptides include mature polypeptides having an amino acid sequence set forth in any one of SEQ ID NOS:4-9 and 45-46. The precursor polypeptides for such exemplary sHuPH20 polypeptides include a signal sequence. Exemplary of the precursors are those set forth in SEQ ID NOS:3 and 38-44, each of which contains a 35 amino acid signal sequence at amino acid positions 1-35. Soluble HuPH20 polypeptides also include those degraded during or after the production and purification methods described herein.

As used herein, soluble rHuPH20 refers to a soluble form of human PH20 that is recombinantly expressed in Chinese Hamster Ovary (CHO) cells. Soluble rHuPH20 is encoded by nucleic acid that includes the signal sequence and is set forth in SEQ ID NO:47. Also included are DNA molecules that are allelic variants thereof and other soluble variants. The nucleic acid encoding soluble rHuPH20 is expressed in CHO cells which secrete the mature polypeptide. As produced in the culture medium there is heterogeneity at the C-terminus so that the product includes a mixture of species that can include one or more of SEQ ID NOS. 4-9 in various abundance. Corresponding allelic variants and other variants also are included, including those corresponding to the precursor human PH20 polypeptides set forth in SEQ ID NOS:48-49. Other variants can have 60%, 70%, 80%, 85%, 90%, 91%, 92%, 93%, 94%, 95%, 96%, 97%, 98%, 99% or more sequence identity with any of SEQ ID NOS. 4 as long they retain a hyaluronidase activity and are soluble.

As used herein, "soluble rHuPH20-expressing cells" refers to any CHO cell that expresses soluble rHuPH20. Exemplary soluble rHuPH20-expressing cells include 2B2 and 3D35M cells. Soluble rHuPH20-expressing cells are CHO cells into which nucleic acid that contains the sequence set forth in SEQ ID NO:55 has been introduced.

As used herein, hyaluronidase activity refers to any activity exhibited by a hyaluronidase polypeptide. Such activities can be tested in vitro and/or in vivo and include, but are not limited to, enzymatic activity, such as to effect cleavage of hyaluronic acid, ability to act as a dispersing or spreading agent and antigenicity. hyaluronidase activity refers to any activity exhibited by a hyaluronidase polypeptide.

As used herein, enzymatic activity refers to the activity of a hyaluronidase, as assessed in in vitro enzymatic assays, to cleave a substrate, such as hyaluronic acid. In vitro assays to determine the enzymatic activity of hyaluronidases, such as soluble rHuPH20, are know in the art and described herein. Exemplary assays include the microturbidity assay described below (see e.g. Example 9 and section I) that measures cleavage of hyaluronic acid by hyaluronidase indirectly by detecting the insoluble precipitate formed when the uncleaved hyaluronic acid binds with serum albumin.

As use herein, specific activity with reference to soluble rHuPH20 is the enzyme activity relative to the amount of soluble rHuPH20, Specific activity is calculated by dividing the enzymatic activity (units/mL) by the protein concentration (mg/mL).

As used herein, "exhibits at least one activity" or "retains at least one activity" refers to the activity exhibited by a variant soluble rHuPH20 as compared to any soluble rHuPH20 set forth in SEQ ID NOS:4-9 under the same conditions. Typically, a variant soluble rHuPH20 that retains or exhibits at least one activity of a soluble rHuPH20 set forth in SEQ ID NOS:4-9 retains at or about 0.5%, 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 90%, 100%, 200%, 300%, 400%, 500% or more of the activity of a soluble rHuPH20 set forth in SEQ ID NOS:4-9. Exemplary activities include, but are not limited to, hyaluronidase activity and enzymatic activity.

As used herein, beaded crosslinked agarose column chromatography refers to chromatography using a column packed with beaded crosslinked agarose. Exemplary of beaded crosslinked agarose is Q Sepharose™.

As used herein, beaded crosslinked phenyl-substituted agarose column chromatography refers to chromatography using a column packed with beaded phenyl-substituted crosslinked agarose. Exemplary of beaded phenyl-substituted crosslinked agarose is Phenyl Sepharose™.

As used herein, amino phenyl boronate column chromatography refers to chromatography using a column packed with amino phenyl boronate agarose.

As used herein, hydroxyapatite column chromatography refers to chromatography using a column packed with hydroxyapatite.

As used herein, harvested cell culture fluid or harvest cell culture fluid (HCCF) refers to the fluid obtained following harvest of the cells from the bioreactor and separation of the cell culture medium from the cells, cell debris and other aggregates. The cell culture that is harvested from the bioreactor can be filtered to clarify the culture, removing the cells, cell debris and other aggregates to leave the harvested cell culture fluid.

As used herein, cell density refers to the number of cells in a given volume of medium.

As used herein, cell culture or culture refers to a cell population that is suspended in a medium under conditions suitable to maintain viability of the cells or grow the cells.

As used herein, medium, cell medium or cell culture medium refers to a solution containing nutrients sufficient to promote the growth of cells in a culture. Typically, these solutions contain essential and non-essential amino acids, vitamins, energy sources, lipids and/or trace elements. The medium also can contain additional supplements, such as hormones, growth factors and growth inhibitors. Reference to cell culture medium included As used herein, the residues of naturally occurring α-amino acids are the residues of those 20 α-amino acids found in nature which are incorporated into protein by the specific recognition of the charged tRNA molecule with its cognate mRNA codon in humans.

As used herein, "in amounts sufficient to increase" when referring to a substance increasing parameters such as cell growth rate, peak cell density, protein synthesis or cell cycle arrest refers to the amount of a substance that effects an increase in one of these parameters compared to that observed in the absence of the substance. The parameters can be assessed in the presence and absence of a substance, and the amount of substance that increases the parameter (such as cell growth rate, peak cell density, protein synthesis or cell cycle arrest) compared to in the absence of the substance can be determined. The growth rate, peak cell density, protein synthesis or cell cycle arrest in the presence of the substance can be increased by at or about 0.5%, 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 90%, 100%, 200%, 300%, 400%, 500% or more compared to the growth rate, peak cell density, protein synthesis or cell cycle arrest in the absence of the substance.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, a peptide refers to a polypeptide that is from 2 to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243: 3552-3559 (1969), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are described herein and are known to those of skill in the art.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

"Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptides, the term "identity" is well known to skilled artisans (Carillo, H. & Lipton, D., *SIAM J Applied Math* 48:1073 (1988)).

As used herein, homologous (with respect to nucleic acid and/or amino acid sequences) means about greater than or equal to 25% sequence homology, typically greater than or equal to 25%, 40%, 50%, 60%, 70%, 80%, 85%, 90% or 95% sequence homology; the precise percentage can be specified if necessary. For purposes herein the terms "homology" and "identity" are often used interchangeably, unless otherwise indicated. In general, for determination of the percentage homology or identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991; Carillo et al. (1988) *SIAM J Applied Math* 48:1073). By sequence homology, the number of conserved amino acids is determined by standard alignment algorithms programs, and can be used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I): 387 (1984)), BLASTP, BLASTN, FASTA (Atschul, S. F., et al., *J Molec Biol* 215:403 (1990)); Guide to Huge Computers, Martin J. Bishop, ed., Academic Press, San Diego, 1994, and Carillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman (1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary, comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide. As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "primer" refers to a nucleic acid molecule that can act as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. It will be appreciated that a certain nucleic acid molecules can serve as a "probe" and as a "primer." A primer, however, has a 3' hydroxyl group for extension. A primer can be used in a variety of methods, including, for example, polymerase chain reaction (PCR), reverse-transcriptase (RT)-PCR, RNA PCR, LCR, multiplex PCR, panhandle PCR, capture PCR, expression PCR, 3' and 5' RACE, in situ PCR, ligation-mediated PCR and other amplification protocols.

As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) or can encode polypeptides having altered amino acid sequence. The term "allelic variant" also is used herein to denote a protein encoded by an allelic variant of a gene. Typically the reference form of the gene encodes a wildtype form and/or predominant form of a polypeptide from a population or single reference member of a species. Typically, allelic variants, which include variants between and among species typically have at least 80%, 90% or greater amino acid identity with a wildtype and/or predominant form from the same species; the degree of identity depends upon the gene and whether comparison is interspecies or intraspecies. Generally, intraspecies allelic variants have at least about 80%, 85%, 90% or 95% identity or greater with a wildtype and/or predominant form, including 96%, 97%, 98%, 99% or greater identity with a wildtype and/or predominant form of a polypeptide. Reference to an allelic variant herein generally refers to variations in proteins among members of the same species.

As used herein, "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include substitutions, deletions and insertions of nucleotides. An allele of a gene also can be a form of a gene containing a mutation.

As used herein, species variants refer to variants in polypeptides among different species, including different mammalian species, such as mouse and human.

As used herein, a splice variant refers to a variant produced by differential processing of a primary transcript of genomic DNA that results in more than one type of mRNA.

As used herein, modification is in reference to modification of a sequence of amino acids of a polypeptide or a sequence of nucleotides in a nucleic acid molecule and includes deletions, insertions, and replacements of amino acids and nucleotides, respectively. Methods of modifying a polypeptide are routine to those of skill in the art, such as by using recombinant DNA methodologies.

As used herein, the term promoter means a portion of a gene containing DNA sequences that provide for the binding of RNA polymerase and initiation of transcription. Promoter sequences are commonly, but not always, found in the 5' non-coding region of genes.

As used herein, isolated or purified polypeptide or protein or biologically-active portion thereof is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

The term substantially free of cellular material includes preparations of proteins in which the protein is separated from cellular components of the cells from which it is isolated or recombinantly-produced. In one embodiment, the term substantially free of cellular material includes preparations of enzyme proteins having less that about 30% (by dry weight) of non-enzyme proteins (also referred to herein as a contaminating protein), generally less than about 20% of non-enzyme proteins or 10% of non-enzyme proteins or less that about 5% of non-enzyme proteins. When the enzyme protein is recombinantly produced, it also is substantially free of culture medium, i.e., culture medium represents less than about or at 20%, 10% or 5% of the volume of the enzyme protein preparation.

As used herein, the term substantially free of chemical precursors or other chemicals includes preparations of enzyme proteins in which the protein is separated from chemical precursors or other chemicals that are involved in the synthesis of the protein. The term includes preparations of enzyme proteins having less than about 30% (by dry weight) 20%, 10%, 5% or less of chemical precursors or non-enzyme chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells.

As used herein the term assessing is intended to include quantitative and qualitative determination in the sense of obtaining an absolute value for the activity of a protease, or a domain thereof, present in the sample, and also of obtaining an index, ratio, percentage, visual or other value indicative of the level of the activity. Assessment can be direct or indirect and the chemical species actually detected need not of course be the proteolysis product itself but can for example be a derivative thereof or some further substance. For example, detection of a cleavage product of a complement protein, such as by SDS-PAGE and protein staining with Coomasie blue.

As used herein, a composition refers to any mixture. It can be a solution, suspension, liquid, powder, paste, aqueous, non-aqueous or any combination thereof. As used herein, a kit is a packaged combination that optionally includes other elements, such as additional reagents and instructions for use of the combination or elements thereof.

As used herein, "disease or disorder" refers to a pathological condition in an organism resulting from cause or condition including, but not limited to, infections, acquired conditions, genetic conditions, and characterized by identifiable symptoms.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease. Treatment also encompasses any pharmaceutical use of a modified interferon and compositions provided herein.

As used herein, a pharmaceutically effective agent, includes any therapeutic agent or bioactive agents, including, but not limited to, for example, anesthetics, vasoconstrictors, dispersing agents, conventional therapeutic drugs, including small molecule drugs and therapeutic proteins.

As used herein, treatment means any manner in which the symptoms of a condition, disorder or disease or other indication, are ameliorated or otherwise beneficially altered.

As used herein, a patient refers to a human subject.

As used herein, an effective amount is the quantity of a therapeutic agent necessary for preventing, curing, ameliorating, arresting or partially arresting a symptom of a disease or disorder.

As used herein, animal includes any animal, such as, but are not limited to primates including humans, gorillas and monkeys; rodents, such as mice and rats; fowl, such as chickens; ruminants, such as goats, cows, deer, sheep; ovine, such as pigs and other animals. Non-human animals exclude humans as the contemplated animal. The hyaluronidases provided herein are from any source, animal, plant, prokaryotic and fungal. Most enzymes are of animal origin, including mammalian origin.

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a compound, comprising "an extracellular domain" includes compounds with one or a plurality of extracellular domains.

As used herein, ranges and amounts can be expressed as "about" a particular value or range. About also includes the exact amount. Hence "about 5 mM" means "about 5 mM" and also "5 mM."

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. OVERVIEW

Provided herein are methods for the large scale production of soluble hyaluronidases, such as soluble human hyaluronidases, including soluble human PH20 (sHuPH20), such as, for example, soluble rHuPH20. The methods typically utilize bioreactors to culture cells that produce the soluble hyaluronidase, such as CHO cells (e.g. DG44 CHO cells). Exemplary of such cells are 2B2 cells, which produce soluble rHuPH20. The volume of cell culture in the bioreactor can range from 1 L to 5000 L or more, but typically is or is about 200, 300, 400, 500, 1000, 1500, 2000, 2500, 3000 or 3500 liters. Prior to inoculation of the bioreactor, the cells are expanded through a series of increasing cell culture volumes to generate the required number of cells for seeding of the bioreactor. Typically, the cell culture in the bioreactor is seeded with $10^5$ to $10^6$ cells/mL, but can be seeded with more or less. The cells are then incubated in the bioreactor for 7, 8, 9, 10, 11, 12, 13, 14, 15, 16, 17, 18, 19 or more days.

During this incubation, feed media is added to the cell culture to supply additional nutrients and supplements. Exemplary supplements or nutrients that can be included in the feed media include, but are not limited to, glucose, glutamine or glutamine-substitute, such as L-Alanyl-L-Glutamine, insulin, and sodium butyrate. The type and amount of supplement added can influence cell growth and protein production. For example, insulin and glutamine or glutamine-substitute can be incorporated into the first feed media added to the cell culture to increase cell growth and peak cell density. Subsequent feed media can be designed to promote protein production more than cell growth. Supplements such as insulin can be excluded or reduced in amount, as can glutamine or glutamine-substitute, such as L-Alanyl-L-Glutamine. In contrast, supplements such as yeast extract that enhance protein synthesis can be increased in amount. In addition, supplements that enhance cell cycle arrest and, therefore, increased protein production, also can be included. Exemplary of such supplements is sodium butyrate.

Following protein production in the bioreactor, the cells are harvested and the soluble hyaluronidase, such as soluble rHuPH20, that has been secreted into the cell culture media is concentrated prior to initiation of the purification process. The soluble hyaluronidase is then purified from the concentrated protein solution using a series of purification steps. Exemplary of purification methods that are used for the methods herein is a combination of ion-exchange chromatography, hydrophobic interaction chromatography and affinity chromatography. The purified protein is then concentrated and diafiltered.

Utilizing the methods described herein, between about 0.5-50 grams of soluble hyaluronidases, such as soluble rHuPH20, is produced per 100 L of cell culture. In some examples, the amount of soluble rHuPH20 produced per 100 L of culture is or is about 1, 2, 3, 4, 5, 10, 15, 20, 30, or 40 grams or more. In some examples, the yield of soluble hyaluronidase following purification can range from between or between about 10% to 50% of the amount produced before purification. For example, the yield following purification can be or be about 10%, 15%, 20%, 25%, 30%, 35%, 40%, 45% or 50% of the amount produced before purification. Generally, the specific activity of soluble rHuPH20 produced using the methods herein is at least or about 80000, 100000, 120000, 140000, 160000 or 180,000 units/mg.

C. HYALURONIDASES

Hyaluronidases are a family of enzymes that degrade hyaluronic acid (also known as hyaluronan or hyaluronate), an essential component of the extracellular matrix and a major constituent of the interstitial barrier. By catalyzing the hydrolysis of hyaluronic acid, hyaluronidase lowers the viscosity of hyaluronic acid, thereby increasing tissue permeability. As such, hyaluronidases have been used, for example, as a spreading or dispersing agent in conjunction with other agents, drugs and proteins to enhance their dispersion and delivery.

1. Structure and Function of Hyaluronidases

There are three general classes of hyaluronidases; mammalian hyaluronidase, bacterial hyaluronidase and hyaluronidase from leeches, other parasites and crustaceans. Mammalian-type hyaluronidases (EC 3.2.1.35) are endo-β-N-acetyl-hexosaminidases that hydrolyze the β1→4 glycosidic bond of hyaluronic acid into various oligosaccharide lengths such as tetrasaccharides and hexasaccharides. They have both hydrolytic and transglycosidase activities and can degrade hyaluronic acid and chondroitin sulfates, such as C4-S and C6-S. Hyaluronidases of this type include, but are not limited to, hyaluronidases from cows (SEQ ID NO:10), yellow jacket wasp (SEQ ID NOS:11 and 12), honey bee (SEQ ID NO:13), white-face hornet (SEQ ID NO:14), paper wasp (SEQ ID NO:15), mouse (SEQ ID NOS:16-18, 29), pig (SEQ ID NOS: 19-20), rat (SEQ ID NOS:21-23, 228), rabbit (SEQ ID NO:24), sheep (SEQ ID NO:25), orangutan (SEQ ID NO:26), cynomolgus monkey (SEQ ID NO:27), guinea pig (SEQ ID NO:30) and human hyaluronidases.

There are six hyaluronidase-like genes in the human genome: HYAL1, HYAL2, HYAL3, HYAL4, HYALP1 and PH20/SPAM1. HYALP1 is a pseudogene, and HYAL3 (SEQ ID NO:36) has not been shown to possess enzyme activity toward any known substrates. HYAL4 (precursor polypeptide set forth in SEQ ID NO:37) is a chondroitinase and exhibits little activity towards hyaluronic acid. HYAL1 (precursor polypeptide set forth in SEQ ID NO:34) is the prototypical acid-active enzyme and PH20 (precursor polypeptide set forth in SEQ ID NO:1) is the prototypical neutral-active enzyme. Acid-active hyaluronidases, such as HYAL1 and HYAL2 (precursor polypeptide set forth in SEQ ID NO:35) generally lack catalytic activity at neutral pH (i.e. pH 7). For example, HYAL1 has little catalytic activity in vitro over pH 4.5 (Frost et al. (1997) Anal Biochemistry 251:263-269). HYAL2 is an acid-active enzyme with a very low specific activity in vitro. The hyaluronidase-like enzymes also can be characterized by those which are generally locked to the plasma membrane via a glycosylphosphatidyl inositol anchor such as human HYAL2 and human PH20 (Danilkovitch-Miagkova, et al. (2003) Proc Natl Acad Sci USA. 100(8): 4580-5), and those which are generally soluble such as human HYAL1 (Frost et al, (1997) Biochem Biophys Res Commun. 236(1):10-5). By catalyzing the hydrolysis of hyaluronic acid, a major constituent of the interstitial barrier, hyaluronidase lowers the viscosity of hyaluronic acid, thereby increasing tissue permeability. It also has been shown to exhibit anti-cancer and anti-carcinogenic activities.

N-linked glycosylation of some hyaluronidases can be very important for their catalytic activity and stability. While altering the type of glycan modifying a glycoprotein can have dramatic affects on a protein's antigenicity, structural folding, solubility, and stability, many enzymes are not thought to require glycosylation for optimal enzyme activity. Hyaluronidases are, therefore, unique in this regard, in that removal of N-linked glycosylation can result in near complete inactivation of the hyaluronidase activity. For such hyaluronidases, the presence of N-linked glycans is critical for generating an active enzyme.

There are seven potential N-linked glycosylation sites at N82, N166, N235, N254, N368, N393, N490 of human PH20 exemplified in SEQ ID NO: 1. Disulfide bonds form between the cysteine residues C60 and C351 and between C224 and C238 to form the core hyaluronidase domain. However, additional cysteines are required in the carboxy terminus for neutral enzyme catalytic activity such that amino acids 36 to 464 of SEQ ID NO:1 contains the minimally active human PH20 hyaluronidase domain. Thus, N-linked glycosylation site N490 is not required for proper hyaluronidase activity.

N-linked oligosaccharides fall into several major types (oligomannose, complex, hybrid, sulfated), all of which have (Man) 3-GlcNAc-GlcNAc-cores attached via the amide nitrogen of Asn residues that fall within-Asn-Xaa-Thr/Ser-sequences (where Xaa is not Pro). Glycosylation at an-Asn-Xaa-Cys-site has been reported for coagulation protein C. In some instances, the hyaluronidase can contain both N-glycosidic and β-glycosidic linkages. For example, rHuPH20 (as produced in the methods described herein) has O-linked oligosaccharides as well as N-linked oligosaccharides.

The methods described herein provide a process for the production and purification of large quantities of a soluble preparation of human PH20 hyaluronidase preparation.

2. PH20

Human PH20 (also known as sperm surface protein PH20), as noted above, is the prototypical neutral-active enzyme that is generally locked to the plasma membrane via a glycosylphosphatidyl inositol (GPI) anchor. It is naturally involved in sperm-egg adhesion and aids penetration by sperm of the layer of cumulus cells by digesting hyaluronic acid. The PH20 mRNA transcript is normally translated to generate a 509 amino acid precursor protein containing a 35 amino acid signal sequence at the N-terminus (amino acid residue positions 1-35). The mature PH20 polypeptide is, therefore, a 474 amino acid polypeptide with an amino acid sequence set forth in SEQ ID NO:2.

Soluble forms of human PH20 (sHuPH20) can be produced and purified using the methods described herein. The generation of sHuPH20 are described in related U.S. patent application Ser. Nos. 10/795,095, 11/065,716 and 11/238,171 (also referred to in these applications as sHASEGP or rHuPH20), and in Examples 1 and 4, below. The soluble forms are produced by expressing nucleic acid encoding C-terminal truncations of the mature PH20 polypeptide that lack the GPI-attachment sites. Soluble forms of human PH20 include soluble rHuPH20, which is produced and purified using the methods provided herein.

3. Therapeutic Uses of Hyaluronidases

Various forms of hyaluronidases have been prepared and approved for therapeutic use in humans. For example, animal-derived hyaluronidase preparations include Vitrase® (ISTA Pharmaceuticals), a purified ovine testicular hyaluronidase, and Amphadase® (Amphastar Pharmaceuticals), a bovine testicular hyaluronidase. Hylenex® (Halozyme Therapeutics) is a human recombinant hyaluronidase produced by genetically engineered Chinese Hamster Ovary (CHO) cells containing nucleic acid encoding for soluble rHuPH20. Approved therapeutic uses for hyaluronidase include use as an adjuvant to increase the absorption and dispersion of other injected drugs, for hypodermoclysis (subcutaneous fluid administration), and as an adjunct in subcutaneous urography for improving resorption of radiopaque agents. In addition to these indications, hyaluronidases, including sHuPH20, can be used as a therapeutic or cosmetic agent for the treatment of additional diseases and conditions.

As noted above, hyaluronidase is a spreading or diffusing substance which modifies the permeability of connective tissue through the hydrolysis of hyaluronic acid, a polysaccharide found in the intercellular ground substance of connective tissue, and of certain specialized tissues, such as the umbilical cord and vitreous humor. When no spreading factor is present, materials injected subcutaneously, such as drugs, proteins, peptides and nucleic acid, spread very slowly. Co-injection with hyaluronidase, however, can cause rapid spreading. The rate of diffusion is proportional to the amount of enzyme, and the extent of diffusion is proportional to the volume of solution. Absorption and dispersion of injected drugs and agents can be enhanced by adding 10-1000 units hyaluronidase to the injection solution. In some examples, 150 U hyaluronidase is added. Hyaluronidases have multiple uses, including and in addition to their use as a spreading agent. Hyaluronidase is commonly used, for example, for peribulbar block in local anesthesia prior ophthalmic surgery. The presence of the enzyme prevents the need for additional blocks and speeds the time to the onset of akinesia (loss of eye movement). Peribulbar and sub-Tenon's block are the most common applications of hyaluronidase for ophthalmic procedures. Hyaluronidase also can promote akinesia in cosmetic surgery, such as blepharoplasties and face lifts. Exemplary therapeutic and cosmetic uses for hyaluronidase are described below.

a. Use as a Spreading Agent

Hyaluronidases, such as soluble rHuPH20 produced using the methods described herein, can be used to promote or enhance the delivery agents and molecules to any of a variety of mammalian tissues in vivo. It can be used to facilitate the diffusion and, therefore, promote the delivery, of small molecule pharmacologic agents as well as larger molecule pharmacologic agents, such as proteins, nucleic acids and ribonucleic acids, and macromolecular compositions than can contain a combination of components including, but not limited to, nucleic acids, proteins, carbohydrates, lipids, lipid-based molecules and drugs. For example, molecules and macromolecular complexes ranging from about 10 nm to about 500 nm in diameter, can exhibit dramatic improvements in delivery through interstitial spaces when the interstitial space has been previously, or is coincidentally, exposed to hyaluronidase (see e.g. U.S. patent application Ser. Nos. 10/795,095, 11/065,716 and 11/238,171).

Examples of pharmaceutical, therapeutic and cosmetic agents and molecules that can be administered with hyaluronidase include, but are not limited to, anesthetics; anti-metabolites, anti-neoplastics and other anti-cancer agents; anti-virals; anti-infectives, including anti-bacterials and other antibiotics, anti-fungals and other anti-infectives; immunomodulatory agents; steroidal and non-steroidal anti-inflammatories; beta blockers; sympathomimetics; ducosanoids, prostaglandins and prostaglandin analogs; miotics, cholinergics and anti-cholinesterases; anti-allergenics and decongestants; hormonal agents; growth factors; immunosuppressants; vaccines and toxoids; immune sera; antibodies; and any combination thereof. In one example, soluble rHuPH20 is administered with a cathepsin, such as cathepsin L.

b. Use in Hypodermoclysis

Hypodermoclysis, the infusion of fluids and electrolytes into the hypodermis of the skin, is a useful and simple hydration technique suitable for mildly to moderately dehydrated adult patients, especially the elderly. Although considered safe and effective, the most frequent adverse effect is mild subcutaneous edema that can be treated by local massage or systemic diuretics. Approximately 3 L can be given in a 24-hour period at two separate sites. Common infusion sites include the chest, abdomen, thighs and upper arms. Solutions used in hypodermoclysis include, for example, normal saline, half-normal saline, glucose with saline and 5% glucose. Potassium chloride also can be added to the solution. The addition of hyaluronidase to the solution can enhance fluid absorption and increase the overall rate of administration.

c. Use in Vitrectomy and Ophthalmic Disorders and Conditions

Hyaluronidase can be used to minimize the detachment or tearing of the retina during vitrectomy. This could cause, for example, the vitreous body to become uncoupled or "disinserted" from the retina, prior to removal of the vitreous body. Such disinsertion or uncoupling of the vitreous body can minimize the likelihood that further tearing or detachment of the retina will occur as the vitreous body is removed.

Hyaluronidase can be used for various ophthalmic applications, including the vitrectomy adjunct application described in U.S. Pat. No. 5,292,509. The use of a highly purified hyaluronidase, such as, for example, soluble rHuPH20 produced and purified by the methods described herein, is preferable for intraocular procedures to minimize immunogenicity and toxicity. In some examples, a pegylated hyaluronidase can be used to prolong residence within the vitreous and prevent localized uptake.

Hyaluronidases can be used to treat and/or prevent ophthalmic disorders by, for example, preventing neovascularization and increasing the rate of clearance from the vitreous of materials toxic to the retina. Hyaluronidase can be administered in an amount effective to liquefy the vitreous humor of the eye without causing toxic damage to the eye. Liquefaction of the vitreous humor increases the rate of liquid exchange from the vitreal chamber. This increase in exchange removes the contaminating materials whose presence can cause ophthalmologic and retinal damage.

Hyaluronidase also can be used to reduce postoperative pressure. Hyaluronic acid has been used in eye primarily as a spacer during cataract and intraocular lens surgical procedures. It also is used in other ocular surgical procedures such as glaucoma, vitreous and retina surgery and in corneal transplantation. A common side effect occurring in postoperative cataract patients is a significant early, and occasionally prolonged, rise in intraocular pressure. Such a condition is sometimes serious, especially in patients with glaucomatous optic disc changes. Hyaluronidase can be co-administered with hyaluronic acid to the eye prior to surgery to reduce postoperative pressure in the eye. The hyaluronidase is administered in an amount effective to reduce the intraocular pressure to pre-operative levels by breaking down the hyaluronic acid without decreasing its effectiveness during surgery nor causing side effects in the patient (U.S. Pat. No. 6,745,776).

Hyaluronidase also can be administered to patients with glaucoma to remove glycosaminoglycans from the trabecular meshwork and reduce intraocular pressure, and can be applied to the vitreous to promote the resolution of vitreous hemorrhages (i.e. extravasation of blood into the vitreous), which can occur in connection with conditions such as diabetic retinopathy, retinal neovascularization, retinal vein occlusion, posterior vitreous detachment, retinal tears, ocular traumas and the like. The presence of vitreous hemorrhages, which are typically slow to resolve, can delay, complicate or prevent procedures that require the retina to be visualized through the vitreous for diagnosis and/or for treatment procedures such as laser photocoagulation and the like which are often primary treatments for conditions such as proliferative diabetic retinopathy.

d. Use in Gene Therapy

The efficacy of most gene delivery vehicles in vivo does not correspond to the efficacy found observed in vitro. Glycosaminoglycans can hinder the transfer and diffusion of DNA and viral vectors into many cell types. The levels such extracellular matrix material can hinder the process considerably. Administration of hyaluronidase can open channels in the extracellular matrix, thus enhancing delivery of gene therapy. For example, hyaluronidase can be administered with collagenase to facilitate transduction of DNA in vivo (Dubensky et al. (1984) Proc Natl Acad Sci USA 81(23): 7529-33). Hyaluronidase also can enhance gene therapy using adeno-associated virus (Favre et al, (2000) Gene Therapy 7(16):1417-20). The channels opened following administration of hyaluronidase are of a size that typically enhance diffusion of smaller molecules such as retroviruses, adenoviruses, adeno-associated viruses and DNA complexes (as well as other therapeutic and pharmacological agents of interest). The pores are not so large, however, as to promote the dislocation and movement of cells.

In some examples, viruses can be engineered to express hyaluronidase to facilitate their replication and spread within a target tissue. The target tissue can be, for example, a cancerous tissue whereby the virus is capable of selective replication within the tumor. The virus also can be a non-lytic virus wherein the virus selectively replicates under a tissue specific promoter. As the viruses replicate, the co-expression of hyaluronidase with viral genes can facilitate the spread of the virus in vivo.

e. Cosmetic Uses

Hyaluronidases can be by administered to remove glycosaminoglycans involved in the accumulation of cellulite and to promote lymphatic flow. In some examples, human hyaluronidases, such as for example, soluble rHuPH20, are used for the treatment of cellulite. The hyaluronidase can be administered through repeated subcutaneous injections, through transdermal delivery in the form of ointments or creams or through the use of injectable slow release formulations to promote the continual degradation of glycosaminoglycans and prevent their return.

Hyaluronidase also can be used to treat conditions such as "pigskin" edema or "orange peel" edema. Hyaluronidases can effect depolymerization of the long mucopolysaccharide chains that can accumulate in the dermis and which are responsible for the retention of bound water and of the slowing, by capillary compression, of the diffusion of organic liquids, which eliminate metabolic wastes. Such retention of water and wastes associated with fat overloading of the lipocytes, constitutes classical "pigskin" edema or "orange peel" edema. Depolymerization can cut the long chains of mucopolysaccharides into shorter chains, resulting in the elimination of the bound water and wastes and restoration of the venous and lymphatic circulation, culminating in the disappearance of local edema.

f. Use in Organ Transplantation

The content of hyaluronic acid in an organ can increase with inflammation. An increased concentration of hyaluronic acid has been observed in tissue from different organs characterized by inflammatory-immunological injury such as alveolitis (Nettelbladt et al. (1991) Am. Rev. Resp. Dis. 139: 759-762) and myocardial infarction (Waldenstrom et al. (1991) J. Clin. Invest. 88(5): 1622-1628). Other examples include allograft rejection after a renal (Ha'llgren et al. (1990) J. Exp. Med. 171: 2063-2076; Wells et al. (1990) Transplantation 50: 240-243), small bowel (Wallander et al. (1993) Transplant. Int. 6: 133-137) or cardiac (Haellgren et al. (1990) J Clin Invest 185:668-673) transplantation; or a myocardial inflammation of viral origin (Waldenstrdm et al. (1993) Eur. J. Clin. Invest. 23: 277-282). The occurrence of interstitial edemas in connection with the grafting of an organ constitutes a severe problem in the field of transplantation surgery. Grafts with interstitial edemas can swell to such a degree that the function is temporarily be lost. In some instances, the swelling can cause disruption of the kidney, resulting in a massive hemorrhage. Hyaluronidases can be used to degrade accumulated glycosaminoglycans in an organ transplant. Removal of such glycosaminoglycans promotes removal of water from the graft and thus enhances organ function.

g. Use in Cancer Treatment

Hyaluronidase has direct anticarcinogenic effects. Hyaluronidase prevents growth of tumors transplanted into mice (De Maeyer et al., (1992) Int. J. Cancer 51:657-660) and inhibits tumor formation upon exposure to carcinogens (Pawlowski et al. (1979) Int. J. Cancer 23:105-109) Hyaluronidase is effective as the sole therapeutic agent in the treatment of brain cancer (gliomas) (WO 198802261). In addition to these effects, hyaluronidases also can be used to enhance penetration of chemotherapeutic agents into solid tumors. They can be injected intratumorally with anti-cancer agents or intravenously for disseminated cancers or hard to reach tumors. The anticancer agent can be a chemotherapeutic, an antibody, a peptide, or a gene therapy vector, virus or DNA. Additionally, hyaluronidase can be used to recruit tumor cells into the cycling pool for sensitization in previously chemorefractory tumors that have acquired multiple drug resistance (St Croix et al., (1998) Cancer Lett September 131(1): 35-44). Hyaluronidases, such as, for example soluble rHuPH20, also can enhance delivery of biologics such as monoclonal antibodies, cytokines and other drugs to tumors that accumulate glycosaminoglycans.

Hyaluronidases can also be used to increase the sensitivity of tumors that are resistant to conventional chemotherapy. For example, hyaluronidase, such as soluble rHuPH20, can be administered to a patient having a tumor associated with a HYAL1 defect in an amount effective to increase diffusion around the tumor site (e.g., to facilitate circulation and/or concentrations of chemotherapeutic agents in and around the tumor site), inhibit tumor cell motility, such as by hyaluronic acid degradation, and/or to lower the tumor cell apoptosis threshold. This can bring the tumor cell(s) to a state of anoikis, which renders the tumor cell more susceptible to the action of chemotherapeutic agents. Administration of hyaluronidase can induce responsiveness of previously chemotherapy-resistant tumors of the pancreas, stomach, colon, ovaries, and breast (Baumgartner et al. (1988) Reg. Cancer Treat. 1:55-58; Zanker et al. (1986) Proc. Amer. Assoc. Cancer Res. 27:390).

In one example, hyaluronidases are used in the treatment of metastatic and non-metastatic cancers, including those that have decreased endogenous hyaluronidase activity relative to non-cancerous cells. Hyaluronidases can be used as a chemotherapeutic agent alone or in combination with other chemotherapeutics. Exemplary cancers include, but are not limited to, small lung cell carcinoma, squamous lung cell carcinoma, and cancers of the breast, ovaries, head and neck, or any other cancer associated with depressed levels of hyaluronidase activity or decreased hyaluronic acid catabolism.

h. Use in Treatment of Glycosaminoglycan Accumulation in the Brain

Hyaluronic acid levels are elevated in a number of cerebrospinal pathologic conditions. Levels of cerebrospinal hyaluronic acid are normally less than 200 µg/L in adults (Laurent et al. (1996) Acta Neurol Scand September 94(3): 194-206), but can elevate to levels of over 8000 µg/L in diseases such as meningitis, spinal stenosis, head injury and cerebral infarction. Hyaluronidases, such as, for example, soluble rHuPH20, can be utilized to degrade critically elevated levels of substrate.

The lack of effective lymphatics in the brain also can lead to life threatening edema following head trauma. Hyaluronic acid accumulation is a result of increased synthesis by hyaluronic acid synthases and decreased degradation. Accumulation of hyaluronic acid can initially serve the beneficial purpose of increasing water content in the damaged tissue to facilitate leukocyte extravasation, but continued accumulation can be lethal. Administration of hyaluronidase, such as intrathecally or intravenously, to a patient suffering from head trauma can serve to remove tissue hyaluronic acid accumulation and the water associated with it.

Hyaluronidases also can be used in the treatment of edema associated with brain tumors, particularly that associated with glioblastoma multiform. The edema associated with brain tumors results from the accumulation of hyaluronic acid in the non-cancerous portions of the brain adjacent the tumor. Administration of hyaluronidase to the sites of hyaluronic acid accumulation (e.g., by intravenous injection or via a shunt) can relieve the edema associated with such malignancies by degrading the excess hyaluronic acid at these sites.

i. Use in Treatment of Glycosaminoglycan Accumulation in Cardiovascular Disease

Hyaluronidase can be used in the treatment of some cardiovascular disease. Administration of hyaluronidase in animal models following experimental myocardial infarct can reduce infarct size (Maclean, et al (1976) Science 194(4261): 199-200). One proposed mechanism by which this can occur is by reducing hyaluronic acid accumulation that occurs following ischemia reperfusion. Reduction of infarct size is believed to occur from increased lymph drainage and increased tissue oxygenation and reduction of myocardial water content.

Hyaluronidases also can be used to limit coronary plaques from arteriosclerosis. Such plaques accumulate glycosaminoglycans and mediate macrophage and foam cell adhesion (Kolodgie et al. (2002) Arterioscler Thromb Vasc Biol. 22(10):1642-8).

j. Use in Pulmonary Disease

Levels of hyaluronic acid in broncheoalveolar lavages (BAL) from normal individuals are generally below 15 ng/ml. However, hyaluronic acid levels in BAL rise dramatically in conditions of respiratory distress (Bjermer et al. (1987) Br Med J (Clin Res Ed) 295(6602):803-6). The increased hyaluronic acid in the lung can prevent oxygen diffusion and gas exchange as well as activating neutrophil and macrophage responses. Purified preparations of soluble rHuPH20, such as those produced using the methods provided herein, can be delivered by either pulmonary or intravenous delivery to patients presenting with such conditions to reduce hyaluronan levels. Hyaluronidases also can be administered to patients suffering from other pulmonary complications that are associated with elevated glycosaminoglycans or to enhance the delivery of other co delivered molecules to the lung.

k. Other Uses

In further examples of its therapeutic use, hyaluronidase can be used for such purposes as an antidote to local necrosis from paravenous injection of necrotic substances such as vinka alkaloids (Few et al. (1987) Amer. J. Matern. Child Nurs. 12, 23-26), treatment of ganglion cysts (Paul et al. (1997) J Hand Surg. 22 (2): 219-21) and treatment of tissue necrosis due to venous insufficiency (Elder et al. (1980) Lancet 648-649). Hyaluronidases also can be used to treat ganglion cysts (also known as a wrist cyst, Bible cyst, or dorsal tendon cyst), which are the most common soft tissue mass of the hand and are fluid filled sacs that can be felt below the skin.

Hyaluronidases can be used in the treatment of spinal cord injury by degrading chondroitin sulfate proteoglycans (CSPGs). Following spinal cord injury, glial scars containing CSPGs are produced by astrocytes. CSPGs play a crucial role in the inhibition of axon growth. In addition, the expression of CSPG has been shown to increase following injury of the central nervous system (CNS). Hyaluronidases also can be utilized for the treatment of herniated disks in a process known as chemonucleolysis. Chondroitinase ABC, an enzyme cleaving similar substrates as hyaluronidase, can induce the reduction of intradiscal pressure in the lumbar spine. There are three types of disk injuries. A protruded disk is one that is intact but bulging. In an extruded disk, the fibrous wrapper has torn and the NP has oozed out, but is still connected to the disk. In a sequestered disk, a fragment of the NP has broken loose from the disk and is free in the spinal canal. Chemonucleolysis is typically effective on protruded and extruded disks, but not on sequestered disk injuries.

D. SOLUBLE rHuPH20-EXPRESSING CELLS

The methods described herein can be used to generate and purify large quantities of soluble rHuPH20, Soluble rHuPH20 is expressed in CHO cells that are grown in large-scale cell culture. Expression is effected using an expression vector that contains the nucleotide sequence encoding the sequence of amino acids set forth in SEQ ID NO:3 (corresponding to amino acids 1 to 482 of the precursor human PH20 polypeptide set forth in SEQ ID NO:1). Following translation, the 35 amino acid signal sequence is cleaved and soluble rHuPH20 is secreted into the medium. The vector also contains an IRES downstream of the soluble rHuPH20 encoding region, a mouse dihydrofolate reductase gene and the SV40 pA sequence. The expression vector was introduced into DG44 cells, which are dihydrofolate reductase deficient (dhfr−) that have been adapted to grow in suspension culture in a chemically defined, animal product-free medium. The resulting soluble rHuPH20-expressing cells include those described in Examples 1 and 4, below, and include cells designated 3D35M, 2B2, 3E10B, 1B3, 5C1, 1G11 and 2G10 cells.

Other cells can be used to produce hyaluronidases similar to rHuPH20. Generally, protein expression systems suitable for the introduction of critical N-linked glycosylation residues on hyaluronidases are used. Such cells include, for example, yeast cells, fungal cells, plant cells, insect cells and mammalian cells. Many cell lines are available for mammalian expression including mouse, rat human, monkey, chicken and hamster cells. Exemplary cell lines include but are not limited to CHO (including DG44 cells and CHO—S cells), Balb/3T3, HeLa, MT2, mouse NS0 (nonsecreting) and other myeloma cell lines, hybridoma and heterohybridoma cell lines, lymphocytes, fibroblasts, Sp2/0, COS, NIH3T3, HEK293, 293S, 2B8, and HKB cells. Cell lines also are available adapted to serum-free media, which facilitates purification of secreted proteins from the cell culture media.

a. 3D35M Cells

Exemplary of soluble rHuPH20-expressing cells are 3D35M cells, described in Example 1, below, and U.S. Patent Publication Nos. 20040268425, 20050260186 and 20060104968. 3D35M cells are dihydrofolate reductase deficient (dhfr−) DG44 CHO cells that express soluble rHuPH20. The cells were transformed with an HZ24 expression vector having the nucleotide sequence set forth in SEQ ID NO:50. This vector contains a CMV promoter driving expression of nucleic acid encoding a 482 amino acid (SEQ ID NO:3) polypeptide that corresponds to amino acid positions 1 to 482 of the full length human PH20 set forth in SEQ ID NO:1. This includes a 35 amino acid N-terminal signal sequence. The vector also contains an internal ribosome entry site (IRES) after the PH20-encoding sequence, followed by a mouse dihydrofolate reductase gene and the SV40 polyadenylation sequence. Following translation, the 482 amino acid polypeptide is processed to remove the 35 amino acid signal sequence, resulting in the secretion of soluble rHuPH20.

Characterization of 3D35M cells demonstrated that nucleic acid region encoding soluble rHuPH20 is present in the cells at a copy number of approximately 318 copies/cells. Soluble rHuPH20 produced from 3D35M cells by the methods herein is a mixture of species that can include one or more of the polypeptides having sequences set forth in SEQ ID NOS:4-9. In an exemplary characterization of these species (described in Example 11), the species set forth in SEQ ID NO:4 was present at an abundance of 0.2%, the species set forth in SEQ ID NO:5 (corresponding to amino acids 1 to 446 of SEQ ID NO:4) was present at an abundance of 18.4%, the species set forth in SEQ ID NO:6 (corresponding to amino acids 1 to 445 of SEQ ID NO:4) was present at an abundance of 11.8%, the species set forth in SEQ ID NO:7 (corresponding to amino acids 1 to 444 of SEQ ID NO:4) was present at an abundance of 56.1%; and the species set forth in SEQ ID NO:8 (corresponding to amino acids 1 to 443 of SEQ ID NO:4) was present at an abundance of 13.6%. Such heterogeneity in the soluble rHuPH20 preparation is likely a result of C-terminal cleavage by peptidases present during the production and purification methods provided herein.

The 3D35M cells can be grown in cell culture medium with or without methotrexate. Additional supplements, such as glutamine, also can be added. In some examples, the cells are grown in cell culture medium containing, for example, 50 nM, 100 nM, 500 nM, 1 µM, or 2 µM methotrexate and lacking hypoxanthine and thymidine. In one example, 3D35M cells are cultured at 37° C. in 5-7% $CO_2$ in culture medium (such as CD CHO Medium, Invitrogen) without hypoxanthine and thymidine and with 100 nM methotrexate and glutamine or a glutamine substitute, such as L-Alanyl-L-Glutamine, a stabilized, dipeptide form of L-glutamine. Other cell culture media appropriate for CHO cells can be used to culture 3D35M cells including, but not limited to, Dulbecco's modified Eagle's medium (DMEM), Eagle's Minimum essential medium (EMEM), Iscove's modified Eagle's medium (IMEM), F12 and RPMI. 3D35M cells grown under such conditions in shaking flasks can produce in excess of 1000 units/mL hyaluronidase activity. When cultured in a bioreactor, such as described in Example 3, below, 3D35M cells can produce soluble rHuPH20 with enzymatic activity in excess of 2000 units/mL.

b. 2B2 Cells

Exemplary of soluble rHuPH20-expressing cells for production of rHuPH20 in the methods provided herein are described in Example 4 and designated 2B2 cells. 2B2 cells were generated by adapting 3D35M cells to higher methotrexate levels (i.e. 20 µM) and selecting clones that grew in the higher methotrexate concentration. This adaptation increased the hyaluronidase activity produced by the cells. DG44 cells are dihydrofolate reductase-deficient (dhfr−) and, therefore, cannot make nucleosides. The expression vector present in 3D35M and 2B2 cells contains, in addition to the PH20 gene, the coding sequence for mouse dihydrofolate reductase. Methotrexate is a strong competitive dihydrofolate reductase inhibitor. Therefore, by increasing the concentration of methotrexate in the culture media, the hyaluronidase-expressing cells are forced to produce more mouse dihydrofolate reductase to remain viable. This can be effected by, for example, gene amplification or rearrangement of the integrated DNA to a more stable and productive arrangement. Thus, forcing an increase in the production of mouse dihydrofolate reductase also can result in an increase in the production of sHuPH20. A comparison of enzymatic activity of soluble rHuPH20 produced by 2B2 cells and 3D35M cells demonstrated that activity was typically between 80% and 100% higher in 2B2 cells (see e.g. Example 5, below) compared to 3D35M cells.

2B2 cells were selected from amongst the cell clones that were isolated following selection with 20 µM methotrexate as the cell line that produced soluble rHuPH20 having the greatest enzymatic activity (see, e.g. Example 4). When characterized, it was observed that the nucleic acid region encoding soluble rHuPH20 was present in 2B2 cells at a copy number of approximately 206 copies/cell. Southern blot analysis of Spe I-, Xba I- and BamH I/Hind III-digested genomic 2B2 cell DNA using a probe specific for the nucleic acid region encoding soluble rHuPH20 revealed the following restriction digest profile: one major hybridizing band of ~7.7 kb and four minor hybridizing bands (~13.9, ~6.6, ~5.7 and ~4.6 kb) with DNA digested with Spe I; one major hybridizing band of ~5.0 kb and two minor hybridizing bands (~43.9 and ~6.5 kb) with DNA digested with Xba I; and one single hybridizing band of ~1.4 kb observed using 2B2 DNA digested with BamH I/Hind III.

2B2 cells can be grown in cell culture medium with or without methotrexate. Additional supplements, such as glutamine, insulin and yeast extract also can be added. In some examples, the cells are grown in cell culture medium containing, for example, 50 nM, 100 nM, 500 nM, 1 µM, 2 µM, 5 µM, 10 µM, 20 µM or more methotrexate and lacking hypoxanthine and thymidine. In one example, 2B2 cells are cultured at 37° C. in 5-7% $CO_2$ in culture medium (such as CD CHO Medium, Invitrogen) without hypoxanthine and thymidine and with 20 μM methotrexate and glutamine or L-alanyl-L-glutamine, a stabilized, dipeptide form of L-glutamine. Other cell culture media appropriate for CHO cells can be used to culture 2B2 cells, including, but not limited to, Dulbecco's modified Eagle's medium (DMEM), Eagle's Minimum essential medium (EMEM), Iscove's modified Eagle's medium (IMEM), F12 and RPMI. 2B2 cells grown under such conditions in shaking flasks can produce in excess of 3000 units/mL hyaluronidase activity. When cultured in a bioreactor, such as described in Example 8, below, 2B2 cells can produce soluble rHuPH20 having enzymatic activity in excess of 17000 units/mL hyaluronidase activity.

Soluble rHuPH20 produced from 2B2 cells by the methods herein is a mixture of species of polypeptides having sequences set forth in SEQ ID NOS:4-9. In an exemplary characterization the soluble rHuPH20 product produced by 2B2 cells (described in Example 11), the species set forth in SEQ ID NO:4 was present at an abundance of 1.9%, the species set forth in SEQ ID NO:5 (corresponding to amino acids 1 to 446 of SEQ ID NO:4) was present at an abundance of 46.7%, the species set forth in SEQ ID NO:6 (corresponding to amino acids 1 to 445 of SEQ ID NO:4) was present at an abundance of 16.7%, the species set forth in SEQ ID NO:7 (corresponding to amino acids 1 to 444 of SEQ ID NO:4) was present at an abundance of 27.8%; and the species set forth in SEQ ID NO:8 (corresponding to amino acids 1 to 443 of SEQ ID NO:4) was present at an abundance of 6.9%. As noted for soluble rHuPH20 produced from 3D35M cells, the heterogeneity in the soluble rHuPH20 preparation from 2B2 cells is likely a result of C-terminal cleavage by peptidases present during the production and purification methods provided herein.

E. CELL CULTURE EXPANSION

The methods described herein employ bioreactors to grow large volumes of cell culture to produce large quantities of soluble rHuPH20. As described in detail below, these methods include a cell expansion phase, a protein production phase, a protein concentration and buffer exchange phase, and a purification phase. The soluble rHuPH20-expressing cells, such as 2B2 cells, are initially expanded from an original inoculum, such as an aliquot of cells from a working cell bank (WCB) or master cell bank (MCB), to a larger volume prior to culture in the bioreactor for the production phase. The final culture volume in the expansion phase is directly proportional to the volume of the bioreactor used in the following production phase. Typically, a larger bioreactor is inoculated using a larger final culture volume from the expansion phase than is a smaller bioreactor.

The soluble rHuPH20-expressing cells are expanded through a series of cultures, each increasing in volume from the previous one, and each being used as the inoculum for the subsequent culture. Exemplary of such cells are 2B2 cells. The original inoculum is typically one in which the purity and identity of the cells and the cell number are defined. These cells can be stored frozen, such as at –20° C., –70° C. or –80° C., or can be maintained in liquid media at, for example, 4° C., or maintained in culture at, for example, 37° C. In some instances, the original inoculum is a master cell bank or working cell bank aliquot that has been stored frozen. In such cases, the inoculum is thawed, such as in a 37° C. waterbath. The original cell inoculum is typically centrifuged and the cells are resuspended in an appropriate cell culture media. For example, 2B2 cells can be resuspended in, and subsequently cultured in, basal media, such as CD CHO media (Invitrogen), or reconstituted powdered CD CGO AGT™ media (Invitrogen), supplemented with 8 mM glutamine or L-alanyl-L-glutamine and 20 μM methotrexate. In another example, cells can be grown in basal media supplemented with 8 mM glutamine or L-alanyl-L-glutamine and 100 mM methotrexate. Any other suitable cell culture media also can be used to expand hyaluronidase-expressing cells. For example, cells can be cultured in Dulbecco's modified Eagle's medium (DMEM), Eagle's Minimum essential medium (EMEM), Iscove's modified Eagle's medium (IMEM), F12, RPMI, or other chemically-defined or undefined media, with or without additional supplements. Typically, the cells are grown in serum-free media, but also can be grown in media containing serum. One of skill in the art could prepare cell culture media using other basal cell culture media to which various nutrients can be supplemented to make the cell culture media in which soluble rHuPH20-expressing cells are cultured.

The cell inoculum is added to the first of a series of increasing volumes of cell culture media, thus expanding the cell culture. Following the initial inoculation, the cells are expanded in a humidified incubator or bioreactor at an appropriate temperature with an appropriate amount of $CO_2$. Typically, the amount of $CO_2$ is between 4% and 9%, typically between 6.0% and 8.0%, such as 7.0% and the temperature is between 35° C. and 39° C., typically between 36° C. and 38° C., such as 37° C. For example, 2B2 and 3D35M cells can be grown in a 37° C. humidified incubator with 7% $CO_2$. The culture can be agitated, such as at 90-130 rpm, during this process. When the cells reach the desired density, such as, for example, greater than $1.0 \times 10^6$ cells/mL (e.g. between $1.5 \times 10^6$ cells/mL and $2.5 \times 10^6$ cells/mL), the cell culture is used to inoculate a larger volume of fresh cell culture media. For example, cells can be inoculated into the next culture at a density of $4 \times 10^4$ to $4 \times 10^6$ cells/mL, typically $2 \times 10^5$ to $6 \times 10^5$ cells/mL, such as $4 \times 10^5$ cells/mL. The process is repeated until the cells have been expanded to the desired volume and cell density for seeding of, for example, $4 \times 10^4$ to $4 \times 10^6$ cells/mL into the bioreactor.

In one example, soluble rHuPH20-expressing cells, such as 2B2 cells, are initially added to approximately 20 mL of fresh cell culture media in a 125 mL shaker flask, resulting in a culture volume of 20-30 mL, typically 25 mL. Following incubation at 37° C., 7% $CO_2$ and expansion of the cells to a density of greater than $1.5 \times 10^6$ cells/mL, fresh media is added to the flask to expand the cell culture to 40 mL. The cells are incubated again until a density of greater than $1.5 \times 10^6$ cells/mL is attained, after which the entire cell culture (approximately 40 mL) is added to fresh media to make 100 mL culture volume in a 125 mL spinner flask. This process is repeated by transferring the entire cell culture (approximately 100 mL) to a 250 mL spinner flask containing sufficient fresh media to make a final culture volume of 200 mL, then a 1 L spinner flask containing sufficient fresh media to make a final culture volume of 800 mL, then a 6 L spinner flask containing sufficient fresh media to make a final culture volume a final volume of 5 L, and finally to a 36 L spinner flask containing sufficient fresh media to make a final culture volume of 32 L. Between each transfer, the cells are incubated until the culture reached a density of greater than $1.5 \times 10^6$ cells/mL. In some examples, a higher cell density is attained following incubation of the final 36 L spinner flask. For example, cells in the 36 L spinner flask can be expanded to a cell density of $3.55 \times 10^6$ cells/mL to $6.05 \times 10^6$ cells/mL. This process can be used to expand soluble rHuPH20-expressing cells before introduction to a 400 L bioreactor (300 L culture volume) for the protein production phase (see, e.g. Example 8). Smaller volumes of cell culture and different cell densities can be used for smaller bioreactors. For example, cells can be expanded to a volume of approximately 20 L with a cell density of between $1.8 \times 10^6$ cells/mL and $2.5 \times 10^6$ cells/mL prior to introduction to a 125 L bioreactor. In another example, soluble rHuPH20-expressing cells are expanded to a volume of approximately 800 mL with a cell density of between $1.5 \times 10^6$ cells/mL and $2.5 \times 10^6$ cells/mL prior to introduction to a 5 L bioreactor.

This process, like any of the processes described herein, also can be scaled-up by one of skill in the art for introduction of the cells into a bioreactor with a culture volume larger than 300 L. For example, the process can be scaled up for introduction of the cells into a bioreactor with a 2500 L culture volume, such as described in Example 12. Thus, in one example of the methods provided herein, following thawing, the cells are serially expanded through a 125 mL shaker flask (working volume of 20-30 mL, such as 25 mL), a 250 mL shaker flask (working volume of 45-55 mL, such as 50 mL), a 1 L shaker flask (working volume of 190-210 mL, such as 200 mL), two 2 L shaker flasks (working volume of 350-450 mL per flask, such as 400 mL per flask), six 2 L shaker flasks (working volume of 350-450 mL per flask, such as 400 mL per flask), a 25 L wave bioreactor (working volume of 14-16 L, such as 15 L), a 100 L wave bioreactor (working volume of 75-85 L, such as 80 L), and a 600 L seed bioreactor (working volume of 440-520 L, such as 480 L).

F. PROTEIN PRODUCTION

Following cell expansion, the soluble rHuPH20-expressing cells are transferred to a bioreactor for the production phase, during which large quantities of soluble rHuPH20 are secreted into the cell media. This phase typically is designed such that the cells growth is maximized in the first half of the bioreactor run, and soluble rHuPH20 production is maximized in the second half of the bioreactor run. The cells are provided with a series of feed media at particular time points throughout the production to regulate this process. The bioreactor conditions also are typically monitored to ensure optimal conditions are maintained throughout the process. The methods described herein for protein can be scaled up or down by one of skill in the art. Further, modifications to, for example, cell media, incubation times, feeding protocols. One of skill in the art can empirically determine the appropriate conditions for protein production for any given bioreactor and cell type.

Bioreactors of different sizes and designs can be utilized in the methods herein. Bioreactors with working volumes of between 1 L and 5000 L or more can be used in the methods herein. In some examples, a 5 L, 36 L, 125 L, 400 L or 3500 L bioreactor is used in the methods herein to culture cells in volumes of approximately 4 L, 23 L, 100 L, 300 L and 2500 L, respectively. Typically, the bioreactor is sterilized prior to the addition of cell culture media or cells. Sterilization can be effected by autoclaving or otherwise treating with steam for some bioreactors, or by treatment with a sterilizing solution, such as dilute sodium hydroxide, dilute nitric acid or sodium hypochlorite. In some examples, the bioreactor is sterilized by steam at 121° C., 20 PSI for 30 minutes. Following sterilization, cell culture media can be added to the bioreactor and then assessed for contamination, such by microbial contamination, after a period of time to ensure that the sterilization process was effective.

The cell culture from the expansion phase, described above, is added to the sterilized bioreactor containing fresh cell culture media. Generally, the soluble rHuPH20-expressing cells are inoculated into the fresh cell culture media at a cell density of $10^4$ to $10^7$ cells/mL, such as $10^5$ to $10^6$ cells/mL. For example, cells can be inoculated at a density of $1 \times 10^4$, $5 \times 10^4$, $1 \times 10^5$, $5 \times 10^5$, $1 \times 10^6$, $4 \times 10^6$, or $1 \times 10^7$ cells/mL. In one example, soluble rHuPH20-expressing cells are inoculated at a cell density of $4 \times 10^5$ cells/mL. The total cell count following inoculation can be, therefore, between $10^7$ and $10^{14}$, depending on the size of the bioreactor and the cell density. For example, a cell culture volume of 100 L can have a cell density following inoculation of approximately $10^9$, $10^{10}$, $10^{11}$ or $10^{12}$ cells. In another example, a cell culture volume of 2500 L can have a cell density following inoculation of approximately $10^{10}$, $10^{11}$, $10^{12}$ or $10^{13}$ cells.

The volumes of inoculating cell culture and fresh culture media used are dependent upon the size of the bioreactor and the cell density of the inoculum. For example, approximately 30 L of soluble rHuPH20-expressing cells, such as 2B2 cells, can be added to a 400 L bioreactor containing 230 L fresh cell culture media, for a total volume of approximately 260 L and an inoculation cell density of $4 \times 10^5$ cells/mL (total cell count of approximately $10^{11}$ cells). This can be scaled up or down as necessary, depending on the bioreactor. For example, approximately 20 L of soluble rHuPH20-expressing cells, such as 3D35M cells, can be added to a 125 L bioreactor containing 65 L fresh cell culture media, for a total volume of approximately 85 L and an inoculation cell density of $4 \times 10^5$ cells/mL (total cell count of approximately $3.4 \times 10^{10}$ cells. In another example, for production in a 3500 L bioreactor, 2B2 cells are added to fresh cell culture media for a total cell culture volume of 1900-2300 L, such as 2100 L.

The fresh cell culture media contains the appropriate supplements to provide the necessary nutrients to the cells to promote cell growth. Supplements that can be added to the basal cell medium include, but are not limited to, glucose, insulin, sodium butyrate, yeast extract and glutamine or a glutamine substitute, such as L-alanyl-L-glutamine. In some instances, the basal medium contains sufficient glucose that no further glucose needs to be added. In other instances, glucose is added to the media later in the production process, such as in a subsequent feed media. The addition of insulin to the medium can promote cell growth and increase peak cell density. Glutamine or glutamine-substitutes, such as or L-alanyl-L-glutamine, can support cell cycle progression and also enhance cell growth. One of skill in the art can empirically determine the amount and quality of the nutrients that can be supplemented to the basal medium. In some examples, glutamine or glutamine-substitute is added to the basal cell culture medium at 1 mM, 2 mM, 3 mM, 4 mM, 5 mM, 6 mM, 7 mM, 8 mM, 9 mM, 10 mM, 15 mM or 20 mM. Insulin can be added to the cell culture medium at, for example, 0.5 mg/L to 50 mg/L, such as 1 mg/L to 40 mg/L, 2 mg to 30 mg/L, or 5 mg/L to 20 mg/L. For example, basal cell culture medium supplemented with 5 mg/L insulin and 8 mM L-alanyl-L-glutamine can be used as the fresh cell culture media into which the soluble rHuPH20-expressing cells are inoculated. Additional supplements, such as antibiotics, anti-fungals, indicators, salts, vitamins, amino acids and growth factors also can be added.

The individual parameters of the bioreactor can be set to maintain optimal conditions throughout the protein production process. The specific parameters that can be set depend on the bioreactor used, and can include, but are not limited to, temperature, pH, dissolved oxygen, impeller speed, vessel pressure, air sparge and air overlay. In one example, the conditions of a 125 L bioreactor containing 100 L cell culture of 3D35M cells are set to; temperature: 37° C.; dissolved oxygen: 25%±10%; impeller speed: 50 RPM; vessel pressure: 3 psi; air sparge: 1 L/minute; air overlay: 1 L/minute, pH: 7.2 In another example, the conditions of a 400 L bioreactor containing an initial cell culture volume of 260 L are set to; temperature: 37° C.; impeller speed 40-55 RPM; vessel pressure: 3 psi; air sparge: 0.5-1.5 L/minute; air overlay: 1 L/minute. In a further example, the conditions of a 3000 L bioreactor containing an initial culture volume of 2100 L are set to; temperature: 37° C. (or between 36.5° C. and 37.5° C.; impeller speed: 35 RPM (or 70-80 RPM); vessel pressure: 5 psi (or 3-7 psi); air sparge: 12 L/minute (or 11-13 L/minute); dissolved oxygen: 25%, or >25%; pH pre inoculation: 7.2 (or pH 7.1-7.3); pH post inoculation: ≦7.2 (or ≦7.3). One of skill in the art can empirically determine the appropriate conditions for growth of a particular soluble rHuPH20-expressing cell in a particular bioreactor.

The soluble rHuPH20-expressing cells are typically cultured in the bioreactor for between 10 and 25 days. In some examples, the soluble rHuPH20-expressing cells are cultured in the bioreactor for 12, 13, 14, 15 or 16 days before harvesting. In other examples, the cells are harvested when the viable cell count (VCC) falls to a particular level, such as, for example, 25%, 30%, 35%, 40%, 45%, 50%, 55%, 60% or 70%. In one example, the cells are harvested when the VCC is between 30% and 35%. In another example, the cells are harvested within 24 hours of the VCC dropping below 50%.

During the bioreactor culture, the cells can be grown as batch cultures, in which the culture is grown to completion without the addition of further nutrients. In other examples, the cells are grown as fed-batch cultures and provided with a series of feed media at particular time points to supplement nutrients and glucose throughout. In some instances, the nutrients provided in the cell culture medium into which the cells were inoculated have depleted by 3, 4, 5, 6, 7 days or more post-inoculation. Thus, providing additional nutrients or supplements can produce higher yields of protein than batch cultures. In one example, cells are provided with feed media on days 6, 9 and 11 post-inoculation. In another example, cells are provided with feed media on days 7, 9 and 11 post-inoculation. In a further example, cells are provided with feed media on days 5, 7, 9 and 11 post-inoculation. The volume of feed media added to the bioreactor culture can range between, for example, 0.5% and 20%, such as 1-20%, 2-15%, 3-10% or 4-5% of the cell culture volume. In some instances, the feed media is added at a volume equivalent to 4% of the cell culture volume.

The addition of various supplements to the feed media also can be used to regulate the growth and/or cell cycle of the cells. Exemplary nutrients and supplements that can be included in the feed media include, but are not limited to, glutamine or glutamine-substitute, such as L-Alanyl-L-Glutamine, insulin, yeast extract, glucose and sodium butyrate or sodium butyrate. Furthermore, the basal media used in the feed media also can be concentrated, thus providing additional nutrients, such as essential amino acids, that may have been depleted during cell culture. The basal media in the feed media can be 2×, 3×, 4×, 5×, 6× or more concentrated. In other examples, the basal media is less concentrated, or the same concentration as the cell culture media in the bioreactor.

The supplements included in the feed media can be used to regulate cell growth and protein production. For example, the first feed media added to the cell culture can include nutrients that enhance cell cycle progression, cell growth and peak cell density. Subsequent feed medias can promote cell growth arrest and/or protein synthesis. The amount of each supplement in each feed media can vary, such as by increasing or decreasing from one feed media to the next, or can be the same from one feed media to the next. In some examples, the amount of a supplement in increased from one feed media to the next, such as by 10%, 20%, 30%, 40%, 50%, 60%, 70%, 80%, 90%, 100%, 150%, 200%, 300%, 400% or more. In other examples, the amount of a supplement in decreased from one feed media to the next, such as by 5%, 10%, 20%, 30%, 40%, 50%, 60%, 70%, 80%, 90% or more. In one example, a supplement is omitted from a feed media. In other examples, the amount of a supplement in the feed media stays the same. One of skill in the art can empirically determine the optimum amount of each supplement for each feed media to promote the desired amount of cell growth and protein production.

Exemplary supplements or nutrients that can be included in the feed media include, but are not limited to, glucose, glutamine or glutamine-substitute, such as L-Alanyl-L-Glutamine, insulin, and sodium butyrate. The type and amount of supplement added can influence cell growth and protein production. For example, insulin and glutamine or glutamine-substitute can be incorporated into the first feed media added to the cell culture to increase cell growth and peak cell density. Subsequent feed media can be designed to promote protein production more than cell growth. Supplements such as insulin can be excluded or reduced in amount, as can glutamine or glutamine-substitute, such as L-Alanyl-L-Glutamine. In contrast, supplements such as yeast extract that enhance protein synthesis can be increased in amount. In addition, supplements that enhance cell cycle arrest and, therefore, increased protein production, also can be included. Exemplary of such supplements is sodium butyrate.

In one example, insulin is added to one or more feed media. The addition of insulin can increase peak cell density by, for example, 2%, 5%, 10%, 15%, 20%, 25%, 30% or more. Although insulin can be incorporated into any feed media, typically, insulin is added to early feed media, such as the first feed media, or the first and second feed media, to promote maximal cell growth in the initial phase of the bioreactor run. For example, a feed media, such as the first feed media, can contain amount of insulin at or about 5 mg/L, 10 mg/L, 15 mg/L, 20 mg/L, 25 mg/L, 30 mg/L, 35 mg/L, 40 mg/L, 45 mg/L, 50 mg/L, 55 mg/L, 60 mg/L or more. In contrast, the amount of insulin added to later feed media can be reduced or can be completely omitted.

Glutamine or glutamine-substitute, such as L-Alanyl-L-Glutamine, also can be added to the feed media. In some instances, the amount of glutamine or glutamine-substitute added to the first feed media is more than the amount of glutamine or glutamine-substitute added to subsequent feed media. In particular examples, the amount of glutamine or glutamine-substitute added to each subsequent feed media is reduced compared to the amount added in the prior feed media. The optimal amount added to each feed media can be determine empirically by one of skill in the art, and can include, for example, concentrations of glutamine or glutamine-substitute at or about 1 mM, 5 mM, 10 mM, 15 mM, 20 mM, 25 mM, 30 mM, 35 mM, 40 mM, 45 mM, 50 mM or more.

Typically, the basal media used in the feed media also is supplemented with glucose. The amount of glucose added to each feed media can be increased or decreased relative to the previous feed media, or can stay approximately constant. In some examples, the amount of glucose added to the feed media is or is about 10 g/L, 15 g/L, 20 g/L, 25 g/L, 30 g/L, 35 g/L, 40 g/L, 45 g/L, 50 g/L, 55 g/L, 60 g/L, 75 g/L, 80 g/L or more.

In addition, supplements that promote protein synthesis also can be included. Such nutrients include, for example, yeast extract. In some instances, the amount of yeast extract included in the feed media is increased during the bioreactor run. For example, the amount of yeast extract in the third feed media can be increased compared to the amount in the second feed media, which can be increased compared to the amount in the second feed media. In some examples, the amount of yeast extract added to the feed media is between 5 and 1000 g/L, such as or as about 10 g/L, 20 g/L, 30 g/L, 40 g/L, 50 g/L, 75 g/L, 100 g/L, 125 g/L, 150 g/L, 175 g/L, 200 g/L, 250 g/L, 300 g/L, 350 g/L, 400 g/L or more.

Supplements that enhance cell cycle arrest and, therefore, increase protein production, also can be included. Typically, such supplements are included in feed media that are added to the bioreactor later in the run and not included in the first feed media. For example, supplements that enhance cell cycle arrest can be added to the second feed media and subsequent feed media. Exemplary of such supplements is sodium butyrate. In some examples, the amount of sodium butyrate added to the feed media is between 0.1 g/L and 10 g/L, such as or as about 0.2 g/L, 0.3 g/L, 0.4 g/L, 0.5 g/L, 0.6 g/L, 0.7 g/L, 0.8 g/L, 0.9 g/L, 1.0 g/L, 1.1 g/L, 1.2 g/L, 1.3 g/L, 1.4 g/L, 1.5 g/L, 1.6 g/L, 1.7 g/L, 1.8 g/L, 1.9 g/L, 2.0 g/L, 2.5 g/L, 3.0 g/L, 3.5 g/L, or more.

Further, any one or more of the bioreactor conditions can be altered during the production phase to optimize protein production. In one example, the temperature is lowered. This can serve to promote cell cycle arrest, prolong cell viability (thereby increasing total protein production), and help stabilize the hyaluronidase that has been secreted. For example, the temperature of the bioreactor can be reduced at each feeding, such as from 37° C. to 36.5° C. on the second feeding, to 36° C. on the third feeding and to 35.5° C. on the fourth feeding. One of skill in the art can empirically determine the appropriate feed media and the time at which to provide the feed, as well as the appropriate conditions in the bioreactor.

In one example, cells are provided with feed media on days 6, 9 and 11 post-inoculation. In another example, cells are provided with feed media on days 7, 9 and 11 post-inoculation. In a further example, cells are provided with feed media on days 5, 7, 9 and 11 post-inoculation. The feed media provided at each time-point can be the same or different, and can include supplements such as, but not limited to, glucose, sodium butyrate, insulin, glutamine or a glutamine substitute and yeast extract. For example, 2B2 cells growing in a 260 L culture in a 400 L bioreactor can be provided with a first feed at day 5 containing 10.4 L of 4× basal media (e.g. CD CHO media) with 33 g/L Glucose, 32 mM L-alanyl-L-glutamine, 16.6 g/L Yeast extract and 33 mg/L Insulin, a second feed at day 7 containing 10.8 L of 2× basal media (e.g. CD CHO media), 33 g/L Glucose, 16 mM L-alanyl-L-glutamine, 33.4 g/L Yeast extract and 0.92 g/L Sodium Butyrate, a third feed at day 9 containing 10.8 L 1× basal media (e.g. CD CHO media), 50 g/L Glucose, 10 mM L-alanyl-L-glutamine, 50 g/L Yeast extract and 1.80 g/L Sodium Butyrate, and a fourth feed at day 11 containing 1× basal media (e.g. CD CHO media), 33 g/L Glucose, 6.6 mM L-alanyl-L-glutamine, 50 g/L Yeast extract and 0.92 g/L Sodium Butyrate. This can be scaled up or down by one of skill in the art for production of rHuPH20 in larger or smaller bioreactors, respectively. Further, one of skill in the art can alter the amount of type of one more supplements added to the media to enhance cell growth and/or protein production.

In another example, the following feed media are provided to cells on days 5, 7, 9 and 11: Feed #1 Medium: basal media+33 g/L Glucose+26.6 mM L-alanyl-L-glutamine+ 83.3 g/L Yeastolate+33 mg/L rHuInsulin; Feed #2: basal media+33 g/L Glucose+13.4 mM L-alanyl-L-glutamine+ 166.7 g/L Yeastolate+0.92 g/L Sodium Butyrate; Feed #3: basal media+50 g/L Glucose+10 mM L-alanyl-L-glutamine+ 250 g/L Yeastolate+1.8 g/L Sodium Butyrate; Feed #4: basal media+33.3 g/L Glucose+6.7 mM L-alanyl-L-glutamine+ 250 g/L Yeastolate+0.92 g/L Sodium butyrate.

G. CELL CULTURE HARVEST, PROTEIN CONCENTRATION AND BUFFER EXCHANGE

Following the protein production phase, the cells are harvested and the soluble rHuPH20 that has been secreted into the cell culture media is concentrated prior to initiation of the purification process. In addition to concentrating the protein, the cell culture media can be exchanged with an appropriate buffer at this time. Multiple systems and processes to effect protein concentration and buffer exchange are known in the art and can be used in the methods herein. Described below are exemplary methods of such, and one of skill in the art will recognize that these methods can be modified or substituted with other effective methods to achieve a satisfactory level of protein concentration and buffer exchange.

The cells are harvested from the bioreactor and processed through a cell removal and clarification system to separate the cell culture fluid containing the hyaluronidase from cells and cell debris. An example of such a system is one that contains a series of filters that allow only the protein to pass though and be collected. Any filter or series of filters capable of separating the hyaluronidase from cells and cell debris can be used. For example, the cell culture harvest can be passed through a series of capsule filters, such a polyethersulfone filters. These can have decreasing pore sizes to incrementally remove, for example, cells, cell debris and smaller particles, such as viruses. In some examples, a series of four filters with pore sizes of 8.0 µm, 0.65 µm, 0.22 µm and 0.22 µm is used to clarify the cell culture to obtain the harvested cell culture fluid (HCCF). Another example of a cell removal and clarification system that can be used in the methods herein is a series of filters that in the first stage contains four modules in parallel, each containing a layer of diatomaceous earth graded to 4-8 µm and a layer of diatomaceous earth graded to 1.4-1.1 µm, followed by a cellulose membrane. The second stage contains a single module containing a layer of diatomaceous earth graded to 0.1-0.11 µM and a layer of diatomaceous earth graded to <0.1 µm followed by a cellulose membrane, and the third stage is a 0.22 µm polyethersulfone capsule filter.

Once the cells and debris have been separated from the HCCF, the protein in the HCCF typically is concentrated and the cell culture media exchanged with an appropriate buffer. The protein can be concentrated by 2×, 3×, 4×, 5×, 6×, 7×, 8×, 9×, 10×, 11×, 12×, 13× or more. In some examples, the protein is concentrated 10×. In other examples, the protein is concentrated 6×. Any method of protein concentration known in the art can be utilized. Exemplary of such methods include concentration using tangential flow filtration (TFF) systems with molecular weight cut off (MWCO) filters. For example, the clarified HCCF can be passed through a series of two 30 kDa MWCO spiral polyethersulfone filters to concentrate the protein 10×. In another example, the HCCF is passed through a series of four 30 kDa MWCO filters. For large-scale production of hyaluronidase, such as, for example, 100 L and 300 L cultures, filters with surface areas of between 0.5 and 5 square meters are typically employed for this purpose. In some examples, filters with a surface area of 1.2 square meters or 2.8 square meters are used.

A buffer exchange is performed following protein concentration. One of skill in the art can empirically determine an appropriate buffer. Exemplary of suitable buffers is a 10 mM Hepes, 25 mM NaCl, pH 7.0 buffer, or a 10 mM Tris, 20 mM Na$_2$SO$_4$, pH 7.5 buffer. Following harvesting, concentration and buffer exchange, the concentrated protein solution is typically passed through another filter, such as a 0.22 µm capsule filter, before being stored in a sterile storage bag.

In some examples, the concentrated protein solution is treated to inactivate any residual virus contamination. Virus inactivation can be effected by any method known in the art. For example, the concentrated protein solution can be mixed with a 10% Triton X-100, 3% tri(n-butyl) phosphate (TNBP), to a final concentration of 1% Triton X-100, 0.3% TNBP, at room temperate for between 15 and 75 minutes. In some examples, the protein is exposed to the viral inactivation solution for 30-45 minutes.

H. PURIFICATION

The soluble rHuPH20 is purified from the concentrated protein solution using a series of purification steps. Many purification techniques are known in the art and can be utilized in the methods herein. Such methods can include, but are not limited to, chromatographic methods such as ion-exchange chromatography, size-exclusion chromatography, affinity chromatography (AC), high performance liquid chromatography (HPLC), reversed phase chromatography (RPC) and hydrophobic interaction chromatography (HIC), and gel filtration methods, or any combination thereof.

Exemplary of purification methods that are used for the methods herein is a combination of ion-exchange chromatography, hydrophobic interaction chromatography and affinity chromatography. In ion-exchange chromatography, the proteins can be separated from a complex solution or mixture based on electrostatic forces between charged functional groups of the proteins and charged functional groups of the chromatography-column matrix. Cation-exchange resins have negatively charged functional groups that attract positively charged functional groups of proteins, and anion-exchange resins have positively charged functional groups that attract negatively charged functional groups of proteins. Proteins bound through electrostatic forces to the matrix can be eluted by increasing the ionic strength of the buffer solution within the chromatography column over time. In hydrophobic interaction chromatography, a protein can be separated from a complex solution or mixture based on its hydrophobicity. A complex solution containing the protein is applied to a chromatography column equilibrated with a high salt buffer that facilitates binding of the protein to the resin. A salt-gradient mobile phase with decreasing ionic strength is then introduced into the chromatography column to release bound proteins from the matrix. Alternatively, hydrophobic interaction chromatography may separate a monomeric protein from a complex solution or mixture by binding hydrophobic impurities, including inactive dimers and aggregates of the protein, while permitting the monomeric protein to flow through the chromatography column relatively unimpeded. In affinity chromatography, a proteins can be separated from a complex solution based on the affinity of the protein for a ligand or ligand-binding entity that is covalently bound to the matrix. Other proteins in the complex solution or mixture with weak affinity, or lacking affinity, for the ligand or ligand-binding entity flow through the chromatography column unimpeded, leaving the protein of interest bound to the matrix. The protein can then be eluted from the chromatography column by altering buffer conditions to decrease the affinity for the ligand or ligand-binding entity.

In one example, the soluble rHuPH20 is purified from the concentrated protein solution by sequential purification through a beaded crosslinked agarose column, such as a Q Sepharose™ column (ion-exchange chromatography), beaded crosslinked phenyl-substituted agarose column, such as a Phenyl Sepharose™ column (hydrophobic interaction chromatography), an Amino Phenyl Boronate column (affinity chromatography) and finally through a Hydroxyapatite column (ion-exchange chromatography). Each of these columns exhibit different binding properties with regards to hyaluronidase, such that the beaded crosslinked agarose column (e.g. Q Sepharose™ column) is a capture step (i.e. soluble rHuPH20 is bound to the resin while some other proteins flow through), the beaded crosslinked phenyl-substituted agarose (e.g. Phenyl Sepharose™ column) is a flow through step (i.e. soluble rHuPH20 flows through the column while some other proteins are captured), the Amino Phenyl Boronate column is another capture step, and the Hydroxyapatite column is a polishing step to further purify the soluble rHuPH20.

Prior to use, the columns are typically sterilized and the equilibrated. Sterilization can be effected by any method known in the art, including, but not limited to, sterilization with 1.0 M NaOH. Equilibration can be effected by the addition of an appropriate buffer to the column, such as a buffer similar to or the same as the buffer used to subsequently wash the column or the buffer in which the protein is contained in prior to loading. One of skill in the art can readily determine buffers suitable for use in equilibrating each column. Exemplary buffers are provided below. Between each chromatography step, the eluted protein can be filtered, such as through a 0.22 µm filter, to remove any contaminating microorganism or large aggregates. In some examples, the filtered eluate is stored, such as in sterile storage bags, prior to use in the next step. Following column chromatography, the purified hyaluronidase can subsequently be subjected to a virus removal step, followed by protein concentration and buffer exchange for final formulation. Exemplary purification methods are described in more detail below.

1. Beaded Crosslinked Agarose Column

The concentrated protein obtained from the of harvested cell culture fluid (HCCF) can be loaded onto a beaded crosslinked agarose column, such as, for example, a Q Sepharose™ column, which is a strong anion exchanger and captures soluble rHuPH20 while allowing other proteins to flow through. The bound soluble rHuPH20 can then be eluted using an appropriate buffer. The dimensions of the column used is typically dependent on the volume of concentrated protein obtained from the HCCF. For example, concentrated protein obtained from culture of hyaluronidase-expressing cells in a 100 L bioreactor culture can be loaded onto a column that is 20 cm high, 14 cm in diameter and contains 3 L resin. In another example, concentrated protein obtained from culture of soluble rHuPH20-expressing cells in a 300 L bioreactor culture can be loaded onto a column that is 29 cm high, 20 cm in diameter and contains 9 L resin. This can be scaled up or down as necessary, depending on the volume of the concentrated protein solution and the expected amount of protein. For example, concentrated protein obtained from culture of soluble rHuPH20-expressing cells in a 20 L bioreactor culture can be loaded onto a Q Sepharose™ column that is 28 cm high, 7 cm in diameter and contains 1.1 L resin, and concentrated protein obtained from culture of soluble rHuPH20-expressing cells in a 2500 L bioreactor culture can be loaded onto a Q Sepharose™ column that is 26 cm high, 63 cm in diameter and contains 81 L resin Prior to loading with the protein, the column is typically equilibrated. Equilibration can be effected by passing through 1, 2, 3, 4, 5, 6, 7, 8, 9 or more column volumes of buffer. In some examples, 5 column volumes of buffer is passed through the column for equilibration. Buffers suitable for equilibration include those similar to the buffers that will be used to wash the column after the protein had been loaded. For example, a beaded crosslinked agarose column, such as a Q Sepharose™ column can be equilibrated with 10 mM Hepes, 25 mM NaCl, pH 7.5. Other neutral pH buffers can be used, as will be recognized by one of skill in the art.

After loading the protein concentrate, the column is washed and the protein eluted. Suitable buffers for washing such columns containing bound soluble rHuPH20 include, for example, 10 mM Hepes, 25 mL NaCl, pH 7.0; 10 mM Hepes, 50 mM NaCl, pH 7.0; and 10 mM Tris, 20 mM $Na_2SO_4$, pH 7.5. The column can be washed with one or more types of buffer. For example, the column can be washed with 20 mM $Na_2SO_4$, pH 7.5 and 10 mM Hepes, 50 mM NaCl, pH 7.0. Typically, washing is effected by passing through 1, 2, 3, 4, 5, 6, 7, 8, 9 or more column volumes of buffer. In some examples, 5 column volumes of buffer is used to wash the column. The soluble rHuPH20 is then eluted using a buffer with a higher salt concentration, such as for example, 10 mM Hepes, 400 mM NaCl, pH 7.0. In some examples, the absorbance at $A_{280}$ is monitored to determine when to collect the eluate, as any absorbance during this process generally indicates the presence of soluble rHuPH20. Thus, in one example, the eluate is collected when the absorbance begins reading is 0.025. Typically, the eluate is filtered through an appropriate filter, such as a 0.22 µm filter, before being stored, such as in a sterile storage bag.

2. Beaded Crosslinked Phenyl-Substituted Agarose Column

Following purification through a beaded crosslinked agarose column, the protein solution can be subjected to hydrophobic interaction chromatography using a beaded crosslinked phenyl-substituted agarose column, such as a Phenyl Sepharose™ column, in which the soluble rHuPH20 flows through the column while other contaminating proteins are captured. The column used in the methods herein can range in size, depending on the volume and amount of protein being purified though it. Exemplary sizes include columns that are 29 cm high, 20 cm in diameter with 9 L resin for use in the purification of soluble rHuPH20 from cells grown in a 100 L bioreactor culture, columns that are 29 cm high, 30 cm in diameter with 19-21 L resin for use in the purification of hyaluronidase from cells grown in a 300 L bioreactor culture, and columns that are 35 cm high, 80 cm in diameter with 176 L resin for use in the purification of soluble rHuPH20 from cells grown in a 2500 L bioreactor culture. One of skill in the art can scale up or down as appropriate.

The sterilized beaded crosslinked phenyl-substituted agarose column, such as a Phenyl Sepharose™ column, can be equilibrated prior to loading of the protein with an appropriate buffer, such as, for example, 5 mM potassium phosphate, 0.5 M ammonium sulfate, 0.1 mM $CaCl_2$, pH 7.0. The protein eluate from the Q Sepharose column purification also is supplemented with ammonium sulfate, potassium phosphate and $CaCl_2$. These can be supplemented to the protein to final concentrations of, for example, about 5 mM potassium phosphate, 0.5 M ammonium sulfate and 0.1 mM $CaCl_2$, pH 7.0. Following loading of the protein, 5 mM potassium phosphate, 0.5 M ammonium sulfate and 0.1 mM $CaCl_2$, pH 7.0 also is added to the column and the flow through filtered is collected, such as in a sterile bag.

3. Amino Phenyl Boronate Column

Following hydrophobic interaction chromatography, the column-purified protein can be loaded onto an Amino Phenyl Boronate column for further purification. Amino Phenyl boronate ligand-mediated chromatography differs from many other ligands used for affinity chromatography. Whereas most ligands bind to a particular binding site on a protein by a mixture of noncovalent interactions, phenyl boronate interacts predominantly by forming a temporary covalent bond with 1,2-cis-diol groups. The boronate ligand will bind to any molecule containing the appropriate group, including soluble rHuPH20, which is highly glycosylated.

The Amino Phenyl Boronate column used in the methods herein can range in size, depending on the volume and amount of protein being purified though it. Exemplary sizes include columns that are 29 cm high, 20 cm in diameter with 6.3 L resin for use in the purification of hyaluronidase from cells grown in a 100 L bioreactor culture, columns that are 29 cm high, 30 cm in diameter with 19-21 L resin for use in the purification of hyaluronidase from cells grown in a 300 L bioreactor culture, and, and columns that are 35 cm high, 80 cm in diameter with 176 L resin for use in the purification of hyaluronidase from cells grown in a 2500 L bioreactor culture. One of skill in the art can scale up or down as appropriate. Buffers suitable for equilibrating the Amino Phenyl Boronate column include, for example, buffers containing 5 mM potassium phosphate, 0.5 M ammonium sulfate, pH 7.0.

Following loading of the Phenyl Sepharose column-purified protein onto the Amino Phenyl Boronate column, the column is washed with suitable wash buffers. Exemplary wash buffers include, but are not limited to, 5 mM potassium phosphate, 0.5 M ammonium sulfate, pH 7.0, and 20 mM bicine, 0.5 M ammonium sulfate, pH 9.0 and 20 mM bicine, 100 mM NaCl, pH 9.0. In one example, the Amino Phenyl Boronate column with the bound hyaluronidase is washed first with 5 mM potassium phosphate, 0.5 M ammonium sulfate, pH 7.0, then with 20 mM bicine, 0.5 M ammonium sulfate, pH 9.0 and finally with 20 mM bicine, 100 mM NaCl, pH 9.0. The bound hyaluronidase can then be eluted, such as with 50 mM Hepes, 100 mM NaCl, pH 7.0. One of skill in the art can modify one or more of the buffers to similarly effect purification. Typically, the eluted soluble rHuPH20 also is filtered to remove any microbial contamination or large aggregates.

4. Hydroxyapatite Column

Following Phenyl Boronate column chromatography, the protein solution containing the soluble rHuPH20 can be loaded onto a Hydroxyapatite column in a final polishing step. Hydroxyapatite is a crystalline form of calcium phosphate with the molecular formula $Ca_{10}(PO_4)_6(OH)_2$. It can be used as a polishing step to separate closely copurifying proteins, operating by mixed-mode ion exchange due to its inclusion of both positively and negatively charged moieties. Various hydroxyapatite chromatographic media are available commercially, and any available form of the material can be used in the methods herein. Examples of hydroxyapatites include, but are not limited to, those that are agglomerated to form particles and sintered at high temperatures into a stable porous ceramic mass. The particle size can vary, such as ranging from about 1 µm to about 1,000 µm in diameter. The porosity also can also vary, such as from about 100 A to about 10,000 A.

The Hydroxyapatite column used in the methods herein can range in size, depending on the volume and amount of protein being purified though it. Exemplary sizes include columns that are 20 cm high, 30 cm in diameter with 13 L resin for use in the purification of hyaluronidase from cells grown in a 300 L bioreactor culture, and columns that are 23 cm high, 80 cm in diameter with 116 L resin for use in the purification of hyaluronidase from cells grown in a 2500 L bioreactor culture. One of skill in the art can scale up or down as appropriate.

For the methods described herein, the Hydroxyapatite column can be equilibrated with 5 mM potassium phosphate, 200 mM NaCl or 5 mM potassium phosphate, 200 mM NaCl, 0.1 mM $CaCl_2$, pH 7.0. Equilibration using solutions such as these make the column compatible with the partially-purified hyaluronidase, which itself is supplemented with potassium phosphate and $CaCl_2$ to final concentrations of 5 mM and 0.1 mM, respectively. Following loading of the protein onto the column, the column can be washed with, for example, 10 mM potassium phosphate, 100 mM NaCl, 0.1 mM $CaCl_2$, pH 7.0, to remove any unbound contaminating proteins. The bound soluble rHuPH20 can then be eluted with an appropriate elution buffer. For example, elution can be effected by the addition of 70 mM potassium phosphate, pH 7.0. In some examples, the eluate is filtered, such as through a 0.22 μm filter.

6. Virus Removal, Protein Concentration and Buffer Exchange

The soluble rHuPH20 obtained flowing column chromatography can be subjected to post-purification steps that serve to formulate the protein in the desired buffer at the desired concentration. The protein also can be subjected to a viral removal step to ensure it is free from contamination and suitable for use as a therapeutic. Viral removal is typically effected with the use of a filter that allows only the soluble protein to pass through while trapping any viruses (and other contaminants that are equal to in size or larger that viruses). Such filters are available commercially, and any can be used in the methods herein. Pores sizes of filters useful for viral removal include, but are not limited to, 10 nm, 15 nm, 20 nm, 25 nm, 30 nm, 40 nm, 50 nm, 60 nm, 75 nm and 100 nm. In one example, the purified hyaluronidase is filtered through a filter containing 20 nm pores. The protein can be pumped into the filter by, for example, peristaltic pump or by use of a pressure tank.

Following viral removal, the soluble rHuPH20 can be concentrated and subjected to buffer exchange. The soluble rHuPH20 can be concentrated by 2×, 3×, 4×, 5×, 6×, 7×, 8×, 9×, 10×, 11×, 12×, 13× or more. In some examples, the protein is concentrated approximately 6×. This can result in, for example, a concentration of between 0.1 mg/mL and 50 mg/mL. In some examples, the purified hyaluronidase is concentrated to approximately 1 mg/mL. In other examples, the purified hyaluronidase is concentrated to approximately 10 mg/mL. Any method of protein concentration known in the art can be utilized. Exemplary of such methods include concentration using tangential flow filtration (TFF) systems with molecular weight cut off (MWCO) filters. For example, the purified hyaluronidase can be passed through a 10 kDa MWCO spiral polyethersulfone filters to concentrate the protein 10×. In another example, the protein is passed through a series of four 30 kDa MWCO filters. For large-scale production of hyaluronidase, such as, for example, 100 L and 300 L cultures, filters with surface areas of between 0.5 and 5 square meters are typically employed for this purpose. In some examples, filters with a surface area of 1.2 square meters or 2.8 square meters are used.

A buffer exchange is generally performed following protein concentration to formulate the protein in the desired buffer for subsequent use, for example, as a therapeutic. One of skill in the art can empirically determine an appropriate buffer. Exemplary of suitable buffers are saline buffers, including, but not limited to, 10 mM Hepes, 130 mM NaCl, pH 7.0, and 10 mM Histidine, 130 mM NaCl, pH 6.0. The purified hyaluronidase can, in some example, be passed through another filter, such as a 0.22 μm capsule filter, before being stored in a sterile environment.

I. FILLING

The methods described herein for the production and purification of soluble rHuPH20 also can include a filling step, in which the purified protein is aseptically filled into smaller containers for long-term storage and use. The soluble rHuPH20 can be filled into the containers as a liquid formulation, or as a powder, such as following lyophilization. For large-scale production, automated filling systems that include, for example, pumps to transfer the protein to the containers and weighing stations to measure the fill volume are typically used and are widely available. Manual or a combination of automated and manual filling of containers also can be performed, however. Suitable containers include, but are not limited to, glass or plastic vials, blister packs, bottles, tubes, inhalers, pumps, bags, syringes, bottles, or any other suitable container. Suitable closures or caps also can be used to seal the container. The filling process can include first passing the soluble rHuPH20 through a filter prior to filling to remove microbial contaminant and larger aggregates or sediment. For example, the protein can be filtered through a 0.22 μm filter before being aliquoted into suitable containers. One of skill in the art can determine the appropriate fill volume and can include, for example, volumes ranging from 0.1 mL to 100 mL. In some examples, vials are aseptically filled with 1 mL, 5 mL or 20 mL soluble rHuPH20. Following capping or closure of the containers, the containers can be stored at an appropriate temperature. In some examples, the containers are flash frozen and stored at between −15° C. and −35° C. In other examples, the containers are refrigerated, such as at between 3° C. and 15° C. Typically, long-term storage of liquids is at lower temperatures to minimize degradation. Soluble rHuPH20 in powder form can be stored for long periods at room temperature without significant degradation.

J. MONITORING AND ASSAYS

The methods described herein can be monitored at one or more steps, measuring one or more conditions, parameters or products at each point. This can ensure that optimal conditions are maintained throughout, and also can be used to assess efficiency and productivity of the process. Monitoring can occur, for example, one or more times during the cell expansion phase, protein production phase (i.e. in the bioreactor), and/or the protein purification stage, as well as any time between, before or after, such as during concentration/buffer exchange procedures or filling. Monitoring can include, but is not limited to, measuring pH, temperature, volumes, contamination, purity, protein concentration, enzyme activity, cell viability and cell number. In addition to monitoring conditions, parameters or products throughout the process, the purified soluble rHuPH20 produced as the end product also can be assessed and characterized with respect to, for example, protein concentration, enzyme activity, impurities, contamination, osmolarity, degradation, post-translational modifications and monosaccharide content.

1. Monitoring the Conditions

The conditions during one or more of the steps in the methods provided herein can be monitored to ensure optimal conditions are maintained throughout the process. If the monitoring demonstrates that the conditions are not within an optimal range, then the conditions can be altered. Conditions that can be monitored vary for each process. For example, during the cell culture phases (i.e. cell expansion and protein production in the bioreactor), conditions to be monitored include, but are not limited to, temperature, cell culture pH, cell culture nutrients (e.g. glucose), $CO_2$ levels and $O_2$ levels.

Typically, the conditions are monitored automatically using in-built systems in, for example the incubator or bioreactor.

During the protein purification stage, conditions that can be monitored include, but are not limited to, pH, conductivity and flow rate. These conditions can be monitored before, during and/or after one or more column chromatography steps. For example, the buffers used to equilibrate, wash or elute the column can be monitored. This can be performed before the buffer is loaded or after the buffer has run through the column.

2. Monitoring Soluble rHuPH20 Production

Soluble rHuPH20 production, and parameters associated with soluble rHuPH20 production, also can be monitored throughout the process. These include, but are not limited to, cell number, cell viability, contamination, protein concentration, enzyme activity, purity, osmolarity, post-translational modifications. Any method to assess these parameters can be used. For example, mammalian cell viability can be assessed by taking a small aliquot of the cell culture and staining with trypan blue, which permeates only damaged cell membranes, thus staining only dead cells. The cells can be visualized under microscope and counted using, for example, a hemocytometer. Other methods include assessing cell viability by measuring metabolic activity. For example, an aliquot of the cell culture can be incubated with a tetrazolium salt (e.g. MTT, XTT or WST-1) that is cleaved into a colored formazan product by metabolically active cells.

Soluble rHuPH20 concentration in a particular sample can be assessed by methods well-known in the art, including but not limited to, enzyme-linked immunosorbant assays (ELISA); SDS-PAGE; Bradford, Lowry, and/or BCA methods; UV absorbance, and other quantifiable protein labeling methods, such as, but not limited to, immunological, radioactive and fluorescent methods and related methods. Additionally, the presence and extent of degradation can be measured by standard techniques such as sodium dodecyl sulfate polyacrylamide gel electrophoresis (SDS-PAGE), Western blotting of electrophoresed hyaluronidase-containing samples and chromatography, such as, for example, RP-HPLC. The purity of a hyaluronidase-containing sample can be assessed by, for example, SDS-PAGE, RP-HPLC, size-exclusion chromatography, anion-exchange chromatography and isoelectric focusing (IEF). Soluble rHuPH20-containing samples, such as samples containing purified hyaluronidase, can be further characterized by assessing the sialic acid and monosaccharide content. This can be accomplished by, for example, hydrolyzing the sample with 40% trifluoroacetic acid, fluorescently labeling the released monosaccharides and separating them using RP-HPLC (see Example 10).

Soluble rHuPH20 produced and purified using the methods provided herein also can be assessed for the presence of post-translational modifications. Such assays are known in the art and include assays to measure glycosylation, hydroxylation, and carboxylation. In an exemplary assay for glycosylation, carbohydrate analysis can be performed, for example, with SDS page analysis of soluble rHuPH20 exposed to hydrazinolysis or endoglycosidase treatment. Hydrazinolysis releases N- and O-linked glycans from glycoproteins by incubation with anhydrous hydrazine, while endoglycosidase release involves PNGase F, which releases most N-glycans from glycoproteins. Hydrazinolysis or endoglycosidase treatment of soluble rHuPH20 polypeptides generates a reducing terminus that can be tagged with a fluorophore or chromophore label. Labeled soluble rHuPH20 polypeptides can be analyzed by fluorophore-assisted carbohydrate electrophoresis (FACE). The fluorescent tag for glycans also can be used for monosaccharide analysis, profiling or fingerprinting of complex glycosylation patterns by HPLC. Exemplary HPLC methods include hydrophilic interaction chromatography, electronic interaction, ion-exchange, hydrophobic interaction, and size-exclusion chromatography. Exemplary glycan probes include, but are not limited to, 3-(acetylamino)-6-aminoacridine (AA-Ac) and 2-aminobenzoic acid (2-AA). Carbohydrate moieties can also be detected through use of specific antibodies that recognize the glycosylated hyaluronidase polypeptide.

An exemplary assay to measure $\beta$-hydroxylation comprises reverse phase HPLC analysis of soluble rHuPH20 polypeptides that have been subjected to alkaline hydrolysis (Przysiecki et al. (1987) PNAS 84:7856-7860). Carboxylation and $\gamma$-carboxylation of hyaluronidase polypeptides can be assessed using mass spectrometry with matrix-assisted laser desorption ionization time-of-flight (MALDI-TOF) analysis, as described in the art (se, e.g. Harvey et al. J Biol Chem 278:8363-8369, Maum et al. Prot Sci 14:1171-1180).

The enzymatic activity of soluble rHuPH20 in a sample can be assessed at any point during the methods described herein. In one example, activity is measured using a microturbidity assay (see e.g. Example 10). This is based on the formation of an insoluble precipitate when hyaluronic acid binds with serum albumin. The activity is measured by incubating soluble rHuPH20 with sodium hyaluronate (hyaluronic acid) for a set period of time (e.g. 10 minutes) and then precipitating the undigested sodium hyaluronate with the addition of acidified serum albumin. The turbidity of the resulting sample is measured at 640 nm after an additional development period. The decrease in turbidity resulting from enzyme activity on the sodium hyaluronate substrate is a measure of the soluble rHuPH20 enzymatic activity. In another example, enzymatic activity is measured using a microtiter assay in which residual biotinylated hyaluronic acid is measured following incubation with the sample containing soluble rHuPH20 (see e.g. Frost and Stern (1997) Anal. Biochem. 251:263-269, U.S. Patent Publication No. 20050260186). The free carboxyl groups on the glucuronic acid residues of hyaluronic acid are biotinylated, and the biotinylated hyaluronic acid substrate is covalently couple to a microtiter plate. Following incubation with the sample containing soluble rHuPH20, the residual biotinylated hyaluronic acid substrate is detected using an avidin-peroxidase reaction, and compared to that obtained following reaction with hyaluronidase standards of known activity. Other assays to measure enzymatic activity also are known in the art and can be used in the methods herein (see e.g. Delpech et al., (1995) Anal. Biochem. 229:35-41; Takahashi et al., (2003) Anal. Biochem. 322:257-263).

The presence of any contamination also can monitored. Contamination can include, but is not limited to, microbial contamination (e.g. viruses, bacteria and mycoplasma), microbial products contamination (e.g. endotoxin), or other process-related impurities. Any suitable method or assay can be used. For example, viruses and bacteria can be cultured using methods well known in the art to determine whether they are present or not in a sample, and if so, in what quantities. Microscopy also can be used to detect microbial contamination. For example, a sample can be assessed for the presence of viruses or bacteria using transmission electron microscopy (TEM). *Mycoplasma* detection can be effected using, for example, biochemical or molecular techniques, including, but not limited to, PCR to amplify mycoplasma-specific nucleic acid, biochemical tests to detect mycoplasmal enzymes and cell-based fluorescence to detect mycoplasmal antigens or nucleic acid.

The presence of microbial products, such as bacterial endotoxins, also can be monitored. An example of a suitable assay for detecting the presence of endotoxin is the *Limulus Amebocyte* Lysate (LAL) assay. Two types of LAL assays can be used: gel clot and photometric (chromogenic and turbometric). LAL is an aqueous extract of blood cells (amebocytes) from the horse shoe crab. Endotoxin triggers a cascade of enzymatic reactions, which result in activated clotting enzyme. In the presence of bacterial endotoxins, at an elevated temperature, the LAL reagent will clot after addition of reagent. The formation of the gel clot is proportional to the concentration of the endotoxin. In the kinetic assay, the proenzyme in the LAL is activated when in contact with endotoxins produced by gram negative bacteria. The rate of activation is directly proportional with the concentration of the endotoxin present. The level of activation can be measured through a subsequent substrate reaction which is measured spectrophotometrically.

K. EXAMPLES

The following examples are included for illustrative purposes only and are not intended to limit the scope of the invention.

Example 1

Generation of a Soluble rHuPH20-Expressing Cell Line

The HZ24 plasmid (set forth in SEQ ID NO:50) was used to transfect Chinese Hamster Ovary (CHO cells) (see e.g. related application Nos. 10/795,095, 11/065,716 and 11/238,171). The HZ24 plasmid vector for expression of soluble rHuPH20 contains a pCI vector backbone (Promega), DNA encoding amino acids 1-482 of human PH20 hyaluronidase (SEQ ID NO:47), an internal ribosomal entry site (IRES) from the ECMV virus (Clontech), and the mouse dihydrofolate reductase (DHFR) gene. The pCI vector backbone also includes DNA encoding the Beta-lactamase resistance gene (AmpR), an f1 origin of replication, a Cytomegalovirus immediate-early enhancer/promoter region (CMV), a chimeric intron, and an SV40 late polyadenylation signal (SV40). The DNA encoding the soluble rHuPH20 construct contains an NheI site and a Kozak consensus sequence prior to the DNA encoding the methionine at amino acid position 1 of the native 35 amino acid signal sequence of human PH20, and a stop codon following the DNA encoding the tyrosine corresponding to amino acid position 482 of the human PH20 hyaluronidase set forth in SEQ ID NO:1), followed by a BamHI restriction site. The construct pCI-PH20-IRES-DHFR-SV40pa (HZ24), therefore, results in a single mRNA species driven by the CMV promoter that encodes amino acids 1-482 of human PH20 (set forth in SEQ ID NO:3) and amino acids 1-186 of mouse dihydrofolate reductase (set forth in SEQ ID NO:51), separated by the internal ribosomal entry site (IRES).

Non-transfected DG44 CHO cells growing in GIBCO Modified CD-CHO media for DHFR(−) cells, supplemented with 4 mM Glutamine and 18 ml/L Plurionic F68/L (Gibco), were seeded at $0.5 \times 10^6$ cells/ml in a shaker flask in preparation for transfection. Cells were grown at 37° C. in 5% $CO_2$ in a humidified incubator, shaking at 120 rpm. Exponentially growing non-transfected DG44 CHO cells were tested for viability prior to transfection.

Sixty million viable cells of the non-transfected DG44 CHO cell culture were pelleted and resuspended to a density of $2 \times 10^7$ cells in 0.7 mL of 2× transfection buffer (2× HeBS: 40 mM Hepes, pH 7.0, 274 mM NaCl, 10 mM KCl, 1.4 mM $Na_2HPO_4$, 12 mM dextrose). To each aliquot of resuspended cells, 0.09 mL (250 μg) of the linear HZ24 plasmid (linearized by overnight digestion with Cla I (New England Biolabs) was added, and the cell/DNA solutions were transferred into 0.4 cm gap BTX (Gentronics) electroporation cuvettes at room temperature. A negative control electroporation was performed with no plasmid DNA mixed with the cells. The cell/plasmid mixes were electroporated with a capacitor discharge of 330 V and 960 μF or at 350 V and 960 μF.

The cells were removed from the cuvettes after electroporation and transferred into 5 mL of Modified CD-CHO media for DHFR(−) cells, supplemented with 4 mM Glutamine and 18 ml/L Plurionic F68/L (Gibco), and allowed to grow in a well of a 6-well tissue culture plate without selection for 2 days at 37° C. in 5% $CO_2$ in a humidified incubator.

Two days post-electroporation, 0.5 mL of tissue culture media was removed from each well and tested for the presence of hyaluronidase activity, using the microturbidity assay described in Example 9.

TABLE 1

Initial Hyaluronidase Activity of
HZ24 Transfected DG44 CHO cells at 40 hours
post-transfection

| | Dilution | Activity Units/ml |
|---|---|---|
| Transfection 1 330 V | 1 to 10 | 0.25 |
| Transfection 2 350 V | 1 to 10 | 0.52 |
| Negative Control | 1 to 10 | 0.015 |

Cells from Transfection 2 (350V) were collected from the tissue culture well, counted and diluted to $1 \times 10^4$ to $2 \times 10^4$ viable cells per mL. A 0.1 mL aliquot of the cell suspension was transferred to each well of five, 96 well round bottom tissue culture plates. One hundred microliters of CD-CHO media (GIBCO) containing 4 mM GlutaMAX™-I supplement (GIBCO™, Invitrogen Corporation) and without hypoxanthine and thymidine supplements were added to the wells containing cells (final volume 0.2 mL).

Ten clones were identified from the 5 plates grown without methotrexate.

TABLE 2

Hyaluronidase activity of identified clones

| Plate/Well ID | Relative Hyaluronidase |
|---|---|
| 1C3 | 261 |
| 2C2 | 261 |
| 3D3 | 261 |
| 3E5 | 243 |
| 3C6 | 174 |
| 2G8 | 103 |
| 1B9 | 304 |
| 2D9 | 273 |
| 4D10 | 302 |

Six HZ24 clones were expanded in culture and transferred into shaker flasks as single cell suspensions. Clones 3D3, 3E5, 2G8, 2D9, 1E11, and 4D10 were plated into 96-well round bottom tissue culture plates using a two-dimensional infinite dilution strategy in which cells were diluted 1:2 down the plate, and 1:3 across the plate, starting at 5000 cells in the top left hand well. Diluted clones were grown in a background of 500 non-transfected DG44 CHO cells per well, to provide necessary growth factors for the initial days in culture. Ten plates were made per subclone, with 5 plates containing 50 nM methotrexate and 5 plates without methotrexate.

Clone 3D-3-produced 24 visual subclones (13 from the no methotrexate treatment, and 11 from the 50 nM methotrexate treatment. Significant hyaluronidase activity was measured in the supernatants from 8 of the 24 subclones (>50 Units/mL), and these 8 subclones were expanded into T-25 tissue culture flasks. Clones isolated from the methotrexate treatment protocol were expanded in the presence of 50 nM methotrexate. Clone 3D35M was further expanded in 500 nM methotrexate giving rise to clones producing in excess of 1,000 Units/ml in shaker flasks (clone 3D35M; or Gen1 3D35M). A master cell bank (MCB) of the 3D35M cells was then prepared.

Example 2

Determination of the Copy Number of the Nucleic Acid Region Encoding Soluble rHuPH20 in 3D35M Cells The copy number of the nucleic acid region encoding soluble rHuPH20 in 3D35M cells was determined by quantitative PCR. Total genomic DNA was extracted from 3D35M cells from the MCB. Six independent dilutions of the DNA were prepared for analysis in duplicate, each of which contained approximately 6.6 ng DNA (equivalent to approximately 100 cells). Negative controls containing no template also were prepared, as were positive controls containing the plasmid and the DNA equivalent of 1000 CHO cells (6.6 ng). The reactions were assembled according to the TaqMan Universal PCR Master Mix Protocol (Applied Biosystems) and run in duplicate. A standard curve was generated using eight dilutions of the HZ24 plasmid, representing a range of approximately $5 \times 10^6$ to 49 copies of plasmid DNA. The standard was diluted in CHO control genomic DNA (equivalent of 100 cells). The reactions were assembled according to the TaqMan Universal PCR Master Mix Protocol (Applied Biosystems) using the HZM3.P1 forward primer and the HZM3.P2 reverse primer (set forth in SEQ ID NOS:52 and 53, respectively) and the HZM3 probe (SEQ ID NO:54), which contained the fluorescent dyes 6FAM (6-carboxyfluorescin) and TAMRA (6-carboxytetramethylrhodamine). The reactions were run in duplicate using the following cycling conditions: 50° C. for 2 minutes, 95° C. for 10 minutes, followed by 40 cycles of 95° C. for 15 seconds and 60° C. for 1 minute. A standard quantitative PCR reaction to assay GAPDH copies for each DNA sample also was performed. Data was collected by the ABI Prism 7700™ Sequence Detection System software version 1.9 (Applied Biosystems).

The target gene copy numbers per cell were calculated as the ratio of target copies (soluble rHuPH20) to normalized copies (GAPDH) for the six dilutions of 3D35M genomic DNA. The Dixon Q Outlier statistics test was applied to the data set. The copy number of the sHuPH20 region in 3D35M cells was found to be 317.87±11.64.

Example 3

Production and Purification of Gen1 soluble rHuPH20

A. 5 L Bioreactor Process

A vial of 3D35M was thawed and expanded from T-25 flasks through 1 L spinner flasks in CD CHO (Invitrogen, Carlsbad Calif.) supplemented with 100 nM Methotrexate and 40 mL/L GlutaMAX™-I (Invitrogen; 200 mM stock solution). Cells were transferred from spinner flasks to a 5 L bioreactor (Braun) at an inoculation density of $4 \times 10^5$ viable cells per ml in 5 L media. Parameters were temperature Setpoint 37° C., pH 7.2 (starting Setpoint), with Dissolved Oxygen Setpoint 25% and an air overlay of 0-100 cc/min. At 168 hrs, 250 ml of Feed #1 Medium (CD CHO with 50 g/L Glucose) was added. At 216 hours, 250 ml of Feed #2 Medium (CD CHO with 50 g/L Glucose and 10 mM Sodium Butyrate) was added, and at 264 hours 250 ml of Feed #2 Medium was added. This process resulted in a final productivity of 1600 Units per ml with a maximal cell density of $6 \times 10^6$ cells/ml. The addition of sodium butyrate was to enhance the production of soluble rHuPH20 in the final stages of production:

Conditioned media from the 3D35M clone was clarified by depth filtration and tangential flow diafiltration into 10 mM Hepes pH 7.0. Soluble rHuPH20 was then purified by sequential chromatography on Q Sepharose (Pharmacia) ion exchange, Phenyl Sepharose (Pharmacia) hydrophobic interaction chromatography, Amino phenyl boronate (ProMedics) and Hydroxyapatite Chromatography (Biorad, Richmond, Calif.).

Soluble rHuPH20 bound to Q Sepharose and eluted at 400 mM NaCl in the same buffer. The eluate was diluted with 2M ammonium sulfate to a final concentration of 500 mM ammonium sulfate and passed through a Phenyl Sepharose (low sub) column, followed by binding under the same conditions to a phenyl boronate resin. The soluble rHuPH20 was eluted from the Phenyl Sepharose resin in Hepes pH 6.9 after washing at pH 9.0 in 50 mM bicine without ammonium sulfate. The eluate was loaded onto a ceramic hydroxyapatite resin at pH 6.9 in 5 mM potassium phosphate and 1 mM $CaCl_2$ and eluted with 80 mM potassium phosphate, pH 7.4 with 0.1 mM $CaCl_2$.

The resultant soluble rHuPH20 possessed a specific activity in excess of 65,000 Units/mg protein by way of the microturbidity assay (see Example 9). Purified soluble rHuPH20 eluted as a single peak from 24 to 26 minutes from a Pharmacia 5RPC styrene divinylbenzene column with a gradient between 0.1% $TFA/H_2O$ and 0.1% TFA/90% acetonitrile/10% $H_2O$ and resolved as a single broad 61 kDa band by SDS electrophoresis that reduced to a sharp 51 kDa band upon treatment with PNGASE-F. N-terminal amino acid sequencing revealed that the leader peptide had been efficiently removed.

B. Upstream Cell Culture Expansion Process into 100 L Bioreactor Cell Culture

A scaled-up process was used to separately purify soluble rHuPH20 from four different vials of 3D35M cell to produce 4 separate batches of sHuPH20; HUA0406C, HUA0410C, HUA0415C and HUA0420C. Each vial was separately expanded and cultured through a 125 L bioreactor, then purified using column chromatography. Samples were taken throughout the process to assess such parameters as enzyme yield. The description of the process provided below sets forth representative specifications for such things as bioreactor starting and feed media volumes, transfer cell densities, and wash and elution volumes. The exact numbers vary slightly with each batch, and are detailed in Tables 3 to 10.

Four vials of 3D35M cells were thawed in a 37° C. water bath, CD CHO containing 100 nM methotrexate and 40 mL/L GlutaMAX™-I was added and the cells were centrifuged. The cells were re-suspended in a 125 mL shake flask with 20 mL of fresh media and placed in a 37° C., 7% $CO_2$ incubator. The cells were expanded up to 40 mL in the 125 mL shake flask. When the cell density reached $1.5-2.5 \times 10^6$ cells/mL, the culture was expanded into a 125 mL spinner flask in a 100 mL culture volume. The flask was incubated at 37° C., 7%

$CO_2$. When the cell density reached $1.5$-$2.5\times10^6$ cells/mL, the culture was expanded into a 250 mL spinner flask in 200 mL culture volume, and the flask was incubated at 37° C., 7% $CO_2$. When the cell density reached $1.5$-$2.5\times10^6$ cells/mL, the culture was expanded into a 1 L spinner flask in 800 mL culture volume and incubated at 37° C., 7% $CO_2$. When the cell density reached $1.5$-$2.5\times10^6$ cells/mL, the culture was expanded into a 6 L spinner flask in 5 L culture volume and incubated at 37° C., 7% $CO_2$. When the cell density reached $1.5$-$2.5\times10^6$ cells/mL, the culture was expanded into a 36 L spinner flask in 20 L culture volume and incubated at 37° C., 7% $CO_2$.

A 125 L reactor was sterilized with steam at 121° C., 20 PSI and 65 L of CD CHO media was added. Before use, the reactor was checked for contamination. When the cell density in the 36 L spinner flasks reached $1.8$-$2.5\times10^6$ cells/mL, 20 L cell culture were transferred from the 36 L spinner flasks to the 125 L bioreactor (Braun), resulting a final volume of 85 L and a seeding density of approximately $4\times10^5$ cells/mL. Parameters were temperature setpoint, 37° C.; pH: 7.2; Dissolved oxygen: 25%±10%; Impeller Speed 50 rpm; Vessel Pressure 3 psi; Air Sparge 1 L/min.; Air Overlay: 1 L/min. The reactor was sampled daily for cell counts, pH verification, media analysis, protein production and retention. Nutrient feeds were added during the run. At Day 6, 3.4 L of Feed #1 Medium (CD CHO+50 g/L Glucose+40 mL/L GlutaMAX™-I) was added, and culture temperature was changed to 36.5° C. At day 9, 3.5 L of Feed #2 (CD CHO+50 g/L Glucose+40 mL/L GlutaMAX™-I+1.1 g/L Sodium Butyrate) was added, and culture temperature was changed to 36° C. At day 11, 3.7 L of Feed #3 (CD CHO+50 g/L Glucose+40 mL/L GlutaMAX™-I+1.1 g/L Sodium Butyrate) was added, and the culture temperature was changed to 35.5° C. The reactor was harvested at 14 days or when the viability of the cells dropped below 50%. The process resulted in production of soluble rHuPH20 with an enzymatic activity of 1600 Units/ml with a maximal cell density of 8 million cells/mL. At harvest, the culture was sampled for mycoplasma, bioburden, endotoxin, and virus in vitro and in vivo, transmission electron microscopy (TEM) for viral particles, and enzyme activity.

The one hundred liter bioreactor cell culture harvest was filtered through a series of disposable capsule filters having a polyethersulfone medium (Sartorius): first through a 8.0 μm depth capsule, a 0.65 μm depth capsule, a 0.22 μm capsule, and finally through a 0.22 μm Sartopore 2000 cm² filter and into a 100 L sterile storage bag. The culture was concentrated 10× using two TFF with Spiral Polyethersulfone 30 kDa MWCO filters (Millipore), followed by a 6× buffer exchange with 10 mM HEPES, 25 mM $Na_2SO_4$, pH 7.0 into a 0.22 μm final filter into a 20 L sterile storage bag. Table 3 provides monitoring data related to the cell culture, harvest, concentration and buffer exchange steps.

TABLE 3

Monitoring data for cell culture, harvest, concentration and buffer exchange steps.

| Parameter | HUA0406C | HUA04010C | HUA0415C | HUA0420C |
| --- | --- | --- | --- | --- |
| Time from thaw to inoculate 100 L bioreactor (days) | 21 | 19 | 17 | 18 |
| 100 L inoculation density (× $10^6$ cells/mL) | 0.45 | 0.33 | 0.44 | 0.46 |
| Doubling time in logarithmic growth (hr) | 29.8 | 27.3 | 29.2 | 23.5 |
| Max. cell density (× $10^6$ cells/mL) | 5.65 | 8.70 | 6.07 | 9.70 |
| Harvest viability (%) | 41 | 48 | 41 | 41 |
| Harvest titer (U/ml) | 1964 | 1670 | 991 | 1319 |
| Time in 100-L bioreactor (days) | 13 | 13 | 12 | 13 |
| Clarified harvest volume (mL) | 81800 | 93300 | 91800 | 89100 |
| Clarified harvest enzyme assay (U/mL) | 2385 | 1768 | 1039 | 1425 |
| Concentrate enzyme assay (U/mL) | 22954 | 17091 | 8561 | 17785 |
| Buffer exchanged concentrate enzyme assay (U/mL) | 15829 | 11649 | 9915 | 8679 |
| Filtered buffer exchanged concentrate enzyme assay (U/mL) | 21550 | 10882 | 9471 | 8527 |
| Buffer exchanged concentrate volume (mL) | 10699 | 13578 | 12727 | 20500 |
| Ratio enzyme units concentration/harvest | 0.87 | 0.96 | 1.32 | 1.4 |

A Q Sepharose (Pharmacia) ion exchange column (3 L resin, Height=20 cm, Diameter=14 cm) was prepared. Wash samples were collected for a determination of pH, conductivity and endotoxin (LAL) assay. The column was equilibrated with 5 column volumes of 10 mM Tris, 20 mM $Na_2SO_4$, pH 7.5. The concentrated, diafiltered harvest was loaded onto the Q column at a flow rate of 100 cm/hr. The column was washed with 5 column volumes of 10 mM Tris, 20 mM $Na_2SO_4$, pH 7.5 and 10 mM Hepes, 50 mM NaCl, pH 7.0. The protein was eluted with 10 mM Hepes, 400 mM NaCl, pH 7.0 and filtered through a 0.22 μm final filter into a sterile bag.

Phenyl-Sepharose (Pharmacia) hydrophobic interaction chromatography was next performed. A Phenyl-Sepharose (PS) column (9.1 L resin, Height=29 cm, Diameter=20 cm) was prepared. The column was equilibrated with 5 column volumes of 5 mM potassium phosphate, 0.5 M ammonium sulfate, 0.1 mM $CaCl_2$, pH 7.0. The protein eluate from above was supplemented with 2M ammonium sulfate, 1 M potassium phosphate and 1 M $CaCl_2$ stock solutions to final concentrations of 5 mM, 0.5 M and 0.1 mM, respectively. The protein was loaded onto the PS column at a flow rate of 100 cm/hr. 5 mM potassium phosphate, 0.5 M ammonium sulfate and 0.1 mM $CaCl_2$ pH 7.0 was added at 100 cm/hr. The flow through was passed through a 0.22 μm final filter into a sterile bag.

The PS-purified protein was the loaded onto an aminophenyl boronate column (ProMedics) (6.3 L resin, Height=20 cm, Diameter=20 cm) that had been equilibrated with 5 column volumes of 5 mM potassium phosphate, 0.5 M ammonium sulfate. The protein was passed through the column at a flow rate of 100 cm/hr, and the column was washed with 5 mM potassium phosphate, 0.5 M ammonium sulfate, pH 7.0. The column was then washed with 20 mM bicine, 100 mM NaCl, pH 9.0 and the protein eluted with 50 mM Hepes, 100 mM NaCl pH 6.9 through a sterile filter and into a 20. L sterile bag. The eluate was tested for bioburden, protein concentration and enzyme activity.

A hydroxyapatite (HAP) column (BioRad) (1.6 L resin, Height=10 cm, Diameter=14 cm) was equilibrated with 5 mM potassium phosphate, 100 mM NaCl, 0.1 mM CaCl$_2$ pH 7.0. Wash samples were collected and tested for pH, conductivity and endotoxin (LAL assay). The aminophenyl boronate purified protein was supplemented with potassium phosphate and CaCl$_2$ to yield final concentrations of 5 mM potassium phosphate and 0.1 mM CaCl$_2$ and loaded onto the HAP column at a flow rate of 100 cm/hr. The column was washed with 5 mM potassium phosphate pH 7.0, 100 mM NaCl, 0.1 mM CaCl$_2$, then 10 mM potassium phosphate pH 7.0, 100 mM NaCl, 0.1 mM CaCl$_2$ pH. The protein was eluted with 70 mM potassium phosphate pH 7.0 and filtered through a 0.22 μm filter into a 5 L sterile storage bag. The eluate was tested for bioburden, protein concentration and enzyme activity.

The HAP-purified protein was then pumped through a 20 nM viral removal filter via a pressure tank. The protein was added to the DV20 pressure tank and filter (Pall Corporation), passing through an Ultipor DV20 Filter with 20 nm pores (Pall Corporation) into a sterile 20 L storage bag. The filtrate was tested for protein concentration, enzyme activity, oligosaccharide, monosaccharide and sialic acid profiling, and process-related impurities. The protein in the filtrate was then concentrated to 1 mg/mL using a 10 kD molecular weight cut off (MWCO) Sartocon Slice tangential flow filtration (TFF) system (Sartorius). The filter was first prepared by washing with a Hepes/saline solution (10 mM Hepes, 130 mM NaCl, pH 7.0) and the permeate was sampled for pH and conductivity. Following concentration, the concentrated protein was sampled and tested for protein concentration and enzyme activity. A 6× buffer exchange was performed on the concentrated protein into the final buffer: 10 mM Hepes, 130 mM NaCl, pH 7.0. The concentrated protein was passed though a 0.22 μm filter into a 20 L sterile storage bag. The protein was sampled and tested for protein concentration, enzyme activity, free sulfhydryl groups, oligosaccharide profiling and osmolarity.

Tables 4 to 10 provide monitoring data related to each of the purification steps described above, for each 3D35M cell lot.

TABLE 4

Q sepharose column data

| Parameter | HUA0406C | HUA0410C | HUA0415C | HUA0420C |
|---|---|---|---|---|
| Load volume (mL) | 10647 | 13524 | 12852 | 20418 |
| Load Volume/Resin Volume ratio | 3.1 | 4.9 | 4.5 | 7.3 |
| Column Volume (mL) | 2770 | 3840 | 2850 | 2880 |
| Eluate volume (mL) | 6108 | 5923 | 5759 | 6284 |
| Protein Conc. of Eluate (mg/mL) | 2.8 | 3.05 | 2.80 | 2.86 |
| Eluate Enzyme Assay (U/mL) | 24493 | 26683 | 18321 | 21052 |
| Enzyme Yield (%) | 65 | 107 | 87 | 76 |

TABLE 5

Phenyl Sepharose column data

| Parameter | HUA0406C | HUA0410C | HUA0415C | HUA0420C |
|---|---|---|---|---|
| Volume Before Stock Solution Addition (mL) | 5670 | 5015 | 5694 | 6251 |
| Load Volume (mL) | 7599 | 6693 | 7631 | 8360 |
| Column Volume (mL) | 9106 | 9420 | 9340 | 9420 |
| Load Volume/Resin Volume ratio | 0.8 | 0.71 | 0.82 | 0.89 |
| Eluate volume (mL) | 16144 | 18010 | 16960 | 17328 |
| Protein Conc of Eluate (mg/mL) | 0.4 | 0.33 | 0.33 | 0.38 |
| Eluate Enzyme Assay (U/mL) | 8806 | 6585 | 4472 | 7509 |
| Protein Yield (%) | 41 | 40 | 36 | 37 |
| Enzyme Yield (%) | 102 | 88 | 82 | 96 |

TABLE 6

Amino Phenyl Boronate column data

| Parameter | HUA0406C | HUA0410C | HUA0415C | HUA0420C |
|---|---|---|---|---|
| Load Volume (mL) | 16136 | 17958 | 16931 | 17884 |
| Load Volume/Resin Volume ratio | 2.99 | 3.15 | 3.08 | 2.98 |

TABLE 6-continued

Amino Phenyl Boronate column data

| Parameter | HUA0406C | HUA0410C | HUA0415C | HUA0420C |
|---|---|---|---|---|
| Column Volume (mL) | 5400 | 5700 | 5500 | 5300 |
| Eluate volume (mL) | 17595 | 22084 | 20686 | 19145 |
| Protein Conc. of Eluate (mg/mL) | 0.0 | 0.03 | 0.03 | 0.04 |
| Protein Conc. of Filtered Eluate (mg/mL) | not tested | 0.03 | 0.00 | 0.04 |
| Eluate Enzyme Assay (U/mL) | 4050 | 2410 | 1523 | 4721 |
| Protein Yield (%) | 0 | 11 | 11 | 12 |
| Enzyme Yield (%) | not determined | 41 | 40 | 69 |

TABLE 7

Hydroxyapatite column data

| Parameter | HUA0406C | HUA0410C | HUA0415C | HUA0420C |
|---|---|---|---|---|
| Volume Before Stock Solution Addition (mL) | 16345 | 20799 | 20640 | 19103 |
| Load Volume/Resin Volume ratio | 10.95 | 13.58 | 14.19 | 12.81 |
| Column Volume (mL) | 1500 | 1540 | 1462 | 1500 |
| Load volume (mL) | 16429 | 20917 | 20746 | 19213 |
| Eluate volume (mL) | 4100 | 2415 | 1936 | 2419 |
| Protein Conc. of Eluate (mg/mL) | not tested | 0.24 | 0.17 | 0.23 |
| Protein Conc. of Filtered Eluate (mg/mL) | NA | NA | 0.17 | NA |
| Eluate Enzyme Assay (U/mL) | 14051 | 29089 | 20424 | 29826 |
| Protein Yield (%) | Not tested | 93 | 53 | 73 |
| Enzyme Yield (%) | 87 | 118 | 140 | 104 |

TABLE 8

DV20 filtration data

| Parameter | HUA0406C | HUA0410C | HUA0415C | HUA0420C |
|---|---|---|---|---|
| Start volume (mL) | 4077 | 2233 | 1917 | 2419 |
| Filtrate Volume (mL) | 4602 | 3334 | 2963 | 3504 |
| Protein Conc. of Filtrate (mg/mL) | 0.1 | NA | 0.09 | NA |
| Protein Conc. of Filtered Eluate (mg/mL) | NA | 0.15 | 0.09 | 0.16 |
| Protein Yield (%) | not tested | 93 | 82 | 101 |

TABLE 9

Final concentration data

| Parameter | HUA0406C | HUA0410C | HUA0415C | HUA0420C |
|---|---|---|---|---|
| Start volume (mL) | 4575 | 3298 | 2963 | 3492 |
| Concentrate Volume (mL) | 562 | 407 | 237 | 316 |
| Protein Conc. of Concentrate (mg/mL) | 0.9 | 1.24 | 1.16 | 1.73 |
| Protein Yield (%) | 111 | 102 | 103 | 98 |

TABLE 10

Buffer Exchange into Final Formulation data

| Parameter | HUA0406C | HUA0410C | HUA0415C | HUA0420C |
|---|---|---|---|---|
| Start Volume (mL) | 562 | 407 | 237 | 316 |
| Final Volume Buffer Exchanged Concentrate (mL) | 594 | 516 | 310 | 554 |
| Protein Conc. of Concentrate (mg/mL) | 1.00 | 0.97 | 0.98 | 1.00 |
| Protein Conc. of Filtered Concentrate (mg/mL) | 0.95 | 0.92 | 0.95 | 1.02 |
| Protein Yield (%) | 118 | 99 | 110 | 101 |

The purified and concentrated soluble rHuPH20 protein was aseptically filled into sterile vials with 5 mL and 1 mL fill volumes. The protein was passed though a 0.22 µm filter to an operator controlled pump that was used to fill the vials using a gravimetric readout. The vials were closed with stoppers and secured with crimped caps. The closed vials were visually inspected for foreign particles and then labeled. Following labeling, the vials were flash-frozen by submersion in liquid nitrogen for no longer than 1 minute and stored at $\leq 15°$ C. ($-20\pm5°$ C.). Production and purification of soluble rHuPH20 using this method yielded approximately 400-700 mg soluble rHuPH20 with a specific activity of 96,000 units/mg to 144,000 units/mg.

Example 4

Production of Gen2 Soluble rHuPH20

The Gen1 3D35M cell line described above was adapted to higher methotrexate levels to produce Gen2 clones. 3D35M cells were seeded from established methotrexate-containing cultures into CD CHO medium containing 8 mM GlutaMAX™-I and 1.0 µM methotrexate. The cells were adapted to a higher methotrexate level by growing and passaging them 9 times over a period of 46 days in a 37° C., 7% $CO_2$ humidified incubator. The amplified population of cells was cloned out by limiting dilution in 96-well tissue culture plates containing medium with 2.0 µM methotrexate. After approximately 4 weeks, clones were identified and clone 3E10B was selected for expansion. 3E10B cells were grown in CD CHO medium containing 8 mM GlutaMAX™-I and 2.0 µM methotrexate for 20 passages, with testing for cell viability by trypan blue staining and counting with a hemocytometer, and enzyme activity by the microturbidity assay (described below in Example 9). A master cell bank (MCB) of the 3E10B cell line was created and frozen and used for subsequent studies.

Amplification of the cell line continued by culturing 3E10B cells in CD CHO medium containing 8 mM GlutaMAX™-I and 4.0 µM methotrexate. After the $12^{th}$ passage, cells were frozen in vials as a research cell bank (RCB). One vial of the RCB was thawed and cultured in medium containing 8.0 µM methotrexate. After 5 days, the methotrexate concentration in the medium was increased to 16.0 µM, then 20.0 µM 18 days later. Cells from the $8^{th}$ passage in medium containing 20.0 µM methotrexate were cloned out by limiting dilution in 96-well tissue culture plates containing CD CHO medium containing 4 mM GlutaMAX™-I and 20.0 µM methotrexate. Clones 1B3, 2B2 and 5C1 were identified 5-6 weeks later. Cells from the $9^{th}$ passage of 3D35M also were cloned out by limiting dilution in 96-well tissue culture plates with CD CHO medium containing 8 mM GlutaMAX™-I and 20.0 µM methotrexate, and clones 1G11, 2E10 and 2G10 were identified.

Cells cultures of each of 1B3, 2B2, 5C1, 1G11, 2E10 and 2G10 were seeded at a density of $4\times10^5$ cells/mL in a volume of 50 mL in 250 mL shaker flasks. The cultures were allowed to grow and decline without additional feeds for 10-14 days to determine the growth rate and productivity of the cells. Samples were taken periodically and assayed for hyaluronidase activity (Tables 11 and 12).

TABLE 11

Hyaluronidase activity of 1B3, 2B2 and 5C1 cells

| Hours post inoculation | Soluble rHuPH20 Enzyme activity in cell culture (units) | | |
|---|---|---|---|
| | 1B3 | 2B2 | 5C1 |
| 74 | | | 382 |
| 95 | | 942 | |
| 101 | | | 582 |
| 142 | | 2287 | |
| 144 | 955 | | |
| 169 | 1200 | | |
| 195 | | | |
| 238 | 1611 | | |
| 242 | | | 2139 |
| 265 | | 3070 | |
| 336 | 2252 | | |

TABLE 12

Hyaluronidase activity of 1B3, 2B2 and 2E10 cells

| Hours post inoculation | Soluble rHuPH20 Enzyme activity in cell culture (units) | | |
|---|---|---|---|
| | 1B3 | 2B2 | 2E10 |
| 98 | 470 | | |
| 123 | | | 1179 |
| 143 | | 2228 | |
| 216 | | | 2814 |
| 290 | 2860 | | |
| 291 | | | 2542 |
| 337 | | 2992 | |

Four cell lines (2B2, 2G10, 1G11 and 2E10) were compared in a study in which all were seeded at a density of $4\times10^5$ cells/mL in a volume of 50 mL in 250 mL shaker flask. All received 10% (v/v) feeds on day 8 and 5% feeds with feed media containing CD CHO medium supplemented with 50 g/L glucose, 40 g/L yeast extract and 1.1 g/L sodium butyrate. The cells were harvested on day 15. Samples were taken periodically and assayed for soluble rHuPH20 enzymatic activity (Table 13).

TABLE 13

Hyaluronidase activity of 2E10, 1G11, 2G10 and 2B2 cells

| Hours post inoculation | Soluble rHuPH20 Enzyme activity in cell culture (units) | | | |
|---|---|---|---|---|
| | 2E10 | 1G11 | 2G10 | 2B2 |
| 122 | 991 | 87 | 1688 | |
| 124 | | | | 878 |
| 194 | 2151 | 1387 | 2430 | |
| 196 | | | | 2642 |
| 285 | 6231 | 3831 | 7952 | |
| 287 | | | | 8822 |
| 364 | 5880 | 2955 | 11064 | |
| 366 | | | | 15684 |

In both the batch and fed-batch conditions, culture of 2B2 ells exhibited higher enzymatic activity, although other cells (e.g. 2G10 cells) also exhibited good enzyme productivity the 2B2 cell line was, therefore, selected for expansion in medium containing 20.0 µM methotrexate. After the $11^{th}$ passage, 2B2 cells were frozen in vials as a research cell bank (RCB).

Example 5

Enzymatic Activity of Soluble rHuPH20 Produced in 3E10B and 2B2 Cells

Soluble rHuPH20 produced by 3E10B and 2B2 cells was assayed for enzymatic activity using the Microturbidity assay (Example 9). Frozen vials of 3E10B and 2B2 cells banks were thawed and the cells were cultured separately for two passages in growth medium (CD CHO medium with 8 mM GlutaMAX™-I and either 2.0 µM methotrexate for 3E10B cells, or 20.0 µM methotrexate for 2B2 cells) in 37° C., 6% $CO_2$ in a humidified incubator. Cells were inoculated into 20 mL growth medium in 125 mL Erlenmeyer flasks (Corning) at $5\times10^5$ cells/mL, and grown for 8 days in 37° C., 6% $CO^2$ in a humidified incubator with a shaker platform rotating at approximately 100 rpm. On days 8 and 10, the cultures received 5% v/v of feed medium containing CD CHO medium supplemented with 50 g/L glucose, 50 g/L Yeast extract, and 2.2 g/L (20 mM) sodium butyrate to initiate the production phase. The cultures were sampled during the production phase on day 8 (190 hours), day 10 (240 hours), day 14 (332 hours), day 15 (258 hours), day 16 (382 hours) and day 18 (427 hours), and the viability was allowed to decline to zero. The samples were then analyzed for hyaluronidase activity.

Tables 14 and 15 set forth the viability (viable cell density (VCD) and percentage viability) and activity (units/flask) of the 3E10B and 2B2 cells at each time point. The enzyme activity of soluble rHuPH20 produced by 2B2 cells was consistently higher than that produced by 3E10B cells. For example, on day 8, the enzyme activity of soluble rHuPH20 produced by 2B2 cells was 69% higher than that of produced by 3E10B cells (2484 units/mL compared to 1469 units/mL). A similar trend was observed throughout the production phase. The viability of the cell cultures declined at a similar rate. When the production rate of the cells was calculated, it was observed that 3E10B cells produced 0.23 picograms soluble rHuPH20 per cell per day (pcd) on day 8 and 0.38 pcd on day 15. In comparison, 2B2 cells produced 0.46 picograms soluble rHuPH20 pcd on day 8 and 0.69 pcd on day 15, which was 100% and 82% higher than production by 3E10B on days 8 and 15, respectively. A master cell bank (MCB) of 2B2 cells was then prepared for subsequent studies.

TABLE 14

Viability and activity of Clone 3E10B

| Hours post inoculation | VCD | % viability | Activity (Units/mL) | Volume (mL) |
|---|---|---|---|---|
| 0 | 5 | 99 | 0 | 20 |
| 190 | 79.8 | 96 | 1469 | 20 |
| 240 | 61.6 | 76 | 2388 | 20 |
| 332 | 16.8 | 22 | 5396 | 20 |
| 358 | 16.4 | 17 | 5628 | 20 |
| 382 | 8.4 | 10 | 6772 | 20 |
| 427 | 0 | 0 | 6476 | 20 |

Total Activity (units) per flask (U/mL times volume (mL)): 129520

TABLE 15

Viability and activity of Clone 2B2

| Hours post inoculation | VCD | % viability | Activity (Units/flask) | Volume (mL) |
|---|---|---|---|---|
| 0 | 5 | 99 | 0 | 20 |
| 190 | 68 | 94 | 2484 | 20 |
| 240 | 77.6 | 89 | 3532 | 20 |
| 332 | 32 | 38 | 8196 | 20 |
| 358 | 15.8 | 17 | 9680 | 20 |
| 382 | 9.8 | 13 | 10788 | 20 |
| 427 | 0 | 0 | 10044 | 20 |

Total Activity (units) per flask (U/mL times volume (mL)): 200880

Example 6

Genetic Stability Testing of 2B2 Cells

A. Determination of Copy Number of the Nucleic Acid Region Encoding Soluble rHuPH20 in 2B2 Cells The copy number of the nucleic acid region encoding soluble rHuPH20 in 2B2 cells was determined by PCR. Total genomic DNA was extracted from $2 \times 10^7$ 2B2 cells from the MCB using a QIAamp DNeasy kit (Qiagen). Genomic DNA also was extracted from DG-44 CHO cells as a negative control. The purity of the extracted DNA was verified by agarose gel electrophoresis and UV spectrophotometry. To generate fragments of DNA (versus high molecular weight DNA), the genomic DNA was sheared by sonication. This ensured more accurate pipetting and template accessibility. Six independent dilutions of the genomic DNA (to amounts dilutions equivalent to approximately 1000 cells/μl) from 2B2 and DG-44 cells were prepared and analyzed in duplicate in two assays; a target assay, which targeted and amplified a sequence specific to the nucleic acid region encoding soluble rHuPH20 plasmid DNA, and an endogenous control, which targeted and amplified GAPDH sequence. The endogenous control was used as a normalizing the results. The target assay included a standard curve generated from a serial dilution of known amounts of the HZ24 plasmid mixed into DG-44 CHO genomic DNA. The endogenous control included a standard curve generated from serial dilutions of DG-44 CHO genomic DNA mixed with HZ24 plasmid DNA. The mammalian genome size was assumed to be $3 \times 10^9$ base pairs. Each assay included a negative control (no template) and a positive control (HZ24 plasmid DNA for the target assay and host cell DNA for the endogenous control normalizing assay). The reactions were prepared using the HZM3.P1 forward primer and the HZM3.P2 reverse primer (set forth in SEQ ID NOS:52 and 53, respectively) and the HZM3 probe (SEQ ID NO:54), which contained the fluorescent dyes 6FAM (6-carboxyfluorescin) and TAMRA (6-carboxytetramethylrhodamine). The samples were amplified using the Applied Biosystems Prism® 7900 Sequence Detection System with standard cycling conditions (50° C. for 2 minutes, 95° C. 10 min, 95° C. 15 seconds and 60° C. for 1 min for 40 cycles).

The target gene copy numbers per cell were calculated as the ratio of target copies to normalized copies (GAPDH) for the six dilutions of 2B2 genomic DNA. The Dixon Q Outlier statistics test was applied to the data set. The copy number of the nucleic acid region encoding soluble rHuPH20 plasmid in 2B2 cells was found to be 206.61±8.35.

B. mRNA Sequence Analysis

The sequence of the PH20 mRNA generated from the HZ24 plasmid in 2132 cells was determined. RNA was extracted from $2 \times 10^7$ 2B2 cells from the MCB using a RNeasy Mini Kit (Qiagen). The sample was treated with DNase I to remove contaminating DNA, and the purity of the RNA was verified by agarose gel electrophoresis and UV spectrophotometry. A reverse transcription reaction using SuperScript™ Reverse Transcriptase (Invitrogen) and a control reaction lacking reverse transcriptase was performed using the extracted RNA and oligo d(t) and random primers. The resulting cDNA products were then used as templates in PCR amplifications. Two different sets of primer pairs were used; AP01/AP03 and AP10/AP12. AP01/AP03 was designed to amplify 1719 base pair region, while primer pair AP10/AP12 was designed to amplify a larger region (1811 base pairs) to obtain the reverse strand sequence of the 3' end. Table 5 sets forth the sequences of the primers. Each PCR reaction included single primer controls, a negative control using the no reverse transcriptase control (described above) as template, and a positive control with control primers and control template. The amplification products were visualized by agarose gel electrophoresis and confirmed to be of the expected size, then purified to, remove excess primers and dNTPs by gel extraction or EXOSAP (USB).

The purified products were sequenced using the BigDye® Terminator v1.1 Cycle Sequencing Kit (Applied Biosystems) and the primers set forth in Table 16. The sequence data were assembled and the derived consensus sequence (SEQ ID NO:55) compared to the reference sequence using Sequencher software version 4.1.2 (Gene Code Corporation). A total of 1449 base pairs of sequence data were generated. The sequence was found to be identical to the reference sequence (SEQ ID NO:47) except for one base pair difference at position 1131, which was observed to be a thymidine (T) instead of the expected cytosine I. This is a silent mutation, with no effect on the amino acid sequence.

TABLE 16

Primers for PCR amplification and sequencing

| Primer name | Sequence | SEQ ID NO. |
|---|---|---|
| AP01 | TTCTCTCCACAGGTGTC | 56 |
| AP02 | AAGATTTCCTTACAAGAC | 57 |
| AP03 | TGGCGAGAGGGGAAAGAC | 58 |
| AP04 | CCATTTATTTGAACACTC | 59 |
| AP06 | CCGAACTCGATTGCGCAC | 60 |
| AP07 | AGCCATTCCCAAATTGTC | 61 |
| AP08 | CTCCCAGTTCAATTACAG | 62 |
| AP09 | CGTTAGCTATGGATCCTC | 63 |
| AP10 | CGAGACAGAGAAGACTCTTGCG | 64 |
| AP12 | CATTCAACAGACCTTGCATTCC | 65 |

C. Southern Blot Analysis of 2B2 Cells

A Southern Blot analysis was performed on 2B2 cells to obtain a structure map. Total DNA was extracted from $1\times10^7$ 2B2 cells and $1\times10^7$ control DG-44 cells using a Maxwell 16® system (Promega). The extracted DNA and a HZ24 plasmid control construct were evaluated for purity by agarose gel electrophoresis. DNA from 2B2 cells, DG-44 cells and the HZ24 plasmid control were digested with Spe I, Xba I, and a double digest using BamH I/Hind III. Another BamH I/Hind digest was performed on the HZ24 plasmid control and the approximately 1.4 kb was purified by gel extraction and radioactively labeled with $\alpha\text{-}^{32}P$ to generate a labeled probe. Approximately 10 μg each of digested 2B2 DNA and DG-44 DNA, and 10 μg DG-44 DNA with 250 pg HZ24 plasmid DNA, was electrophoresed on an agarose gel. An image was take on the gel following electrophoresis, then a Southern blot transfer was performed. The nylon membrane was hybridized with the labeled probe then washed at room temperature for 30 minutes then twice at 55° C. for 30 minutes. An initial autoradiograph was exposed for 24 hours and visually inspected. It was determined that a longer exposure was needed, so a second autoradiograph was exposed for 3 days for a darker exposure of the hybridized bands. After developing the film, the bans were sized using an AlphaImager® (Alpha Innotech).

No hybridizing bands were observed for the DG-44 negative control digest and single hybridizing bands of expected sizes were observed in the HZ24 digests (BamH I/Hind III digest: ~1.4 kb; Spe I digest: ~6.6 kb; Xba I digest: ~6.5 kb). There was one major hybridizing band of ~7.7 kb and four minor hybridizing bands (~13.9, ~6.6, ~5.7 and ~4.6 kb) observed using 2B2 DNA digested with Spe I, one major hybridizing band of ~5.0 kb and two minor hybridizing bands (~13.9 and ~6.5 kb) observed using 2B2 DNA digested with Xba I, and one single hybridizing band of ~1.4 kb observed using 2B2 DNA digested with BamH I/Hind III. The presence of the single ~1.4 kb hybridizing band in the BamH I/Hind III indicated that there were no large sequence insertions or deletions within the probed region. The results from the single Xba I and Spe I digests indicate that there are multiple integration sites of the HZ24 plasmid in the genome if the 2B2 cells.

Example 7

Production of Gen2 Soluble rHuPH20 in 30 L Bioreactor Cell Culture

Soluble rHuPH20 was produced and purified from 2B2 cells using a 36 L bioreactor (30 L culture volume) to determine optimal processes for scale-up to a 400 L bioreactor (300 L culture volume). Four separate 36 L bioreactor runs are detailed below in sections A to D.

A. Production and Characterization of Soluble rHuPH20 Lots 056-099 and 056-100

A vial of 2B2 ($1\times10^7$ cells) was thawed and cultured at 37° C., 7% $CO_2$ for 8 passages in CD CHO (Invitrogen, Carlsbad, Calif.) supplemented with 20 μM methotrexate and 40 mL/L GlutaMAX™-I (Invitrogen), after which it was expanded to 600 mL. One week later, the culture was expanded to 5 L in CD CHO medium supplemented with 40 mL/L GlutaMAX™-I and no methotrexate. A 36 L bioreactor containing 25 L CD CHO medium supplemented with 1 L GlutaMAX™-I and 30 mL gentamicin sulfate was inoculated with the 5 L culture at an initial seeding density of $3.6\times10^5$ cell/mL. The agitation set point of the bioreactor was set to 75 RPM; temperature: 37° C.; pH: 7.15; dissolved oxygen: 30%. The bioreactor received filtered air overlay and an air/oxygen/$CO_2$ sparge, as controlled by an Applikon controller.

The culture was fed 7 times throughout the bioreactor run, at 161, 184, 237, 256, 280, 304 and 328 hours post inoculation. The feed media were filtered into the bioreactor via peristaltic pump. The content of each feed media and the bioreactor feed parameters throughout the run are provided in Tables 17 and 18, respectively.

TABLE 17

| | Feed Media formulations | | | | | | |
|---|---|---|---|---|---|---|---|
| Component | Feed #1 | Feed #2 | Feed #3 | Feed #4 | Feed #5 | Feed #6 | Feed #7 |
| CD CHO liquid medium | 1 L | 1 L | 1 L | 1 L | 1 L | 1 L | 1 L |
| GlutaMAX ™-I | 120 mL | 80 mL | 40 mL | 40 mL | 40 mL | 30 mL | 30 mL |
| CD CHO AGT powder | 48.6 g | 24.3 g | 0 | 0 | 0 | 0 | 0 |

TABLE 17-continued

Feed Media formulations

| Component | Feed #1 | Feed #2 | Feed #3 | Feed #4 | Feed #5 | Feed #6 | Feed #7 |
|---|---|---|---|---|---|---|---|
| Yeastolate Ultrafiltrate (200 g/L) | 150 mL | 300 mL | 300 mL | 150 mL | 150 ml | 0 | 0 |
| Sodium butyrate | 1.65 g | 2.35 g | 1.65 g | 1.65 g | 1.65 g | 1.65 g | 1.65 g |

TABLE 18

Bioreactor Parameters

| Hours | VCD | % viability | pH | Hyaluronidase Units | Vol (L) | Glucose | Feed |
|---|---|---|---|---|---|---|---|
| 0 | 3.6 | 97 | 7.28 | 0 | 31 | 6000 | — |
| 15 | 6.2 | 94 | 7.45 | 117 | 31 | 5780 | — |
| 44 | 11.3 | 97 | 7.15 | 290 | 31 | 5320 | — |
| 88 | 25.6 | 97 | 6.85 | 517 | 31 | 3430 | — |
| 115 | 42.6 | 95 | 6.75 | 1132 | 31 | 2920 | — |
| 139 | 56.4 | 96 | 6.74 | 1320 | 31 | 2220 | — |
| 161 | 71.9 | 97 | 6.82 | 2296 | 31 | 520 | Feed #1 |
| 184 | 83.9 | 96 | 6.81 | 2748 | 32 | 610 | Feed #2 |
| 213 | 82.7 | 96 | 6.87 | 3396 | 33 | 1190 | — |
| 237 | 80.5 | 89 | 7.21 | 4450 | 33 | 200 | Feed #3 |
| 256 | 62.3 | 71 | 7.03 | 4750 | 34 | 240 | Feed #4 |
| 280 | 52.7 | 66 | 7.01 | 5030 | 35 | 600 | Feed #5 |
| 304 | 44.6 | 59 | 7.00 | 5970 | 36 | 560 | Feed #6 |
| 328 | 33.3 | 47 | 7.00 | 7240 | 37 | 570 | Feed #7 |
| 351 | 26.1 | 34 | 7.00 | 7360 | 37 | 250 | — |

The bioreactor was harvested and filtered through a system that contained a series of capsule filters (Sartorius) with pore sizes of 8 μm, 0.65 μm, 0.45 μm and 0.22 μm, respectively. The harvest was performed using a peristaltic pump and completed in approximately 5 hours, yielding approximately 32 L of harvested cell culture fluid (HCCF). The HCCF was supplemented with EDTA and Tris to final concentrations of 10 mM each, pH 7.6. The HCCF was then stored at 2-8° C. before being concentrated and subjected to a buffer exchange.

To concentrate the protein, a 2.5 ft² Millipore spiral wound cartridge with a 30 kDa MWCO was first equilibrated in 150 mM NaCl, 10 mM Hepes, 10 mM EDTA, pH 7.5. Fifteen L of HCCF was concentrated 15× to 1 L. The concentrate was 10× buffer exchanged with the 150 mM NaCl, 10 mM Hepes, 10 mM EDTA, pH 7.5 buffer, and the retentate was filtered through a 0.2 μm capsule into a 2 L storage bag, for a final volume of 1.1 L. The retentate was then stored at 2-8° C.

The concentrated and buffer exchanged protein solution was then purified using column chromatography through a Q Sepharose column, a phenyl Sepharose column, an Amino Phenyl column and a Hydroxyapatite column. The hyaluronidase units in the protein solution before and after each chromatography step were assessed and used to determine the yield for each step.

Briefly, a Q sepharose column with a 1.1 L column bed was sanitized with 2.8 L 1.0 N NaOH and stored in 0.1 N NaOH prior to use. It was then cleaned with 2.5 L of 10 mM Hepes, 400 mM NaCl, pH 7.0, rinsed in 4.1 L sterile water for injection (SWFI) and equilibrated with 2.5 L of 10 mM Hepes, 25 mM NaCl, pH 7.0. The buffer exchanged protein (1 L at 170,160 units/mL) was loaded onto the column. The flowthrough was 1.0 L at 479 units/mL, indicating that nearly all of the product bound the resin. The column was washed with 4 L of 10 mM Hepes, 25 mM NaCl, pH 7.0, and 4.2 L of 10 mM Hepes, 50 mM NaCl, pH 7.0. The product was then eluted in 3.0 L of 10 mM Hepes, 400 mM NaCl, pH 7.0, yielding 3 L at 49,940 units/mL, and filtered through a 0.2 μm filter.

A Phenyl Sepharose column with a 2.1 L column bed was sanitized with 4.8 L 1.0 N NaOH and stored in 0.1 N NaOH prior to use. It was then rinsed with 5.0 L SWFI and cleaned with 4.6 L of 5 mM potassium phosphate, 0.5 M ammonium sulfate and rinsed again with 6.8 L SWFI. The column was then equilibrated in 5.5 L of 5 mM potassium phosphate, 0.5 M ammonium sulfate. To the eluate from the Q Sepharose column, 10.3 mL of 1 M potassium phosphate monobasic, 10.3 mL 1 M potassium phosphate dibasic and 0.42 mL 1 mL CaCl₂ was added. This was then loaded onto the column and the flow through and chase (1 L of 5 mM potassium phosphate, 0.5 mM ammonium sulfate) were collected, yielding 7.4 L at 20,030 units/mL. The product was filtered through a 0.2 μm filter.

An Amino Phenyl Boronate column with a 1.8 L column bed was sanitized with 4.5 L 1.0 N NaOH and stored in 0.1 N NaOH prior to use. It was then rinsed with 3.9 L SWFI, cleaned with 4.2 L of 5 mM potassium phosphate, 0.5 M ammonium sulfate and rinsed again with 4.0 L SWFI. The column was then equilibrated with 7.5 L of 5 mM potassium phosphate, 0.5 M ammonium sulfate. The flow through material from the Phenyl Sepharose column was loaded onto the Amino Phenyl Boronate column after being supplemented with ammonium sulfate to a final concentration of 0.5 M. The column was washed with 6.5 L of 5 mM potassium phosphate pH 7.0, then with 7.8 L of 20 mM bicine, pH 9.0 then with 9.0 L of 20 mM bicine, 100 mM NaCl, pH 9.0. The product was eluted with 4.8 L 50 mM Hepes, 100 mM NaCl, pH 7.0, resulting in 4.8 L at 22,940 units/mL, and filtered through a 0.2 μm filter.

An Hydroxyapatite column with a 0.8 L column bed was sanitized with 2.7 L 1.0 N NaOH and stored in 0.1 N NaOH prior to use. The column was neutralized with 2.1 L of 200 mM potassium phosphate, pH 7.0 then equilibrated in 2.2 L of 5 mM potassium phosphate, 100 mM NaCl. To the eluate from the Amino Phenyl Boronate column, 9.1 mL of 1 M potassium phosphate monobasic, 9.1 mL 1 M potassium phosphate dibasic and 0.452 mL 1 mL CaCl₂ was added. This was then loaded onto the column and the flow through was 4.5 L at 10 units/mL, indicating good binding of the soluble HuPH20. The column was washed with 3.3 L of 5 mM potassium phosphate, 100 mM NaCl, 0.5 M ammonium sulfate, pH 7.0, then with 2.9 L of 10 mM potassium phosphate, 100 mM NaCl, 0.5 M ammonium sulfate, pH 7.0. The product was eluted with 1.0 L of 70 mM potassium phosphate, pH 7.0, resulting in 1 L at 130,000 units/mL, and filtered through a 0.2 μm filter.

The purified product was concentrated using a 2.5 ft² Millipore 30 kDa MWCO cartridge that had been equilibrated in 130 mM NaCl, 10 mM Hepes, pH 7.0. The product was concentrated 74 mL, and buffer exchanged 10× with the 130 mM NaCl, 10 mM Hepes, pH 7.0 buffer then filtered through a 0.2 μm filter. $A_{280}$ measurements were performed and indicated that the protein concentration was 11.3 mg/mL. An additional 9.6 mL of 130 mM NaCl, 10 mM Hepes, pH 7.0 buffer was added to bring the protein concentration to 10 mg/mL (Lot 056-99). Ten mL of the mg/mL protein solution was diluted in the buffer to yield a 1 mg/mL solution (Lot 056-100. Both solutions were filtered through a 0.2 μm filter.

The formulated product was filled into 10 mL and 1 mL glass vials, the combined total of which yielded 761 mg soluble rHuPH20. The vials were frozen at −80° C. then transferred to −20° C. for storage. Lot 056-99 and 056-100 were then characterized with respect to activity and purity. Lots 056-99 and 056-100 exhibited 1,350,786 units/mL and 129,982 units/mL enzyme activity, and 13,000 units/mg and 12,400 units/mg specific activity (calculated from enzyme activity and protein concentration). The purity of the soluble rHuPH20 samples was determined by SDS-PAGE, IsoElectric Focusing (IEF), reverse phase high pressure liquid chromatography (RP-HPLC), size-exclusion chromatography (SEC) and anion-exchange chromatography. As determined by RP-HPLC, purity of the two Lots was observed to be approximately 95%. As determined by SEC, purity of the two Lots was observed to be approximately 99%. Endotoxin levels were shown to be EU/mL and 0.1 EU/mL for lots 056-99 and 056-100, respectively. Osmolarity was measured to be 271 mOsm/kg and 291 mOsm/kg for lots 056-99 and 056-100, respectively.

B. Modifications to Increase Soluble rHuPH20 Production: Bioreactor Batch 2B2-20K.5

Modifications were made to the method described above in section A. These modifications were intended to increase the product yield and improve the efficiency and scalability of manufacturing. The manufacturing steps described below include thaw of frozen cells from the research cell bank, expansion of cells in continuous culture, operation of fed-batch bioreactor system, harvest and clarification of cell culture fluid, and concentration and buffer exchange of bulk product. The modifications include, for example, the addition of recombinant human insulin to the bioreactor medium to increase the growth rate and product expression levels of the cells. Also, the number of feeds has been reduced from 7 to 5. Other modifications of the methods described above also were made.

A vial of 2B2 ($1×10^7$ cells) was thawed and cultured in CD CHO (Invitrogen, Carlsbad, Calif.) supplemented with 20 μM methotrexate and 40 mL/L GlutaMAX™-I (Invitrogen), after which it was expanded to 100 mL, 450 ml then to 4.5 L in CD CHO medium supplemented with 40 mL/L GlutaMAX™-I and no methotrexate. A 36 L bioreactor containing 20 L CD CHO medium supplemented with 800 L GlutaMAX™-I, 30 mL gentamicin sulfate and 100 mg recombinant human insulin was inoculated with 3.6 L 2B2 culture at an initial seeding density of $4.3×10^5$ cell/mL. The agitation set point of the bioreactor was set to 80 RPM; temperature: 37° C.; pH: 7.15; dissolved oxygen: 25%. The bioreactor received filtered air overlay and an air/oxygen/$CO_2$ sparge, as controlled by an Applikon controller.

The culture was fed 5 times throughout the 13 day bioreactor run, at 117, 143, 196, 235, and 283 hours post inoculation. The feed media were filtered into the bioreactor via peristaltic pump. The content of each feed media and the bioreactor feed parameters throughout the run are provided in Tables 19 and 20, respectively.

TABLE 19

Feed Media formulations

| Component | Initial bioreactor medium | Feed #1 | Feed #2 | Feed #3 | Feed #4 | Feed #5 |
|---|---|---|---|---|---|---|
| CD CHO liquid medium | 12 L | 0 | 0 | 0 | 0 | 0 |
| GlutaMAX ™-I | 800 mL | 120 mL | 80 mL | 40 mL | 40 mL | 40 mL |
| CD CHO AGT powder | 194.4 g | 97.2 g | 48.6 g | 24.3 g | 24.3 g | 24.3 g |
| SWFI | 8 L | 800 mL | 900 mL | 700 mL | 700 mL | 700 mL |
| Yeastolate Ultrafiltrate (200 g/L) | 0 | 0 | 0 | 200 mL | 200 mL | 200 mL |
| Dextrose | 0 | 30 g | 60 g | 40 g | 40 g | 40 g |
| Gentamicin | 30 mL | 0 | 0 | 0 | 0 | 0 |
| rHuInsulin | 25 mL | 0 | 0 | 0 | 0 | 0 |
| Sodium butyrate | 0 | 0 | 0 | 2.2 g | 1.1 g | 1.1 g |

TABLE 20

Bioreactor Parameters

| Hours | VCD | % viability | pH | Hyaluronidase Units | Vol (L) | Glucose | Feed |
|---|---|---|---|---|---|---|---|
| 0 | 4.3 | 98 | 7.28 | 0 | 25 | 8820 | — |
| 55 | 17.1 | 99 | 7.07 | 580 | 25 | 4950 | — |
| 94 | 40.6 | 99 | 6.77 | 1059 | 25 | 3800 | — |
| 117 | 57.5 | 99 | 6.76 | 1720 | 25 | 2310 | Feed #1 |
| 143 | 88.8 | 99 | 6.75 | 3168 | 26 | 2770 | Feed #2 |
| 167 | 93.7 | 99 | 6.80 | 6982 | 27 | 3830 | — |
| 196 | 96.2 | 97 | 6.89 | 4560 | 27 | 2060 | Feed #3 |
| 222 | 78.9 | 85 | 6.83 | 4920 | 28 | 2720 | — |
| 235 | 80 | 76 | 6.81 | 5670 | 28 | 1870 | Feed #4 |
| 260 | 54.3 | 65 | 6.76 | 5865 | 29 | 2930 | — |

TABLE 20-continued

Bioreactor Parameters

| Hours | VCD | % viability | pH | Hyaluronidase Units | Vol (L) | Glucose | Feed |
|---|---|---|---|---|---|---|---|
| 283 | 38.7 | 44 | 6.73 | 6540 | 29 | 1880 | Feed #5 |
| 308 | 37.3 | 39 | 6.78 | 8460 | 29 | 2400 | — |
| 313 | 33.7 | 34 | 6.78 | 8190 | 29 | 2300 | — |

The bioreactor was harvested and filtered through a system that contained a series of Millipore Pod filters D0HC (0.5 m$^2$) and A1HC stacks, which contain layers of graded-pore-size diatomaceous earth, followed by final filtration through capsule filter (Sartorius Sartobran 300) into a 50 L storage bag. The harvest was performed using a peristaltic pump and completed in approximately 2 hours, yielding approximately 30 L of harvested cell culture fluid (HCCF). Twenty-eight L HCCF was supplemented with EDTA and Tris to final concentrations of 10 mM each, and a pH 7.5. The remaining 2 l HCCF was left without Tris/EDTA, to assess the effect of adding Tris/EDTA on the concentration/buffer exchange step. The HCCF was then stored at 2-8° C. before being concentrated and subjected to a buffer exchange.

To concentrate the protein, a 0.1 m$^2$ Millipore Pellicon 2 biomax A screen cassette with a 30 kDa MWCO was first equilibrated in 20 mM Na$_2$SO$_4$, 10 mM Tris, pH 7.5. 2 L of HCCF with and without Tris/EDTA was concentrated 10× and buffer exchanged 10× with the 20 mM Na$_2$SO$_4$, 10 mM Tris, pH 7.5 buffer. The protein levels were measured by absorbance at A$_{260}$. The remaining HCCF (approximately 26.5 L) was then concentrated and subjected to buffer exchange. Two 0.1 m$^2$ Millipore Pellicon 2 biomax A screen cassettes with a 30 kDa MWCO were assembled in the TFF system and equilibrated in 20 mM Na$_2$SO$_4$, 10 mM Tris, pH 7.5. The HCCF was concentrated approximately 10× to 2.5 L, and buffer exchanged 10× with 20 mM Na$_2$SO$_4$, 10 mM Tris, pH 7.5. The retentate was filtered through a 0.2 µm vacuum filter into 1 L and 500 mL storage bags, for a final volume of 2.6 L. The retentate was then stored at 2-8° C. Samples taken during the concentration and buffer exchange process were analyzed by RP-HPLC to determine the effect of the addition of Tris/EDTA to the sample. It was observed that the addition of Tris/EDTA facilitated a more efficient processing step.

C. Production and Characterization of Soluble rHuPH20 Lots 056-122 and 056-123 (Bioreactor Batch 2B2-20K.6).

Modifications described above in section C were incorporated into the manufacturing steps to produce and purify two lots of soluble rHuPH20; Lots 056-122 and 056-123. The process described below include thaw of frozen cells from the research cell bank HZ24-2B2; expansion of cells in continuous culture; operation of 36 L fed-batch bioreactor system at the 30 L scale; cell removal, clarification, and buffer exchange of bulk product; 4-step column chromatography; and formulation, fill, and finish operations.

A vial of 2B2 (1×10$^7$ cells) was thawed and cultured at 37° C., 7% CO$_2$ in CD CHO (Invitrogen, Carlsbad, Calif.) supplemented with 20 µM methotrexate and 40 mL/L GlutaMAX™-I (Invitrogen), after which it was expanded to 400 mL then 4.4 L in CD CHO medium supplemented with 40 mL/L GlutaMAX™-I and no methotrexate. A 36 L bioreactor (Bellco 1964 series) containing 20 L CD CHO medium supplemented with 800 L GlutaMAX™-1,100 mg recombinant human insulin and 30 mL gentamicin sulfate was inoculated with the 4 L culture at an initial seeding density of 4.9×10$^5$ cell/mL. The agitation set point of the bioreactor was set to 80 RPM; temperature: 37° C.; pH: 7.15; dissolved oxygen: 25%. The bioreactor received filtered air overlay and an air/oxygen/CO$_2$ sparge, as controlled by an Applikon ADI 1030 controller.

The culture was fed 4 times throughout the 13 day bioreactor run, at 127, 163, 208 and hours post inoculation. The feed media were filtered into the bioreactor via peristaltic pump. The temperature setpoint of the bioreactor was reduced from 37° C. to 36.5° C. on day 7, to 36.0° C. on day 9 and finally to 35.5° C. on day 11. The content of each feed media and the bioreactor feed parameters throughout the run are provided in Tables 21 and 22, respectively.

TABLE 21

Feed Media formulations

| Component | Initial bioreactor medium | Feed #1 | Feed #2 | Feed #3 | Feed #4 |
|---|---|---|---|---|---|
| CD CHO AGT powder (Invitrogen; part #: 10743-029; lot # 1366333) | 0 | 97.2 g | 48.6 g | 24.3 g | 24.3 g |
| CD CHO AGT powder (Invitrogen; part #: 10743-029; lot # 1320613) | 267.3 g | 0 | 0 | 0 | 0 |
| CD CHO AGT powder (Invitrogen; part #: 12490-017; lot # 1300803) | 218.7 g | 0 | 0 | 0 | 0 |
| SWFI | 20 L | 700 mL | 700 mL | 600 mL | 600 mL |
| GlutaMAX ™-I (Invitrogen) | 800 mL | 160 mL | 80 mL | 60 mL | 40 mL |
| Yeastolate Ultrafiltrate (Invitrogen; 200 g/L) | 0 | 100 mL | 200 mL | 300 mL | 300 mL |
| Dextrose (D-glucose) | 0 | 40 g | 40 g | 60 g | 40 g |
| Gentamicin | 30 mL | 0 | 0 | 0 | 0 |
| rHuInsulin | 100 mg | 40 mg | 0 | 0 | 0 |
| Sodium butyrate | 0 | 0 | 1.1 g | 2.2 g | 1.1 g |

TABLE 22

Bioreactor Parameters

| Hours | Viable cell density (×10⁵ cells/mL) | % viability | pH | Hyaluronidase Units | Vol (L) | Glucose | Feed |
|---|---|---|---|---|---|---|---|
| 0 | 4.9 | 92 | 7.26 | 79 | 25 | 7780 | — |
| 24 | 9.2 | 95 | 7.21 | 141 | 25 | 6060 | — |
| 48 | 17.3 | 97 | 7.13 | 243 | 25 | 5280 | — |
| 72 | 33 | 99 | 6.82 | 407 | 25 | 3910 | — |
| 98 | 49.3 | 99 | 6.77 | 658 | 25 | 3200 | — |
| 127 | 67 | 98 | 6.83 | 1296 | 25 | 1610 | Feed #1 |
| 144 | 88.1 | 98 | 6.78 | 1886 | 26 | 2860 | — |
| 163 | 92.4 | 99 | 6.89 | 2439 | 26 | 1680 | Feed #2 |
| 192 | 91 | 97 | 6.85 | 3140 | 27 | 1480 | — |
| 208 | 92.7 | 96 | 6.91 | 3188 | 27 | 230 | Feed #3 |
| 235 | 70 | 76 | 6.86 | 5118 | 28 | 1940 | — |
| 261 | 63 | 61 | 6.84 | 5862 | 28 | 280 | Feed #4 |
| 291 | 36.4 | 45 | 6.76 | 7072 | 29 | 1570 | — |
| 307 | 29.3 | 32 | 6.81 | 8160 | 29 | 1250 | Harvest |

The bioreactor was harvested and filtered through a system that contained a series of Millipore Pod filters D0HC (0.5 m²) and A1HC stacks (0.1 m²), which contain layers of graded-pore-size diatomaceous earth, followed by final filtration through capsule filter (Sartorius Sartobran 300) into 20 L storage bags. The harvest was performed using a peristaltic pump and completed in approximately 1 hour, yielding approximately 34 L of harvested cell culture fluid (HCCF). This includes the 29 L bioreactor volume plus approximately 5 L PBS chase. The HCCF was supplemented with EDTA and Tris to final concentrations of 10 mM each, and a final pH of 7.5. The HCCF was then stored at 2-8° C. before being concentrated and subjected to a buffer exchange.

To concentrate the protein, a 7.0 ft² Sartorius Sartocon 2 crossflow cassette with a 30 kDa MWCO was first equilibrated in 20 mM $Na_2SO_4$, 10 mM Tris, pH 7.5. 34 L of HCCF was concentrated 10× to 3 L and buffer exchanged 10× with the 20 mM $Na_2SO_4$, 10 mM Tris, pH 7.5 buffer. The retentate was filtered through a 0.2 μm capsule filter into a 5 L storage bags for a final volume of 3.0 L. The retentate was then stored at 2-8° C.

The concentrated and buffer exchanged protein solution was then purified using column chromatography through a Q Sepharose column, a phenyl Sepharose column, an Amino Phenyl column and a Hydroxyapatite column. The hyaluronidase units in the protein solution before and after each chromatography step were assessed and used to determine the yield for each step.

Briefly, a Q sepharose column with a 1.1 L column bed, diameter 7 cm, height 28 cm was sanitized with 2.1 L 1.0 N NaOH and stored in 0.1 N NaOH prior to use. It was then cleaned with 2.5 L of 10 mM Hepes, 400 mM NaCl, pH 7.0, rinsed in 4.5 L sterile water for injection (SWFI) and equilibrated with 4.3 L of 10 mM Hepes, 25 mM NaCl, pH 7.0. The buffer exchanged protein (3 L at 94,960 hyaluronidase units/mL) was loaded onto the column. The flowthrough and first wash was 5830 mL at 75 hyaluronidase units/mL, indicating that nearly all of the product (99.8%) bound the resin. The column was washed with 4.2 L of 10 mM Hepes, 25 mM NaCl, pH 7.0, and 4.6 L of 10 mM Hepes, 50 mM NaCl, pH 7.0. The product was then eluted in 2.9 L of 10 mM Hepes, 400 mM NaCl, pH 7.0, yielding 2880 mL at 96,080 units/mL, and filtered through a 0.2 μm filter.

A Phenyl Sepharose column with a 2.2 L column bed (height 28 cm, diameter 10 cm) was sanitized with 5.0 L 1.0 N NaOH and stored in 0.1 N NaOH prior to use. It was then rinsed with 4.5 L SWFI and cleaned with 4.6 L of 5 mM potassium phosphate, 0.5 M ammonium sulfate and rinsed again with 6.8 L SWFI. The column was then equilibrated in 4.6 L of 5 mM potassium phosphate, 0.5 mM ammonium sulfate. To the eluate from the Q Sepharose column, 9.6 mL of 1 M potassium phosphate monobasic, 9.6 mL 1 M potassium phosphate dibasic and 0.4 mL 1 mL $CaCl_2$ was added. This was then loaded onto the column and the flow through and chase (5 mM potassium phosphate, 0.5 mM ammonium sulfate) were collected, yielding 6905 mL at 36,280 units/mL. The product was filtered through a 0.2 μm filter.

An Amino Phenyl Boronate column with a 2.2 L column bed (height 29 cm, diameter 10 cm) was sanitized with 3.8 L 1.0 N NaOH and stored in 0.1 N NaOH prior to use. It was then rinsed with 5.0 L SWFI, cleaned with 5.0 L of 5 mM potassium phosphate, 0.5 M ammonium sulfate and rinsed again with 5.0 L SWFI. The column was then equilibrated with 5.0 L of 5 mM potassium phosphate, 0.5 M ammonium sulfate. The flow through material from the Phenyl Sepharose column was loaded onto the Amino Phenyl Boronate column. The column was washed with 9.9 L of 5 mM potassium phosphate, 0.5M ammonium sulfate, pH 7.0, then with 9.7 L of 20 mM bicine, 0.5 M ammonium sulfate, pH 9.0 then with 9.9 L of 20 mM bicine, 100 mM NaCl, pH 9.0. The product was eluted with 5.0 L 50 mM Hepes, 100 mM NaCl, pH 7.0, resulting in 4460 mL at 48,400 units/mL, and filtered through a 0.2 μm filter.

A Hydroxyapatite column with a 1.1 L column bed (diameter 7 cm, height 28 cm) was sanitized with 2.7 L 1.0 N NaOH and stored in 0.1 N NaOH prior to use. The column was neutralized with 2.1 L of 200 mM potassium phosphate, pH 7.0, then equilibrated in 2.2 L of 5 mM potassium phosphate, 100 mM NaCl. To the eluate from the Amino Phenyl Boronate column, 11.2 mL of 1 M potassium phosphate monobasic, 11.2 mL 1 M potassium phosphate dibasic and 0.45 mL 1 mL $CaCl_2$ was added. This was then loaded onto the column and subsequently washed with 3.5 L of 5 mM potassium phosphate, 100 mM NaCl, 0.5 M ammonium sulfate, pH 7.0, then with 3.5 L of 10 mM potassium phosphate, 100 mM NaCl, 0.5 M ammonium sulfate, pH 7.0. The product was eluted with 1.4 L of 70 mM potassium phosphate, pH 7.0, resulting in 1260 mL at 152,560 units/mL, and filtered through a 0.2 μm filter.

The purified product was concentrated using a 0.05 ft² Millipore 30 kDa MWCO cartridge that had been equilibrated in 130 mM NaCl, 10 mM Hepes, pH 7.0. The product was concentrated from 1250 mL at 1.04/mg/mL to 120 mL and buffer exchanged 10× with the 130 mM NaCl, 10 mM Hepes, pH 7.0 buffer then filtered through a 0.2 µm filter. $A_{280}$ measurements were performed and indicated that the soluble rHuPH20 concentration of the remaining 118 ml was 11.45 mg/mL. An additional 17 mL of 130 mM NaCl, 10 mM Hepes, pH 7.0 buffer was added to bring the protein concentration to 10 mg/mL (Lot 056-122). Ten mL of the 10 mg/mL protein solution was diluted in the buffer to yield a 1 mg/mL solution (Lot 056-123. Both solutions were filtered through a 0.2 µm filter.

The formulated product was filled into 10 mL and 1 mL glass vials, the combined total of which yielded 1308 mg soluble rHuPH20. The vials were frozen at −80° C. then transferred to −20° C. for storage. Lot 056-122 and 056-123 were then characterized with respect to activity and purity. Lots 056-122 and 056-123 exhibited 1,376,992 units/mL and 129,412 units/mL enzyme activity, and 136,900 units/mg and 124,400 units/mg specific activity (calculated from enzyme activity and protein concentration). The purity of the soluble rHuPH20 samples was determined by SDS-PAGE, IsoElectric Focusing (IEF), reverse phase high pressure liquid chromatography (RP-HPLC), size-exclusion chromatography (SEC) and anion-exchange chromatography. As determined by RP-HPLC, purity of the two Lots was observed to be approximately 96.2%. As determined by SEC, purity of the two Lots was observed to be greater than 99%. Endotoxin levels were shown to be EU/mL and 0.09 EU/mL for lots 056-122 and 056-123, respectively. Osmolarity was measured to be 265 mOsm/kg and 256 mOsm/kg for lots 056-122 and 056-123, respectively. The pH of each was 7.2.

D. Reproducibility of the Production Process of Gen 2 Soluble rHuPH20 in 30 L Bioreactor Cell Culture The process described above for Batch 2B2-20K.6 was used for a subsequent batch to demonstrate the reproducibility of the process. The process was modified slightly by the incorporation of a viral inactivation step immediately prior to the column chromatography steps.

A vial of 2B2 cells ($1 \times 10^7$ cells) was thawed and cultured at 37° C., 7% $CO_2$ for 7 passages in CD CHO (Invitrogen, Carlsbad, Calif.) supplemented with 20 µM Methotrexate and 40 mL/L GlutaMAX™-I (Invitrogen), after which it was expanded to 400 mL then 4.4 L in CD CHO medium supplemented with 40 mL/L GlutaMAX™-I and no methotrexate. A 36 L bioreactor (Bellco 1964 series) containing 20 L CD CHO medium supplemented with 800 mL GlutaMAX™-1, 100 mg recombinant human insulin and 300 mg gentamicin sulfate was inoculated with 3 L culture at an initial seeding density of $4.7 \times 10^5$ cell/mL. The agitation set point of the bioreactor was set to 80 RPM; temperature: 37° C.; pH: 7.15; dissolved oxygen: 25%. The bioreactor received filtered air overlay and an air/oxygen/$CO_2$ sparge, as controlled by an Applikon ADI 1030 controller.

The culture was fed 4 times throughout the 13 day bioreactor run, at 127, 163, 208 and hours post inoculation. The feed media were filtered into the bioreactor via peristaltic pump. The temperature setpoint of the bioreactor was reduced from 37° C. to 36.5° C. on day 7, to 36.0° C. on day 9 and finally to 35.5° C. on day 11. The content of each feed media and the bioreactor feed parameters throughout the run are provided in Tables 23 and 24, respectively.

TABLE 23

Feed Media formulations

| Component | Initial bioreactor medium | Feed #1 | Feed #2 | Feed #3 | Feed #4 |
|---|---|---|---|---|---|
| CD CHO liquid medium (Invitrogen) | 20 L | 0 | 0 | 0 | 0 |
| CD CHO AGT powder | 0 g | 97.2 g | 48.6 g | 24.3 g | 24.3 g |
| SWFI | 0 | 700 mL | 700 mL | 600 mL | 600 mL |
| GlutaMAX ™-I (Invitrogen) | 800 mL | 160 mL | 80 mL | 60 mL | 40 mL |
| Yeastolate Ultrafiltrate (Invitrogen; 200 g/L) | 0 | 100 mL | 200 mL | 300 mL | 300 mL |
| Dextrose (D-glucose) | 0 | 40 g | 40 g | 60 g | 50 g |
| Gentamicin | 300 mg | 0 | 0 | 0 | 0 |
| rHuInsulin | 100 mg | 40 mg | 0 | 0 | 0 |
| Sodium butyrate | 0 | 0 | 1.1 g | 2.2 g | 1.1 g |

TABLE 24

Bioreactor Parameters

| Hours | Viable cell density ($\times 10^5$ cells/mL) | % viability | pH | Hyaluronidase Units | Vol (L) | Glucose | Feed |
|---|---|---|---|---|---|---|---|
| 0 | 4.7 | 98 | 7.28 | 113 | 24 | 8200 | — |
| 24 | 8.9 | 98 | 7.23 | 202 | 24 | 6160 | — |
| 50 | 19.3 | 97 | 7.15 | 332 | 24 | 5480 | — |
| 76 | 36.7 | 99 | 6.85 | 680 | 24 | 3620 | — |
| 120 | 73.6 | 99 | 6.76 | 1619 | 24 | 2100 | Feed #1 |
| 145 | 84.3 | 99 | 6.75 | 2842 | 25 | 2660 | — |

TABLE 24-continued

Bioreactor Parameters

| Hours | Viable cell density ($\times 10^5$ cells/mL) | % viability | pH | Hyaluronidase Units | Vol (L) | Glucose | Feed |
|---|---|---|---|---|---|---|---|
| 165 | 98.8 | 99 | 6.87 | 3756 | 25 | 840 | Feed #2 |
| 190 | 95.3 | 99 | 6.85 | 4773 | 26 | 1330 | — |
| 201 | 105 | 97 | 6.90 | 5484 | 26 | 270 | Feed #3 |
| 214 | 95.9 | 93 | 6.82 | 6344 | 27 | 2590 | — |
| 242 | 81.2 | 81 | 6.75 | 7890 | 27 | 1350 | Feed #4 |
| 268 | 51.9 | 48 | 6.65 | 10398 | 28 | 2500 | — |
| 287 | 38.4 | 41 | 6.70 | 11864 | 28 | 2170 | — |
| 308 | 31.6 | 31 | 6.66 | 12864 | 28 | 1850 | Harvest |

The bioreactor was harvested and filtered through a system that contained a series of Millipore Pod filters D0HC (0.5 m$^2$) and A1HC stacks (0.1 m$^2$), which contain layers of graded-pore-size diatomaceous earth, followed by final filtration through capsule filter (Sartorius Sartobran 300) into 20 L storage bags. The harvest was performed using a peristaltic pump and completed in approximately 75 minutes, yielding approximately 30 L of harvested cell culture fluid (HCCF). This includes the 28 L bioreactor volume plus approximately 2 L PBS chase. The HCCF was supplemented with EDTA and Tris to final concentrations of 10 mM each, and a final pH of 7.5. The HCCF was then stored at 2-8° C. before being concentrated and subjected to a buffer exchange.

To concentrate the protein, a Sartorius Slice system with 3×1.0 ft$^2$ Sartocon Slice crossflow cassettes (30 kDa MWCO) was first equilibrated in 20 mM Na$_2$SO$_4$, mM Tris, pH 7.5. Thirty liters of HCCF was concentrated 10× to 3 L and buffer exchanged 10× with the 20 mM Na$_2$SO$_4$, 10 mM Tris, pH 7.5 buffer. The average flux rate during the concentration was 115 mL/minute and the average transmembrane pressure was 16 psig. The average flux rate during the diafiltration was 150 mL/minute and the average transmembrane pressure was 15 psig. The retentate was filtered through a 0.2 μm vacuum filter systems into a 5 L storage bags for a final volume of 3.0 L. The retentate was then stored at 2-8° C.

Viral inactivation was performed by mixing 235 mL of a filtered solution of 10% w/w Triton X-100, 35 w/w Tri-butyl phosphate in SWFI with 2.15 L of room-temperature concentrated and buffer exchanged protein in a glass spinner flask stirring at 30-40 rpm. After 45 minutes, the protein solution was loaded onto the Q sepharose column (as described below). The loading took 24 minutes, which resulted in a total exposure time to the detergent solution of 69 minutes.

The Q sepharose column with a 1.1 L column bed, diameter 7 cm, height 28 cm was sanitized with 2.1 L 1.0 N NaOH and stored in 0.1 N NaOH prior to use. It was then cleaned with 2.5 L of 10 mM Hepes, 400 mM NaCl, pH 7.0, rinsed in 4.5 L sterile water for injection (SWFI) and equilibrated with 4.5 L of 10 mM Hepes, 25 mM NaCl, pH 7.0. The buffer exchanged, viral inactivated protein (2385 mL at 133,040 hyaluronidase units/mL) was loaded onto the column. The column was washed with 4.5 L of 10 mM Hepes, 25 mM NaCl, pH 7.0, and 4.5 L of 10 mM Hepes, 50 mM NaCl, pH 7.0. The product was then eluted in 2.5 L of 10 mM Hepes, 400 mM NaCl, pH 7.0, yielding 2500 mL at 133,680 units/mL, and filtered through a 0.2 μm filter.

A Phenyl Sepharose column with a 2.2 L column bed (height 28 cm, diameter 10 cm) was sanitized with 5.0 L 1.0 N NaOH and stored in 0.1 N NaOH prior to use. It was then rinsed with 6.0 L SWFI and equilibrated in 4.6 L of 5 mM potassium phosphate, 0.5 mM ammonium sulfate. To elute the column, 9.6 mL of 1 M potassium phosphate monobasic, 9.6 mL 1 M potassium phosphate dibasic and 0.4 mL 1 mL CaCl$_2$ was added. This was then loaded onto the column and the flow through and chase (5 mM potassium phosphate, 0.5 mM ammonium sulfate) were collected, yielding 6450 mL at 43,840 units/mL. The product was filtered through a 0.2 μm filter.

An Amino Phenyl Boronate column with a 2.2 L column bed (height 29 cm, diameter 10 cm) was sanitized with 3.5 L 1.0 N NaOH and stored in 0.1 N NaOH prior to use. It was then rinsed with 5.0 L SWFI and equilibrated with 9.0 L of 5 mM potassium phosphate, 0.5 M ammonium sulfate. The flow through material from the Phenyl Sepharose column was loaded onto the Amino Phenyl Boronate column. The column was washed with 9.9 L of 5 mM potassium phosphate, 0.5 M ammonium sulfate, pH 7.0, then with 9.9 L of 20 mM bicine, 0.5 M ammonium sulfate, pH 9.0. The product was eluted with 4.4 L 50 mM Hepes, 100 mM NaCl, pH 7.0, yielding 4389 mL at 33,840 units/mL, and filtered through a 0.2 μm filter.

A Hydroxyapatite column with a 1.1 L column bed (diameter 7 cm, height 28 cm) was sanitized with 2.1 L 1.0 N NaOH and stored in 0.1 N NaOH prior to use. The column was neutralized with 3.6 L of 200 mM potassium phosphate, pH 7.0, then equilibrated in 3.2 L of 5 mM potassium phosphate, 100 mM NaCl. To the eluate from the Amino Phenyl Boronate column, 11 mL of 1 M potassium phosphate monobasic, 11 mL 1 M potassium phosphate dibasic and 0.44 mL 1 mL CaCl$_2$ was added. This was then loaded onto the column and subsequently washed with 4.8 L of 5 mM potassium phosphate, 100 mM NaCl, 0.5 M ammonium sulfate, pH 7.0, then with 3.8 L of 10 mM potassium phosphate, 100 mM NaCl, 0.5 M ammonium sulfate, pH 7.0. The product was eluted with 1.5 L of 70 mM potassium phosphate, pH 7.0, resulting in 1500 mL at 114,320 units/mL, and filtered through a 0.2 μm filter.

The purified product was concentrated using a 0.05 ft$^2$ Millipore 30 kDa MWCO cartridge that had been equilibrated in 130 mM NaCl, 10 mM Hepes, pH 7.0. The product was concentrated from 1500 mL at 0.961 mg/mL to 125 mL and buffer exchanged 10× with the 130 mM NaCl, 10 mM Hepes, pH 7.0 buffer then filtered through a 0.2 μm filter. A$_{280}$ measurements were performed and indicated that the protein concentration of the remaining 122 ml was 11.431 mg/mL. An additional 17.5 mL of 130 mM NaCl, 10 mM Hepes, pH 7.0 buffer was added to bring the protein concentration to 10 mg/mL (Lot 056-135). Ten mL of the 10 mg/mL protein solution was diluted in the buffer to yield a 1 mg/mL solution (Lot 056-136). Both solutions were filtered through a 0.2 μm filter.

The formulated product was filled into 5 mL and 1 mL glass vials, the combined total of which yielded 1324 mg soluble rHuPH20. The vials were frozen at −80° C. then transferred to −20° C. for storage. Lot 056-135 and 056-136 were then characterized with respect to activity and purity. Lots 056-135 and 056-136 exhibited 1,301,010 units/mL and 127,661 units/mL enzyme activity, and 121,600 units/mg and 127,700 units/mg specific activity (calculated from enzyme activity and protein concentration). The purity of the soluble rHuPH20 samples was determined by SDS-PAGE, IsoElectric Focusing (IEF), reverse phase high pressure liquid chromatography (RP-HPLC), size-exclusion chromatography (SEC) and anion-exchange chromatography. As determined by RP-HPLC, purity of the two Lots was observed to be between 93.5% and 93.7%. As determined by SEC, purity of the two Lots was observed to be greater than 99%. Endotoxin levels were shown to be EU/mL and 0.09 EU/mL for lots 056-135 and 056-136, respectively. Osmolarity was measured to be 255 mOsm/kg and 260 mOsm/kg for lots 056-135 and 056-136, respectively. The pH of each was 7.2.

Example 8

A. Production of Gen2 Soluble rHuPH20 in 300 L Bioreactor Cell Culture

The production and purification methods detailed in Example 7, above, were scaled-up for production using a 400 L bioreactor. A vial of 2B2 cells ($1 \times 10^7$ cells) was thawed and expanded from shaker flasks through 36 L spinner flasks in CD CHO (Invitrogen, Carlsbad, Calif.) supplemented with 20 μM methotrexate and 8 mM GlutaMAX™-I (Invitrogen). Briefly, the a vial of cells was thawed in a 37° C. water bath, media was added and the cells were centrifuged. The cells were re-suspended in a 125 mL shake flask with 20 mL of fresh media and placed in a 37° C., 7% $CO_2$ incubator. The cells were expanded up to 40 mL in the 125 mL shake flask. When the cell density reached greater than $1.5 \times 10^6$ cells/mL, the culture was expanded into a 125 mL spinner flask in a 100 mL culture volume. The flask was incubated at 37° C., 7% $CO_2$. When the cell density reached greater than $1.5 \times 10^6$ cells/mL, the culture was expanded into a 250 mL spinner flask in 200 mL culture volume, and the flask was incubated at 37° C., 7% $CO_2$. When the cell density reached greater than $1.5 \times 10^6$ cells/mL, the culture was expanded into a 1 L spinner flask in 800 mL culture volume and incubated at 37° C., 7% $CO_2$. When the cell density reached greater than $1.5 \times 10^6$ cells/mL the culture was expanded into a 6 L spinner flask in 5000 mL culture volume and incubated at 37° C., 7% $CO_2$. When the cell density reached greater than $1.5 \times 10^6$ cells/mL the culture was expanded into a 36 L spinner flask in 32 L culture volume and incubated at 37° C., 7% $CO_2$.

A 400 L reactor was sterilized by steam at 121° C. for 30 minutes and 230 mL of CD CHO media supplemented with 8 mM GlutaMAX™-I and 5 mg/L rHuInsulin was added. Before use, the reactor was checked for contamination. Approximately 30 L cells were transferred from the 36 L spinner flasks to the 400 L bioreactor (Braun) at an inoculation density of $4.0 \times 10^5$ viable cells per ml and a total volume of 260 L. Parameters were temperature setpoint, 37° C.; Impeller Speed 40-55 RPM; Vessel Pressure: 3 psi; Air Sparge 0.5-1.5 L/Min.; Air Overlay: 3 L/min. The reactor was sampled daily for cell counts, pH verification, media analysis, protein production and retention. Also, during the run nutrient feeds were added. At 120 hrs (day 5), 10.4 L of Feed #1 Medium (4×CD CHO+33 g/L Glucose+160 mL/L GlutaMAX™-I+16.6 g/L Yeastolate+33 mg/L rHuInsulin) was added. At 168 hours (day 7), 10.8 L of Feed #2 (2×CD CHO+33 g/L Glucose+80 mL/L GlutaMAX™-I+33.4 g/L Yeastolate+0.92 g/L Sodium Butyrate) was added, and culture temperature was changed to 36.5° C. At 216 hours (day 9), 10.8 L of Feed #3 (1×CD CHO+50 g/L Glucose+50 mL/L GlutaMAX™-I+50 g/L Yeastolate+1.80 g/L Sodium Butyrate) was added, and culture temperature was changed to 36° C. At 264 hours (day 11), 10.8 L of Feed #4 (1× CD CHO+33 g/L Glucose+33 mL/L GlutaMAX™-I+50 g/L Yeastolate+0.92 g/L Sodium Butyrate) was added, and culture temperature was changed to 35.5° C. The addition of the feed media was observed to dramatically enhance the production of soluble rHuPH20 in the final stages of production. The reactor was harvested at 14 days or when the viability of the cells dropped below 40%. The process resulted in a final productivity of 17,000 Units per ml with a maximal cell density of 12 million cells/mL. At harvest, the culture was sampled for mycoplasma, bioburden, endotoxin and viral in vitro and in vivo, TEM for viral particles and enzyme activity.

The culture was pumped by a peristaltic pump through four Millistak filtration system modules (Millipore) in parallel, each containing a layer of diatomaceous earth graded to 4-8 μm and a layer of diatomaceous earth graded to 1.4-1.1 μm, followed by a cellulose membrane, then through a second single Millistak filtration system (Millipore) containing a layer of diatomaceous earth graded to 0.4-0.11 μm and a layer of diatomaceous earth graded to <0.1 μm, followed by a cellulose membrane, and then through a 0.22 μm final filter into a sterile single use flexible bag with a 350 L capacity. The harvested cell culture fluid was supplemented with 10 mM EDTA and 10 mM Tris to a pH of 7.5. The culture was concentrated 10× with a model tangential flow filtration (TFF) apparatus using four Sartoslice TFF 30 kDa molecular weight cut-off (MWCO) polyether sulfone (PES) filters (Sartorius), followed by a 10× buffer exchange with 10 mM Tris, 20 mM $Na_2SO_4$, pH 7.5 into a 0.22 μm final filter into a 50 L sterile storage bag.

The concentrated, diafiltered harvest was inactivated for virus. Prior to viral inactivation, a solution of 10% Triton X-100, 3% tri(n-butyl) phosphate (TNBP) was prepared. The concentrated, diafiltered harvest was exposed to 1% Triton X-100, 0.3% TNBP for 1 hour in a 36 L glass reaction vessel immediately prior to purification on the Q column.

B. Purification of Gen2 sHuPH20

A Q Sepharose (Pharmacia) ion exchange column (9 L resin, H=29 cm, D=20 cm) was prepared. Wash samples were collected for a determination of pH, conductivity and endotoxin (LAL) assay. The column was equilibrated with 5 column volumes of 10 mM Tris, 20 mM $Na_2SO4$, pH 7.5. Following viral inactivation, the concentrated, diafiltered harvest was loaded onto the Q column at a flow rate of 100 cm/hr. The column was washed with 5 column volumes of 10 mM Tris, 20 mM $Na_2SO_4$, pH 7.5 and 10 mM Hepes, 50 mM NaCl, pH 7.0. The protein was eluted with 10 mM Hepes, 400 mM NaCl, pH 7.0 into a 0.22 μm final filter into sterile bag. The eluate sample was tested for bioburden, protein concentration and enzyme activity. $A_{280}$ absorbance reading were taken at the beginning and end of the exchange.

Phenyl-Sepharose (Pharmacia) hydrophobic interaction chromatography was next performed. A Phenyl-Sepharose (PS) column (19-21 L resin, H=29 cm, D=30 cm) was prepared. The wash was collected and sampled for pH, conductivity and endotoxin (LAL assay). The column was equilibrated with 5 column volumes of 5 mM potassium phosphate, 0.5 M ammonium sulfate, 0.1 mM $CaCl_2$, pH 7.0. The protein eluate from above was supplemented with 2M ammonium sulfate, 1 M potassium phosphate and 1 M CaCl$_2$ stock solutions to yield final concentrations of 5 mM, 0.5 M and 0.1 mM, respectively. The protein was loaded onto the PS column at a flow rate of 100 cm/hr. 5 mM potassium phosphate, 0.5 M ammonium sulfate and 0.1 mM CaCl$_2$ pH 7.0 was added at 100 cm/hr. The flow through was passed through a 0.22 μm final filter into a sterile bag. The flow through was sampled for bioburden, protein concentration and enzyme activity.

An aminophenyl boronate column (ProMedics; 21 L resin, H=29 cm, D=30 cm) was prepared. The wash was collected and sampled for pH, conductivity and endotoxin (LAL assay). The column was equilibrated with 5 column volumes of 5 mM potassium phosphate, 0.5 M ammonium sulfate. The PS purified protein was loaded onto the aminophenyl boronate column at a flow rate of 100 cm/hr. The column was washed with 5 mM potassium phosphate, 0.5 M ammonium sulfate, pH 7.0. The column was washed with 20 mM bicine, 0.5 M ammonium sulfate, pH 9.0. The column was washed with 20 mM bicine, 100 mM sodium chloride, pH 9.0. The protein was eluted with 50 mM Hepes, 100 mM NaCl, pH 6.9 and passed through a sterile filter into a sterile bag. The eluted sample was tested for bioburden, protein concentration and enzyme activity.

The hydroxyapatite (HAP) column (BioRad; 13 L resin, H=20 cm, D=30 cm) was prepared. The wash was collected and test for pH, conductivity and endotoxin (LAL assay). The column was equilibrated with 5 mM potassium phosphate, 100 mM NaCl, 0.1 mM CaCl$_2$, pH 7.0. The aminophenyl boronate purified protein was supplemented to final concentrations of 5 mM potassium phosphate and 0.1 mM CaCl$_2$ and loaded onto the HAP column at a flow rate of 100 cm/hr. The column was washed with 5 mM potassium phosphate, pH 7, 100 mM NaCl, 0.1 mM CaCl$_2$. The column was next washed with 10 mM potassium phosphate, pH 7, 100 mM NaCl, 0.1 mM CaCl$_2$. The protein was eluted with 70 mM potassium phosphate, pH 7.0 and passed through a 0.22 μm sterile filter into a sterile bag. The eluted sample was tested for bioburden, protein concentration and enzyme activity.

The HAP purified protein was then passed through a viral removal filter. The sterilized Virosart filter (Sartorius) was first prepared by washing with 2 L of 70 mM potassium phosphate, pH 7.0. Before use, the filtered buffer was sampled for pH and conductivity. The HAP purified protein was pumped via a peristaltic pump through the 20 nM viral removal filter. The filtered protein in 70 mM potassium phosphate, pH 7.0 was passed through a 0.22 μm final filter into a sterile bag. The viral filtered sample was tested for protein concentration, enzyme activity, oligosaccharide, monosaccharide and sialic acid profiling (as described in Examples 9 to 10, below).

The protein in the filtrate was then concentrated to 10 mg/mL using a 10 kD molecular weight cut off (MWCO) Sartocon Slice tangential flow filtration (TFF) system (Sartorius). The filter was first prepared by washing with 10 mM histidine, 130 mM NaCl, pH 6.0 and the permeate was sampled for pH and conductivity. Following concentration, the concentrated protein was sampled and tested for protein concentration and enzyme activity. A 6× buffer exchange was performed on the concentrated protein into the final buffer: 10 mM histidine, 130 mM NaCl, pH 6.0. Following buffer exchange, the concentrated protein was passed though a 0.22 μm filter into a 20 L sterile storage bag. The protein was sampled and tested for protein concentration, enzyme activity, free sulfhydryl groups, oligosaccharide profiling and osmolarity (as described in Examples 9 to 10, below).

The sterile filtered bulk protein was then aseptically dispensed at 20 mL into 30 mL sterile Teflon vials (Nalgene). The vials were then flash frozen and stored at −20±5° C. Production and purification of soluble rHuPH20 using this method yielded approximately 11 and 15 grams, with specific activity of 95,000 units/mg to 120,000 units/mg.

C. Comparison of Production and Purification of Gen1 and Gen2 sHuPH20

The production and purification of Gen2 soluble rHuPH20 in a 300 L bioreactor cell culture contained some changes in the protocols compared to the production and purification Gen1 soluble rHuPH20 in a 100 L bioreactor cell culture (described in Example 4). Table 25 sets forth exemplary differences, in addition to simple scale up changes, between the methods.

TABLE 25

Exemplary differences between Gen1 and Gen2 soluble rHuPH20 production and purification using the 100 L and 300 L bioreactor cell culture methods

| Process Difference | Gen1 soluble rHuPH20 | Gen2 soluble rHuPH20 |
|---|---|---|
| Cell line | 3D35M | 2B2 |
| Media used to expand cell inoculum | Contains 0.10 μM methotrexate (0.045 mg/L) | Contains 20 μM methotrexate (9 mg/L) |
| Media in 6 L cultures onwards | Contains 0.10 μM methotrexate | Contains no methotrexate |
| 36 L spinner flask | No instrumentation 20 L operating volume. | Equipped with instrumentation that monitors and controls pH, dissolved oxygen, sparge and overlay gas flow rate. 32 L operating volume |
| Final operating volume in bioreactor | Approx. 100 L in a 125 L bioreactor (initial culture volume + 65 L) | Approx. 300 L in a 400 L bioreactor (initial culture volume + 260 L) |
| Culture media in final bioreactor | No rHuInsulin | 5.0 mg/L rHuInsulin |
| Media feed volume | Scaled at 4% of the bioreactor cell culture volume i.e. 3.4, 3.5 and 3.7 L, resulting in a target | Scaled at 4% of the bioreactor cell culture volume i.e. 10.4, 10.8, 11.2 and 11.7 L, resulting |

TABLE 25-continued

Exemplary differences between Gen1 and Gen2 soluble rHuPH20 production and purification using the 100 L and 300 L bioreactor cell culture methods

| Process Difference | Gen1 soluble rHuPH20 | Gen2 soluble rHuPH20 |
| --- | --- | --- |
| | bioreactor volume of ~92 L. | in a target bioreactor volume of ~303 L. |
| Media feed | Feed #1 Medium: CD CHO + 50 g/L Glucose + 8 mM GlutaMAX ™-I<br>Feed #2 (CD CHO + 50 g/L Glucose + 8 mM GlutaMAX ™-I + 1.1 g/L Sodium Butyrate<br>Feed #3: CD CHO + 50 g/L Glucose + 8 mM GlutaMAX ™-I + 1.1 g/L Sodium Butyrate | Feed #1 Medium: 4x CD CHO + 33 g/L Glucose + 32 mM GlutaMAX ™-I + 16.6 g/L Yeastolate + 33 mg/L rHuInsulin<br>Feed #2: 2x CD CHO + 33 g/L Glucose + 16 mM GlutaMAX ™-I + 33.4 g/L Yeastolate + 0.92 g/L Sodium Butyrate<br>Feed #3: 1x CD CHO + 50 g/L Glucose + 10 mM GlutaMAX ™-I + 50 g/L Yeastolate + 1.80 g/L Sodium Butyrate<br>Feed #4: 1 × CD CHO + 33 g/L Glucose + 6.6 mM GlutaMAX ™-I + 50 g/L Yeastolate + 0.92 g/L Sodium Butyrate |
| Filtration of bioreactor cell culture | Four polyethersulfone filters (8.0 μm, 0.65 μm, 0.22 μm and 0.22 μm) in series<br>100 L storage bag | $1^{st}$ stage - Four modules in parallel, each with a layer of diatomaceous earth graded to 4-8 μm and a layer of diatomaceous earth graded to 1.4-1.1 μm, followed by a cellulose membrane.<br>$2^{nd}$ stage - single module containing a layer of diatomaceous earth graded to 0.4-0.11 μm and a layer of diatomaceous earth graded to <0.1 μm, followed by a cellulose membrane.<br>$3^{rd}$ stage - 0.22 μm polyethersulfone filter<br>300 L storage bag<br>Harvested cell culture is supplemented with 10 mM EDTA, 10 mM Tris to a pH of 7.5. |
| Concentration and buffer exchange prior to chromatography | Concentrate with 2 TFF with Millipore Spiral Polyethersulfone 30K MWCO Filter<br>Buffer Exchange the Concentrate 6× with 10 mM Hepes, 25 mM NaCl, pH 7.0<br>20 L sterile storage bag | Concentrate using four Sartorius Sartoslice TFF 30K MWCO Filter<br>Buffer Exchange the Concentrate 10× with 10 mM Tris, 20 mM Na2SO4, pH 7.5<br>50 L sterile storage bag |
| Viral inactivation prior to chromatography | None | Viral inactivation performed with the addition of a 1% Triton X-100, 0.3% Tributyl Phosphate, pH 7.5, |
| $1^{st}$ purification step (Q sepharose) | No absorbance reading | A280 measurements at the beginning and end |
| Viral filtration after chromatography | Pall DV-20 filter (20 nm) | Sartorius Virosart filter (20 nm) |
| Concentration and buffer exchange after chromatography | Hepes/saline pH 7.0 buffer<br>Protein concentrated to 1 mg/ml | Histidine/saline, pH 6.0 buffer<br>Protein concentrated to 10 mg/ml |
| Vial filling | 5 mL and 1 mL fill volumes<br>Stored at - ≦30° C.<br>Glass/rubber stopper | 20 mL fill volumes<br>Stored at ≦20° C.<br>Teflon/screw cap |
| Soluble rHuPH20 yield | Approx. 400-700 mg | Approx. 11-25 g |

Example 9

Determination of Enzymatic Activity of Soluble rHuPH20

Enzymatic activity of soluble rHuPH20 in samples such as cell cultures, purification fractions and purified solutions was determined using a turbidometric assay, which based on the formation of an insoluble precipitate when hyaluronic acid binds with serum albumin. The activity is measured by incubating soluble rHuPH20 with sodium hyaluronate (hyaluronic acid) for a set period of time (10 minutes) and then precipitating the undigested sodium hyaluronate with the addition of acidified serum albumin. The turbidity of the resulting sample is measured at 640 nm after a 30 minute development period. The decrease in turbidity resulting from enzyme activity on the sodium hyaluronate substrate is a measure of the soluble rHuPH20 enzymatic activity. The method is run using a calibration curve generated with dilutions of a soluble rHuPH20 assay working reference standard, and sample activity measurements are made relative to this calibration curve.

Dilutions of the sample were prepared in Enzyme Diluent Solutions. The Enzyme Diluent Solution was prepared by dissolving 33.0±0.05 mg of hydrolyzed gelatin in 25.0 mL of the 50 mM PIPES Reaction Buffer (140 mM NaCl, 50 mM PIPES, pH 5.5) and 25.0 mL of SWFI, and diluting 0.2 mL of 25% Buminate solution into the mixture and vortexing for 30 seconds. This was performed within 2 hours of use and stored on ice until needed. The samples were diluted to an estimated 1-2 U/mL. Generally, the maximum dilution per step did not exceed 1:100 and the initial sample size for the first dilution was not be less than 20 µL. The minimum sample volumes needed to perform the assay were: In-process Samples, FPLC Fractions: 80 µL; Tissue Culture Supernatants: 1 mL; Concentrated Material 80 µL; Purified or Final Step Material: 80 L. The dilutions were made in triplicate in a Low Protein Binding 96-well plate, and 30 µL of each dilution was transferred to Optilux black/clear bottom plates (BD BioSciences).

Dilutions of known soluble rHuPH20 with a concentration of 2.5 U/mL were prepared in Enzyme Diluent Solution to generate a standard curve and added to the Optilux plate in triplicate. The dilutions included 0 U/mL, 0.25 U/mL, 0.5 U/mL, 1.0 U/mL, 1.5 U/mL, 2.0 U/mL, and 2.5 U/mL. "Reagent blank" wells that contained 60 µL of Enzyme Diluent Solution were included in the plate as a negative control. The plate was then covered and warmed on a heat block for 5 minutes at 37° C. The cover was removed and the plate was shaken for 10 seconds. After shaking, the plate was returned to the plate to the heat block and the MULTIDROP 384 Liquid Handling Device was primed with the warm 0.25 mg/mL sodium hyaluronate solution (prepared by dissolving 100 mg of sodium hyaluronate (LifeCore Biomedical) in 20.0 mL of SWFI. This was mixed by gently rotating and/or rocking at 2-8° C. for 2-4 hours, or until completely dissolved). The reaction plate was transferred to the MULTIDROP 384 and the reaction was initiated by pressing the start key to dispense 30 µL sodium hyaluronate into each well. The plate was then removed from the MULTIDROP 384 and shaken for 10 seconds before being transferred to a heat block with the plate cover replaced. The plate was incubated at 37° C. for 10 minutes The MULTIDROP 384 was prepared to stop the reaction by priming the machine with Serum Working Solution and changing the volume setting to 240 µL. (25 mL of Serum Stock Solution [1 volume of Horse Serum (Sigma) was diluted with 9 volumes of 500 mM Acetate Buffer Solution and the pH was adjusted to 3.1 with hydrochloric acid] in 75 mL of 500 mM Acetate Buffer Solution). The plate was removed from the heat block and placed onto the MULTIDROP 384 and 240 µL of serum Working Solutions was dispensed into the wells. The plate was removed and shaken on a plate reader for 10 seconds. After a further 15 minutes, the turbidity of the samples was measured at 640 nm and the enzyme activity (in U/mL) of each sample was determined by fitting to the standard curve.

Specific activity (Units/mg) was calculated by dividing the enzyme activity (U/ml) by the protein concentration (mg/mL).

Example 10

Determination of Sialic Acid and Monosaccharide Content

The sialic acid and monosaccharide content of soluble rHuPH20 can be assessed by reverse phase liquid chromatography (RPLC) following hydrolysis with trifluoroacetic acid. In one example, the sialic acid and monosaccharide content of purified hyaluronidase lot # HUB0701E (1.2 mg/mL; produced and purified essentially as described in Example 8) was determined. Briefly, 100 µg sample was hydrolyzed with 40% (v/v) trifluoroacetic acid at 100° C. for 4 hours in duplicate. Following hydrolysis, the samples were dried down and resuspended in 300 µL water. A 45 µL aliquot from each re-suspended sample was transferred to a new tube and dried down, and 10 µL of a 10 mg/mL sodium acetate solution was added to each. The released monosaccharides were fluorescently labeled by the addition of 50 µL of a solution containing 30 mg/mL 2-aminobenzoic acid, 20 mg/mL sodium cyanoborohydride, approximately 40 mg/mL sodium acetate and 20 mg/mL boric acid in methanol. The mixture was incubated for 30 minutes at 80° C. in the dark. The derivitization reaction was quenched by the addition of 440 µL of mobile phase A (0.2% (v/v) n-butylamine, 0.5% (v/v) phosphoric acid, 1% (v/v) tetrahydrofuran). A matrix blank of water also was hydrolyzed and derivatized as described for the hyaluronidase sample as a negative control. The released monosaccharides were separated by RPLC using an Octadecyl ($C_{18}$) reverse phase column (4.6×250 mm, 5 µm particle size; J. T. Baker) and monitored by fluorescence detection (360 nm excitation, 425 nm emission). Quantitation of the monosaccharide content was made by comparison of the chromatograms from the hyaluronidase sample with chromatograms of monosaccharide standards including N-D-glucosamine (GlcN), N-D-galactosamine (GalN), galactose, fucose and mannose. Table 26 presents the molar ratio of each monosaccharide per hyaluronidase molecule.

TABLE 26

Monosaccharide content of soluble rHuPH20

| Lot | Replicate | GlcN | GalN | Galactose | Mannose | Fucose |
|---|---|---|---|---|---|---|
| HUB0701E | 1 | 14.28 | 0.07* | 6.19 | 25.28 | 2.69 |
|  | 2 | 13.66 | 0.08* | 6.00 | 24.34 | 2.61 |
|  | Average | 13.97 | 0.08* | 6.10 | 24.81 | 2.65 |

*GalN results were below the limit of detection

Example 11

C-Terminal Heterogeneity of Soluble rHuPH20 from 3D35M and 2B2 Cells

C-terminal sequencing was performed on two lots of sHuPH20 produced and purified from 3D35M cells in a 100 L bioreactor volume (Lot HUA0505MA) and 2B2 cells in a 300 L bioreactor volume (Lot HUB0701EB). The lots were separately digested with endoproteinase Asp-N, which specifically cleaves peptide bonds N-terminally at aspartic and cysteic acid. This releases the C-terminal portion of the soluble rHuPH20 at the aspartic acid at position 431 of SEQ ID NO:4. The C-terminal fragments were separated and characterized to determine the sequence and abundance of each population in Lot HUA0505MA and Lot HUB0701EB.

It was observed that the soluble rHuPH20 preparations from 3D35M cells and 2B2 cells displayed heterogeneity, and contained polypeptides that differed from one another in their C-terminal sequence (Tables 27 and 28). This heterogeneity is likely the result of C-terminal cleavage of the expressed 447 amino acid polypeptide (SEQ ID NO:4) by peptidases present in the cell culture medium or other solutions during the production and purification process. The polypeptides in the soluble rHuPH20 preparations have amino acid sequences corresponding to amino acids 1-447, 1-446, 1-445, 1-444 and 1-443 of the soluble rHuPH20 sequence set forth SEQ ID NO:4. The full amino acid sequence of each of these polypeptides is forth in SEQ ID NOS: 4 to 8, respectively. As noted in tables 27 and 28, the abundance of each polypeptide in the soluble rHuPH20 preparations from 3D35M cells and 2B2 cells differs.

TABLE 27

Analysis of C-terminal fragments from Lot HUA0505MA

| Fragment | Amino acid position (relative to SEQ ID NO: 4) | Sequence | Theor. Mass | Exp. Mass | Error | Elution time | Abundance |
|---|---|---|---|---|---|---|---|
| D28a | 431-447 | DAFKLPPMETEEPQIFY (SEQ ID NO: 66) | 2053.97 | 2054.42 | 0.45 | 99.87 | 0.2% |
| D28b | 431-446 | DAFKLPPMETEEPQIF (SEQ ID NO: 67) | 1890.91 | 1891.28 | 0.37 | 97.02 | 18.4% |
| D28c | 431-445 | DAFKLPPMETEEPQI (SEQ ID NO: 68) | 1743.84 | 1744.17 | 0.33 | 86.4 | 11.8% |
| D28d | 431-444 | DAFKLPPMETEEPQ (SEQ ID NO: 69) | 1630.70 | 1631.07 | 0.32 | 74.15 | 56.1% |
| D28e | 431-443 | DAFKLPPMETEEP (SEQ ID NO: 70) | 1502.70 | 1502.98 | 0.28 | 77.36 | 13.6% |
| D28f | 431-442 | DAFKLPPMETEE (SEQ ID NO: 71) | 1405.64 | ND | N/A | N/A | 0.0% |

TABLE 28

Analysis of C-terminal fragments from Lot HUB0701EB

| Fragment | Amino acid position (relative to SEQ ID NO: 4) | Sequence | Theor. Mass | Exp. Mass | Error | Elution time | Abundance |
|---|---|---|---|---|---|---|---|
| D28a | 431-477 | DAFKLPPMETEEPQIFY (SEQ ID NO: 66) | 2053.97 | 2054.42 | 0.45 | 99.89 | 1.9% |
| D28b | 431-446 | DAFKLPPMETEEPQIF (SEQ ID NO: 67) | 1890.91 | 1891.36 | 0.45 | 96.92 | 46.7% |
| D28c | 431-445 | DAFKLPPMETEEPQI (SEQ ID NO: 68) | 1743.84 | 1744.24 | 0.40 | 85.98 | 16.7% |
| D28d | 431-444 | DAFKLPPMETEEPQ (SEQ ID NO: 69) | 1630.70 | 1631.14 | 0.39 | 73.9 | 27.8% |
| D28e | 431-443 | DAFKLPPMETEEP (SEQ ID NO: 70) | 1502.70 | 1503.03 | 0.33 | 77.02 | 6.9% |
| D28f | 431-442 | DAFKLPPMETEE (SEQ ID NO: 71) | 1405.64 | ND | N/A | N/A | 0.0% |

Example 12

Production and Purification of Soluble rHuPH20 in 2500 L Bioreactor Cell Culture The production and purification of soluble rHuPH20 can be scaled up from a 300 L batch-fed bioreactor process (described in Example 8) to a 2500 L batch-fed bioreactor process. Like production of rHuPH20 in a 300 L bioreactor cell culture, the production of rHuPH20 in a 2500 L bioreactor cell culture is performed by first thawing and expanding a vial of 2B2 cells, culturing in a bioreactor, harvesting and clarifying the culture, concentrating and buffer-exchanging the harvest, followed by viral inactivation. The rHuPH20 is then purified from the concentrate using a series of purification steps that utilize Q sepharose, Phenyl sepharose, aminophenyl boronate and hydroxyapatite boronate, followed by viral filtration.

1. Cell Culture Expansion

To generate higher cell numbers required for seeding the 2500 L bioreactor cell culture compared to the 300 L culture, the cell culture is serially expanded through a 125 mL shaker flask, a 250 mL shaker, a 1 L shaker flask, two 2 L shaker flasks, six 2 L shaker flasks, a 25 L WAVE Bioreactor™ (GE Healthcare Life Sciences), a 100 L WAVE Bioreactor™, and a 600 L stirred tank seed bioreactor (ABEC, Inc. Bethlehem, Pa.; Stainless Technology division). At each expansion, the target seeding density is $4 \times 10^5$ cells/mL The temperature throughout the expansion is 37° C. (or between 36° C. and 38° C.) with 7% $CO_2$ (or between 6-8% $CO_2$). The flasks are agitated at approximately 110 RPM (or 90-130 RPM), the 25 L and 100 L WAVE Bioreactor™ are rocked at 20 RPM (or 15-25 or 18-22 RPM, respectively) and the 600 L seed bioreactor is agitated at 90 RPM (or 85-95 RPM).

First, a vial of 2B2 cells ($1 \times 10^7$ cells) from the working cell bank is thawed in a 37° C. water bath for approximately 2 minutes (preferably no more than 5 minutes) before media is added and the cells are centrifuged. The cells are re-suspended to approximately 25 mL (or between 20-30 mL) with fresh media (CD CHO AGT™ with 40 mL/L (8 mM) GlutaMAX™-1 and 20 µM methotrexate in a 125 mL shaker flask and placed in a 37° C., 7% $CO_2$ incubator. When the cell density reaches approximately $8 \times 10^5$ cells/mL, the culture is transferred into a 250 mL shake flask in a 50 mL culture volume (or 45-55 mL). Following incubation, when the cell density reaches approximately $1.6 \times 10^6$ cells/mL, the culture is expanded into a 1 L flask in 200 mL culture volume (or 190-210 mL) and incubated. When the cell density in the 1 L flask reaches approximately $1.6 \times 10^6$ cells/mL, the culture is expanded into 2×2 L flasks, each with a total culture volume of approximately 400 mL (or between 350-450 mL per flask), and incubated. When the cell density in the 2 L flasks reaches approximately $1.2 \times 10^6$ cells/mL, the culture is expanded into 6×2 L flasks, each with a total culture volume of approximately 400 mL (or between 350-450 mL per flask), and incubated. When the cell density in the 2 L flasks reaches approximately $2.5 \times 10^6$ cells/mL, the culture is expanded into a 25 L WAVE Bioreactor™, with a total culture volume of approximately 15 L (or between 14-16 L) and incubated with an air flow of 1.5 L/minute.

When the cell density in the 25 L WAVE Bioreactor™ reaches approximately $2.2 \times 10^6$ cells/mL, the culture is expanded into a 100 L WAVE Bioreactor™, with a total culture volume of approximately 80 L (or between 75-85 L), using CD-CHO AGT™ media that is supplemented with 3.6 g/L methotrexate, 40 mL/L GlutaMAX™-I and 1 mL/L 1N NaOH, and incubated with an air flow of 1.5 L/minute. When the cell density in the 100 L WAVE Bioreactor™ reaches approximately $2.6 \times 10^6$ cells/mL, the culture is expanded into a 600 L seed bioreactor ABEC, Inc. Bethlehem, Pa.; Stainless Technology division) with a total culture volume of approximately 480 L (or between 440-520 L) using CD-CHO AGT™ media that is supplemented with 40 mL/L GlutaMAX™-I and incubated until the cell density in the 600 L bioreactor reaches approximately $1.6 \times 10^6$ cells/mL.

2. rHuPH20 Production

A 3500 L bioreactor with a total volume of 3523 L and a working volume of 500-2500 L (ABEC, Inc, Bethlehem, Pa.) is used for high yield production of rHuPH20. Following sterilization, approximately 1800-2000 L CD-CHO AGT™ media containing 24.3 g/L powdered CD-CHO AGT™, supplemented with 40 mL/L GlutaMAX™-I and 5 mg/L rHuInsulin is added to the bioreactor. Parameters are set to: temperature setpoint, 37° C.; Impeller Speed 75 RPM; Vessel Pressure: 5 psi; Air Sparge 18 L/min; dissolved oxygen: 25%; pH 9.2. Before use, the reactor is checked for contamination. Approximately between 300-500 L of cells (depending on cell count) from the 600 L seed bioreactor culture are inoculated into the cell culture medium in the 3500 L bioreactor at an inoculation density of $4.0 \times 10^5$ viable cells per ml, to reach a total volume of 2100 L. During the 14 day cell incubation, the bioreactor is sampled daily for cell viability, cell density, pH verification, and enzymatic activity. Temperature and dissolved oxygen also are monitored closely.

Nutrient feeds are added during the 14 day bioreactor run, each at approximately 4% v/v. At day 5, approximately 84 L (or 4% v/v) of Feed #1 Medium (81 g/L powdered CD-CHO AGT™+33 g/L Glucose+13.3 mL/L GlutaMAX™-I+83.3 g/L Yeastolate+33 mg/L rHuInsulin) is added. At day 7, approximately 87 L (or 4% v/v) of Feed #2 (40.5 g/L powdered CD-CHO AGT™+33 g/L Glucose+66.7 mL/L GlutaMAX™-I+166.7 g/L Yeastolate+0.92 g/L Sodium butyrate) is added, and culture temperature is changed to 36.5° C. At day 9, approximately 91 L (or 4% v/v) of Feed #3 (20.3 g/L powdered CD-CHO AGT™+50 g/L Glucose+50 mL/L GlutaMAX™-I+250 g/L Yeastolate+1.8 g/L Sodium butyrate) is added, and culture temperature is changed to 36° C. At day 11, approximately 94 L (or 4% v/v) of Feed #4 (20.3 g/L powdered CD-CHO AGT™+33.3 g/L Glucose+33.3 mL/L GlutaMAX™-I+250 g/L Yeastolate+0.92 g/L Sodium butyrate) is added, and culture temperature is changed to 35.5° C. The reactor is harvested at 14 days, yielding 2400-2600 L harvest (typically approximately 2500 L).

The culture is pressure transferred through 20 Millistak filtration system modules (Millipore) in parallel, each containing a layer of diatomaceous earth graded to 4-8 µm and a layer of diatomaceous earth graded to 1.4-1.1 µm, followed by a cellulose membrane, then through a second Millistak filtration system (Millipore) containing 10 modules, each with a layer of diatomaceous earth graded to 0.4-0.11 µm and a layer of diatomaceous earth graded to <0.1 µm, followed by a cellulose membrane, and then through a 0.22 µm final filter into a sterile single use flexible bag with a 350 L capacity. The harvested cell culture fluid is supplemented with 10 mM EDTA and 10 mM Tris, pH 8.4, to a target pH of 7.5. The culture is concentrated 10× with a tangential flow filtration (TFF) apparatus (Pall) using 18-21 $m^2$ of Sartoslice TFF 30 kDa molecular weight cut-off (MWCO) polyether sulfone (PES) filters (Sartorius), followed by a 10× buffer exchange with 10 mM Tris, 20 mM $Na_2SO_4$, pH 7.5 into a 0.22 µM final filter into a 350 L sterile storage bag.

The concentrated, diafiltered harvest is inactivated for virus. Prior to viral inactivation, a solution of 10% Triton X-100, 3% tri(n-butyl) phosphate (TNBP) was prepared. The concentrated, diafiltered harvest was exposed to 1% Triton X-100, 0.3% TNBP up to 2 hours in 500 L stainless steel reaction vessels immediately prior to purification on the Q column.

B. Purification of Gen2 rHuPH20

A Q Sepharose (Pharmacia) ion exchange column (81 L resin, H=26 cm, D=63 cm) is prepared. The column is equilibrated with 5 column volumes of 10 mM Tris, 20 mM $Na_2SO_4$, pH 7.5. Following viral inactivation, the concentrated, diafiltered, viral-inactivated harvest of approximately 250 L is loaded onto the Q column at a flow rate of 150 cm/hr. The column is washed with 5 column volumes of 10 mM Tris, 20 mM $Na_2SO_4$, pH 7.5 and 10 mM Hepes, 50 mM NaCl, pH 7.0. The protein is eluted with 10 mM Hepes, 400 mM NaCl, pH 7.0 into a 0.22 µfinal filter into sterile bag. The eluate sample is tested for bioburden, protein concentration and enzyme activity. $A_{280}$ absorbance reading were taken at the beginning and end of the exchange.

Phenyl-Sepharose (Pharmacia) hydrophobic interaction chromatography is next performed. A Phenyl-Sepharose (PS) column (176 L resin, H=35 cm, D=80 cm) is prepared. The column is equilibrated with 5 column volumes of 5 mM potassium phosphate, 0.5 M ammonium sulfate, 0.1 mM $CaCl_2$, pH 7.0. The protein eluate from above is supplemented with 2M ammonium sulfate, 1 M potassium phosphate and 1 M $CaCl_2$ stock solutions to yield final concentrations of 5 mM, 0.5 M and 0.1 mM, respectively. The protein is loaded onto the PS column at a flow rate of 100 cm/hr. 5 mM potassium phosphate, 0.5 M ammonium sulfate and 0.1 mM $CaCl_2$ pH 7.0 was added at 100 cm/hr. The flow through is passed through a 0.22 µm final filter into a sterile bag. The flow through is sampled for bioburden, protein concentration and enzyme activity.

An aminophenyl boronate column (ProMedics; 176 L resin, H=35 cm, D=80 cm) is then prepared. The column is equilibrated with 5 column volumes of 5 mM potassium phosphate, 0.5 M ammonium sulfate. The PS-purified protein is loaded onto the aminophenyl boronate column at a flow rate of 50 cm/hr. The flow rate was increased to 100 cm/hr for the remainder of the process. The column was first washed with 5 mM potassium phosphate, 0.5 M ammonium sulfate, pH 7.0, then 20 mM bicine, 0.5 M ammonium sulfate, pH 9.0, and then with 20 mM bicine, 100 mM sodium chloride, pH 9.0. The protein is eluted with 50 mM Hepes, 100 mM NaCl, pH 6.9 and passed through a sterile filter into a sterile bag. The eluted sample is tested for bioburden, protein concentration and enzyme activity.

The hydroxyapatite (HAP) column (BioRad; 116 L resin, H=23 cm, D=80 cm) is prepared. The column is equilibrated with 5 mM potassium phosphate, 100 mM NaCl, 0.1 mM $CaCl_2$, pH 7.0. The aminophenyl boronate purified protein is supplemented to final concentrations of 5 mM potassium phosphate and 0.1 mM $CaCl_2$ and loaded onto the HAP column at a flow rate of 100 cm/hr. The column is first washed with 5 mM potassium phosphate, pH 7, 100 mM NaCl, 0.1 mM $CaCl_2$, then 10 mM potassium phosphate, pH 7, 100 mM NaCl, 0.1 mM $CaCl_2$. The protein is eluted with 70 mM potassium phosphate, pH 7.0 and passed through a 0.22 µm sterile filter into a sterile bag. The eluted sample is tested for bioburden, protein concentration and enzyme activity.

The HAP purified protein is then passed through a viral removal filter. The sterilized Viosart filter (Sartorius) is first prepared by washing with 2 L of 70 mM potassium phosphate, pH 7.0. The HAP purified protein is pumped via a peristaltic pump through the 20 nM viral removal filter. The filtered protein in 70 mM potassium phosphate, pH 7.0 is then passed through a 0.22 µm final filter into a sterile bag. The viral filtered sample is tested for protein concentration, enzyme activity, oligosaccharide, monosaccharide and sialic acid profiling (as described in Examples 9 to 10, below).

The protein in the filtrate was then concentrated 8-12× using three 10 kD molecular weight cut off (MWCO) Sartocon PES cassettes, each with a filter surface area of 0.7 $m^2$, for a total surface area of 2.1 $m^2$. Following concentration, the concentrated protein was sampled and tested for protein concentration and enzyme activity. A 10× diafiltration is then performed on the concentrated protein. This can be performed one of two ways: 1) using a 20 mM histidine, 130 mM NaCl, pH 6.5 buffer and 1% polysorbate 80; or 2) using a 10 mM histidine, 130 mM NaCl, pH 6.5 buffer. The concentrated, diafiltered bulk protein is at a concentration of approximately 10 mg/mL. Following buffer exchange, the concentrated protein is passed though a 0.22 µm filter into a 20 L sterile storage bag.

The sterile filtered bulk protein is then aseptically dispensed at 400 mL into 1 L sterile PFA Nalgene bottles. The bottles are then flash frozen in a liquid nitrogen bath and stored at less that −20° C. for the bulk protein that does not contain the polysorbate 80, and less that −70° C. for the bulk protein that does contain the polysorbate 80.

Table 29 sets forth some exemplary differences between production of rHuPH20 in a 300 L and 2500 L bioreactor culture

TABLE 29

Exemplary differences between production of rHuPH20 in a 300 L and 2500 L bioreactor culture

| Process Difference | 300 L cell culture | 2500 L cell culture |
|---|---|---|
| Cell line | 2B2 | 2B2 |
| Media used to expand cell inoculum | Contains 20 µM methotrexate (9 mg/L) | Contains 20 µM methotrexate (9 mg/L) |
| Cell expansion | Expanded through 125 mL flask, 250 mL flask, 1 L flask, 6 L flask and 36 L flask. | Expanded through 125 mL flask, 250 mL flask, 1 L flask, 2 × 2 L shaker flasks, 6 × 2 L shaker flasks, 25 L WAVE Bioreactor ™, 100 L WAVE Bioreactor ™, and a 600 L stirred tank seed bioreactor |
| Final operating volume in bioreactor | Approx. 300 L in a 400 L bioreactor | Approx. 2500 L in a 3500 L bioreactor |
| Culture media in at bioreactor inoculation | CD CHO with 5.0 mg/L rHuInsulin | CD CHO AGT ™ with 5.0 mg/L rHuInsulin |

TABLE 29-continued

Exemplary differences between production of rHuPH20 in a 300 L and 2500 L bioreactor culture

| Process Difference | 300 L cell culture | 2500 L cell culture |
| --- | --- | --- |
| Media feed volume | 40 mL/L (8 mM) GlutaMAX ™-I Scaled at 4% of the bioreactor cell culture volume i.e. approximately 10.4, 10.8, 11.2 and 11.7 L, resulting in a target bioreactor volume of ~300 L. | 40 mL/L (8 mM) GlutaMAX ™-I Scaled at 4% of the bioreactor cell culture volume i.e. approximately 84, 87, 91, and 94 L, resulting in a target bioreactor volume of ~2500 L. |
| Media feed | Feed #1 Medium: 4x CD CHO + 33 g/L Glucose + 32 mM GlutaMAX ™-I + 16.6 g/L Yeastolate + 33 mg/L rHuInsulin Feed #2: 2x CD CHO + 33 g/L Glucose + 16 mM GlutaMAX ™-I + 33.4 g/L Yeastolate + 0.92 g/L Sodium Butyrate Feed #3: 1x CD CHO + 50 g/L Glucose + 10 mM GlutaMAX ™-I + 50 g/L Yeastolate + 1.80 g/L Sodium Butyrate Feed #4: 1x CD CHO + 33 g/L Glucose + 6.7 mM GlutaMAX ™-I + 50 g/L Yeastolate + 0.92 g/L Sodium Butyrate | Feed #1 Medium: 81 g/L powdered CD-CHO AGT ™ + 33 g/L Glucose + 26.6 mM GlutaMAX ™-I + 83.3 g/L Yeastolate + 33 mg/L rHuInsulin Feed #2: 40.5 g/L powdered CD-CHO AGT ™ + 33 g/L Glucose + 13.4 mM GlutaMAX ™-I + 166.7 g/L Yeastolate + 0.92 g/L Sodium butyrate Feed #3: 20.3 g/L powdered CD-CHO AGT ™ + 50 g/L Glucose + 10 mM GlutaMAX ™-I + 250 g/L Yeastolate + 1.8 g/L Sodium butyrate Feed #4: 20.3 g/L powdered CD-CHO AGT ™ + 33.3 g/L Glucose + 6.7 mM GlutaMAX ™-I + 250 g/L Yeastolate + 0.92 g/L Sodium butyrate |
| Filtration of bioreactor cell culture | $1^{st}$ stage - 4 modules in parallel, each with a layer of diatomaceous earth graded to 4-8 μm and a layer of diatomaceous earth graded to 1.4-1.1 μm, followed by a cellulose membrane. $2^{nd}$ stage - single module containing a layer of diatomaceous earth graded to 0.4-0.11 μm and a layer of diatomaceous earth graded to <0.1 μm, followed by a cellulose membrane. $3^{rd}$ stage - 0.22 μm polyethersulfone filter 300 L storage bag | 1 t stage - 20 modules in parallel, each with a layer of diatomaceous earth graded to 4-8 μm and a layer of diatomaceous earth graded to 1.4-1.1 μm, followed by a cellulose membrane. $2^{nd}$ stage - 10 modules containing a layer of diatomaceous earth graded to 0.4-0.11 μm and a layer of diatomaceous earth graded to <0.1 μm, followed by a cellulose membrane. $3^{rd}$ stage - 0.22 μm polyethersulfone filter 350 L storage bag |
| Concentration and buffer exchange prior to chromatography | Concentrate using four Sartorius Sartoslice TFF 30K MWCO Filter Buffer Exchange the Concentrate 10x with 10 mM Tris, 20 mM Na2SO4, pH 7.5 50 L sterile storage bag | Concentrate with 2 TFF with Millipore Spiral Polyethersulfone 30K MWCO Filter Buffer Exchange the Concentrate 6x with 10 mM Hepes, 25 mM NaCl, pH 7.0 20 L sterile storage bag |
| Q sepharose column | 9 L resin, H = 29 cm, D = 20 cm | 81 L resin, H = 26 cm, D = 63 cm |
| A Phenyl-Sepharose (PS) column | 19-21 L resin, H = 29 cm, D = 30 cm | 176 L resin, H = 35 cm, D = 80 cm |
| aminophenyl boronate column | 21 L resin, H = 29 cm, D = 30 cm | 176 L resin, H = 35 cm, D = 80 cm |
| hydroxyapatite (HAP) column | 13 L resin, H = 20 cm, D = 30 cm | 116 L resin, H = 23 cm, D = 80 cm |
| Protein Concentration | Single 10 kD MWCO Sartocon Slice tangential flow filtration (TFF) 6x buffer exchange with 10 mM histidine, 130 mM | Three 10 kD molecular weight cut off (MWCO) Sartocon PES cassettes 10x diafiltration with: 1) 20 mM histidine, 130 mM |

TABLE 29-continued

Exemplary differences between production of rHuPH20 in a 300 L and 2500 L bioreactor culture

| Process Difference | 300 L cell culture | 2500 L cell culture |
|---|---|---|
| | NaCl, pH 6.0 | NaCl, pH 6.5 buffer and 1% polysorbate 80; or 2) 10 mM histidine, 130 mM NaCl, pH 6.5 buffer. |
| Vial filling | 20 mL fill volumes Stored at ≦20° C. | 400 mL fill volumes Stored at ≦20° C. if protein does not polysorbate 80, or ≦70° C. if protein does contain polysorbate 80 |

Since modifications will be apparent to those of skill in this art, it is intended that this invention be limited only by the scope of the appended claims.

The invention claimed is:

1. A method for producing soluble rHuPH20, comprising:
a) inoculating cell medium in a bioreactor with an inoculum of cells that encode soluble rHuPH20 to produce a cell culture, wherein:
the cells comprise between 150 and 300 copies of nucleic acid encoding soluble rHuPH20;
the bioreactor contains at least 100 liters of cell culture;
about $10^{10}$-$10^{11}$ cells are inoculated per 100 liters cell culture; and
the cells are cultured at a set temperature;
b) feeding the cells with a first feed medium containing glucose, L-alanyl-L-glutamine, human insulin and yeast extract in amounts sufficient to increase cell growth and peak cell density, and to increase soluble rHuPH20 synthesis, wherein the feed medium is added to the culture at a volume of 0.5% or about 0.5% to 20% or about 20% of the cell culture volume;
c) feeding the cells with a second feed medium containing glucose, L-alanyl-L-glutamine, yeast extract and sodium butyrate in amounts sufficient to increase soluble rHuPH20 synthesis and induce cell cycle arrest; and
lowering the temperature compared to the temperature in step a) to a temperature sufficient to increase cell cycle arrest, increase cell viability and stabilize the soluble hyaluronidase; wherein:
the amount of L-alanyl-L-glutamine is decreased compared to the amount of L-alanyl-L-glutamine in step b);
the amount of yeast extract is increased compared to the amount of yeast extract in step b); and
the feed medium is added to the culture at a volume of 0.5% or about 0.5% to 20% of the cell culture volume;
d) feeding the cells with a third feed medium containing glucose, L-alanyl-L-glutamine, yeast extract and sodium butyrate in amounts sufficient to increase soluble rHuPH20 synthesis and increase cell cycle arrest, and
lowering the temperature compared to the temperature in step c) to a temperature sufficient to increase cell cycle arrest, increase cell viability and stabilize the soluble hyaluronidase; wherein:
the amount of L-alanyl-L-glutamine decreased compared to the amount of L-alanyl-L-glutamine in step c);
the amounts of yeast extract, glucose and sodium butyrate are increased compared to the amounts of yeast extract, glucose and sodium butyrate in step c); and
the feed medium is added to the culture at a volume of 0.5% or about 0.5% to 20% of the cell culture volume;
e) feeding the cells with a fourth feed medium containing glucose, L-alanyl-L-glutamine, yeast extract and sodium butyrate in amounts sufficient to increase soluble rHuPH20 synthesis and increase cell cycle arrest, and
lowering the temperature compared to the temperature in step d) to a temperature sufficient to increase cell cycle arrest, increase cell viability and stabilize the soluble hyaluronidase; wherein:
the amount of L-alanyl-L-glutamine and glucose is decreased compared to the amount of L-alanyl-L-glutamine and glucose in step d);
the amount of sodium butyrate is decreased compared to the amount of sodium butyrate in step d); and
the feed medium is added to the culture at a volume of 0.5% or about 0.5% to 20% of the cell culture volume;
f) continuing to culture the cells until viability drops below at least or about 50%;
g) obtaining the harvest cell culture fluid; and
h) purifying the rHuPH20 from the harvest cell culture fluid.

2. The method of claim 1, wherein the temperature in step a) is or is about 37° C.

3. The method of claim 1, wherein the temperature in step c) is or is about 36.5° C.

4. The method of claim 1, wherein the temperature in step d) is 36° C.

5. The method of claim 1, wherein the temperature in step e) is 35.5° C.

6. The method of claim 1, wherein the harvest cell culture fluid is filtered prior to purification.

7. The method of claim 1, wherein the soluble rHuPH20 purification is effected by column chromatography.

8. The method of claim 7, wherein the column chromatography comprises beaded crosslinked agarose column chromatography, beaded crosslinked phenyl-substituted agarose column chromatography, amino phenyl boronate column chromatography and hydroxyapatite column chromatography.

9. The method of claim 1, wherein the feed medium is added to the culture at a volume of 4% or about 4% of the cell culture volume.

10. A method for producing soluble rHuPH20, comprising:
a) inoculating cell medium in a bioreactor with an inoculum of cells that encode soluble rHuPH20 to produce a cell culture, wherein:
the cells comprise between 150 and 300 copies of nucleic acid encoding soluble rHuPH20;
the bioreactor contains at least 100 liters of cell culture;
the inoculation cell density is at or about $4 \times 10^5$ cells/mL; and
the cells are cultured at or at about 37° C.;
b) feeding the cells with a first feed medium containing or containing about 33 g/L glucose, 32 mM L-alanyl-L-glutamine, 16.6 g/L yeast extract and 33 mg/L insulin, wherein the feed medium is added to the culture at a volume of 4% or about 4% of the cell culture volume;
c) feeding the cells with a second feed medium containing or containing about 33 g/L glucose, 16 mM L-alanyl-L-glutamine, 33.4 g/L yeast extract and 0.92 g/L sodium butyrate, wherein the feed medium is added to the culture at a volume of 4% or about 4% of the cell culture volume; and
the temperature is lowered to 36.5° C.;
d) feeding the cells with a third feed medium containing or containing about 50 g/L glucose, 10 mM L-alanyl-L-glutamine, 50 g/L yeast extract and 1.8 g/L sodium butyrate, wherein the feed medium is added to the culture at a volume of 4% or about 4% of the cell culture volume; and
the temperature is lowered to 36° C.;
e) feeding the cells with a fourth feed medium containing or containing about 33 g/L glucose, 6.6 mM L-alanyl-L-glutamine, 50 g/L yeast extract and 0.92 g/L sodium butyrate, wherein the feed medium is added to the culture at a volume of 4% or about 4% of the cell culture volume; and
the temperature is lowered to 36° C.;
f) continuing to culture the cells until viability drops below at least or about 50%;
g) obtaining the harvest cell culture fluid;
h) filtering the harvest cell culture fluid;
i) purifying the rHuPH20 from the harvest culture fluid using beaded crosslinked agarose column chromatography, beaded crosslinked phenyl-substituted agarose column chromatography, amino phenyl boronate column chromatography and hydroxyapatite column chromatography.

11. A method for producing soluble rHuPH20, comprising:
a) inoculating cell medium in a bioreactor with an inoculum of cells that encode soluble rHuPH20 to produce a cell culture, wherein:
the cells comprise between 150 and 300 copies of nucleic acid encoding soluble rHuPH20;
the bioreactor contains at least 100 liters of cell culture;
the inoculation cell density is at or about $4 \times 10^5$ cells/mL; and
the cells are cultured at or about 37° C.;
b) feeding the cells with a first feed medium containing or containing about 33 g/L glucose, 32 mM L-alanyl-L-glutamine, 83.3 g/L yeast extract and 33 mg/L insulin, wherein the feed medium is added to the culture at a volume of 4% or about 4% of the cell culture volume;
c) feeding the cells with a second feed medium containing or containing about 33 g/L glucose, 13 mM L-alanyl-L-glutamine, 166.7 g/L yeast extract and 0.92 g/L sodium butyrate, wherein the feed medium is added to the culture at a volume of at or about 4% of the cell culture volume; and
the temperature is lowered to 36.5° C.;
d) feeding the cells with a third feed medium containing or containing about 50 g/L glucose, 10 mM L-alanyl-L-glutamine; 250 g/L yeast extract and 1.8 g/L sodium butyrate, wherein the feed medium is added to the culture at a volume of 4% or about 4% of the cell culture volume; and
the temperature is lowered to 36° C.;
e) feeding the cells with a fourth feed medium containing or containing about 33 g/L glucose, 6.7 mM L-alanyl-L-glutamine, 250 g/L yeast extract and 0.92 g/L sodium butyrate, wherein the feed medium is added to the culture at a volume of 4% or about 4% of the cell culture volume; and
the temperature is lowered to 36° C.;
f) continuing to culture the cells until viability drops below at least or about 50%;
g) obtaining the harvest cell culture fluid;
h) filtering the harvest cell culture fluid; and
i) purifying the rHuPH20 from the harvest culture fluid using beaded crosslinked agarose column chromatography, beaded crosslinked phenyl-substituted agarose column chromatography, amino phenyl boronate column chromatography and hydroxyapatite column chromatography.

12. The method of claim 1, wherein at least or about 0.5, 1, 5, 10, 15, 20, 25, 30, 35 or 40 grams of soluble rHuPH20 is produced per 100 L of cell culture.

13. The method of claim 1, wherein the specific activity of the soluble rHuPH20 is at least or about 80000, 100000, 120000, 140000, 160000 or 180,000 units/mg.

14. The method of claim 1, wherein the volume of cell culture in the bioreactor is or is about 200, 300, 400, 500, 1000, 1500, 2000, 2500, 3000 or 3500 liters.

15. The method of claim 1, wherein the cells that encode soluble rHuPH20 are DG44 CHO cells.

16. The method of claim 1, wherein the rHuPH20 is encoded by nucleic acid set forth in SEQ ID NO:47.

* * * * *

UNITED STATES PATENT AND TRADEMARK OFFICE
CERTIFICATE OF CORRECTION

PATENT NO. : 8,187,855 B2
APPLICATION NO. : 12/735868
DATED : May 29, 2012
INVENTOR(S) : Baker et al.

Page 1 of 3

It is certified that error appears in the above-identified patent and that said Letters Patent is hereby corrected as shown below:

At column 2, line 64, please replace "step d) is 35.5°C" with --step e) is 35.5°C--.

At column 3, line 30, please replace "temperature is lowered to 36°C" with --temperature is lowered to 35.5°C--.

At column 3, line 67, please replace "temperature is lowered to 36°C" with --temperature is lowered to 35.5°C--.

Column 225, lines 16 to 61 should read
10. A method for producing soluble rHuPH20, comprising:
a) inoculating cell medium in a bioreactor with an inoculum of cells that encode soluble rHuPH20 to produce a cell culture, wherein:
the cells comprise between 150 and 300 copies of nucleic acid encoding soluble rHuPH20;
the bioreactor contains at least 100 liters of cell culture;
the inoculation cell density is at or about $4 \times 10^5$ cells/mL; and
the cells are cultured at or at about 37 °C;
b) feeding the cells with a first feed medium containing or containing about 33 g/L glucose, 32 mM L-alanyl-L-glutamine, 16.6 g/L yeast extract and 33 mg/L insulin, wherein the feed medium is added to the culture at a volume of 4 % or about 4% of the cell culture volume;
c) feeding the cells with a second feed medium containing or containing about 33 g/L glucose, 16 mM L-alanyl-L-glutamine, 33.4 g/L yeast extract and 0.92 g/L sodium butyrate, wherein the feed medium is added to the culture at a volume of 4 % or about 4 % of the cell culture volume; and
the temperature is lowered to 36.5 °C;
d) feeding the cells with a third feed medium containing or containing about 50 g/L glucose, 10 mM L-alanyl-L-glutamine, 50 g/L yeast extract and 1.8 g/L sodium butyrate, wherein the feed medium is added to the culture at a volume of 4 % or about 4% of the cell culture volume; and Signed and Sealed this
Eighth Day of January, 2013

David J. Kappos
*Director of the United States Patent and Trademark Office* the temperature is lowered to 36 °C;
e)     feeding the cells with a fourth feed medium containing or containing about 33 g/L glucose, 6.6 mM L-alanyl-L-glutamine, 50 g/L yeast extract and 0.92 g/L sodium butyrate, wherein the feed medium is added to the culture at a volume of 4 % or about 4% of the cell culture volume; and the temperature is lowered to 35.5 °C;
f)     continuing to culture the cells until viability drops below at least or about 50%;
g)     obtaining the harvest cell culture fluid;
h)     filtering the harvest cell culture fluid;
i)     purifying the rHuPH20 from the harvest culture fluid using beaded crosslinked agarose column chromatography, beaded crosslinked phenyl-substituted agarose column chromatography, amino phenyl boronate column chromatography and hydroxyapatite column chromatography.

Column 226, lines 1 to 46 should read

11.     A method for producing soluble rHuPH20, comprising:
a)     inoculating cell medium in a bioreactor with an inoculum of cells that encode soluble rHuPH20 to produce a cell culture, wherein:

the cells comprise between 150 and 300 copies of nucleic acid encoding soluble rHuPH20;

the bioreactor contains at least 100 liters of cell culture;

the inoculation cell density is at or about $4 \times 10^5$ cells/mL; and the cells are cultured at or about 37 °C;
b)     feeding the cells with a first feed medium containing or containing about 33 g/L glucose, 32 mM L-alanyl-L-glutamine, 83.3 g/L yeast extract and 33 mg/L insulin, wherein the feed medium is added to the culture at a volume of 4 % or about 4% of the cell culture volume;
c)     feeding the cells with a second feed medium containing or containing about 33 g/L glucose, 13 mM L-alanyl-L-glutamine, 166.7 g/L yeast extract and 0.92 g/L sodium butyrate, wherein the feed medium is added to the culture at a volume of at or about 4% of the cell culture volume; and the temperature is lowered to 36.5 °C;
d)     feeding the cells with a third feed medium containing or containing about 50 g/L glucose, 10 mM L-alanyl-L-glutamine, 250 g/L yeast extract and 1.8 g/L sodium butyrate, wherein the feed medium is added to the culture at a volume of 4 % or about 4% of the cell culture volume; and the temperature is lowered to 36 °C;
e)     feeding the cells with a fourth feed medium containing or containing about 33 g/L glucose, 6.7 mM L-alanyl-L-glutamine, 250 g/L yeast extract and 0.92 g/L sodium butyrate, wherein the feed medium is added to the culture at a volume of 4 % or about 4% of the cell culture volume; and the temperature is lowered to 35.5 °C;

f) continuing to culture the cells until viability drops below at least or about 50%;
g) obtaining the harvest cell culture fluid;
h) filtering the harvest cell culture fluid; and
i) purifying the rHuPH20 from the harvest culture fluid using beaded crosslinked agarose column chromatography, beaded crosslinked phenyl-substituted agarose column chromatography, amino phenyl boronate column chromatography and hydroxyapatite column chromatography.

SEQUENCE LISTING

<160> NUMBER OF SEQ ID NOS: 71

<210> SEQ ID NO 1
<211> LENGTH: 509
<212> TYPE: PRT
<213> ORGANISM: Homo sapiens
<220> FEATURE:
<223> OTHER INFORMATION: precursor human PH20

<400> SEQUENCE: 1

```
Met Gly Val Leu Lys Phe Lys His Ile Phe Phe Arg Ser Phe Val Lys
  1               5                  10                  15

Ser Ser Gly Val Ser Gln Ile Val Phe Thr Phe Leu Leu Ile Pro Cys
             20                  25                  30

Cys Leu Thr Leu Asn Phe Arg Ala Pro Pro Val Ile Pro Asn Val Pro
         35                  40                  45

Phe Leu Trp Ala Trp Asn Ala Pro Ser Glu Phe Cys Leu Gly Lys Phe
     50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220
```

```
Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
            245                 250                 255

Thr Ala Leu Tyr Pro Ser Ile Tyr Leu Asn Thr Gln Gln Ser Pro Val
        260                 265                 270

Ala Ala Thr Leu Tyr Val Arg Asn Arg Val Arg Glu Ala Ile Arg Val
    275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505

<210> SEQ ID NO 2
<211> LENGTH: 474
<212> TYPE: PRT
<213> ORGANISM: Homo sapiens
<220> FEATURE:
<223> OTHER INFORMATION: Mature PH20

<400> SEQUENCE: 2

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
```

```
                85                  90                  95
Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
                195                 200                 205

Lys Arg Asn Asp Asp Leu Ser Trp Leu Trp Asn Glu Ser Thr Ala Leu
                210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270

Phe Thr Asp Gln Val Leu Lys Phe Leu Ser Gln Asp Glu Leu Val Tyr
                275                 280                 285

Thr Phe Gly Glu Thr Val Ala Leu Gly Ala Ser Gly Ile Val Ile Trp
                290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
                370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln Ile Phe Tyr Asn
                435                 440                 445

Ala Ser Pro Ser Thr Leu Ser Ala Thr Met Phe Ile Val Ser Ile Leu
450                 455                 460

Phe Leu Ile Ile Ser Ser Val Ala Ser Leu
465                 470

<210> SEQ ID NO 3
<211> LENGTH: 482
<212> TYPE: PRT
<213> ORGANISM: Homo sapiens
<220> FEATURE:
```

<223> OTHER INFORMATION: precursor soluble rHuPH20

<400> SEQUENCE: 3

```
Met Gly Val Leu Lys Phe Lys His Ile Phe Phe Arg Ser Phe Val Lys
 1               5                  10                  15

Ser Ser Gly Val Ser Gln Ile Val Phe Thr Phe Leu Leu Ile Pro Cys
             20                  25                  30

Cys Leu Thr Leu Asn Phe Arg Ala Pro Pro Val Ile Pro Asn Val Pro
         35                  40                  45

Phe Leu Trp Ala Trp Asn Ala Pro Ser Glu Phe Cys Leu Gly Lys Phe
     50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
```

```
                       405                 410                 415
Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445

Val Lys Asp Thr Asp Ala Val Asp Val Cys Ile Ala Asp Gly Val Cys
            450                 455                 460

Ile Asp Ala Phe Leu Lys Pro Pro Met Glu Thr Glu Glu Pro Gln Ile
465                 470                 475                 480

Phe Tyr

<210> SEQ ID NO 4
<211> LENGTH: 447
<212> TYPE: PRT
<213> ORGANISM: Homo sapiens
<220> FEATURE:
<223> OTHER INFORMATION: soluble rHuPH20 1-447

<400> SEQUENCE: 4

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285
```

-continued

Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln Ile Phe Tyr
435                 440                 445

<210> SEQ ID NO 5
<211> LENGTH: 446
<212> TYPE: PRT
<213> ORGANISM: Homo sapiens
<220> FEATURE:
<223> OTHER INFORMATION: soluble rHuPH20 1-446

<400> SEQUENCE: 5

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
                35                  40                  45

Thr Gly Gln Gly Val Thr Ile Phe Tyr Val Asp Arg Leu Gly Tyr Tyr
50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
                115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
                195                 200                 205

Lys Arg Asn Asp Asp Leu Ser Trp Leu Trp Asn Glu Ser Thr Ala Leu

```
                 210                 215                 220
Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
        290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln Ile Phe
            435                 440                 445

<210> SEQ ID NO 6
<211> LENGTH: 445
<212> TYPE: PRT
<213> ORGANISM: Homo sapiens
<220> FEATURE:
<223> OTHER INFORMATION: soluble rHuPH20 1-445

<400> SEQUENCE: 6

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140
```

```
Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
            165                 170                 175

Pro Asn His Leu Trp Gly Tyr Tyr Leu Phe Pro Asp Cys Tyr Asn His
        180                 185                 190

His Tyr Lys Lys Pro Gly Tyr Asn Gly Ser Cys Phe Asn Val Glu Ile
    195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
            245                 250                 255

Pro Asp Ala Lys Ser Pro Leu Pro Val Phe Ala Tyr Thr Arg Ile Val
        260                 265                 270

Phe Thr Asp Gln Val Leu Lys Phe Leu Ser Gln Asp Glu Leu Val Tyr
    275                 280                 285

Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
            325                 330                 335

Ala Ala Lys Met Cys Ser Gln Val Leu Cys Gln Glu Gln Gly Val Cys
        340                 345                 350

Ile Arg Lys Asn Trp Asn Ser Ser Asp Tyr Leu His Leu Asn Pro Asp
    355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
            405                 410                 415

Thr Asp Ala Val Asp Val Cys Ile Ala Asp Gly Val Cys Ile Asp Ala
        420                 425                 430

Phe Leu Lys Pro Pro Met Glu Thr Glu Glu Pro Gln Ile
    435                 440                 445

<210> SEQ ID NO 7
<211> LENGTH: 444
<212> TYPE: PRT
<213> ORGANISM: Homo sapiens
<220> FEATURE:
<223> OTHER INFORMATION: soluble rHuPH20 1-444

<400> SEQUENCE: 7

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60
```

```
Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                 85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln
        435                 440

<210> SEQ ID NO 8
<211> LENGTH: 443
<212> TYPE: PRT
<213> ORGANISM: Homo sapiens
<220> FEATURE:
<223> OTHER INFORMATION: soluble rHuPH20 1-443
```

<400> SEQUENCE: 8

```
Leu Asn Phe Arg Ala Pro Pro Val Ile Pro Asn Val Pro Phe Leu Trp
 1               5                  10                  15
Ala Trp Asn Ala Pro Ser Glu Phe Cys Leu Gly Lys Phe Asp Glu Pro
            20                  25                  30
Leu Asp Met Ser Leu Phe Ser Phe Ile Gly Ser Pro Arg Ile Asn Ala
        35                  40                  45
Thr Gly Gln Gly Val Thr Ile Phe Tyr Val Asp Arg Leu Gly Tyr Tyr
    50                  55                  60
Pro Tyr Ile Asp Ser Ile Thr Gly Val Thr Val Asn Gly Gly Ile Pro
65                  70                  75                  80
Gln Lys Ile Ser Leu Gln Asp His Leu Asp Lys Ala Lys Lys Asp Ile
                85                  90                  95
Thr Phe Tyr Met Pro Val Asp Asn Leu Gly Met Ala Val Ile Asp Trp
            100                 105                 110
Glu Glu Trp Arg Pro Thr Trp Ala Arg Asn Trp Lys Pro Lys Asp Val
        115                 120                 125
Tyr Lys Asn Arg Ser Ile Glu Leu Val Gln Gln Asn Val Gln Leu
    130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
Pro Asn His Leu Trp Gly Tyr Tyr Leu Phe Pro Asp Cys Tyr Asn His
            180                 185                 190
His Tyr Lys Lys Pro Gly Tyr Asn Gly Ser Cys Phe Asn Val Glu Ile
        195                 200                 205
Lys Arg Asn Asp Asp Leu Ser Trp Leu Trp Asn Glu Ser Thr Ala Leu
    210                 215                 220
Tyr Pro Ser Ile Tyr Leu Asn Thr Gln Gln Ser Pro Val Ala Ala Thr
225                 230                 235                 240
Leu Tyr Val Arg Asn Arg Val Arg Glu Ala Ile Arg Val Ser Lys Ile
                245                 250                 255
Pro Asp Ala Lys Ser Pro Leu Pro Val Phe Ala Tyr Thr Arg Ile Val
            260                 265                 270
Phe Thr Asp Gln Val Leu Lys Phe Leu Ser Gln Asp Glu Leu Val Tyr
        275                 280                 285
Thr Phe Gly Glu Thr Val Ala Leu Gly Ala Ser Gly Ile Val Ile Trp
    290                 295                 300
Gly Thr Leu Ser Ile Met Arg Ser Met Lys Ser Cys Leu Leu Leu Asp
305                 310                 315                 320
Asn Tyr Met Glu Thr Ile Leu Asn Pro Tyr Ile Ile Asn Val Thr Leu
                325                 330                 335
Ala Ala Lys Met Cys Ser Gln Val Leu Cys Gln Glu Gln Gly Val Cys
            340                 345                 350
Ile Arg Lys Asn Trp Asn Ser Ser Asp Tyr Leu His Leu Asn Pro Asp
        355                 360                 365
Asn Phe Ala Ile Gln Leu Glu Lys Gly Gly Lys Phe Thr Val Arg Gly
    370                 375                 380
Lys Pro Thr Leu Glu Asp Leu Glu Gln Phe Ser Glu Lys Phe Tyr Cys
385                 390                 395                 400
Ser Cys Tyr Ser Thr Leu Ser Cys Lys Glu Lys Ala Asp Val Lys Asp
                405                 410                 415
```

-continued

```
Thr Asp Ala Val Asp Val Cys Ile Ala Asp Gly Val Cys Ile Asp Ala
                420                 425                 430
Phe Leu Lys Pro Pro Met Glu Thr Glu Glu Pro
            435                 440

<210> SEQ ID NO 9
<211> LENGTH: 442
<212> TYPE: PRT
<213> ORGANISM: Homo sapiens
<220> FEATURE:
<223> OTHER INFORMATION: soluble rHuPH20 1-442

<400> SEQUENCE: 9

Leu Asn Phe Arg Ala Pro Pro Val Ile Pro Asn Val Pro Phe Leu Trp
  1               5                  10                  15
Ala Trp Asn Ala Pro Ser Glu Phe Cys Leu Gly Lys Phe Asp Glu Pro
                 20                  25                  30
Leu Asp Met Ser Leu Phe Ser Phe Ile Gly Ser Pro Arg Ile Asn Ala
             35                  40                  45
Thr Gly Gln Gly Val Thr Ile Phe Tyr Val Asp Arg Leu Gly Tyr Tyr
         50                  55                  60
Pro Tyr Ile Asp Ser Ile Thr Gly Val Thr Val Asn Gly Gly Ile Pro
 65                  70                  75                  80
Gln Lys Ile Ser Leu Gln Asp His Leu Asp Lys Ala Lys Lys Asp Ile
                 85                  90                  95
Thr Phe Tyr Met Pro Val Asp Asn Leu Gly Met Ala Val Ile Asp Trp
            100                 105                 110
Glu Glu Trp Arg Pro Thr Trp Ala Arg Asn Trp Lys Pro Lys Asp Val
        115                 120                 125
Tyr Lys Asn Arg Ser Ile Glu Leu Val Gln Gln Asn Val Gln Leu
    130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
Pro Asn His Leu Trp Gly Tyr Tyr Leu Phe Pro Asp Cys Tyr Asn His
            180                 185                 190
His Tyr Lys Lys Pro Gly Tyr Asn Gly Ser Cys Phe Asn Val Glu Ile
        195                 200                 205
Lys Arg Asn Asp Asp Leu Ser Trp Leu Trp Asn Glu Ser Thr Ala Leu
    210                 215                 220
Tyr Pro Ser Ile Tyr Leu Asn Thr Gln Gln Ser Pro Val Ala Ala Thr
225                 230                 235                 240
Leu Tyr Val Arg Asn Arg Val Arg Glu Ala Ile Arg Val Ser Lys Ile
                245                 250                 255
Pro Asp Ala Lys Ser Pro Leu Pro Val Phe Ala Tyr Thr Arg Ile Val
            260                 265                 270
Phe Thr Asp Gln Val Leu Lys Phe Leu Ser Gln Asp Glu Leu Val Tyr
        275                 280                 285
Thr Phe Gly Glu Thr Val Ala Leu Gly Ala Ser Gly Ile Val Ile Trp
    290                 295                 300
Gly Thr Leu Ser Ile Met Arg Ser Met Lys Ser Cys Leu Leu Leu Asp
305                 310                 315                 320
Asn Tyr Met Glu Thr Ile Leu Asn Pro Tyr Ile Ile Asn Val Thr Leu
                325                 330                 335
Ala Ala Lys Met Cys Ser Gln Val Leu Cys Gln Glu Gln Gly Val Cys
```

```
                    340             345             350
Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
        370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu
        435                 440

<210> SEQ ID NO 10
<211> LENGTH: 450
<212> TYPE: PRT
<213> ORGANISM: Bos taurus
<220> FEATURE:
<223> OTHER INFORMATION: hyaluronidase

<400> SEQUENCE: 10

Met Arg Pro Phe Ser Leu Glu Val Ser Leu His Leu Pro Trp Ala Met
1               5                   10                  15

Ala Ala His Leu Leu Pro Val Cys Thr Leu Phe Leu Asn Leu Leu Ser
            20                  25                  30

Met Thr Gln Gly Ser Arg Asp Pro Val Val Pro Asn Gln Pro Phe Thr
        35                  40                  45

Thr Ile Trp Asn Ala Asn Thr Glu Trp Cys Met Lys Lys His Gly Val
    50                  55                  60

Asp Val Asp Ile Ser Ile Phe Asp Val Val Thr Asn Pro Gly Gln Thr
65                  70                  75                  80

Phe Arg Gly Pro Asn Met Thr Ile Phe Tyr Ser Ser Gln Leu Gly Thr
                85                  90                  95

Tyr Pro Tyr Tyr Thr Ser Ala Gly Glu Pro Val Phe Gly Gly Leu Pro
            100                 105                 110

Gln Asn Ala Ser Leu Asn Ala His Leu Ala Arg Thr Phe Gln Asp Ile
        115                 120                 125

Leu Ala Ala Met Pro Glu Pro Arg Phe Ser Gly Leu Ala Val Ile Asp
    130                 135                 140

Trp Glu Ala Trp Arg Pro Arg Trp Ala Phe Asn Trp Asp Thr Lys Asp
145                 150                 155                 160

Ile Tyr Arg Gln Arg Ser Arg Ala Leu Val Gln Lys Gln His Pro Asp
                165                 170                 175

Trp Leu Ala Pro Arg Val Glu Ala Ala Ala Gln Asp Gln Phe Glu Gly
            180                 185                 190

Ala Ala Glu Glu Trp Met Ala Gly Thr Leu Lys Leu Gly Gln Ala Leu
        195                 200                 205

Arg Pro Gln Gly Leu Trp Gly Phe Tyr Asn Phe Pro Glu Cys Tyr Asn
    210                 215                 220

Tyr Asp Phe Lys Ser Pro Asn Tyr Thr Gly Arg Cys Pro Leu Asn Ile
225                 230                 235                 240

Cys Ala Gln Asn Asp Gln Leu Gly Trp Leu Trp Gly Gln Ser Arg Ala
                245                 250                 255

Leu Tyr Pro Ser Ile Tyr Leu Pro Ala Ala Leu Glu Gly Thr Lys Lys
            260                 265                 270
```

Thr Gln Met Phe Val Gln His Arg Val Ala Glu Ala Phe Arg Val Ala
            275                 280                 285

Ala Gly Ala Gly Asp Pro Lys Leu Pro Val Leu Pro Tyr Met Gln Leu
        290                 295                 300

Phe Tyr Asp Met Thr Asn His Phe Leu Pro Ala Glu Leu Glu His
305                 310                 315                 320

Ser Leu Gly Glu Ser Ala Ala Gln Gly Ala Ala Gly Val Val Leu Trp
                325                 330                 335

Val Ser Trp Leu Ser Thr Ser Thr Lys Glu Ser Cys Gln Ala Ile Lys
            340                 345                 350

Glu Tyr Val Asp Thr Thr Leu Gly Pro Ser Ile Leu Asn Val Thr Ser
        355                 360                 365

Gly Ala Arg Leu Cys Ser Gln Val Leu Cys Ser Gly His Gly Arg Cys
    370                 375                 380

Ala Arg Arg Pro Ser Tyr Pro Lys Ala Arg Leu Ile Leu Asn Ser Thr
385                 390                 395                 400

Ser Phe Ser Ile Lys Pro Thr Pro Gly Gly Gly Pro Leu Thr Leu Gln
                405                 410                 415

Gly Ala Leu Ser Leu Glu Asp Arg Leu Arg Met Ala Val Glu Phe Glu
            420                 425                 430

Cys Arg Cys Tyr Arg Gly Trp Arg Gly Thr Arg Cys Glu Gln Trp Gly
        435                 440                 445

Met Trp
    450

<210> SEQ ID NO 11
<211> LENGTH: 331
<212> TYPE: PRT
<213> ORGANISM: Vespula vulgaris
<220> FEATURE:
<223> OTHER INFORMATION: hyaluronidase A

<400> SEQUENCE: 11

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
                20                  25                  30

Asn Ile Lys Arg Asn Ser Lys Asp Phe Gln Gly Asp Lys Ile Ala
            35                  40                  45

Ile Phe Tyr Asp Pro Gly Glu Phe Pro Ala Leu Leu Ser Leu Lys Asp
    50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125

Ser Ile Asp Leu Val Arg Asn Glu His Pro Thr Trp Asn Lys Lys Met
    130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

```
Trp Gly Tyr Tyr Gly Tyr Pro Tyr Cys Phe Asn Met Ser Pro Asn Asn
            180                 185                 190

Leu Val Pro Glu Cys Asp Val Thr Ala Met His Glu Asn Asp Lys Met
            195                 200                 205

Ser Trp Leu Phe Asn Asn Gln Asn Val Leu Leu Pro Ser Val Tyr Val
210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
            275                 280                 285

Gly Gly Asp Gly Ile Ile Ile Trp Gly Ser Ser Ser Asp Val Asn Ser
            290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330

<210> SEQ ID NO 12
<211> LENGTH: 340
<212> TYPE: PRT
<213> ORGANISM: Vespula vulgaris
<220> FEATURE:
<223> OTHER INFORMATION: hyaluronidase B

<400> SEQUENCE: 12

Asp Arg Thr Ile Trp Pro Lys Lys Gly Phe Ser Ile Tyr Trp Asn Ile
1               5                   10                  15

Pro Thr His Phe Cys His Asn Phe Gly Val Tyr Phe Lys Glu Leu Lys
            20                  25                  30

Gln Phe Asn Ile Lys Tyr Asn Ser Met Asn Asn Phe Arg Gly Glu Thr
        35                  40                  45

Ile Ser Leu Phe Tyr Asp Pro Gly Asn Phe Pro Ser Met Val Leu Leu
50                  55                  60

Lys Asn Gly Thr Tyr Glu Ile Arg Asn Glu Gly Val Pro Gln Lys Gly
65                  70                  75                  80

Asn Leu Thr Ile His Leu Glu Gln Phe Thr Lys Glu Leu Asp Glu Ile
                85                  90                  95

Tyr Pro Lys Lys Ile Ala Gly Gly Ile Gly Val Ile His Phe His Asn
            100                 105                 110

Trp Arg Pro Ile Phe Arg Arg Asn Val Asp Asn Leu Lys Ile Asn Lys
        115                 120                 125

Asp Ile Ser Ile Asp Leu Val Arg Lys Glu His Pro Lys Trp Asp Lys
130                 135                 140

Ser Met Ile Glu Lys Glu Ala Ser Asn Arg Phe Glu Thr Ser Ala Lys
145                 150                 155                 160

Ile Phe Met Glu Lys Thr Leu Lys Leu Ala Lys Glu Ile Arg Lys Lys
                165                 170                 175

Thr Glu Trp Gly Tyr His Gly Tyr Pro His Cys Leu Ser Gly Ser Thr
            180                 185                 190

Asp Lys Pro Ser Phe Asp Cys Asp Ala Leu Ser Met Ser Glu Asn Asp
        195                 200                 205

Lys Met Ser Trp Leu Phe Asn Asn Gln Asn Val Leu Leu Pro Ser Ile
```

-continued

```
                210                 215                 220
Tyr Leu Lys Asn Val Leu Lys Pro Asp Glu Lys Ile His Leu Val Gln
225                 230                 235                 240

Glu Arg Leu Lys Glu Ala Ile Arg Ile Ser Lys Asn Phe Lys His Leu
                245                 250                 255

Pro Lys Val Leu Pro Tyr Trp Trp Tyr Thr Tyr Gln Asp Lys Glu Ser
                260                 265                 270

Ile Phe Leu Thr Glu Ala Asp Val Lys Asn Thr Phe Lys Glu Ile Leu
            275                 280                 285

Thr Asn Gly Ala Asp Gly Ile Ile Ile Trp Gly Val Ser Tyr Glu Leu
        290                 295                 300

Thr Asp Arg Lys Arg Cys Glu Lys Leu Lys Glu Tyr Leu Met Lys Ile
305                 310                 315                 320

Leu Gly Pro Ile Ala Phe Lys Val Thr Lys Ala Val Lys Glu Asn Thr
                325                 330                 335

Pro Leu Asn Phe
            340
```

<210> SEQ ID NO 13
<211> LENGTH: 382
<212> TYPE: PRT
<213> ORGANISM: Apis mellifera
<220> FEATURE:
<223> OTHER INFORMATION: hyaluronidase

<400> SEQUENCE: 13

```
Met Ser Arg Pro Leu Val Ile Thr Glu Gly Met Met Ile Gly Val Leu
1               5                   10                  15

Leu Met Leu Ala Pro Ile Asn Ala Leu Leu Gly Phe Val Gln Ser
            20                  25                  30

Thr Pro Asp Asn Asn Lys Thr Val Arg Glu Phe Asn Val Tyr Trp Asn
        35                  40                  45

Val Pro Thr Phe Met Cys His Lys Tyr Gly Leu Arg Phe Glu Glu Val
50                  55                  60

Ser Glu Lys Tyr Gly Ile Leu Gln Asn Trp Met Asp Lys Phe Arg Gly
65                  70                  75                  80

Glu Glu Ile Ala Ile Leu Tyr Asp Pro Gly Met Phe Pro Ala Leu Leu
                85                  90                  95

Lys Asp Pro Asn Gly Asn Val Val Ala Arg Asn Gly Gly Val Pro Gln
            100                 105                 110

Leu Gly Asn Leu Thr Lys His Leu Gln Val Phe Arg Asp His Leu Ile
        115                 120                 125

Asn Gln Ile Pro Asp Lys Ser Phe Pro Gly Val Gly Val Ile Asp Phe
130                 135                 140

Glu Ser Trp Arg Pro Ile Phe Arg Gln Asn Trp Ala Ser Leu Gln Pro
145                 150                 155                 160

Tyr Lys Lys Leu Ser Val Glu Val Val Arg Arg Glu His Pro Phe Trp
                165                 170                 175

Asp Asp Gln Arg Val Glu Gln Glu Ala Lys Arg Arg Phe Glu Lys Tyr
            180                 185                 190

Gly Gln Leu Phe Met Glu Glu Thr Leu Lys Ala Ala Lys Arg Met Arg
        195                 200                 205

Pro Ala Ala Asn Trp Gly Tyr Tyr Ala Tyr Pro Tyr Cys Tyr Asn Leu
210                 215                 220

Thr Pro Asn Gln Pro Ser Ala Gln Cys Glu Ala Thr Thr Met Gln Glu
225                 230                 235                 240
```

```
Asn Asp Lys Met Ser Trp Leu Phe Glu Ser Glu Asp Val Leu Leu Pro
            245                 250                 255

Ser Val Tyr Leu Arg Trp Asn Leu Thr Ser Gly Glu Arg Val Gly Leu
        260                 265                 270

Val Gly Gly Arg Val Lys Glu Ala Leu Arg Ile Ala Arg Gln Met Thr
            275                 280                 285

Thr Ser Arg Lys Lys Val Leu Pro Tyr Tyr Trp Tyr Lys Tyr Gln Asp
    290                 295                 300

Arg Arg Asp Thr Asp Leu Ser Arg Ala Asp Leu Glu Ala Thr Leu Arg
305                 310                 315                 320

Lys Ile Thr Asp Leu Gly Ala Asp Gly Phe Ile Ile Trp Gly Ser Ser
                325                 330                 335

Asp Asp Ile Asn Thr Lys Ala Lys Cys Leu Gln Phe Glu Tyr Leu
            340                 345                 350

Asn Asn Glu Leu Gly Pro Ala Val Lys Arg Ile Ala Leu Asn Asn Asn
        355                 360                 365

Ala Asn Asp Arg Leu Thr Val Asp Val Ser Val Asp Gln Val
370                 375                 380

<210> SEQ ID NO 14
<211> LENGTH: 331
<212> TYPE: PRT
<213> ORGANISM: Dolichovespula maculata
<220> FEATURE:
<223> OTHER INFORMATION: hyaluronidase

<400> SEQUENCE: 14

Ser Glu Arg Pro Lys Arg Val Phe Asn Ile Tyr Trp Asn Val Pro Thr
1               5                   10                  15

Phe Met Cys His Gln Tyr Gly Leu Tyr Phe Asp Glu Val Thr Asn Phe
            20                  25                  30

Asn Ile Lys His Asn Ser Lys Asp Asp Phe Gln Gly Asp Lys Ile Ser
        35                  40                  45

Ile Phe Tyr Asp Pro Gly Glu Phe Pro Ala Leu Leu Pro Leu Lys Glu
50                  55                  60

Gly Asn Tyr Lys Ile Arg Asn Gly Gly Val Pro Gln Glu Gly Asn Ile
65                  70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
            100                 105                 110

Pro Ile Phe Arg Gln Asn Trp Gly Asn Met Met Ile His Lys Lys Phe
        115                 120                 125

Ser Ile Asp Leu Val Arg Asn Glu His Pro Phe Trp Asp Lys Lys Met
    130                 135                 140

Ile Glu Leu Glu Ala Ser Lys Arg Phe Glu Lys Tyr Ala Arg Leu Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Asp Cys Asp Ala Thr Ala Met Leu Glu Asn Asp Lys Met
        195                 200                 205

Ser Trp Leu Phe Asn Asn Gln Asn Val Leu Leu Pro Ser Val Tyr Ile
    210                 215                 220
```

```
Arg His Glu Leu Thr Pro Asp Gln Arg Val Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Asp Thr Asn Thr Phe
            260                 265                 270

Leu Thr Glu Thr Asp Val Lys Lys Thr Phe Gln Glu Ile Ala Ile Asn
        275                 280                 285

Gly Gly Asp Gly Ile Ile Ile Trp Gly Ser Ser Asp Val Asn Ser
    290                 295                 300

Leu Ser Lys Cys Lys Arg Leu Arg Glu Tyr Leu Leu Thr Val Leu Gly
305                 310                 315                 320

Pro Ile Thr Val Asn Val Thr Glu Thr Val Asn
            325                 330
```

<210> SEQ ID NO 15
<211> LENGTH: 367
<212> TYPE: PRT
<213> ORGANISM: Polistes annularis
<220> FEATURE:
<223> OTHER INFORMATION: hyaluronidase

<400> SEQUENCE: 15

```
Tyr Val Ser Leu Ser Pro Asp Ser Val Phe Asn Ile Ile Thr Asp Asp
1               5                   10                  15

Ile Ser His Gln Ile Leu Ser Arg Ser Asn Cys Glu Arg Ser Lys Arg
            20                  25                  30

Pro Lys Arg Val Phe Ser Ile Tyr Trp Asn Val Pro Thr Phe Met Cys
        35                  40                  45

His Gln Tyr Gly Met Asn Phe Asp Glu Val Thr Asp Phe Asn Ile Lys
    50                  55                  60

His Asn Ser Lys Asp Asn Phe Arg Gly Glu Thr Ile Ser Ile Tyr Tyr
65                  70                  75                  80

Asp Pro Gly Lys Phe Pro Ala Leu Met Pro Leu Lys Asn Gly Asn Tyr
                85                  90                  95

Glu Glu Arg Asn Gly Gly Val Pro Gln Arg Gly Asn Ile Thr Ile His
            100                 105                 110

Leu Gln Gln Phe Asn Glu Asp Leu Asp Lys Met Thr Pro Asp Lys Asn
        115                 120                 125

Phe Gly Gly Ile Gly Val Ile Asp Phe Glu Arg Trp Lys Pro Ile Phe
    130                 135                 140

Arg Gln Asn Trp Gly Asn Thr Glu Ile His Lys Lys Tyr Ser Ile Glu
145                 150                 155                 160

Leu Val Arg Lys Glu His Pro Lys Trp Ser Glu Ser Met Ile Glu Ala
                165                 170                 175

Glu Ala Thr Lys Lys Phe Glu Lys Tyr Ala Arg Tyr Phe Met Glu Glu
            180                 185                 190

Thr Leu Lys Leu Ala Lys Lys Thr Arg Lys Arg Ala Lys Trp Gly Tyr
        195                 200                 205

Tyr Gly Phe Pro Tyr Cys Tyr Asn Val Thr Pro Asn Asn Pro Gly Pro
    210                 215                 220

Asp Cys Asp Ala Lys Ala Thr Ile Glu Asn Asp Arg Leu Ser Trp Met
225                 230                 235                 240

Tyr Asn Asn Gln Glu Ile Leu Phe Pro Ser Val Tyr Val Arg His Glu
                245                 250                 255

Gln Lys Pro Glu Glu Arg Val Tyr Leu Val Gln Gly Arg Ile Lys Glu
```

-continued

```
                        260                 265                 270
Ala Val Arg Ile Ser Asn Asn Leu Glu His Ser Pro Ser Val Leu Ala
                275                 280                 285

Tyr Trp Trp Tyr Val Tyr Gln Asp Lys Met Asp Ile Tyr Leu Ser Glu
            290                 295                 300

Thr Asp Val Glu Lys Thr Phe Gln Glu Ile Val Thr Asn Gly Gly Asp
305                 310                 315                 320

Gly Ile Ile Ile Trp Gly Ser Ser Asp Val Asn Ser Leu Ser Lys
                325                 330                 335

Cys Lys Arg Leu Arg Glu Tyr Leu Leu Asn Thr Leu Gly Pro Phe Ala
                340                 345                 350

Val Asn Val Thr Glu Thr Val Asn Gly Arg Ser Ser Leu Asn Phe
                355                 360                 365

<210> SEQ ID NO 16
<211> LENGTH: 462
<212> TYPE: PRT
<213> ORGANISM: Mus musculus
<220> FEATURE:
<223> OTHER INFORMATION: hyaluronidase

<400> SEQUENCE: 16

Met Leu Gly Leu Thr Gln His Ala Gln Lys Val Trp Arg Met Lys Pro
1               5                   10                  15

Phe Ser Pro Glu Val Ser Pro Gly Ser Ser Pro Ala Thr Ala Gly His
                20                  25                  30

Leu Leu Arg Ile Ser Thr Leu Phe Leu Thr Leu Leu Glu Leu Ala Gln
            35                  40                  45

Val Cys Arg Gly Ser Val Val Ser Asn Arg Pro Phe Ile Thr Val Trp
        50                  55                  60

Asn Gly Asp Thr His Trp Cys Leu Thr Glu Tyr Gly Val Asp Val Asp
65                  70                  75                  80

Val Ser Val Phe Asp Val Val Ala Asn Lys Glu Gln Ser Phe Gln Gly
                85                  90                  95

Ser Asn Met Thr Ile Phe Tyr Arg Glu Glu Leu Gly Thr Tyr Pro Tyr
                100                 105                 110

Tyr Thr Pro Thr Gly Glu Pro Val Phe Gly Gly Leu Pro Gln Asn Ala
            115                 120                 125

Ser Leu Val Thr His Leu Ala His Thr Phe Gln Asp Ile Lys Ala Ala
        130                 135                 140

Met Pro Glu Pro Asp Phe Ser Gly Leu Ala Val Ile Asp Trp Glu Ala
145                 150                 155                 160

Trp Arg Pro Arg Trp Ala Phe Asn Trp Asp Ser Lys Asp Ile Tyr Arg
                165                 170                 175

Gln Arg Ser Met Glu Leu Val Gln Ala Glu His Pro Asp Trp Pro Glu
                180                 185                 190

Thr Leu Val Glu Ala Ala Ala Lys Asn Gln Phe Gln Glu Ala Ala Glu
            195                 200                 205

Ala Trp Met Ala Gly Thr Leu Gln Leu Gly Gln Val Leu Arg Pro Arg
        210                 215                 220

Gly Leu Trp Gly Tyr Tyr Gly Phe Pro Asp Cys Tyr Asn Asn Asp Phe
225                 230                 235                 240

Leu Ser Leu Asn Tyr Thr Gly Gln Cys Pro Val Phe Val Arg Asp Gln
                245                 250                 255

Asn Asp Gln Leu Gly Trp Leu Trp Asn Gln Ser Tyr Ala Leu Tyr Pro
                260                 265                 270
```

```
Ser Ile Tyr Leu Pro Ala Ala Leu Met Gly Thr Gly Lys Ser Gln Met
            275                 280                 285

Tyr Val Arg His Arg Val Gln Glu Ala Leu Arg Val Ala Ile Val Ser
        290                 295                 300

Arg Asp Pro His Val Pro Val Met Pro Tyr Val Gln Ile Phe Tyr Glu
305                 310                 315                 320

Met Thr Asp Tyr Leu Leu Pro Leu Glu Glu Leu Glu His Ser Leu Gly
                325                 330                 335

Glu Ser Ala Ala Gln Gly Val Ala Gly Ala Val Leu Trp Leu Ser Ser
            340                 345                 350

Asp Lys Thr Ser Thr Lys Glu Ser Cys Gln Ala Ile Lys Ala Tyr Met
        355                 360                 365

Asp Ser Thr Leu Gly Pro Phe Ile Val Asn Val Thr Ser Ala Ala Leu
370                 375                 380

Leu Cys Ser Glu Ala Leu Cys Ser Gly His Gly Arg Cys Val Arg His
385                 390                 395                 400

Pro Ser Tyr Pro Glu Ala Leu Leu Thr Leu Asn Pro Ala Ser Phe Ser
                405                 410                 415

Ile Glu Leu Thr His Asp Gly Arg Pro Pro Ser Leu Lys Gly Thr Leu
            420                 425                 430

Ser Leu Lys Asp Arg Ala Gln Met Ala Met Lys Phe Arg Cys Arg Cys
        435                 440                 445

Tyr Arg Gly Trp Arg Gly Lys Trp Cys Asp Lys Arg Gly Met
450                 455                 460

<210> SEQ ID NO 17
<211> LENGTH: 473
<212> TYPE: PRT
<213> ORGANISM: Mus musculus
<220> FEATURE:
<223> OTHER INFORMATION: Hyaluronidase 2

<400> SEQUENCE: 17

Met Arg Ala Gly Leu Gly Pro Ile Ile Thr Leu Ala Leu Val Leu Glu
1               5                   10                  15

Val Ala Trp Ala Gly Glu Leu Lys Pro Thr Ala Pro Pro Ile Phe Thr
            20                  25                  30

Gly Arg Pro Phe Val Val Ala Trp Asn Val Pro Thr Gln Glu Cys Ala
        35                  40                  45

Pro Arg His Lys Val Pro Leu Asp Leu Arg Ala Phe Asp Val Lys Ala
    50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Thr Ser Val
                85                  90                  95

His Gly Gly Val Pro Gln Asn Gly Ser Leu Cys Ala His Leu Pro Met
            100                 105                 110

Leu Lys Glu Ser Val Glu Arg Tyr Ile Gln Thr Gln Glu Pro Gly Gly
        115                 120                 125

Leu Ala Val Ile Asp Trp Glu Glu Trp Arg Pro Val Trp Val Arg Asn
130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Val Met Lys Gln Ala Gln
                165                 170                 175
```

```
Tyr Glu Phe Glu Phe Ala Ala Arg Gln Phe Met Leu Asn Thr Leu Arg
                180                 185                 190

Tyr Val Lys Ala Val Arg Pro Gln His Leu Trp Gly Phe Tyr Leu Phe
            195                 200                 205

Pro Asp Cys Tyr Asn His Asp Tyr Val Gln Asn Trp Glu Ser Tyr Thr
        210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Val His Ser Arg Asn Phe Val Ser Phe Arg Val
            260                 265                 270

Arg Glu Ala Leu Arg Val Ala His Thr His His Ala Asn His Ala Leu
        275                 280                 285

Pro Val Tyr Val Phe Thr Arg Pro Thr Tyr Thr Arg Gly Leu Thr Gly
        290                 295                 300

Leu Ser Gln Val Asp Leu Ile Ser Thr Ile Gly Glu Ser Ala Ala Leu
305                 310                 315                 320

Gly Ser Ala Gly Val Ile Phe Trp Gly Asp Ser Glu Asp Ala Ser Ser
                325                 330                 335

Met Glu Thr Cys Gln Tyr Leu Lys Asn Tyr Leu Thr Gln Leu Leu Val
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Asn
        370                 375                 380

Thr Phe Leu His Leu Asn Ala Ser Ser Phe Arg Leu Val Pro Gly His
385                 390                 395                 400

Thr Pro Ser Glu Pro Gln Leu Arg Pro Glu Gly Gln Leu Ser Glu Ala
                405                 410                 415

Asp Leu Asn Tyr Leu Gln Lys His Phe Arg Cys Gln Cys Tyr Leu Gly
            420                 425                 430

Trp Gly Gly Glu Gln Cys Gln Arg Asn Tyr Lys Gly Ala Ala Gly Asn
        435                 440                 445

Ala Ser Arg Ala Trp Ala Gly Ser His Leu Thr Ser Leu Leu Gly Leu
450                 455                 460

Val Ala Val Ala Leu Thr Trp Thr Leu
465                 470

<210> SEQ ID NO 18
<211> LENGTH: 412
<212> TYPE: PRT
<213> ORGANISM: Mus musculus
<220> FEATURE:
<223> OTHER INFORMATION: hyalurinidase 3

<400> SEQUENCE: 18

Met Ile Met His Leu Gly Leu Met Met Val Val Gly Leu Thr Leu Cys
1               5                   10                  15

Leu Met His Gly Gln Ala Leu Leu Gln Val Pro Glu His Pro Phe Ser
                20                  25                  30

Val Val Trp Asn Val Pro Ser Ala Arg Cys Lys Ala His Phe Gly Val
            35                  40                  45

His Leu Pro Leu Asp Ala Leu Gly Ile Val Ala Asn His Gly Gln His
        50                  55                  60

Phe His Gly Gln Asn Ile Ser Ile Phe Tyr Lys Asn Gln Phe Gly Leu
```

```
            65                  70                  75                  80
Tyr Pro Tyr Phe Gly Pro Arg Gly Thr Ala His Asn Gly Gly Ile Pro
                85                  90                  95
Gln Ala Val Ser Leu Asp His His Leu Ala Arg Ala Ala His Gln Ile
            100                 105                 110
Leu His Ser Leu Gly Ser Ser Phe Ala Gly Leu Ala Val Leu Asp Trp
        115                 120                 125
Glu Glu Trp Tyr Pro Leu Trp Ala Gly Asn Trp Gly Pro His Arg Gln
    130                 135                 140
Val Tyr Leu Ala Ala Ser Trp Val Trp Thr Gln Gln Met Phe Pro Gly
145                 150                 155                 160
Leu Asp Pro Gln Glu Gln Leu His Lys Ala His Thr Ser Phe Glu Gln
                165                 170                 175
Ala Ala Arg Ala Leu Met Glu Tyr Thr Leu Gln Leu Gly Arg Thr Leu
            180                 185                 190
Arg Pro Ser Gly Leu Trp Gly Phe Tyr Arg Tyr Pro Ala Cys Gly Asn
        195                 200                 205
Gly Trp His Lys Met Ala Ser Asn Tyr Thr Gly His Cys His Ala Ala
    210                 215                 220
Ile Thr Thr Gln Asn Thr Gln Leu Arg Trp Leu Trp Ala Ala Ser Ser
225                 230                 235                 240
Ala Leu Phe Pro Ser Ile Tyr Leu Pro Pro Arg Leu Pro Leu Ala Tyr
                245                 250                 255
Arg Gln Ala Phe Val Arg His Arg Leu Glu Glu Ala Phe Arg Val Ala
            260                 265                 270
Leu Leu Glu His Ser His Pro Leu Pro Val Leu Ala Tyr Ser Arg Leu
        275                 280                 285
Thr His Arg Ser Ser Gly Arg Phe Leu Ser Leu Asp Asp Leu Met Gln
    290                 295                 300
Thr Ile Gly Val Ser Ala Ala Leu Gly Thr Ala Gly Val Val Leu Trp
305                 310                 315                 320
Gly Asp Leu Ser Phe Ser Ser Ser Glu Glu Lys Cys Trp Arg Leu His
                325                 330                 335
Asp Tyr Leu Val Gly Thr Leu Gly Pro Tyr Val Ile Asn Val Thr Lys
            340                 345                 350
Ala Asp Met Ala Cys Ser His Gln Arg Cys His Gly His Gly Arg Cys
        355                 360                 365
Ala Arg Lys Asp Pro Gly Gln Met Glu Ala Phe Leu His Leu Gln Pro
    370                 375                 380
Asp Asp Ser Leu Gly Ala Trp Asn Ser Phe Arg Cys His Cys Tyr Ser
385                 390                 395                 400
Gly Trp Ala Gly Pro Thr Cys Leu Glu Pro Lys Pro
                405                 410

<210> SEQ ID NO 19
<211> LENGTH: 435
<212> TYPE: PRT
<213> ORGANISM: Sus scrofa
<220> FEATURE:
<223> OTHER INFORMATION: hyalauronidase

<400> SEQUENCE: 19

Met Ala Ala His Leu Leu Pro Ile Cys Thr Leu Phe Leu Asn Leu Leu
 1               5                  10                  15
Ser Val Ala Gln Gly Ser Arg Asp Pro Val Val Leu Asn Arg Pro Phe
            20                  25                  30
```

```
Thr Thr Ile Trp Asn Ala Asn Thr Gln Trp Cys Leu Lys Arg His Gly
        35                  40                  45

Val Asp Val Asp Val Ser Val Phe Glu Val Val Asn Pro Gly Gln
50                      55                  60

Thr Phe Arg Gly Pro Asn Met Thr Ile Phe Tyr Ser Ser Gln Leu Gly
65                      70                  75                  80

Thr Tyr Pro Tyr Tyr Thr Ser Ala Gly Glu Pro Val Phe Gly Gly Leu
                85                  90                  95

Pro Gln Asn Ala Ser Leu Asp Val His Leu Asn Arg Thr Phe Lys Asp
                100                 105                 110

Ile Leu Ala Ala Met Pro Glu Ser Asn Phe Ser Gly Leu Ala Val Ile
            115                 120                 125

Asp Trp Glu Ala Trp Arg Pro Arg Trp Ala Phe Asn Trp Asp Ala Lys
    130                 135                 140

Asp Ile Tyr Arg Gln Arg Ser Arg Ala Leu Val Gln Lys Gln His Pro
145                 150                 155                 160

Asp Trp Pro Ala Pro Trp Val Glu Ala Ala Gln Asp Gln Phe Gln
                165                 170                 175

Glu Ala Ala Gln Thr Trp Met Ala Gly Thr Leu Lys Leu Gly Gln Thr
                180                 185                 190

Leu Arg Pro His Gly Leu Trp Gly Phe Tyr Gly Phe Pro Asp Cys Tyr
            195                 200                 205

Asn Tyr Asp Phe Gln Ser Ser Asn Tyr Thr Gly Gln Cys Pro Pro Gly
            210                 215                 220

Val Ser Ala Gln Asn Asp Gln Leu Gly Trp Leu Trp Gly Gln Ser Arg
225                 230                 235                 240

Ala Leu Tyr Pro Ser Ile Tyr Leu Pro Ser Ala Leu Glu Gly Thr Asn
                245                 250                 255

Lys Thr Gln Leu Tyr Val Gln His Arg Val Asn Glu Ala Phe Arg Val
            260                 265                 270

Ala Ala Ala Ala Gly Asp Pro Asn Leu Pro Val Leu Pro Tyr Ala Gln
            275                 280                 285

Ile Phe His Asp Met Thr Asn Arg Leu Leu Ser Arg Glu Glu Leu Glu
            290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ser Ile
                325                 330                 335

Lys Glu Tyr Val Asp Thr Thr Leu Gly Pro Phe Ile Leu Asn Val Thr
                340                 345                 350

Ser Gly Ala Leu Leu Cys Ser Gln Ala Val Cys Ser Gly His Gly Arg
                355                 360                 365

Cys Val Arg Arg Pro Ser His Thr Glu Ala Leu Pro Ile Leu Asn Pro
370                 375                 380

Ser Ser Phe Ser Ile Lys Pro Thr Pro Gly Gly Pro Leu Thr Leu
385                 390                 395                 400

Gln Gly Ala Leu Ser Leu Lys Asp Arg Val Gln Met Ala Glu Glu Phe
                405                 410                 415

Gln Cys Arg Cys Tyr Pro Gly Trp Arg Gly Thr Trp Cys Glu Gln Gln
            420                 425                 430

Gly Thr Arg
        435
```

```
<210> SEQ ID NO 20
<211> LENGTH: 419
<212> TYPE: PRT
<213> ORGANISM: Sus scrofa
<220> FEATURE:
<223> OTHER INFORMATION: hyaluronidase 3

<400> SEQUENCE: 20
```

Met Thr Met Gln Leu Gly Leu Ala Leu Val Leu Gly Val Ala Met Cys
 1               5                  10                  15

Leu Gly Cys Gly Gln Pro Leu Leu Arg Ala Pro Glu Arg Pro Phe Cys
            20                  25                  30

Val Leu Trp Asn Val Pro Ser Ala Arg Cys Lys Ala Arg Phe Gly Val
        35                  40                  45

His Leu Pro Leu Glu Ala Leu Gly Ile Thr Ala Asn His Gly Gln Arg
50                  55                  60

Phe His Gly Gln Asn Ile Thr Ile Phe Tyr Lys Ser Gln Leu Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Arg Ala Ala Tyr Gln Ile
            100                 105                 110

His Arg Ser Leu Arg Pro Gly Phe Thr Gly Leu Ala Val Leu Asp Trp
        115                 120                 125

Glu Glu Trp Cys Pro Leu Trp Ala Gly Asn Trp Gly Arg Arg Gln Ala
130                 135                 140

Tyr Gln Ala Ala Ser Cys Ala Trp Ala Gln Arg Val Tyr Pro Asn Leu
145                 150                 155                 160

Asp Pro Gln Glu Gln Leu Cys Lys Ala Arg Ala Gly Phe Glu Glu Ala
                165                 170                 175

Ala Arg Ala Leu Met Glu Asp Thr Leu Arg Leu Gly Arg Met Leu Arg
            180                 185                 190

Pro His Gly Leu Trp Gly Phe Tyr His Tyr Pro Ala Cys Gly Asn Gly
        195                 200                 205

Trp His Gly Thr Ala Ser Asn Tyr Thr Gly His Cys His Ala Ala Ala
210                 215                 220

Leu Ala Arg Asn Thr Gln Leu Tyr Trp Leu Trp Ala Ala Ser Ser Ala
225                 230                 235                 240

Leu Phe Pro Ser Ile Tyr Leu Pro Pro Gly Leu Pro Pro Ala Tyr His
                245                 250                 255

Gln Ala Phe Val Arg Tyr Arg Leu Glu Ala Phe Arg Val Ala Leu
            260                 265                 270

Val Gly His Pro His Pro Leu Pro Val Leu Ala Tyr Ala Arg Leu Thr
        275                 280                 285

His Arg Asn Ser Gly Arg Phe Leu Ser Gln Asp Glu Leu Val Gln Thr
290                 295                 300

Ile Gly Val Ser Ala Ala Leu Gly Ala Ser Gly Val Val Leu Trp Gly
305                 310                 315                 320

Asp Leu Ser Phe Ser Ser Glu Glu Glu Cys Trp His Leu Arg Gly
                325                 330                 335

Tyr Leu Val Gly Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Trp Gln Asp Pro Gly Gln Leu Lys Val Phe Leu His Leu His Pro Gly
370                 375                 380

```
Gly Ser Pro Gly Ala Trp Glu Ser Phe Ser Cys Arg Cys Tyr Trp Gly
385                 390                 395                 400

Trp Ala Gly Pro Thr Cys Gln Glu Pro Arg Pro Glu Leu Gly Pro Glu
            405                 410                 415

Glu Ala Thr

<210> SEQ ID NO 21
<211> LENGTH: 449
<212> TYPE: PRT
<213> ORGANISM: Rattus norvegicus
<220> FEATURE:
<223> OTHER INFORMATION: hyaluronidase 1

<400> SEQUENCE: 21

Met Lys Pro Phe Ser Pro Glu Val Ser Pro Asp Pro Cys Pro Ala Thr
1               5                   10                  15

Ala Ala His Leu Leu Arg Thr Tyr Thr Leu Phe Leu Thr Leu Leu Glu
            20                  25                  30

Leu Ala Gln Gly Cys Arg Gly Ser Met Val Ser Asn Arg Pro Phe Ile
        35                  40                  45

Thr Val Trp Asn Ala Asp His Trp Cys Leu Lys Asp His Gly Val
50                  55                  60

Asp Val Asp Val Ser Val Phe Asp Val Val Ala Asn Lys Glu Gln Asn
65                  70                  75                  80

Phe Gln Gly Pro Asn Met Thr Ile Phe Tyr Arg Glu Glu Leu Gly Thr
                85                  90                  95

Tyr Pro Tyr Tyr Thr Pro Thr Gly Glu Pro Val Phe Gly Gly Leu Pro
            100                 105                 110

Gln Asn Ala Ser Leu Val Thr His Leu Ala His Ala Phe Gln Asp Ile
        115                 120                 125

Lys Ala Ala Met Pro Glu Pro Asp Phe Ser Gly Leu Ala Val Ile Asp
130                 135                 140

Trp Glu Ala Trp Arg Pro Arg Trp Ala Phe Asn Trp Asp Ser Lys Asp
145                 150                 155                 160

Ile Tyr Gln Gln Arg Ser Met Glu Leu Val Arg Ala Glu His Pro Asp
                165                 170                 175

Trp Pro Glu Thr Leu Val Glu Ala Glu Ala Gln Gly Gln Phe Gln Glu
            180                 185                 190

Ala Ala Glu Ala Trp Met Ala Gly Thr Leu Gln Leu Gly Gln Val Leu
        195                 200                 205

Arg Pro Arg Gly Leu Trp Gly Tyr Tyr Gly Phe Pro Asp Cys Tyr Asn
210                 215                 220

Tyr Asp Phe Leu Ser Pro Asn Tyr Thr Gly Gln Cys Ser Leu Ser Ile
225                 230                 235                 240

His Asp Gln Asn Asp Gln Leu Gly Trp Leu Trp Asn Gln Ser Tyr Ala
                245                 250                 255

Leu Tyr Pro Ser Ile Tyr Leu Pro Ala Ala Leu Met Gly Thr Gly Lys
            260                 265                 270

Ser Gln Met Tyr Val Arg Tyr Arg Val Gln Glu Ala Phe Arg Leu Ala
        275                 280                 285

Leu Val Ser Arg Asp Pro His Val Pro Ile Met Pro Tyr Val Gln Ile
290                 295                 300

Phe Tyr Glu Lys Thr Asp Tyr Leu Leu Pro Leu Glu Glu Leu Glu His
305                 310                 315                 320

Ser Leu Gly Glu Ser Ala Ala Gln Gly Ala Ala Gly Ala Val Leu Trp
```

```
                    325                 330                 335
Ile Ser Ser Glu Lys Thr Ser Thr Lys Glu Ser Cys Gln Ala Ile Lys
                340                 345                 350

Ala Tyr Met Asp Ser Thr Leu Gly Pro Phe Ile Leu Asn Val Thr Ser
            355                 360                 365

Ala Ala Leu Leu Cys Ser Glu Ala Leu Cys Ser Gly Arg Gly Arg Cys
        370                 375                 380

Val Arg His Pro Ser Tyr Pro Glu Ala Leu Leu Thr Leu Ser Pro Ala
385                 390                 395                 400

Ser Phe Ser Ile Glu Pro Thr His Asp Gly Arg Pro Leu Ser Leu Lys
                405                 410                 415

Gly Thr Leu Ser Leu Lys Asp Arg Ala Gln Met Ala Met Lys Phe Lys
            420                 425                 430

Cys Arg Cys Tyr Arg Gly Trp Ser Gly Glu Trp Cys Lys Lys Gln Asp
        435                 440                 445

Met

<210> SEQ ID NO 22
<211> LENGTH: 473
<212> TYPE: PRT
<213> ORGANISM: Rattus norvegicus
<220> FEATURE:
<223> OTHER INFORMATION: hyaluronidase 2

<400> SEQUENCE: 22

Met Arg Ala Gly Leu Gly Pro Ile Ile Thr Leu Ala Leu Val Leu Glu
  1               5                  10                  15

Val Ala Trp Ala Ser Glu Leu Lys Pro Thr Ala Pro Pro Ile Phe Thr
                 20                  25                  30

Gly Arg Pro Phe Val Val Ala Trp Asn Val Pro Thr Gln Glu Cys Ala
             35                  40                  45

Pro Arg His Lys Val Pro Leu Asp Leu Arg Ala Phe Asp Val Glu Ala
         50                  55                  60

Thr Pro Asn Glu Gly Phe Phe Asn Gln Asn Ile Thr Thr Phe Tyr Tyr
 65                  70                  75                  80

Asp Arg Leu Gly Leu Tyr Pro Arg Phe Asp Ala Ala Gly Met Ser Val
                 85                  90                  95

His Gly Gly Val Pro Gln Asn Gly Ser Leu Cys Ala His Leu Pro Met
            100                 105                 110

Leu Lys Glu Ala Val Glu Arg Tyr Ile Gln Thr Gln Glu Pro Ala Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Ile Val Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Asp Ser Tyr Thr
    210                 215                 220

Gly Arg Cys Pro Asp Val Glu Val Ala Gln Asn Asp Gln Leu Ala Trp
225                 230                 235                 240
```

```
Leu Trp Ala Glu Asn Thr Ala Leu Phe Pro Ser Val Tyr Leu Asp Lys
            245                 250                 255

Thr Leu Ala Ser Ser Lys His Ser Arg Asn Phe Val Ser Phe Arg Val
        260                 265                 270

Gln Glu Ala Leu Arg Val Ala His Thr His His Ala Asn His Ala Leu
    275                 280                 285

Pro Val Tyr Val Phe Thr Arg Pro Thr Tyr Thr Arg Arg Leu Thr Glu
290                 295                 300

Leu Asn Gln Met Asp Leu Ile Ser Thr Ile Gly Glu Ser Ala Ala Leu
305                 310                 315                 320

Gly Ser Ala Gly Val Ile Phe Trp Gly Asp Ser Val Tyr Ala Ser Ser
                325                 330                 335

Met Glu Asn Cys Gln Asn Leu Lys Lys Tyr Leu Thr Gln Thr Leu Val
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Ser
    370                 375                 380

Thr Phe Leu His Leu Ser Pro Ser Ser Phe Arg Leu Val Pro Gly Arg
385                 390                 395                 400

Thr Pro Ser Glu Pro Gln Leu Arg Pro Glu Gly Glu Leu Ser Glu Asp
                405                 410                 415

Asp Leu Ser Tyr Leu Gln Met His Phe Arg Cys His Cys Tyr Leu Gly
            420                 425                 430

Trp Gly Gly Glu Gln Cys Gln Trp Asn His Lys Arg Ala Ala Gly Asp
        435                 440                 445

Ala Ser Arg Ala Trp Ala Gly Ala His Leu Ala Ser Leu Leu Gly Leu
    450                 455                 460

Val Ala Met Thr Leu Thr Trp Thr Leu
465                 470

<210> SEQ ID NO 23
<211> LENGTH: 412
<212> TYPE: PRT
<213> ORGANISM: Rattus norvegicus
<220> FEATURE:
<223> OTHER INFORMATION: hyaluronidase 3

<400> SEQUENCE: 23

Met Ile Thr Gln Leu Gly Leu Thr Leu Val Val Gly Leu Thr Leu Cys
1               5                   10                  15

Leu Val His Val Gln Ala Leu Leu Gln Val Pro Glu Phe Pro Phe Ser
            20                  25                  30

Val Leu Trp Asn Val Pro Ser Ala Arg Cys Lys Thr Arg Phe Gly Val
        35                  40                  45

His Leu Pro Leu Asp Ala Leu Gly Ile Ile Ala Asn His Gly Gln Arg
    50                  55                  60

Phe His Gly Gln Asn Ile Thr Ile Phe Tyr Lys Asn Gln Phe Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Gln Ala His Gln Ile
            100                 105                 110

Leu His Asn Leu Gly Ser Ser Phe Ala Gly Leu Ala Val Leu Asp Trp
        115                 120                 125

Glu Glu Trp Tyr Pro Leu Trp Ala Gly Asn Trp Gly Thr His Arg Gln
```

```
            130                 135                 140
Val Tyr Gln Ala Ala Ser Trp Ala Trp Ala Gln Gln Met Phe Pro Asp
145                 150                 155                 160

Leu Asn Pro Gln Glu Gln Leu His Lys Ala Gln Thr Gly Phe Glu Gln
                165                 170                 175

Ala Ala Arg Ala Leu Met Glu His Thr Leu Arg Leu Gly Gln Met Leu
            180                 185                 190

Arg Pro His Gly Leu Trp Gly Phe Tyr Arg Tyr Pro Val Cys Gly Asn
        195                 200                 205

Gly Trp His Asn Met Ala Ser Asn Tyr Thr Gly His Cys His Pro Ala
    210                 215                 220

Ile Ile Thr Arg Asn Thr Gln Leu Arg Trp Leu Trp Ala Ala Ser Ser
225                 230                 235                 240

Ala Leu Phe Pro Ser Ile Tyr Leu Pro Pro Arg Leu Pro Pro Ala Tyr
                245                 250                 255

His Gln Thr Phe Val Arg His Arg Leu Glu Glu Ala Phe Arg Val Ala
            260                 265                 270

Leu Thr Gly His Ala His Pro Leu Pro Val Leu Ala Tyr Val Arg Leu
        275                 280                 285

Thr His Arg Ser Ser Gly Arg Phe Leu Ser Leu Asp Asp Leu Met Gln
    290                 295                 300

Thr Ile Gly Val Ser Ala Leu Gly Ala Ala Gly Val Val Leu Trp
305                 310                 315                 320

Gly Asp Leu Ser Val Ser Ser Glu Glu Cys Trp Arg Leu His
                325                 330                 335

Asp Tyr Leu Val Gly Thr Leu Gly Pro Tyr Val Ile Asn Val Thr Lys
            340                 345                 350

Ala Ala Thr Ala Cys Ser His Gln Arg Cys His Gly His Gly Arg Cys
        355                 360                 365

Ser Trp Lys Asp Pro Gly Gln Met Glu Ala Phe Leu His Leu Gln Pro
    370                 375                 380

Asp Asp Asn Leu Gly Ala Trp Lys Ser Phe Arg Cys Arg Cys Tyr Leu
385                 390                 395                 400

Gly Trp Ser Gly Pro Thr Cys Leu Glu Pro Lys Pro
                405                 410

<210> SEQ ID NO 24
<211> LENGTH: 545
<212> TYPE: PRT
<213> ORGANISM: Oryctolagus cuniculus
<220> FEATURE:
<223> OTHER INFORMATION: PH20

<400> SEQUENCE: 24

Met Gly Val Leu Lys Phe Lys His Ile Phe Phe Gly Ser Ala Val Glu
1               5                   10                  15

Leu Ser Gly Val Phe Gln Ile Val Phe Ile Phe Leu Leu Ile Pro Cys
                20                  25                  30

Cys Leu Thr Ala Asn Phe Arg Ala Pro Pro Val Ile Pro Asn Val Pro
            35                  40                  45

Phe Leu Trp Ala Trp Asn Ala Pro Thr Glu Phe Cys Leu Gly Lys Ser
        50                  55                  60

Gly Glu Pro Leu Asp Met Ser Leu Phe Ser Leu Phe Gly Ser Pro Arg
65              70                  75                  80

Lys Asn Lys Thr Gly Gln Gly Ile Thr Ile Phe Tyr Val Asp Arg Leu
                85                  90                  95
```

```
Gly Tyr Tyr Pro Tyr Ile Asp Pro His Thr Gly Ala Ile Val His Gly
                100                 105                 110

Arg Ile Pro Gln Leu Gly Pro Leu Gln Gln His Leu Thr Lys Leu Arg
            115                 120                 125

Gln Glu Ile Leu Tyr Tyr Met Pro Lys Asp Asn Val Gly Leu Ala Val
        130                 135                 140

Ile Asp Trp Glu Glu Trp Leu Pro Thr Trp Leu Arg Asn Trp Lys Pro
145                 150                 155                 160

Lys Asp Ile Tyr Arg Ile Lys Ser Ile Glu Leu Val Lys Ser Gln His
                165                 170                 175

Pro Gln Tyr Asn His Ser Tyr Ala Thr Glu Lys Ala Lys Arg Asp Phe
            180                 185                 190

Glu Lys Ala Gly Lys Asp Phe Met Glu Glu Thr Leu Lys Leu Gly Arg
        195                 200                 205

Leu Leu Arg Pro Asn His Leu Trp Gly Tyr Tyr Leu Phe Pro Asp Cys
    210                 215                 220

Tyr Asn His His Tyr Asp Lys Pro Asn Leu Tyr Lys Gly Ser Cys Phe
225                 230                 235                 240

Asp Ile Glu Lys Lys Arg Asn Asp Asp Leu Ser Trp Leu Trp Lys Glu
                245                 250                 255

Ser Thr Ala Leu Phe Pro Ser Val Tyr Leu Thr Ser Arg Ala Arg Ser
            260                 265                 270

Ala Thr Ala Leu Ser Lys Leu Tyr Val Val Arg Asn Arg Val His Glu
        275                 280                 285

Ala Ile Arg Val Ser Lys Ile Pro Asp Asp Lys Ser Pro Leu Pro Asn
    290                 295                 300

Phe Val Tyr Thr Arg Leu Val Phe Thr Asp Gln Ile Phe Gln Phe Leu
305                 310                 315                 320

Ser His His Asp Leu Val Tyr Thr Ile Gly Glu Ile Val Ala Leu Gly
                325                 330                 335

Ala Ser Gly Ile Val Val Trp Gly Ser Gln Ser Leu Ala Arg Ser Met
            340                 345                 350

Lys Ser Cys Leu His Leu Asp Asn Tyr Met Lys Thr Ile Leu Asn Pro
        355                 360                 365

Tyr Leu Ile Asn Val Thr Leu Ala Ala Lys Met Cys Asn Gln Val Leu
    370                 375                 380

Cys Gln Glu Gln Gly Val Cys Thr Arg Lys Asn Trp Asn Pro Asn Asp
385                 390                 395                 400

Tyr Leu His Leu Asn Pro Gly Asn Phe Ala Ile Gln Leu Gly Ser Asn
                405                 410                 415

Gly Thr Tyr Lys Val Asp Gly Lys Pro Thr Leu Thr Asp Leu Glu Gln
            420                 425                 430

Phe Ser Lys Asn Phe Gln Cys Ser Cys Tyr Thr Asn Leu Asn Cys Lys
        435                 440                 445

Glu Arg Thr Asp Met Asn Asn Val Arg Thr Val Asn Val Cys Ala Val
    450                 455                 460

Glu Asn Val Cys Ile Asp Thr Asn Val Gly Pro Gln Ala Val Thr Tyr
465                 470                 475                 480

Ala Pro Lys Glu Lys Lys Asp Val Ala His Ile Leu Ser Asn Thr Thr
                485                 490                 495

Ser Ile Asn Ser Ser Thr Thr Met Ser Leu Pro Phe Pro Arg Lys His
            500                 505                 510

Val Ser Gly Cys Leu Leu Val Leu Cys Met Tyr Ser Gln Tyr Leu Asn
```

```
                515                 520                 525
Ile Cys Tyr Arg Leu Val Ala Ile Gly Ile Gln His Gly Tyr Tyr Leu
530                 535                 540

Lys
545

<210> SEQ ID NO 25
<211> LENGTH: 476
<212> TYPE: PRT
<213> ORGANISM: Ovis aries
<220> FEATURE:
<223> OTHER INFORMATION: hyaluronidase 2

<400> SEQUENCE: 25

Met Trp Thr Gly Leu Gly Pro Ala Val Thr Ala Leu Val Leu Val
 1               5                  10                  15

Val Ala Trp Ala Thr Glu Leu Lys Pro Thr Ala Pro Ile Phe Thr
            20                  25                  30

Gly Arg Pro Phe Val Val Ala Trp Asp Val Pro Thr Gln Asp Cys Gly
            35                  40                  45

Pro Arg His Lys Met Pro Leu Asp Pro Lys Asp Met Lys Ala Phe Asp
50                  55                  60

Val Gln Ala Ser Pro Asn Glu Gly Phe Val Asn Gln Asn Ile Thr Ile
65                  70                  75                  80

Phe Tyr Arg Asp Arg Leu Gly Met Tyr Pro His Phe Asn Ser Val Gly
                85                  90                  95

Arg Ser Val His Gly Gly Val Pro Gln Asn Gly Ser Leu Trp Val His
                100                 105                 110

Leu Glu Met Leu Lys Gly His Val Glu His Tyr Ile Arg Thr Gln Glu
                115                 120                 125

Pro Ala Gly Leu Ala Val Ile Asp Trp Glu Asp Trp Arg Pro Val Trp
                130                 135                 140

Val Arg Asn Trp Gln Asp Lys Asp Val Tyr Arg Arg Leu Ser Arg Gln
145                 150                 155                 160

Leu Val Ala Ser His His Pro Asp Trp Pro Pro Glu Arg Ile Val Lys
                165                 170                 175

Glu Ala Gln Tyr Glu Phe Glu Phe Ala Ala Arg Gln Phe Met Leu Glu
                180                 185                 190

Thr Leu Arg Phe Val Lys Ala Phe Arg Pro Arg His Leu Trp Gly Phe
                195                 200                 205

Tyr Leu Phe Pro Asp Cys Tyr Asn His Asp Tyr Val Gln Asn Trp Glu
                210                 215                 220

Thr Tyr Thr Gly Arg Cys Pro Asp Val Glu Val Ser Arg Asn Asp Gln
225                 230                 235                 240

Leu Ser Trp Leu Trp Ala Glu Ser Thr Ala Leu Phe Pro Ser Val Tyr
                245                 250                 255

Leu Glu Glu Thr Leu Ala Ser Ser Thr His Gly Arg Asn Phe Val Ser
                260                 265                 270

Phe Arg Val Gln Glu Ala Leu Arg Val Ala Asp Val His His Ala Asn
                275                 280                 285

His Ala Leu Pro Val Tyr Val Phe Thr Arg Pro Thr Tyr Ser Arg Gly
                290                 295                 300

Leu Thr Gly Leu Ser Glu Met Asp Leu Ile Ser Thr Ile Gly Glu Ser
305                 310                 315                 320

Ala Ala Leu Gly Ala Ala Gly Val Ile Leu Trp Gly Asp Ala Gly Phe
                325                 330                 335
```

-continued

```
Thr Thr Ser Asn Glu Thr Cys Arg Arg Leu Lys Asp Tyr Leu Thr Arg
            340                 345                 350

Ser Leu Val Pro Tyr Val Val Asn Val Ser Trp Ala Ala Gln Tyr Cys
            355                 360                 365

Ser Trp Ala Gln Cys His Gly His Gly Arg Cys Val Arg Arg Asp Pro
            370                 375                 380

Asn Ala His Thr Phe Leu His Leu Ser Ala Ser Ser Phe Arg Leu Val
385                 390                 395                 400

Pro Ser His Ala Pro Asp Glu Pro Arg Leu Arg Pro Glu Gly Glu Leu
            405                 410                 415

Ser Trp Ala Asp Arg Asn His Leu Gln Thr His Phe Arg Cys Gln Cys
            420                 425                 430

Tyr Leu Gly Trp Gly Gly Glu Gln Cys Gln Trp Asp Arg Arg Arg Ala
            435                 440                 445

Ala Gly Gly Ala Ser Gly Ala Trp Ala Gly Ser His Leu Thr Gly Leu
            450                 455                 460

Leu Ala Val Ala Val Leu Ala Phe Thr Trp Thr Ser
465                 470                 475

<210> SEQ ID NO 26
<211> LENGTH: 414
<212> TYPE: PRT
<213> ORGANISM: Pongo pygmaeus
<220> FEATURE:
<223> OTHER INFORMATION: hyaluronidase 3

<400> SEQUENCE: 26

Met Thr Thr Arg Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Lys Ser Arg Phe Gly Val
            35                  40                  45

His Leu Pro Leu Asn Ala Leu Gly Ile Ile Ala Asn Arg Gly Gln His
        50                  55                  60

Phe His Gly Gln Asn Met Thr Ile Phe Tyr Lys Asn Gln Leu Gly Leu
65                  70                  75                  80

Tyr Pro Tyr Phe Gly Pro Lys Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
            130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220
```

```
Leu Ala Arg Asn Thr Gln Leu His Trp Leu Trp Ala Ser Ser Ala
225                 230                 235                 240

Leu Phe Pro Ser Ile Tyr Leu Pro Pro Arg Leu Pro Ala His His
            245                 250                 255

Gln Ala Phe Val Arg His Arg Leu Glu Glu Ala Phe Arg Val Ala Leu
        260                 265                 270

Val Gly His Leu Pro Val Leu Ala Tyr Val Arg Leu Thr His Arg Arg
    275                 280                 285

Ser Gly Arg Phe Leu Ser Gln Asp Asp Leu Val Gln Thr Ile Gly Val
290                 295                 300

Ser Ala Ala Leu Gly Ala Ala Gly Val Val Leu Trp Gly Asp Leu Ser
305                 310                 315                 320

Leu Ser Ser Ser Glu Glu Glu Cys Trp His Leu His Asp Tyr Leu Val
                325                 330                 335

Asp Thr Leu Gly Pro Tyr Gly Ile Asn Val Thr Arg Ala Ala Met Ala
            340                 345                 350

Cys Ser His Gln Arg Cys His Gly His Gly Arg Cys Ala Arg Arg Asp
            355                 360                 365

Pro Gly Gln Met Glu Ala Phe Leu His Leu Trp Pro Asp Gly Ser Leu
    370                 375                 380

Gly Asp Trp Lys Ser Phe Ser Cys His Cys Tyr Trp Gly Trp Ala Gly
385                 390                 395                 400

Pro Thr Cys Gln Glu Pro Arg Leu Gly Pro Lys Glu Ala Val
                405                 410

<210> SEQ ID NO 27
<211> LENGTH: 510
<212> TYPE: PRT
<213> ORGANISM: Macaca fascicularis
<220> FEATURE:
<223> OTHER INFORMATION: PH20

<400> SEQUENCE: 27

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Ile Ile Pro Asn Val Pro
        35                  40                  45

Phe Leu Trp Ala Trp Asn Ala Pro Ser Glu Phe Cys Leu Gly Lys Phe
    50                  55                  60

Asn Glu Pro Leu Asp Met Ser Leu Phe Thr Leu Met Gly Ser Pro Arg
65                  70                  75                  80

Ile Asn Val Thr Gly Gln Gly Val Thr Ile Phe Tyr Val Asp Arg Leu
                85                  90                  95

Gly Tyr Tyr Pro Tyr Ile Asp Leu Thr Thr Gly Val Thr Val His Gly
            100                 105                 110

Gly Ile Pro Gln Lys Val Ser Leu Gln Asp His Leu Asp Lys Ser Lys
        115                 120                 125

Gln Asp Ile Leu Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Pro Gln Ala Thr Asp Lys Ala Lys Gln Glu Phe
```

```
                    180                 185                 190
Glu Lys Ala Gly Lys Asp Phe Met Leu Glu Thr Ile Lys Leu Gly Arg
                195                 200                 205

Ser Leu Arg Pro Asn His Leu Trp Gly Tyr Tyr Leu Phe Pro Asp Cys
    210                 215                 220

Tyr Asn His His Tyr Arg Lys Pro Gly Tyr Asn Gly Ser Cys Phe Asp
225                 230                 235                 240

Val Glu Ile Lys Arg Asn Asp Leu Ser Trp Leu Trp Asn Glu Ser
                245                 250                 255

Thr Ala Leu Tyr Pro Ser Ile Tyr Leu Asn Thr Gln Gln Ser Val Val
            260                 265                 270

Val Ala Thr Leu Tyr Val Arg Asn Arg Val Arg Glu Ala Ile Arg Val
        275                 280                 285

Ser Lys Ile Pro Asp Ala Lys Asn Pro Leu Pro Val Phe Val Tyr Ala
    290                 295                 300

Arg Leu Val Phe Thr Asp Gln Val Leu Lys Phe Leu Ser Arg Glu Glu
305                 310                 315                 320

Leu Val Ser Thr Leu Gly Glu Thr Val Ala Leu Gly Ala Ser Gly Ile
                325                 330                 335

Val Ile Trp Gly Ser Leu Ser Ile Thr Arg Ser Met Lys Ser Cys Leu
            340                 345                 350

Leu Leu Asp Thr Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asp Trp Asn Ser Ser Asp Tyr Leu His Leu
385                 390                 395                 400

Asn Pro Asp Asn Phe Asp Ile Arg Leu Glu Lys Gly Lys Phe Thr
                405                 410                 415

Val His Gly Lys Pro Thr Val Glu Asp Leu Glu Glu Phe Ser Glu Lys
            420                 425                 430

Phe Tyr Cys Ser Cys Tyr Thr Asn Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Ser Leu Lys Pro Pro Val Glu Thr Gly Ser Pro Pro
465                 470                 475                 480

Ile Phe Tyr Asn Thr Ser Ser Ser Thr Val Ser Thr Thr Met Phe Ile
                485                 490                 495

Val Asn Ile Leu Phe Leu Ile Ile Ser Ser Val Ala Ser Leu
            500                 505                 510

<210> SEQ ID NO 28
<211> LENGTH: 529
<212> TYPE: PRT
<213> ORGANISM: Cavia porcellus
<220> FEATURE:
<223> OTHER INFORMATION: PH20

<400> SEQUENCE: 28

Met Gly Ala Phe Thr Phe Lys His Ser Phe Gly Ser Phe Val Glu
1               5                   10                  15

Cys Ser Gly Val Leu Gln Thr Val Phe Ile Phe Leu Leu Ile Pro Cys
                20                  25                  30

Cys Leu Ala Asp Lys Arg Ala Pro Pro Leu Ile Pro Asn Val Pro Leu
            35                  40                  45
```

```
Leu Trp Val Trp Asn Ala Pro Thr Glu Phe Cys Ile Gly Gly Thr Asn
     50                  55                  60

Gln Pro Leu Asp Met Ser Phe Phe Ser Ile Val Gly Thr Pro Arg Lys
 65                  70                  75                  80

Asn Ile Thr Gly Gln Ser Ile Thr Leu Tyr Tyr Val Asp Arg Leu Gly
                     85                  90                  95

Tyr Tyr Pro Tyr Ile Asp Pro His Thr Gly Ala Ile Val His Gly Gly
                100                 105                 110

Leu Pro Gln Leu Met Asn Leu Gln Gln His Leu Arg Lys Ser Arg Gln
                115                 120                 125

Asp Ile Leu Phe Tyr Met Pro Thr Asp Ser Val Gly Leu Ala Val Ile
                130                 135                 140

Asp Trp Glu Glu Trp Arg Pro Thr Trp Thr Arg Asn Trp Arg Pro Lys
145                 150                 155                 160

Asp Ile Tyr Arg Asn Lys Ser Ile Glu Leu Val Lys Ser Gln His Pro
                165                 170                 175

Gln Tyr Asn His Ser Tyr Ala Val Ala Val Ala Lys Arg Asp Phe Glu
                180                 185                 190

Arg Thr Gly Lys Ala Phe Met Leu Glu Thr Leu Lys Leu Gly Lys Ser
                195                 200                 205

Leu Arg Pro Ser Ser Leu Trp Gly Tyr Tyr Leu Phe Pro Asp Cys Tyr
210                 215                 220

Asn Thr His Phe Thr Lys Pro Asn Tyr Asp Gly His Cys Pro Pro Ile
225                 230                 235                 240

Glu Leu Gln Arg Asn Asn Asp Leu Gln Trp Leu Trp Asn Asp Ser Thr
                245                 250                 255

Ala Leu Tyr Pro Ser Val Tyr Leu Thr Ser Arg Val Arg Ser Ser Gln
                260                 265                 270

Asn Gly Ala Leu Tyr Val Arg Asn Arg Val His Glu Ser Ile Arg Val
                275                 280                 285

Ser Lys Leu Met Asp Asp Lys Asn Pro Leu Pro Ile Tyr Val Tyr Ile
290                 295                 300

Arg Leu Val Phe Thr Asp Gln Thr Thr Thr Phe Leu Glu Leu Asp Asp
305                 310                 315                 320

Leu Val His Ser Val Gly Glu Ile Val Pro Leu Gly Val Ser Gly Ile
                325                 330                 335

Ile Ile Trp Gly Ser Leu Ser Leu Thr Arg Ser Leu Val Ser Cys Ile
                340                 345                 350

Gly Leu Glu Asn Tyr Met Lys Gly Thr Leu Leu Pro Tyr Leu Ile Asn
                355                 360                 365

Val Thr Leu Ala Ala Lys Met Cys Gly Gln Val Leu Cys Lys Asn Gln
370                 375                 380

Gly Ile Cys Thr Arg Lys Asp Trp Asn Thr Asn Thr Tyr Leu His Leu
385                 390                 395                 400

Asn Ala Thr Asn Phe Asp Ile Glu Leu Gln Gln Asn Gly Lys Phe Val
                405                 410                 415

Val His Gly Lys Pro Ser Leu Glu Asp Leu Gln Glu Phe Ser Lys Asn
                420                 425                 430

Phe His Cys Ser Cys Tyr Thr Asn Val Ala Cys Lys Asp Arg Leu Asp
                435                 440                 445

Val His Asn Val Arg Ser Val Asn Val Cys Thr Ala Asn Asn Ile Cys
                450                 455                 460

Ile Asp Ala Val Leu Asn Phe Pro Ser Leu Asp Asp Asp Asp Glu Pro
```

```
                465                 470                 475                 480
Pro Ile Thr Asp Asp Thr Ser Gln Asn Gln Asp Ser Ile Ser Asp Ile
                    485                 490                 495

Thr Ser Ser Ala Pro Pro Ser Ser His Ile Leu Pro Lys Asp Leu Ser
                500                 505                 510

Trp Cys Leu Phe Leu Leu Ser Ile Phe Ser Gln His Trp Lys Tyr Leu
                515                 520                 525

Leu

<210> SEQ ID NO 29
<211> LENGTH: 512
<212> TYPE: PRT
<213> ORGANISM: Rattus norvegicus
<220> FEATURE:
<223> OTHER INFORMATION: PH20

<400> SEQUENCE: 29

Met Gly Glu Leu Gln Phe Lys Trp Leu Phe Trp Arg Ser Phe Ala Glu
  1               5                  10                  15

Ser Gly Gly Thr Phe Gln Thr Val Leu Ile Phe Leu Phe Ile Pro Tyr
                 20                  25                  30

Ser Leu Thr Val Asp Tyr Arg Ala Thr Pro Val Leu Ser Asp Thr Thr
             35                  40                  45

Phe Val Trp Val Trp Asn Val Pro Thr Glu Ala Cys Val Glu Asn Val
 50                  55                  60

Thr Glu Pro Ile Asp Leu Ser Phe Phe Ser Leu Ile Gly Ser Pro Arg
 65                  70                  75                  80

Lys Thr Ala Ile Gly Gln Pro Val Thr Leu Phe Tyr Val Asp Arg Leu
                 85                  90                  95

Gly Asn Tyr Pro His Ile Asp Ala Gln Gln Thr Glu His His Gly Gly
            100                 105                 110

Ile Pro Gln Lys Gly Asp Leu Thr Thr His Leu Val Lys Ala Lys Glu
            115                 120                 125

Asp Val Glu Arg Tyr Ile Pro Thr Asp Lys Leu Gly Leu Ala Ile Ile
130                 135                 140

Asp Trp Glu Glu Trp Arg Pro Thr Trp Met Arg Asn Trp Thr Pro Lys
145                 150                 155                 160

Asp Ile Tyr Arg Asn Lys Ser Ile Glu Leu Val Gln Ala Ala Asp Pro
                165                 170                 175

Ala Ile Asn Ile Thr Glu Ala Thr Val Arg Ala Lys Ala Gln Phe Glu
            180                 185                 190

Gly Ala Ala Lys Glu Phe Met Glu Gly Thr Leu Lys Leu Gly Lys His
        195                 200                 205

Ile Arg Pro Lys His Leu Trp Gly Phe Tyr Leu Phe Pro Asp Cys Tyr
    210                 215                 220

Asn Asn Lys Phe Gln Val Asp Asn Tyr Asp Gly Gln Cys Pro Asp Val
225                 230                 235                 240

Glu Lys Lys Arg Asn Asp Asp Leu Asp Trp Leu Trp Lys Glu Ser Thr
                245                 250                 255

Gly Leu Tyr Pro Ser Val Tyr Leu Lys Lys Asp Leu Lys Ser Ser Arg
            260                 265                 270

Lys Ala Thr Leu Tyr Val Arg Tyr Arg Val Leu Glu Ser Ile Arg Val
        275                 280                 285

Ser Lys Val Ser Asp Glu Ser Asn Pro Val Pro Ile Phe Val Tyr Ile
    290                 295                 300
```

```
Arg Leu Val Phe Thr Asp His Val Ser Glu Tyr Leu Leu Glu Asp Asp
305                 310                 315                 320

Leu Val Asn Thr Ile Gly Glu Ile Val Ala Gln Gly Thr Ser Gly Ile
            325                 330                 335

Ile Ile Trp Asp Ala Met Ser Leu Ala Gln Arg Ser Ala Gly Cys Pro
            340                 345                 350

Ile Leu Arg Gln Tyr Met Lys Thr Thr Leu Asn Pro Tyr Ile Val Asn
            355                 360                 365

Val Thr Leu Ala Ala Lys Met Cys Ser Gln Thr Leu Cys Lys Glu Lys
            370                 375                 380

Gly Met Cys Ser Arg Lys Thr Glu Ser Ser Asp Ala Tyr Leu His Leu
385                 390                 395                 400

Asp Pro Ser Ser Phe Ser Ile Asn Val Thr Glu Ala Gly Lys Tyr Glu
                405                 410                 415

Val Leu Gly Lys Pro Glu Val Lys Asp Leu Glu Tyr Phe Ser Glu His
                420                 425                 430

Phe Lys Cys Ser Cys Phe Ser Lys Met Thr Cys Glu Glu Thr Ser Asp
            435                 440                 445

Met Arg Ser Ile Gln Asp Val Asn Val Cys Met Gly Asp Asn Val Cys
450                 455                 460

Ile Lys Ala Thr Leu Gly Pro Asn Ser Ala Phe His Leu Leu Pro Gly
465                 470                 475                 480

Lys Gly Leu Leu Leu Met Thr Thr Leu Ala His Ile Leu His His Leu
                485                 490                 495

Pro His Asp Ile Phe Val Phe Pro Trp Lys Met Leu Val Ser Thr Pro
                500                 505                 510

<210> SEQ ID NO 30
<211> LENGTH: 512
<212> TYPE: PRT
<213> ORGANISM: Mus musculus
<220> FEATURE:
<223> OTHER INFORMATION: PH20

<400> SEQUENCE: 30

Met Gly Glu Leu Arg Phe Lys His Leu Phe Trp Gly Ser Phe Val Glu
1               5                   10                  15

Ser Gly Gly Thr Phe Gln Thr Val Leu Ile Phe Leu Leu Ile Pro Cys
            20                  25                  30

Ser Leu Thr Val Asp Tyr Arg Ala Ala Pro Ile Leu Ser Asn Thr Thr
        35                  40                  45

Phe Leu Trp Ile Trp Asn Val Pro Thr Glu Arg Cys Val Gly Asn Val
50                  55                  60

Asn Asp Pro Ile Asp Leu Ser Phe Phe Ser Leu Ile Gly Ser Pro Arg
65                  70                  75                  80

Lys Thr Ala Thr Gly Gln Pro Val Thr Leu Phe Tyr Val Asp Arg Leu
                85                  90                  95

Gly Leu Tyr Pro His Ile Asp Ala Asn Gln Ala Glu His Tyr Gly Gly
            100                 105                 110

Ile Pro Gln Arg Gly Asp Tyr Gln Ala His Leu Arg Lys Ala Lys Thr
        115                 120                 125

Asp Ile Glu His Tyr Ile Pro Asp Lys Leu Gly Leu Ala Ile Ile
    130                 135                 140

Asp Trp Glu Glu Trp Arg Pro Thr Trp Leu Arg Asn Trp Lys Pro Lys
145                 150                 155                 160

Asp Asn Tyr Arg Asn Lys Ser Ile Glu Leu Val Gln Ser Thr Asn Pro
```

```
                    165                 170                 175
Gly Leu Ser Ile Thr Glu Ala Thr Gln Lys Ala Ile Gln Gln Phe Glu
            180                 185                 190

Glu Ala Gly Arg Lys Phe Met Glu Gly Thr Leu His Leu Gly Lys Phe
            195                 200                 205

Leu Arg Pro Asn Gln Leu Trp Gly Tyr Tyr Leu Phe Pro Asp Cys Tyr
            210                 215                 220

Asn Asn Lys Phe Gln Asp Pro Lys Tyr Asp Gly Gln Cys Pro Ala Val
225                 230                 235                 240

Glu Lys Lys Arg Asn Asp Asn Leu Lys Trp Leu Trp Lys Ala Ser Thr
                245                 250                 255

Gly Leu Tyr Pro Ser Val Tyr Leu Lys Lys Asp Leu Lys Ser Asn Arg
            260                 265                 270

Gln Ala Thr Leu Tyr Val Arg Tyr Arg Val Val Glu Ala Ile Arg Val
            275                 280                 285

Ser Lys Val Gly Asn Ala Ser Asp Pro Val Pro Ile Phe Val Tyr Ile
            290                 295                 300

Arg Leu Val Phe Thr Asp Arg Thr Ser Glu Tyr Leu Leu Glu Asp Asp
305                 310                 315                 320

Leu Val Asn Thr Ile Gly Glu Ile Val Ala Leu Gly Thr Ser Gly Ile
                325                 330                 335

Ile Ile Trp Asp Ala Met Ser Leu Ala Gln Arg Ala Ala Gly Cys Pro
            340                 345                 350

Ile Leu His Lys Tyr Met Gln Thr Thr Leu Asn Pro Tyr Ile Val Asn
            355                 360                 365

Val Thr Leu Ala Ala Lys Met Cys Ser Gln Thr Leu Cys Asn Glu Lys
            370                 375                 380

Gly Met Cys Ser Arg Arg Lys Glu Ser Ser Asp Val Tyr Leu His Leu
385                 390                 395                 400

Asn Pro Ser His Phe Asp Ile Met Leu Thr Glu Thr Gly Lys Tyr Glu
                405                 410                 415

Val Leu Gly Asn Pro Arg Val Gly Asp Leu Glu Tyr Phe Ser Glu His
            420                 425                 430

Phe Lys Cys Ser Cys Phe Ser Arg Met Thr Cys Lys Glu Thr Ser Asp
            435                 440                 445

Val Lys Asn Val Gln Asp Val Asn Val Cys Val Gly Asp Asn Val Cys
            450                 455                 460

Ile Lys Ala Lys Val Glu Pro Asn Pro Ala Phe Tyr Leu Leu Pro Gly
465                 470                 475                 480

Lys Ser Leu Leu Phe Met Thr Thr Leu Gly His Val Leu Tyr His Leu
                485                 490                 495

Pro Gln Asp Ile Phe Val Phe Pro Arg Lys Thr Leu Val Ser Thr Pro
            500                 505                 510

<210> SEQ ID NO 31
<211> LENGTH: 807
<212> TYPE: PRT
<213> ORGANISM: Staphylococcus aureus
<220> FEATURE:
<223> OTHER INFORMATION: hyaluronidase

<400> SEQUENCE: 31

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30
```

Asp Lys His Gln Ile Ala Val Ala Asp Thr Asn Val Gln Thr Pro Asp
            35                  40                  45

Tyr Glu Lys Leu Arg Asn Thr Trp Leu Asp Val Asn Tyr Gly Tyr Asp
 50                  55                  60

Lys Tyr Asp Glu Asn Asn Pro Asp Met Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
            115                 120                 125

Arg Asn Pro Lys Thr Thr Leu Asn Thr Asp Glu Asn Lys Lys Lys Val
130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
            195                 200                 205

Glu Lys Lys Lys Phe Thr Ala Pro Ile Lys Thr Phe Ala Pro Asp Ser
            210                 215                 220

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
            275                 280                 285

Tyr Lys Asp Gly Ser Tyr Ile Asp His Gln Asp Val Pro Tyr Thr Gly
            290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
            355                 360                 365

Ser His Ser Ala Ser Ala Thr Val Met Lys Ser Leu Leu Arg Leu Ser
            370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
            435                 440                 445

Asp Arg Val Thr Tyr His Asn Lys Asp Leu Asp Phe Ala Phe Gly Leu

```
                450             455             460
Ser Met Thr Ser Lys Asn Val Ala Arg Tyr Glu Ser Ile Asn Gly Glu
465             470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
                500                 505                 510

Lys Arg Leu Ser Gly Thr Thr Thr Leu Asp Asn Glu Ile Leu Lys Asp
                515                 520                 525

Thr Asp Asp Lys Lys Ser Ser Lys Thr Phe Val Gly Thr Lys Val
530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
                580                 585                 590

Thr Thr Ile Glu Asn Arg Lys Ala Asn Gly Tyr Thr Leu Tyr Thr Asp
                595                 600                 605

Asp Lys Gln Thr Thr Asn Ser Asp Asn Gln Glu Asn Asn Ser Val Phe
610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
                645                 650                 655

Glu Ile Asn Lys Ser Gln Lys Asp Thr Gln Lys Thr Asp Glu Tyr Tyr
                660                 665                 670

Glu Val Thr Gln Lys His Ser Asn Ser Asp Asn Lys Tyr Gly Tyr Val
                675                 680                 685

Leu Tyr Pro Gly Leu Ser Lys Asp Val Phe Lys Thr Lys Lys Asp Glu
                690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
                740                 745                 750

Leu Lys Lys Lys Asp Asp Asn Thr Tyr Glu Cys Ser Phe Tyr Asn Pro
                755                 760                 765

Glu Ser Thr Asn Ser Ala Ser Asp Ile Glu Ser Lys Ile Ser Met Thr
770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805
```

<210> SEQ ID NO 32
<211> LENGTH: 371
<212> TYPE: PRT
<213> ORGANISM: Streptococcus pyogenes bacteriophage H4489A
<220> FEATURE:
<223> OTHER INFORMATION: hyaluronidase

<400> SEQUENCE: 32

```
Met Thr Glu Asn Ile Pro Leu Arg Val Gln Phe Lys Arg Met Ser Ala
1               5                   10                  15
```

Asp Glu Trp Ala Arg Ser Asp Val Ile Leu Glu Gly Glu Ile Gly
            20                  25                  30

Phe Glu Thr Asp Thr Gly Phe Ala Lys Phe Gly Asp Gly Gln Asn Thr
        35                  40                  45

Phe Ser Lys Leu Lys Tyr Leu Thr Gly Pro Lys Gly Pro Lys Gly Asp
 50                  55                  60

Thr Gly Leu Gln Gly Lys Thr Gly Thr Gly Pro Arg Gly Pro Ala
 65                  70                  75                  80

Gly Lys Pro Gly Thr Thr Asp Tyr Asp Gln Leu Gln Asn Lys Pro Asp
                85                  90                  95

Leu Gly Ala Phe Ala Gln Lys Glu Glu Thr Asn Ser Lys Ile Thr Lys
            100                 105                 110

Leu Glu Ser Ser Lys Ala Asp Lys Ser Ala Val Tyr Ser Lys Ala Glu
        115                 120                 125

Ser Lys Ile Glu Leu Asp Lys Lys Leu Ser Leu Thr Gly Gly Ile Val
130                 135                 140

Thr Gly Gln Leu Gln Phe Lys Pro Asn Lys Ser Gly Ile Lys Pro Ser
145                 150                 155                 160

Ser Ser Val Gly Gly Ala Ile Asn Ile Asp Met Ser Lys Ser Glu Gly
                165                 170                 175

Ala Ala Met Val Met Tyr Thr Asn Lys Asp Thr Thr Asp Gly Pro Leu
            180                 185                 190

Met Ile Leu Arg Ser Asp Lys Asp Thr Phe Asp Gln Ser Ala Gln Phe
        195                 200                 205

Val Asp Tyr Ser Gly Lys Thr Asn Ala Val Asn Ile Val Met Arg Gln
210                 215                 220

Pro Ser Ala Pro Asn Phe Ser Ser Ala Leu Asn Ile Thr Ser Ala Asn
225                 230                 235                 240

Glu Gly Gly Ser Ala Met Gln Ile Arg Gly Val Glu Lys Ala Leu Gly
                245                 250                 255

Thr Leu Lys Ile Thr His Glu Asn Pro Asn Val Glu Ala Lys Tyr Asp
            260                 265                 270

Glu Asn Ala Ala Ala Leu Ser Ile Asp Ile Val Lys Lys Gln Lys Gly
        275                 280                 285

Gly Lys Gly Thr Ala Ala Gln Gly Ile Tyr Ile Asn Ser Thr Ser Gly
290                 295                 300

Thr Ala Gly Lys Met Leu Arg Ile Arg Asn Lys Asn Glu Asp Lys Phe
305                 310                 315                 320

Tyr Val Gly Pro Asp Gly Gly Phe His Ser Gly Ala Asn Ser Thr Val
                325                 330                 335

Ala Gly Asn Leu Thr Val Lys Asp Pro Thr Ser Gly Lys His Ala Ala
            340                 345                 350

Thr Lys Asp Tyr Val Asp Glu Lys Ile Ala Glu Leu Lys Lys Leu Ile
        355                 360                 365

Leu Lys Lys
    370

<210> SEQ ID NO 33
<211> LENGTH: 1628
<212> TYPE: PRT
<213> ORGANISM: Clostridium perfringens
<220> FEATURE:
<223> OTHER INFORMATION: hyaluronidase

<400> SEQUENCE: 33

-continued

```
Met Asn Lys Asn Ile Arg Lys Ile Ile Thr Ser Thr Val Leu Ala Ala
 1               5                  10                  15
Met Thr Ile Ser Val Leu Pro Ser Asn Leu Val Val Phe Ala Thr Asp
            20                  25                  30
Gly Ile Thr Glu Asn Phe Tyr Glu Ile Tyr Pro Lys Pro Gln Glu Ile
                35                  40                  45
Ser Tyr Ser Gly Gly Glu Phe Gln Ile Ser Asp Glu Ile Asn Ile Val
        50                  55                  60
Tyr Asp Asp Gly Ile Asp Thr Tyr Thr Lys Lys Arg Val Asp Glu Val
 65                  70                  75                  80
Leu Glu Ala Ser Asn Leu Glu Ala Thr Val Ser Asn Glu Ile Val Pro
                85                  90                  95
Gly Lys Thr Asn Phe Leu Val Gly Ile Asn Glu Ser Gly Gly Val Val
                100                 105                 110
Asp Asn Tyr Phe Asn Lys Asn Ile Pro His Asp Glu Ser Phe Phe Asp
            115                 120                 125
Glu Lys Met Asp Ala Asn Ile Val Ser Val Lys Asp Gly Val Ile Gly
        130                 135                 140
Val Ile Gly Glu Asp Thr Asp Ser Ala Phe Tyr Gly Val Thr Thr Leu
145                 150                 155                 160
Lys His Val Phe Asn Gln Leu Glu Glu Gly Asn Lys Ile Gln Ser Phe
                165                 170                 175
Arg Ala Asp Asp Tyr Ala Glu Val Ala His Arg Gly Phe Ile Glu Gly
            180                 185                 190
Tyr Tyr Gly Asn Pro Trp Ser Asn Glu Asp Arg Ala Glu Leu Met Lys
        195                 200                 205
Phe Gly Gly Asp Tyr Lys Leu Asn Gln Tyr Val Phe Ala Pro Lys Asp
210                 215                 220
Asp Pro Tyr His Asn Ser Lys Trp Arg Asp Leu Tyr Pro Glu Glu Lys
225                 230                 235                 240
Leu Ser Glu Ile Lys Lys Leu Ala Gln Val Gly Asn Glu Thr Lys Asn
                245                 250                 255
Arg Tyr Val Tyr Ala Leu His Pro Phe Met Asn Asn Pro Val Arg Phe
            260                 265                 270
Asp Thr Glu Glu Asn Tyr Gln Asn Asp Leu Gly Val Ile Lys Ala Lys
        275                 280                 285
Phe Thr Gln Leu Leu Glu Asn Asp Val Arg Gln Phe Ala Ile Leu Ala
290                 295                 300
Asp Asp Ala Ser Ala Pro Ala Gln Gly Ala Ser Met Tyr Val Lys Leu
305                 310                 315                 320
Leu Thr Asp Leu Thr Arg Trp Leu Glu Glu Gln Gln Ser Thr Tyr Pro
                325                 330                 335
Asp Leu Lys Thr Asp Leu Met Phe Cys Pro Ser Asp Tyr Tyr Gly Asn
            340                 345                 350
Gly Ser Ser Ala Gln Leu Lys Glu Leu Asn Lys Ala Glu Asp Asn Val
        355                 360                 365
Ser Ile Val Met Thr Gly Gly Arg Ile Trp Gly Glu Val Asp Glu Asn
370                 375                 380
Phe Ala Asn Asn Phe Met Asn Asn Ile Ser Thr Glu Gly His Pro Gly
385                 390                 395                 400
Arg Ala Pro Phe Phe Trp Ile Asn Trp Pro Cys Ser Asp Asn Ser Lys
                405                 410                 415
Gln His Leu Ile Met Gly Gly Asn Asp Thr Phe Leu His Pro Gly Val
            420                 425                 430
```

```
Asp Pro Ser Lys Ile Asp Gly Ile Val Leu Asn Pro Met Gln Gln Ala
            435                 440                 445

Glu Ala Asn Lys Ser Ala Leu Phe Ala Ile Ala Asp Tyr Ala Trp Asn
        450                 455                 460

Ile Trp Asp Asn Lys Glu Ala Asp Glu Asn Trp Asn Asp Ser Phe
465                 470                 475                 480

Lys Tyr Met Asp His Gly Thr Ala Glu Thr Asn Ser Ser Leu Ala
                485                 490                 495

Leu Arg Glu Ile Ser Lys His Met Ile Asn Gln Asn Met Asp Gly Arg
                500                 505                 510

Val Arg Pro Leu Gln Glu Ser Val Glu Leu Ala Pro Lys Leu Glu Ala
            515                 520                 525

Phe Lys Gln Lys Tyr Asp Ser Gly Ala Ser Ile Lys Glu Asp Ala Leu
            530                 535                 540

Glu Leu Ile Ala Glu Phe Thr Asn Leu Gln Lys Ala Ala Asp Tyr Tyr
545                 550                 555                 560

Lys Asn Asn Pro Gly Asn Glu Arg Thr Arg Asp Gln Ile Ile Tyr Trp
                565                 570                 575

Leu Asn Cys Trp Glu Asp Thr Met Asp Ala Ala Ile Gly Tyr Leu Lys
                580                 585                 590

Ser Ala Ile Ala Ile Glu Glu Gly Asp Glu Ala Ala Trp Ala Asn
            595                 600                 605

Tyr Ser Glu Ala Gln Gly Ala Phe Glu Lys Ser Lys Thr Tyr Gly Phe
            610                 615                 620

His Tyr Val Asp His Thr Glu Tyr Ala Glu Val Gly Val Gln His Ile
625                 630                 635                 640

Val Pro Phe Ile Lys Ser Met Gly Gln Asn Leu Ser Val Val Ile Gly
                645                 650                 655

Ser Ile Val Asp Pro Asn Arg Ile Ile Ala Thr Tyr Ile Ser Asn Arg
                660                 665                 670

Gln Asp Ala Pro Thr Gly Asn Pro Asp Asn Ile Phe Asp Asn Asn Ala
            675                 680                 685

Ser Thr Glu Leu Val Tyr Lys Asn Pro Asn Arg Ile Asp Val Gly Thr
            690                 695                 700

Tyr Val Gly Val Lys Tyr Ser Asn Pro Ile Thr Leu Asn Asn Val Glu
705                 710                 715                 720

Phe Leu Met Gly Ala Asn Ser Asn Pro Asn Asp Thr Met Gln Lys Ala
                725                 730                 735

Lys Ile Gln Tyr Thr Val Asp Gly Arg Glu Trp Ile Asp Leu Glu Glu
            740                 745                 750

Gly Val Glu Tyr Thr Met Pro Gly Ala Ile Lys Val Glu Asn Leu Asp
            755                 760                 765

Leu Lys Val Arg Gly Val Arg Leu Ile Ala Thr Glu Ala Arg Glu Asn
            770                 775                 780

Thr Trp Leu Gly Val Arg Asp Ile Asn Val Asn Lys Lys Glu Asp Ser
785                 790                 795                 800

Asn Ser Gly Val Glu Phe Asn Pro Ser Leu Ile Arg Ser Glu Ser Trp
                805                 810                 815

Gln Val Tyr Glu Gly Asn Glu Ala Asn Leu Leu Asp Gly Asp Asn
            820                 825                 830

Thr Gly Val Trp Tyr Lys Thr Leu Asn Gly Asp Thr Ser Leu Ala Gly
            835                 840                 845

Glu Phe Ile Gly Leu Asp Leu Gly Lys Glu Ile Lys Leu Asp Gly Ile
```

```
            850                 855                 860
Arg Phe Val Ile Gly Lys Asn Gly Gly Ser Ser Asp Lys Trp Asn
865                 870                 875                 880
Lys Phe Lys Leu Glu Tyr Ser Leu Asp Asn Glu Ser Trp Thr Thr Ile
                    885                 890                 895
Lys Glu Tyr Asp Lys Thr Gly Ala Pro Ala Gly Lys Asp Val Ile Glu
                    900                 905                 910
Glu Ser Phe Glu Thr Pro Ile Ser Ala Lys Tyr Ile Arg Leu Thr Asn
                    915                 920                 925
Met Glu Asn Ile Asn Lys Trp Leu Thr Phe Ser Glu Phe Ala Ile Ile
            930                 935                 940
Ser Asp Glu Leu Glu Asn Ala Gly Asn Lys Glu Asn Val Tyr Thr Asn
945                 950                 955                 960
Thr Glu Leu Asp Leu Leu Ser Leu Ala Lys Glu Asp Val Thr Lys Leu
                    965                 970                 975
Ile Pro Thr Asp Asp Ile Ser Leu Asn His Gly Glu Tyr Ile Gly Val
                    980                 985                 990
Lys Leu Asn Arg Ile Lys Asp Leu Ser Asn Ile Asn Leu Glu Ile Ser
                    995                 1000                1005
Asn Asp Thr Gly Leu Lys Leu Gln Ser Ser Met Asn Gly Val Glu Trp
            1010                1015                1020
Thr Glu Ile Thr Asp Lys Asn Thr Leu Glu Asp Gly Arg Tyr Val Arg
1025                1030                1035                1040
Leu Ile Asn Thr Ser Asn Glu Ala Val Asn Phe Asn Leu Thr Lys Phe
                    1045                1050                1055
Glu Val Asn Ser Asn Glu Val Tyr Glu Pro Ser Leu Val Asp Ala Tyr
                    1060                1065                1070
Val Gly Asp Asp Gly Ala Lys Lys Ala Val Asp Gly Asp Leu Lys Thr
                    1075                1080                1085
Arg Val Lys Phe Leu Gly Ala Pro Ser Thr Gly Asp Thr Ile Val Tyr
                    1090                1095                1100
Asp Leu Gly Gln Glu Ile Leu Val Asp Asn Leu Lys Tyr Val Val Leu
1105                1110                1115                1120
Asp Thr Glu Val Asp His Val Arg Asp Gly Lys Ile Gln Leu Ser Leu
                    1125                1130                1135
Asp Gly Glu Thr Trp Thr Asp Ala Ile Thr Ile Gly Asp Gly Val Glu
            1140                1145                1150
Asn Gly Val Asp Asp Met Phe Ser Thr Pro Leu Lys Asn Gly Tyr Lys
            1155                1160                1165
His Gly Asn Gln Ser Gly Gly Ile Val Pro Ile Asp Ser Ala Tyr Val
            1170                1175                1180
Glu Gly Asp Asn Leu Asn Gln Lys Ala Arg Tyr Val Arg Ile Leu Phe
1185                1190                1195                1200
Thr Ala Pro Tyr Arg His Arg Trp Thr Val Ile Asn Glu Leu Met Ile
                    1205                1210                1215
Asn Asn Gly Glu Tyr Ile Ser Thr Val Asn Asp Pro Thr Tyr Ile Ser
                    1220                1225                1230
Asn Pro Ile Glu Glu Arg Gly Phe Ala Pro Ser Asn Leu Arg Asp Gly
                    1235                1240                1245
Asn Leu Thr Thr Ser Tyr Lys Pro Asn Thr Asn Asn Gly Glu Ile Ser
            1250                1255                1260
Glu Gly Ser Ile Thr Tyr Arg Leu Ser Glu Lys Thr Asp Val Arg Lys
1265                1270                1275                1280
```

```
Val Thr Ile Val Gln Ser Gly Ser Ser Ile Ser Asn Ala Lys Val Met
            1285                1290                1295

Ala Arg Val Gly Asp Gly Ser Glu Asn Val Thr Asp Gln Trp Val Gln
            1300                1305                1310

Leu Gly Thr Leu Ser Asn Ser Leu Asn Glu Phe Ile Asn Arg Asp Tyr
            1315                1320                1325

Asn Asn Ile Tyr Glu Ile Lys Ile Glu Trp Thr Asp Val Ala Pro Asn
            1330                1335                1340

Ile Tyr Glu Ile Ile Thr Leu Asn Gln Glu Phe Glu Phe Pro Val Asn
1345                1350                1355                1360

Asp Ser Leu Lys Ala Lys Tyr Asp Glu Leu Ile Asn Leu Ser Gly Asp
            1365                1370                1375

Glu Tyr Thr Leu Ser Ser Phe Glu Thr Leu Lys Glu Ala Leu Asn Glu
            1380                1385                1390

Ala Lys Ser Ile Leu Asp Asp Ser Asn Ser Ser Gln Lys Lys Ile Asp
            1395                1400                1405

Lys Ala Leu Glu Lys Leu Asn Lys Ala Glu Glu Arg Leu Asp Leu Arg
            1410                1415                1420

Ala Thr Asp Phe Glu Asp Phe Asn Lys Val Leu Thr Leu Gly Asn Ser
1425                1430                1435                1440

Leu Val Glu Glu Glu Tyr Thr Ala Glu Ser Trp Ala Leu Phe Ser Glu
            1445                1450                1455

Val Leu Glu Ala Ala Asn Glu Ala Asn Lys Asn Lys Ala Asp Tyr Thr
            1460                1465                1470

Gln Asp Gln Ile Asn Gln Ile Val Ile Asp Leu Asp Ala Ser Ile Lys
            1475                1480                1485

Ala Leu Val Lys Glu Thr Pro Glu Val Asp Lys Thr Asn Leu Gly Glu
            1490                1495                1500

Leu Ile Asn Gln Gly Lys Ser Leu Leu Asp Glu Ser Val Glu Gly Phe
1505                1510                1515                1520

Asn Val Gly Glu Tyr His Lys Gly Ala Lys Asp Gly Leu Thr Val Glu
            1525                1530                1535

Ile Asn Lys Ala Glu Glu Val Phe Asn Lys Glu Asp Ala Thr Glu Glu
            1540                1545                1550

Glu Ile Asn Leu Ala Lys Glu Ser Leu Glu Gly Ala Ile Ala Arg Phe
            1555                1560                1565

Asn Ser Leu Leu Ile Glu Glu Ser Thr Gly Asp Phe Asn Gly Asn Gly
            1570                1575                1580

Lys Ile Asp Ile Gly Asp Leu Ala Met Val Ser Lys Asn Ile Gly Ser
1585                1590                1595                1600

Thr Thr Asn Thr Ser Leu Asp Leu Asn Lys Asp Gly Ser Ile Asp Glu
            1605                1610                1615

Tyr Glu Ile Ser Phe Ile Asn His Arg Ile Leu Asn
            1620                1625

<210> SEQ ID NO 34
<211> LENGTH: 435
<212> TYPE: PRT
<213> ORGANISM: Homo sapiens
<220> FEATURE:
<223> OTHER INFORMATION: Hyaluronidase-1 [Precursor]

<400> SEQUENCE: 34

Met Ala Ala His Leu Leu Pro Ile Cys Ala Leu Phe Leu Thr Leu Leu
 1               5                   10                  15

Asp Met Ala Gln Gly Phe Arg Gly Pro Leu Leu Pro Asn Arg Pro Phe
```

```
            20                  25                  30
Thr Thr Val Trp Asn Ala Asn Thr Gln Trp Cys Leu Glu Arg His Gly
            35                  40                  45

Val Asp Val Asp Val Ser Val Phe Asp Val Val Ala Asn Pro Gly Gln
 50                  55                  60

Thr Phe Arg Gly Pro Asp Met Thr Ile Phe Tyr Ser Ser Gln Leu Gly
 65              70                  75                  80

Thr Tyr Pro Tyr Tyr Thr Pro Thr Gly Glu Pro Val Phe Gly Gly Leu
                 85                  90                  95

Pro Gln Asn Ala Ser Leu Ile Ala His Leu Ala Arg Thr Phe Gln Asp
                100                 105                 110

Ile Leu Ala Ala Ile Pro Ala Pro Asp Phe Ser Gly Leu Ala Val Ile
            115                 120                 125

Asp Trp Glu Ala Trp Arg Pro Arg Trp Ala Phe Asn Trp Asp Thr Lys
            130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
                180                 185                 190

Leu Arg Pro Arg Gly Leu Trp Gly Phe Tyr Gly Phe Pro Asp Cys Tyr
            195                 200                 205

Asn Tyr Asp Phe Leu Ser Pro Asn Tyr Thr Gly Gln Cys Pro Ser Gly
            210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
                260                 265                 270

Ala Val Ala Ala Gly Asp Pro Asn Leu Pro Val Leu Pro Tyr Val Gln
            275                 280                 285

Ile Phe Tyr Asp Thr Thr Asn His Phe Leu Pro Leu Asp Glu Leu Glu
            290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
                340                 345                 350

Ser Gly Ala Leu Leu Cys Ser Gln Ala Leu Cys Ser Gly His Gly Arg
            355                 360                 365

Cys Val Arg Arg Thr Ser His Pro Lys Ala Leu Leu Leu Leu Asn Pro
            370                 375                 380

Ala Ser Phe Ser Ile Gln Leu Thr Pro Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
            435
```

<210> SEQ ID NO 35
<211> LENGTH: 473
<212> TYPE: PRT
<213> ORGANISM: Homo sapiens
<220> FEATURE:
<223> OTHER INFORMATION: Hyaluronidase-2 [Precursor]

<400> SEQUENCE: 35

```
Met Arg Ala Gly Pro Gly Pro Thr Val Thr Leu Ala Leu Val Leu Ala
 1               5                  10                  15

Val Ala Trp Ala Met Glu Leu Lys Pro Thr Ala Pro Pro Ile Phe Thr
             20                  25                  30

Gly Arg Pro Phe Val Val Ala Trp Asp Val Pro Thr Gln Asp Cys Gly
         35                  40                  45

Pro Arg Leu Lys Val Pro Leu Asp Leu Asn Ala Phe Asp Val Gln Ala
     50                  55                  60

Ser Pro Asn Glu Gly Phe Val Asn Gln Asn Ile Thr Ile Phe Tyr Arg
 65                  70                  75                  80

Asp Arg Leu Gly Leu Tyr Pro Arg Phe Asp Ser Ala Gly Arg Ser Val
                 85                  90                  95

His Gly Gly Val Pro Gln Asn Val Ser Leu Trp Ala His Arg Lys Met
            100                 105                 110

Leu Gln Lys Arg Val Glu His Tyr Ile Arg Thr Gln Glu Ser Ala Gly
        115                 120                 125

Leu Ala Val Ile Asp Trp Glu Asp Trp Arg Pro Val Trp Val Arg Asn
    130                 135                 140

Trp Gln Asp Lys Asp Val Tyr Arg Arg Leu Ser Arg Gln Leu Val Ala
145                 150                 155                 160

Ser Arg His Pro Asp Trp Pro Pro Asp Arg Ile Val Lys Gln Ala Gln
                165                 170                 175

Tyr Glu Phe Glu Phe Ala Ala Gln Gln Phe Met Leu Glu Thr Leu Arg
            180                 185                 190

Tyr Val Lys Ala Val Arg Pro Arg His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
                245                 250                 255

Thr Leu Ala Ser Ser Arg His Gly Arg Asn Phe Val Ser Phe Arg Val
            260                 265                 270

Gln Glu Ala Leu Arg Val Ala Arg Thr His His Ala Asn His Ala Leu
        275                 280                 285

Pro Val Tyr Val Phe Thr Arg Pro Thr Tyr Ser Arg Arg Leu Thr Gly
    290                 295                 300

Leu Ser Glu Met Asp Leu Ile Ser Thr Ile Gly Glu Ser Ala Ala Leu
305                 310                 315                 320

Gly Ala Ala Gly Val Ile Leu Trp Gly Asp Ala Gly Tyr Thr Thr Ser
                325                 330                 335

Thr Glu Thr Cys Gln Tyr Leu Lys Asp Tyr Leu Thr Arg Leu Leu Val
            340                 345                 350

Pro Tyr Val Val Asn Val Ser Trp Ala Thr Gln Tyr Cys Ser Arg Ala
        355                 360                 365

Gln Cys His Gly His Gly Arg Cys Val Arg Arg Asn Pro Ser Ala Ser
```

```
                370                 375                 380
Thr Phe Leu His Leu Ser Thr Asn Ser Phe Arg Leu Val Pro Gly His
385                 390                 395                 400

Ala Pro Gly Glu Pro Gln Leu Arg Pro Val Gly Glu Leu Ser Trp Ala
                405                 410                 415

Asp Ile Asp His Leu Gln Thr His Phe Arg Cys Gln Cys Tyr Leu Gly
                420                 425                 430

Trp Ser Gly Glu Gln Cys Gln Trp Asp His Arg Gln Ala Ala Gly Gly
                435                 440                 445

Ala Ser Glu Ala Trp Ala Gly Ser His Leu Thr Ser Leu Leu Ala Leu
                450                 455                 460

Ala Ala Leu Ala Phe Thr Trp Thr Leu
465                 470

<210> SEQ ID NO 36
<211> LENGTH: 417
<212> TYPE: PRT
<213> ORGANISM: Homo sapiens
<220> FEATURE:
<223> OTHER INFORMATION: Hyaluronidase-3 [Precursor]

<400> SEQUENCE: 36

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
                20                  25                  30

Val Leu Trp Asn Val Pro Ser Ala His Cys Glu Ala Arg Phe Gly Val
                35                  40                  45

His Leu Pro Leu Asn Ala Leu Gly Ile Ile Ala Asn Arg Gly Gln His
                50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
                100                 105                 110

His His Ser Leu Arg Pro Gly Phe Ala Gly Pro Ala Val Leu Asp Trp
                115                 120                 125

Glu Glu Trp Cys Pro Leu Trp Ala Gly Asn Trp Gly Arg Arg Arg Ala
130                 135                 140

Tyr Gln Ala Ala Ser Trp Ala Trp Ala Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
                180                 185                 190

Pro His Gly Leu Trp Gly Phe Tyr His Tyr Pro Ala Cys Gly Asn Gly
                195                 200                 205

Trp His Ser Met Ala Ser Asn Tyr Thr Gly Arg Cys His Ala Ala Thr
                210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
                260                 265                 270
```

Val Gly His Arg His Pro Leu Pro Val Leu Ala Tyr Val Arg Leu Thr
            275                 280                 285

His Arg Arg Ser Gly Arg Phe Leu Ser Gln Asp Asp Leu Val Gln Ser
        290                 295                 300

Ile Gly Val Ser Ala Ala Leu Gly Ala Ala Gly Val Val Leu Trp Gly
305                 310                 315                 320

Asp Leu Ser Leu Ser Ser Glu Glu Glu Cys Trp His Leu His Asp
                325                 330                 335

Tyr Leu Val Asp Thr Leu Gly Pro Tyr Val Ile Asn Val Thr Arg Ala
                340                 345                 350

Ala Met Ala Cys Ser His Gln Arg Cys His Gly His Gly Arg Cys Ala
            355                 360                 365

Arg Arg Asp Pro Gly Gln Met Glu Ala Phe Leu His Leu Trp Pro Asp
        370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415

Val

<210> SEQ ID NO 37
<211> LENGTH: 481
<212> TYPE: PRT
<213> ORGANISM: Homo sapiens
<220> FEATURE:
<223> OTHER INFORMATION: Hyaluronidase-4

<400> SEQUENCE: 37

Met Lys Val Leu Ser Glu Gly Gln Leu Lys Leu Cys Val Val Gln Pro
1               5                   10                  15

Val His Leu Thr Ser Trp Leu Leu Ile Phe Phe Ile Leu Lys Ser Ile
            20                  25                  30

Ser Cys Leu Lys Pro Ala Arg Leu Pro Ile Tyr Gln Arg Lys Pro Phe
        35                  40                  45

Ile Ala Ala Trp Asn Ala Pro Thr Asp Gln Cys Leu Ile Lys Tyr Asn
50                  55                  60

Leu Arg Leu Asn Leu Lys Met Phe Pro Val Ile Gly Ser Pro Leu Ala
65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
            100                 105                 110

Pro Gln Asn Ile Ser Leu Gln Val His Leu Glu Lys Ala Asp Gln Asp
        115                 120                 125

Ile Asn Tyr Tyr Ile Pro Ala Glu Asp Phe Ser Gly Leu Ala Val Ile
130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
            180                 185                 190

Glu Ser Ala Lys Ala Phe Met Lys Glu Thr Ile Lys Leu Gly Ile Lys
        195                 200                 205

Ser Arg Pro Lys Gly Leu Trp Gly Tyr Tyr Leu Tyr Pro Asp Cys His

-continued

```
                210                 215                 220
Asn Tyr Asn Val Tyr Ala Pro Asn Tyr Ser Gly Ser Cys Pro Glu Asp
225                 230                 235                 240

Glu Val Leu Arg Asn Glu Leu Ser Trp Leu Trp Asn Ser Ser Ala
            245                 250                 255

Ala Leu Tyr Pro Ser Ile Gly Val Trp Lys Ser Leu Gly Asp Ser Glu
            260                 265                 270

Asn Ile Leu Arg Phe Ser Lys Phe Arg Val His Glu Ser Met Arg Ile
            275                 280                 285

Ser Thr Met Thr Ser His Asp Tyr Ala Leu Pro Val Phe Val Tyr Thr
            290                 295                 300

Arg Leu Gly Tyr Arg Asp Glu Pro Leu Phe Phe Leu Ser Lys Gln Asp
305                 310                 315                 320

Leu Val Ser Thr Ile Gly Glu Ser Ala Ala Leu Gly Ala Ala Gly Ile
                325                 330                 335

Val Ile Trp Gly Asp Met Asn Leu Thr Ala Ser Lys Ala Asn Cys Thr
                340                 345                 350

Lys Val Lys Gln Phe Val Ser Ser Asp Leu Gly Ser Tyr Ile Ala Asn
            355                 360                 365

Val Thr Arg Ala Ala Glu Val Cys Ser Leu His Leu Cys Arg Asn Asn
            370                 375                 380

Gly Arg Cys Ile Arg Lys Met Trp Asn Ala Pro Ser Tyr Leu His Leu
385                 390                 395                 400

Asn Pro Ala Ser Tyr His Ile Glu Ala Ser Glu Asp Gly Glu Phe Thr
                405                 410                 415

Val Lys Gly Lys Ala Ser Asp Thr Asp Leu Ala Val Met Ala Asp Thr
            420                 425                 430

Phe Ser Cys His Cys Tyr Gln Gly Tyr Glu Gly Ala Asp Cys Arg Glu
            435                 440                 445

Ile Lys Thr Ala Asp Gly Cys Ser Gly Val Ser Pro Ser Pro Gly Ser
            450                 455                 460

Leu Met Thr Leu Cys Leu Leu Leu Ala Ser Tyr Arg Ser Ile Gln
465                 470                 475                 480

Leu
```

<210> SEQ ID NO 38
<211> LENGTH: 467
<212> TYPE: PRT
<213> ORGANISM: Homo sapiens
<220> FEATURE:
<223> OTHER INFORMATION: sHuPH20 precursor 1-467

<400> SEQUENCE: 38

```
Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95
```

```
Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
            210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
            290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445

Val Lys Asp Thr Asp Ala Val Asp Val Cys Ile Ala Asp Gly Val Cys
450                 455                 460

Ile Asp Ala
465
```

<210> SEQ ID NO 39
<211> LENGTH: 477
<212> TYPE: PRT
<213> ORGANISM: Homo sapiens
<220> FEATURE:
<223> OTHER INFORMATION: sHuPH20 precursor 1-477

<400> SEQUENCE: 39

```
Met Gly Val Leu Lys Phe Lys His Ile Phe Phe Arg Ser Phe Val Lys
 1               5                  10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
             35                  40                  45

Phe Leu Trp Ala Trp Asn Ala Pro Ser Glu Phe Cys Leu Gly Lys Phe
 50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
            290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415
```

-continued

Val Arg Gly Lys Pro Thr Leu Glu Asp Leu Glu Gln Phe Ser Glu Lys
            420             425             430

Phe Tyr Cys Ser Cys Tyr Ser Thr Leu Ser Cys Lys Glu Lys Ala Asp
            435             440             445

Val Lys Asp Thr Asp Ala Val Asp Val Cys Ile Ala Asp Gly Val Cys
            450             455             460

Ile Asp Ala Phe Leu Lys Pro Pro Met Glu Thr Glu Glu
465             470             475

<210> SEQ ID NO 40
<211> LENGTH: 478
<212> TYPE: PRT
<213> ORGANISM: Homo sapiens
<220> FEATURE:
<223> OTHER INFORMATION: sHuPH20 precursor 1-478

<400> SEQUENCE: 40

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
        50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu

-continued

```
                305                 310                 315                 320
Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
        370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro
465                 470                 475

<210> SEQ ID NO 41
<211> LENGTH: 479
<212> TYPE: PRT
<213> ORGANISM: Homo sapiens
<220> FEATURE:
<223> OTHER INFORMATION: sHuPH20 precursor 1-479

<400> SEQUENCE: 41

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205
```

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
        290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln
465                 470                 475

<210> SEQ ID NO 42
<211> LENGTH: 480
<212> TYPE: PRT
<213> ORGANISM: Homo sapiens
<220> FEATURE:
<223> OTHER INFORMATION: sHuPH20 precursor 1-480

<400> SEQUENCE: 42

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

```
Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
        130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
450                 455                 460

Ile Asp Ala Phe Leu Lys Pro Met Glu Thr Glu Glu Pro Gln Ile
465                 470                 475                 480
```

<210> SEQ ID NO 43
<211> LENGTH: 481
<212> TYPE: PRT
<213> ORGANISM: Homo sapiens
<220> FEATURE:
<223> OTHER INFORMATION: sHuPH20 precursor 1-481

<400> SEQUENCE: 43

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

```
Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Pro Gln Ile
465                 470                 475                 480

Phe

<210> SEQ ID NO 44
<211> LENGTH: 483
<212> TYPE: PRT
<213> ORGANISM: Homo sapiens
<220> FEATURE:
<223> OTHER INFORMATION: sHuPH20 precursor 1-483

<400> SEQUENCE: 44

Met Gly Val Leu Lys Phe Lys His Ile Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
            85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
    290                 295                 300
```

-continued

```
Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
            325                 330                 335

Val Ile Trp Gly Thr Leu Ser Ile Met Arg Ser Met Lys Ser Cys Leu
        340                 345                 350

Leu Leu Asp Asn Tyr Met Glu Thr Ile Leu Asn Pro Tyr Ile Ile Asn
    355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn

<210> SEQ ID NO 45
<211> LENGTH: 432
<212> TYPE: PRT
<213> ORGANISM: Homo sapiens
<220> FEATURE:
<223> OTHER INFORMATION: sHuPH20 mature 36-467

<400> SEQUENCE: 45

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
```

```
                    180                 185                 190
His Tyr Lys Lys Pro Gly Tyr Asn Gly Ser Cys Phe Asn Val Glu Ile
                195                 200                 205

Lys Arg Asn Asp Asp Leu Ser Trp Leu Trp Asn Glu Ser Thr Ala Leu
            210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

<210> SEQ ID NO 46
<211> LENGTH: 448
<212> TYPE: PRT
<213> ORGANISM: Homo sapiens
<220> FEATURE:
<223> OTHER INFORMATION: sHuPH20 mature 36-483

<400> SEQUENCE: 46

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125
```

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

```
<210> SEQ ID NO 47
<211> LENGTH: 1446
<212> TYPE: DNA
<213> ORGANISM: Homo sapiens
<220> FEATURE:
<223> OTHER INFORMATION: DNA encoding soluble rHuPH20 "precursor"

<400> SEQUENCE: 47
atgggagtgc taaaattcaa gcacatcttt ttcagaagct tgttaaaatc aagtggagta      60
tcccagatag ttttcacctt ccttctgatt ccatgttgct tgactctgaa tttcagagca     120
cctcctgtta ttccaaatgt gcctttcctc tgggcctgga atgccccaag tgaattttgt     180
cttggaaaat ttgatgagcc actagatatg agcctcttct ctttcatagg aagccccaga     240
ataaacgcca ccgggcaagg tgttacaata ttttatgttg atagacttgg ctactatcct     300
```

```
tacatagatt caatcacagg agtaactgtg aatggaggaa tcccccagaa gatttcctta      360
caagaccatc tggacaaagc taagaaagac attacatttt atatgccagt agacaatttg      420
ggaatggctg ttattgactg ggaagaatgg agacccactt gggcaagaaa ctggaaacct      480
aaagatgttt acaagaatag gtctattgaa ttggttcagc aacaaaatgt acaacttagt      540
ctcacagagg ccactgagaa agcaaaacaa gaatttgaaa aggcagggaa ggatttcctg      600
gtagagacta taaaattggg aaaattactt cggccaaatc acttgtgggg ttattatctt      660
tttccggatt gttacaacca tcactataag aaacccggtt acaatggaag ttgcttcaat      720
gtagaaataa aagaaatga tgatctcagc tggttgtgga atgaaagcac tgctctttac       780
ccatccattt atttgaacac tcagcagtct cctgtagctg ctacactcta tgtgcgcaat      840
cgagttcggg aagccatcag agtttccaaa atacctgatg caaaaagtcc acttccggtt      900
tttgcatata cccgcatagt ttttactgat caagttttga aattcctttc tcaagatgaa      960
cttgtgtata catttggcga aactgttgct ctgggtgctt ctggaattgt aatatgggga     1020
accctcagta taatgcgaag tatgaaatct tgcttgctcc tagacaatta catggagact     1080
atactgaatc cttacataat caacgtcaca ctagcagcca aaatgtgtag ccaagtgctt     1140
tgccaggagc aaggagtgtg tataaggaaa aactggaatt caagtgacta tcttcacctc     1200
aacccagata attttgctat tcaacttgag aaaggtggaa agttcacagt acgtggaaaa     1260
ccgacacttg aagacctgga gcaatttttct gaaaaatttt attgcagctg ttatagcacc     1320
ttgagttgta aggagaaagc tgatgtaaaa gacactgatg ctgttgatgt gtgtattgct     1380
gatggtgtct gtatagatgc ttttctaaaa cctcccatgg agacagaaga acctcaaatt     1440
ttctac                                                                1446

<210> SEQ ID NO 48
<211> LENGTH: 509
<212> TYPE: PRT
<213> ORGANISM: Homo sapiens
<220> FEATURE:
<223> OTHER INFORMATION: PH20 variant P48A

<400> SEQUENCE: 48

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Ala
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160
```

```
Lys Asp Val Tyr Lys Asn Arg Ser Ile Glu Leu Val Gln Gln Asn
            165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
210             215                 220

Tyr Asn His His Tyr Lys Lys Pro Gly Tyr Asn Gly Ser Cys Phe Asn
225             230                 235                 240

Val Glu Ile Lys Arg Asn Asp Asp Leu Ser Trp Leu Trp Asn Glu Ser
            245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
            290                 295                 300

Arg Ile Val Phe Thr Asp Gln Val Leu Lys Phe Leu Ser Gln Asp Glu
305             310                 315                 320

Leu Val Tyr Thr Phe Gly Glu Thr Val Ala Leu Gly Ala Ser Gly Ile
            325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
            370                 375                 380

Gly Val Cys Ile Arg Lys Asn Trp Asn Ser Ser Asp Tyr Leu His Leu
385             390                 395                 400

Asn Pro Asp Asn Phe Ala Ile Gln Leu Glu Lys Gly Gly Lys Phe Thr
            405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445

Val Lys Asp Thr Asp Ala Val Asp Val Cys Ile Ala Asp Gly Val Cys
450             455                 460

Ile Asp Ala Phe Leu Lys Pro Pro Met Glu Thr Glu Glu Pro Gln Ile
465             470                 475                 480

Phe Tyr Asn Ala Ser Pro Ser Thr Leu Ser Ala Thr Met Phe Ile Val
            485                 490                 495

Ser Ile Leu Phe Leu Ile Ile Ser Ser Val Ala Ser Leu
            500                 505

<210> SEQ ID NO 49
<211> LENGTH: 509
<212> TYPE: PRT
<213> ORGANISM: Homo sapiens
<220> FEATURE:
<223> OTHER INFORMATION: precursor PH20 variant L499W

<400> SEQUENCE: 49

Met Gly Val Leu Lys Phe Lys His Ile Phe Phe Arg Ser Phe Val Lys
1               5                   10                  15
```

```
Ser Ser Gly Val Ser Gln Ile Val Phe Thr Phe Leu Leu Ile Pro Cys
            20              25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
 50              55                  60

Asp Glu Pro Leu Asp Met Ser Leu Phe Ser Phe Ile Gly Ser Pro Arg
 65              70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
 130                 135                 140

Ile Asp Trp Glu Glu Trp Arg Pro Thr Trp Ala Arg Asn Trp Lys Pro
 145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
 210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
 290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
 370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445
```

```
Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Trp Phe Leu Ile Ile Ser Ser Val Ala Ser Leu
            500                 505

<210> SEQ ID NO 50
<211> LENGTH: 6630
<212> TYPE: DNA
<213> ORGANISM: Artificial Sequence
<220> FEATURE:
<223> OTHER INFORMATION: HZ24 vector

<400> SEQUENCE: 50
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccccattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga agagactctt gcgtttctga taggcaccta ttggtcttac     960
tgacatccac tttgcctttc tctccacagg tgtccactcc cagttcaatt acagctctta    1020
aggctagagt acttaatacg actcactata ggctagcatg ggagtgctaa aattcaagca    1080
catctttttc agaagctttg ttaaatcaag tggagtatcc cagatagttt tcaccttcct    1140
tctgattcca tgttgcttga ctctgaattt cagagcacct cctgttattc caaatgtgcc    1200
tttcctctgg gcctggaatg ccccaagtga attttgtctt ggaaaatttg atgagccact    1260
agatatgagc ctcttctctt tcataggaag cccccgaata aacgccaccg ggcaaggtgt    1320
tacaatattt tatgttgata gacttggcta ctatccttac atagattcaa tcacaggagt    1380
aactgtgaat ggaggaatcc cccagaagat ttccttacaa gaccatctgg acaaagctaa    1440
gaaagacatt acattttata tgccagtaga caatttggga atggctgtta ttgactggga    1500
agaatggaga cccacttggg caagaaactg gaaacctaaa gatgtttaca gaataggtc     1560 tattgaattg gttcagcaac aaaatgtaca acttagtctc acagaggcca ctgagaaagc    1620
aaaacaagaa tttgaaaagg cagggaagga tttcctggta gagactataa aattgggaaa    1680
attacttcgg ccaaatcact gtgggggtta ttatctttttt ccggattgtt acaaccatca    1740
```

```
ctataagaaa cccggttaca atggaagttg cttcaatgta gaaataaaaa gaaatgatga    1800
tctcagctgg ttgtggaatg aaagcactgc tctttaccca tccatttatt tgaacactca    1860
gcagtctcct gtagctgcta cactctatgt gcgcaatcga gttcgggaag ccatcagagt    1920
ttccaaaata cctgatgcaa aaagtccact tccggttttt gcatataccc gcatagtttt    1980
tactgatcaa gttttgaaat tcctttctca agatgaactt gtgtatacat ttggcgaaac    2040
tgttgctctg ggtgcttctg gaattgtaat atggggaacc ctcagtataa tgcgaagtat    2100
gaaatcttgc ttgctcctag acaattacat ggagactata ctgaatcctt acataatcaa    2160
cgtcacacta gcagccaaaa tgtgtagcca agtgctttgc caggagcaag gagtgtgtat    2220
aaggaaaaac tggaattcaa gtgactatct tcacctcaac ccagataatt ttgctattca    2280
acttgagaaa ggtggaaagt tcacagtacg tggaaaaccg acacttgaag acctggagca    2340
attttctgaa aaattttatt gcagctgtta tagcaccttg agttgtaagg agaaagctga    2400
tgtaaaagac actgatgctg ttgatgtgtg tattgctgat ggtgtctgta tagatgcttt    2460
tctaaaacct cccatggaga cagaagaacc tcaaattttc tactgaggat ccatagctaa    2520
cgcccctctc cctccccccc ccctaacgtt actggccgaa gccgcttgga ataaggccgg    2580
tgtgcgtttg tctatatgtt attttccacc atattgccgt cttttggcaa tgtgagggcc    2640
cggaaacctg gccctgtctt cttgacgagc attcctaggg gtctttcccc tctcgccaaa    2700
ggaatgcaag gtctgttgaa tgtcgtgaag gaagcagttc ctctggaagc ttcttgaaga    2760
caaacaacgt ctgtagcgac cctttgcagg cagcggaacc ccccacctgg cgacaggtgc    2820
ctctgcggcc aaaagccacg tgtataagat acacctgcaa aggcggcaca ccccagtgc    2880 cacgttgtga gttggatagt tgtggaaaga gtcaaatggc tctcctcaag cgtattcaac    2940
aaggggctga aggatgccca gaaggtaccc cattgtatgg gatctgatct ggggcctcgg    3000
tgcacatgct ttcatgtgt ttagtcgagg ttaaaaaaac gtctaggccc cccgaaccac    3060
ggggacgtgg ttttccttg aaaaacacga tgataagctt gccacaaccc acagcggccg    3120
ctgccatcat ggttcgacca ttgaactgca tcgtcgccgt gtcccaaaat atggggattg    3180
gcaagaacgg agacctaccc tggcctccgc tcaggaacga gttcaagtac ttccaaagaa    3240
tgaccacaac ctcttcagtg gaaggtaaac agaatctggt gattatgggt aggaaaacct    3300
ggttctccat tcctgagaag aatcgacctt taaaggacag aattaatata gttctcagta    3360
gagaactcaa agaaccacca cgaggagctc attttcttgc caaagttttg gatgatgcct    3420
taagacttat tgaacaaccg gaattggcaa gtaaagtaga catggtttgg atagtcggag    3480
gcagttctgt ttaccaggaa gccatgaatc aaccaggcca cctcagactc tttgtgacaa    3540
ggatcatgca ggaatttgaa agtgacacgt ttttcccaga aattgatttg ggggaaatata    3600 aacttctccc agaatccca ggcgtcctct ctgaggtcca ggaggaaaaa ggcatcaagt    3660
ataagtttga agtctacgag aagaaagact aaacgcgtgg tacctctaga gtcgacccgg    3720
gcggccgctt cgagcagaca tgataagata cattgatgag tttggacaaa ccacaactag    3780
aatgcagtga aaaaaatgct ttatttgtga aatttgtgat gctattgctt tatttgtaac    3840
cattataagc tgcaataaac aagttaacaa caacaattgc attcatttta tgtttcaggt    3900 tcaggggag atgtgggagg ttttttaaag caagtaaaac ctctacaaat gtggtaaaat    3960
cgataaggat ccgggctggc gtaatagcga agaggcccgc accgatcgcc cttcccaaca    4020
gttgcgcagc ctgaatggcg aatggacgcg ccctgtagcg gcgcattaag cgcggcgggt    4080
gtggtggtta cgcgcagcgt gaccgctaca cttgccagcg ccctagcgcc cgctcctttc    4140
```

```
gctttcttcc cttcctttct cgccacgttc gccggctttc cccgtcaagc tctaaatcgg   4200 gggctcccett tagggttccg atttagtgct ttacggcacc tcgaccccaa aaaacttgat   4260
tagggtgatg gttcacgtag tgggccatcg ccctgataga cggttttttcg ccctttgacg   4320 ttggagtcca cgttctttaa tagtggactc ttgttccaaa ctggaacaac actcaaccct   4380
atctcggtct attcttttga tttataaggg attttgccga tttcggccta ttggttaaaa   4440
aatgagctga tttaacaaaa atttaacgcg aattttaaca aaatattaac gcttacaatt   4500
tcctgatgcg gtattttctc cttacgcatc tgtgcggtat ttcacaccgc atatggtgca   4560
ctctcagtac aatctgctct gatgccgcat agttaagcca gccccgacac ccgccaacac   4620
ccgctgacgc gccctgacgg gcttgtctgc tcccggcatc cgcttacaga caagctgtga   4680
ccgtctccgg gagctgcatg tgtcagaggt tttaccgtc atcaccgaaa cgcgcgagac   4740
gaaagggcct cgtgatacgc ctatttttat aggttaatgt catgataata atggtttctt   4800
agacgtcagg tggcactttt cggggaaatg tgcgcggaac ccctatttgt ttatttttct   4860
aaatacattc aaatatgtat ccgctcatga acaataacc ctgataaatg cttcaataat   4920
attgaaaaag gaagagtatg agtattcaac atttccgtgt cgcccttatt cccttttttg   4980
cggcattttg ccttcctgtt tttgctcacc cagaaacgct ggtgaaagta aaagatgctg   5040
aagatcagtt gggtgcacga gtgggttaca tcgaactgga tctcaacagc ggtaagatcc   5100
ttgagagttt tcgccccgaa gaacgttttc caatgatgag cacttttaaa gttctgctat   5160
gtggcgcggt attatcccgt attgacgccg ggcaagagca actcggtcgc cgcatacact   5220
attctcagaa tgacttggtt gagtactcac cagtcacaga aaagcatctt acggatggca   5280
tgacagtaag agaattatgc agtgctgcca taaccatgag tgataacact gcggccaact   5340
tacttctgac aacgatcgga ggaccgaagg agctaaccgc ttttttgcac aacatggggg   5400
atcatgtaac tcgccttgat cgttgggaac cggagctgaa tgaagccata ccaaacgacg   5460
agcgtgacac cacgatgcct gtagcaatgg caacaacgtt gcgcaaacta ttaactggcg   5520
aactacttac tctagcttcc cggcaacaat taatagactg gatggaggcg gataaagttg   5580
caggaccact tctgcgctcg gcccttccgg ctggctggtt tattgctgat aaatctggag   5640
ccggtgagcg tgggtctcgc ggtatcattg cagcactggg gccagatggt aagccctccc   5700
gtatcgtagt tatctacacg acggggagtc aggcaactat ggatgaacga atagacaga   5760 tcgctgagat aggtgcctca ctgattaagc attggtaact gtcagaccaa gtttactcat   5820
atatacttta gattgattta aaacttcatt tttaatttaa aaggatctag gtgaagatcc   5880
tttttgataa tctcatgacc aaaatccctt aacgtgagtt ttcgttccac tgagcgtcag   5940
accccgtaga aaagatcaaa ggatcttctt gagatccttt ttttctgcgc gtaatctgct   6000
gcttgcaaac aaaaaaacca ccgctaccag cggtggtttg tttgccggat caagagctac   6060
caactctttt tccgaaggta actggcttca gcagagcgca gataccaaat actgttcttc   6120
tagtgtagcc gtagttaggc caccacttca agaactctgt agcaccgcct acatacctcg   6180
ctctgctaat cctgttacca gtggctgctg ccagtggcga taagtcgtgt cttaccgggt   6240
tggactcaag acgatagtta ccggataagg cgcagcggtc gggctgaacg gggggttcgt   6300
gcacacagcc cagcttggag cgaacgacct acaccgaact gagatacta cagcgtgagc   6360 tatgagaaag cgccacgctt cccgaaggga gaaggcgga caggtatccg gtaagcggca   6420
gggtcggaac aggagagcgc acgagggagc ttccagggggg aaacgcctgg tatctttata   6480
gtcctgtcgg gtttcgccac tctgacttg agcgtcgatt tttgtgatgc tcgtcagggg   6540
```

-continued

```
ggcggagcct atggaaaaac gccagcaacg cggccttttt acggttcctg gccttttgct    6600
ggccttttgc tcacatggct cgacagatct                                     6630
```

<210> SEQ ID NO 51
<211> LENGTH: 186
<212> TYPE: PRT
<213> ORGANISM: Mus musculus
<220> FEATURE:
<223> OTHER INFORMATION: dihydrofolate reductase

<400> SEQUENCE: 51

```
Val Arg Pro Leu Asn Cys Ile Val Ala Val Ser Gln Asn Met Gly Ile
 1               5                  10                  15

Gly Lys Asn Gly Asp Leu Pro Trp Pro Pro Leu Arg Asn Glu Phe Lys
            20                  25                  30

Tyr Phe Gln Arg Met Thr Thr Thr Ser Ser Val Glu Gly Lys Gln Asn
        35                  40                  45

Leu Val Ile Met Gly Arg Lys Thr Trp Phe Ser Ile Pro Glu Lys Asn
    50                  55                  60

Arg Pro Leu Lys Asp Arg Ile Asn Ile Val Leu Ser Arg Glu Leu Lys
65                  70                  75                  80

Glu Pro Pro Arg Gly Ala His Phe Leu Ala Lys Ser Leu Asp Asp Ala
                85                  90                  95

Leu Arg Leu Ile Glu Gln Pro Glu Leu Ala Ser Lys Val Asp Met Val
            100                 105                 110

Trp Ile Val Gly Gly Ser Ser Val Tyr Gln Glu Ala Met Asn Gln Pro
        115                 120                 125

Gly His Leu Arg Leu Phe Val Thr Arg Ile Met Gln Glu Phe Glu Ser
    130                 135                 140

Asp Thr Phe Phe Pro Glu Ile Asp Leu Gly Lys Tyr Lys Leu Leu Pro
145                 150                 155                 160

Glu Tyr Pro Gly Val Leu Ser Glu Val Gln Glu Lys Gly Ile Lys
                165                 170                 175

Tyr Lys Phe Glu Val Tyr Glu Lys Lys Asp
            180                 185
```

<210> SEQ ID NO 52
<211> LENGTH: 23
<212> TYPE: DNA
<213> ORGANISM: Artificial Sequence
<220> FEATURE:
<223> OTHER INFORMATION: HZM3.P1 forward primer

<400> SEQUENCE: 52

```
tttgaacact cagcagtctc ctg                                              23
```

<210> SEQ ID NO 53
<211> LENGTH: 20
<212> TYPE: DNA
<213> ORGANISM: Artificial Sequence
<220> FEATURE:
<223> OTHER INFORMATION: HZM3.P2 reverse primer

<400> SEQUENCE: 53

```
aactctgatg gcttcccgaa                                                  20
```

<210> SEQ ID NO 54
<211> LENGTH: 28
<212> TYPE: DNA
<213> ORGANISM: Artificial Sequence
<220> FEATURE:
<223> OTHER INFORMATION: HZM3 probe

<400> SEQUENCE: 54
agctgctaca ctctatgtgc gcaatcga                                              28

<210> SEQ ID NO 55
<211> LENGTH: 1449
<212> TYPE: DNA
<213> ORGANISM: Homo sapiens
<220> FEATURE:
<223> OTHER INFORMATION: PH20 mRNA sequence from 3D35M cells

<400> SEQUENCE: 55

```
atgggagtgc taaaattcaa gcacatcttt ttcagaagct tgttaaaatc aagtggagta      60
tcccagatag ttttcacctt ccttctgatt ccatgttgct tgactctgaa tttcagagca     120
cctcctgtta ttccaaatgt gcctttcctc tgggcctgga atgccccaag tgaattttgt     180
cttggaaaat ttgatgagcc actagatatg agcctcttct ctttcatagg aagcccccga     240
ataaacgcca ccgggcaagg tgttacaata ttttatgttg atagacttgg ctactatcct     300
tacatagatt caatcacagg agtaactgtg aatggaggaa tcccccagaa gatttcctta     360
caagaccatc tggacaaagc taagaaagac attacatttt atatgccagt agacaatttg     420
ggaatggctg ttattgactg ggaagaatgg agacccactt gggcaagaaa ctggaaacct     480
aaagatgttt acaagaatag gtctattgaa ttggttcagc aacaaaatgt acaacttagt     540
ctcacagagg ccactgagaa agcaaaacaa gaatttgaaa aggcagggaa ggatttcctg     600
gtagagacta aaaattggg aaaattactt cggccaaatc acttgtgggg ttattatctt     660
tttccggatt gttacaacca tcactataag aaacccggtt acaatggaag ttgcttcaat     720
gtagaaataa aagaaatga tgatctcagc tggttgtgga atgaaagcac tgctctttac     780
ccatccattt atttgaacac tcagcagtct cctgtagctg ctacactcta tgtgcgcaat     840
cgagttcggg aagccatcag agtttccaaa ataccttgatg caaaaagtcc acttccggtt     900
tttgcatata cccgcatagt ttttactgat caagttttga aattcctttc tcaagatgaa     960
cttgtgtata catttggcga aactgttgct ctgggtgctt ctggaattgt aatatgggga    1020
accctcagta taatgcgaag tatgaaatct tgcttgctcc tagacaatta catggagact    1080
atactgaatc cttacataat caacgtcaca ctagcagcca aaatgtgtag tcaagtgctt    1140
tgccaggagc aaggagtgtg tataaggaaa aactggaatt caagtgacta tcttcacctc    1200
aacccagata attttgctat tcaacttgag aaaggtggaa agttcacagt acgtggaaaa    1260
ccgacacttg aagacctgga gcaattttct gaaaaatttt attgcagctg ttatagcacc    1320
ttgagttgta aggagaaagc tgatgtaaaa gacactgatg ctgttgatgt gtgtattgct    1380
gatggtgtct gtatagatgc ttttctaaaa cctcccatgg agacagaaga acctcaaatt    1440
ttctactga                                                            1449
```

<210> SEQ ID NO 56
<211> LENGTH: 17
<212> TYPE: DNA
<213> ORGANISM: Artificial Sequence
<220> FEATURE:
<223> OTHER INFORMATION: AP01

<400> SEQUENCE: 56
ttctctccac aggtgtc                                                         17

```
<210> SEQ ID NO 57
<211> LENGTH: 18
<212> TYPE: DNA
<213> ORGANISM: Artificial Sequence
<220> FEATURE:
<223> OTHER INFORMATION: AP02

<400> SEQUENCE: 57
aagatttcct tacaagac                                                   18

<210> SEQ ID NO 58
<211> LENGTH: 18
<212> TYPE: DNA
<213> ORGANISM: Artificial Sequence
<220> FEATURE:
<223> OTHER INFORMATION: AP03

<400> SEQUENCE: 58
tggcgagagg ggaaagac                                                   18

<210> SEQ ID NO 59
<211> LENGTH: 18
<212> TYPE: DNA
<213> ORGANISM: Artificial Sequence
<220> FEATURE:
<223> OTHER INFORMATION: AP04

<400> SEQUENCE: 59
ccatttattt gaacactc                                                   18

<210> SEQ ID NO 60
<211> LENGTH: 18
<212> TYPE: DNA
<213> ORGANISM: Artificial Sequence
<220> FEATURE:
<223> OTHER INFORMATION: AP06

<400> SEQUENCE: 60
ccgaactcga ttgcgcac                                                   18

<210> SEQ ID NO 61
<211> LENGTH: 18
<212> TYPE: DNA
<213> ORGANISM: Artificial Sequence
<220> FEATURE:
<223> OTHER INFORMATION: AP07

<400> SEQUENCE: 61
agccattccc aaattgtc                                                   18

<210> SEQ ID NO 62
<211> LENGTH: 18
<212> TYPE: DNA
<213> ORGANISM: Artificial Sequence
<220> FEATURE:
<223> OTHER INFORMATION: AP08

<400> SEQUENCE: 62
ctcccagttc aattacag                                                   18

<210> SEQ ID NO 63
<211> LENGTH: 18
<212> TYPE: DNA
<213> ORGANISM: Artificial Sequence
<220> FEATURE:
<223> OTHER INFORMATION: AP09

<400> SEQUENCE: 63
```

```
cgttagctat ggatcctc                                              18

<210> SEQ ID NO 64
<211> LENGTH: 22
<212> TYPE: DNA
<213> ORGANISM: Artificial Sequence
<220> FEATURE:
<223> OTHER INFORMATION: AP10

<400> SEQUENCE: 64
cgagacagag aagactcttg cg                                         22

<210> SEQ ID NO 65
<211> LENGTH: 22
<212> TYPE: DNA
<213> ORGANISM: Artificial Sequence
<220> FEATURE:
<223> OTHER INFORMATION: AP12

<400> SEQUENCE: 65
cattcaacag accttgcatt cc                                         22

<210> SEQ ID NO 66
<211> LENGTH: 17
<212> TYPE: PRT
<213> ORGANISM: Homo sapiens
<220> FEATURE:
<223> OTHER INFORMATION: C-terminal peptide cleaved from soluble rHuPH20
      aa 431-447

<400> SEQUENCE: 66

Asp Ala Phe Lys Leu Pro Pro Met Glu Thr Glu Glu Pro Gln Ile Phe
 1               5                  10                  15

Tyr

<210> SEQ ID NO 67
<211> LENGTH: 16
<212> TYPE: PRT
<213> ORGANISM: Homo sapiens
<220> FEATURE:
<223> OTHER INFORMATION: C-terminal peptide cleaved from soluble rHuPH20
      aa 431-446

<400> SEQUENCE: 67

Asp Ala Phe Lys Leu Pro Pro Met Glu Thr Glu Glu Pro Gln Ile Phe
 1               5                  10                  15

<210> SEQ ID NO 68
<211> LENGTH: 15
<212> TYPE: PRT
<213> ORGANISM: Homo sapiens
<220> FEATURE:
<223> OTHER INFORMATION: C-terminal peptide cleaved from soluble rHuPH20
      aa 431-445

<400> SEQUENCE: 68

Asp Ala Phe Lys Leu Pro Pro Met Glu Thr Glu Glu Pro Gln Ile
 1               5                  10                  15

<210> SEQ ID NO 69
<211> LENGTH: 14
<212> TYPE: PRT
<213> ORGANISM: Homo sapiens
<220> FEATURE:
<223> OTHER INFORMATION: C-terminal peptide cleaved from soluble rHuPH20
      aa 431-444
```

```
-continued

<400> SEQUENCE: 69

Asp Ala Phe Lys Leu Pro Pro Met Glu Thr Glu Glu Pro Gln
1               5                   10

<210> SEQ ID NO 70
<211> LENGTH: 13
<212> TYPE: PRT
<213> ORGANISM: Homo sapiens
<220> FEATURE:
<223> OTHER INFORMATION: C-terminal peptide cleaved from soluble rHuPH20
      aa 431-443

<400> SEQUENCE: 70

Asp Ala Phe Lys Leu Pro Pro Met Glu Thr Glu Glu Pro
1               5                   10

<210> SEQ ID NO 71
<211> LENGTH: 12
<212> TYPE: PRT
<213> ORGANISM: Homo sapiens
<220> FEATURE:
<223> OTHER INFORMATION: C-terminal peptide cleaved from soluble rHuPH20
      aa 431-442

<400> SEQUENCE: 71

Asp Ala Phe Lys Leu Pro Pro Met Glu Thr Glu Glu
1               5                   10
```